(12) United States Patent
Butler et al.

(10) Patent No.: US 10,028,692 B2
(45) Date of Patent: Jul. 24, 2018

(54) ADJUSTABLE CONNECTOR, IMPROVED FLUID FLOW AND REDUCED CLOTTING RISK

(71) Applicant: OptiScan Biomedical Corporation, Hayward, CA (US)

(72) Inventors: Michael Butler, Dublin, CA (US); Eugene Lim, Lafayette, CA (US); Craig Johnson, Dublin, CA (US)

(73) Assignee: OptiScan Biomedical Corporation, Hayward, CA (US)

( * ) Notice: Subject to any disclaimer, the term of this patent is extended or adjusted under 35 U.S.C. 154(b) by 300 days.

(21) Appl. No.: 14/259,940

(22) Filed: Apr. 23, 2014

(65) Prior Publication Data

US 2014/0236047 A1   Aug. 21, 2014

Related U.S. Application Data

(63) Continuation of application No. 13/068,121, filed on May 3, 2011, now Pat. No. 8,731,639, which is a (Continued)

(51) Int. Cl.
*A61M 39/10* (2006.01)
*A61B 5/15* (2006.01)
(Continued)

(52) U.S. Cl.
CPC ...... *A61B 5/150992* (2013.01); *A61B 5/0059* (2013.01); *A61B 5/1455* (2013.01);
(Continued)

(58) Field of Classification Search
None
See application file for complete search history.

(56) References Cited

U.S. PATENT DOCUMENTS 1,649,673 A   12/1926   Dyck
2,797,149 A   6/1957    Skeggs
(Continued)

FOREIGN PATENT DOCUMENTS

EP   0549341   6/1993
EP   1 747 796  1/2007
(Continued)

OTHER PUBLICATIONS

Billman et. al., "Clinical Performance of an In line Ex-Vivo Point of Care Monitor: A Multicenter Study," Clinical Chemistry 48:11, pp. 2030-2043, 2002.
(Continued)

*Primary Examiner* — Katherine Fernandez
*Assistant Examiner* — Bradley Impink
(74) *Attorney, Agent, or Firm* — Knobbe Martens Olson & Bear LLP

(57) ABSTRACT

Methods and systems for determining the concentration of one or more analytes from a sample such as blood or plasma are described. The systems described herein can be configured to withdraw a sample from a source of fluid, direct a first portion of the withdrawn sample to an analyte monitoring system and return a second portion of the sample. The analyte monitoring system can be connected to the fluid source via a connector that is configured to improve fluid flow and reduce blood clotting risk. These goals can be accomplished, for example, by employing coatings in or on a connector, positioning a resilient substance at or near the junction, by reducing dead space volume, by using resiliency to improve fit, by extending a portion of one connector to better mate with a portion of another connector, etc.

36 Claims, 74 Drawing Sheets
(6 of 74 Drawing Sheet(s) Filed in Color)

Related U.S. Application Data continuation-in-part of application No. 12/804,336, filed on Jul. 20, 2010, now Pat. No. 8,731,638.

(60) Provisional application No. 61/330,812, filed on May 3, 2010, provisional application No. 61/227,040, filed on Jul. 20, 2009.

(51) Int. Cl.
| | | |
|---|---|---|
| *A61B 5/00* | (2006.01) | |
| *A61B 5/145* | (2006.01) | |
| *A61B 5/1455* | (2006.01) | |
| *A61B 5/153* | (2006.01) | |
| *A61B 5/155* | (2006.01) | |
| *A61B 5/157* | (2006.01) | |
| *A61M 39/26* | (2006.01) | |

(52) U.S. Cl.
CPC ...... *A61B 5/14532* (2013.01); *A61B 5/14546* (2013.01); *A61B 5/15003* (2013.01); *A61B 5/153* (2013.01); *A61B 5/155* (2013.01); *A61B 5/157* (2013.01); *A61B 5/150229* (2013.01); *A61B 5/150389* (2013.01); *A61B 5/150503* (2013.01); *A61B 5/150755* (2013.01); *A61B 5/412* (2013.01); *A61M 39/10* (2013.01); *A61M 39/1011* (2013.01); *A61M 39/26* (2013.01); *A61B 5/14557* (2013.01); *A61B 2560/0437* (2013.01); *A61M 2039/1027* (2013.01); *A61M 2039/1033* (2013.01); *A61M 2039/263* (2013.01); *A61M 2205/0222* (2013.01); *A61M 2205/0238* (2013.01)

(56) References Cited

U.S. PATENT DOCUMENTS

| | | |
|---|---|---|
| 3,634,039 A | 1/1972 | Brondy |
| 3,806,086 A | 4/1974 | Cloyd |
| 4,151,845 A | 5/1979 | Clemens |
| 4,506,987 A | 3/1985 | Daughton et al. |
| 4,573,968 A | 3/1986 | Parker |
| 4,595,021 A | 6/1986 | Shimizu |
| 4,619,640 A * | 10/1986 | Potolsky ............... A61M 39/10 128/912 |
| 4,657,529 A | 4/1987 | Prince et al. |
| 4,690,437 A | 9/1987 | Anderson, Jr. |
| 4,745,950 A | 5/1988 | Mathieu |
| 4,919,596 A | 4/1990 | Slate et al. |
| 4,929,243 A | 5/1990 | Koch et al. |
| 4,940,527 A | 7/1990 | Kazlauskas et al. |
| 4,946,455 A | 8/1990 | Rosen |
| 4,966,162 A | 10/1990 | Wang |
| 5,108,380 A | 4/1992 | Herlitze et al. |
| 5,156,596 A | 10/1992 | Balbierz |
| 5,165,406 A | 11/1992 | Wong |
| 5,169,120 A | 12/1992 | Guthrie, Jr. et al. |
| 5,195,980 A | 3/1993 | Catlin |
| 5,230,706 A | 7/1993 | Duquette |
| 5,269,771 A | 12/1993 | Thomas et al. |
| 5,322,518 A | 6/1994 | Schneider et al. |
| 5,334,159 A | 8/1994 | Turkel |
| 5,353,837 A | 10/1994 | Faust |
| 5,380,306 A | 1/1995 | Brinson |
| 5,380,665 A | 1/1995 | Cusack et al. |
| 5,405,339 A * | 4/1995 | Kohnen ............... A61M 39/12 285/239 |
| 5,437,650 A | 8/1995 | Larkin et al. |
| 5,441,487 A | 8/1995 | Vedder |
| 5,478,331 A | 12/1995 | Heflin et al. |
| 5,492,147 A | 2/1996 | Challender et al. |
| 5,520,666 A | 5/1996 | Choudhury et al. |
| 5,531,699 A | 7/1996 | Tomba et al. |
| 5,549,577 A | 8/1996 | Siegel et al. |
| 5,555,908 A | 9/1996 | Edwards et al. |
| 5,603,706 A | 2/1997 | Wyatt et al. |
| 5,669,891 A | 9/1997 | Vaillancourt |
| 5,685,866 A | 11/1997 | Lopez |
| 5,697,899 A | 12/1997 | Hillman et al. |
| 5,700,248 A | 12/1997 | Lopez |
| 5,738,144 A | 4/1998 | Rogers |
| 5,738,663 A | 4/1998 | Lopez |
| 5,758,643 A | 6/1998 | Wong et al. |
| 5,776,113 A | 7/1998 | Daugherty et al. |
| 5,785,693 A | 7/1998 | Haining |
| 5,788,215 A | 8/1998 | Ryan |
| 5,817,007 A | 10/1998 | Fodgaard et al. |
| 5,820,614 A | 10/1998 | Erskine et al. |
| 5,839,715 A | 11/1998 | Leinsing |
| 5,848,997 A | 12/1998 | Erskine et al. |
| 5,901,942 A | 5/1999 | Lopez |
| 5,902,253 A | 5/1999 | Pfeiffer et al. |
| 5,950,986 A | 9/1999 | Daugherty et al. |
| 5,954,313 A | 9/1999 | Ryan |
| 5,967,490 A | 10/1999 | Pike |
| 6,017,318 A | 1/2000 | Gauthier et al. |
| 6,040,578 A | 3/2000 | Malin et al. |
| 6,056,331 A | 5/2000 | Benett et al. |
| 6,063,062 A | 5/2000 | Paradis |
| 6,101,406 A | 8/2000 | Hacker et al. |
| 6,113,068 A | 9/2000 | Ryan |
| 6,158,458 A | 12/2000 | Ryan |
| 6,168,137 B1 | 1/2001 | Paradis |
| 6,171,287 B1 | 1/2001 | Lynn et al. |
| 6,200,287 B1 | 3/2001 | Keller et al. |
| 6,224,575 B1 | 5/2001 | Garvin |
| 6,228,069 B1 | 5/2001 | Barth et al. |
| 6,260,890 B1 | 7/2001 | Mason |
| 6,261,065 B1 | 7/2001 | Nayak et al. |
| 6,261,282 B1 | 7/2001 | Jepson et al. |
| 6,262,798 B1 | 7/2001 | Shepherd et al. |
| 6,273,869 B1 | 8/2001 | Vaillancourt |
| 6,299,131 B1 | 10/2001 | Ryan |
| 6,312,647 B1 | 11/2001 | Spears |
| 6,364,869 B1 | 4/2002 | Bonaldo |
| 6,450,992 B1 | 9/2002 | Cassidy, Jr. |
| 6,482,188 B1 | 11/2002 | Rogers et al. |
| 6,543,745 B1 | 4/2003 | Enerson |
| 6,546,269 B1 | 4/2003 | Kurnik |
| 6,599,273 B1 | 7/2003 | Lopez |
| 6,609,696 B2 | 8/2003 | Enerson |
| 6,612,624 B1 * | 9/2003 | Segal .................... A61M 39/10 285/330 |
| 6,620,119 B1 | 9/2003 | Utterberg |
| 6,666,839 B2 | 12/2003 | Utterberg |
| 6,695,816 B2 | 2/2004 | Cassidy, Jr. |
| 6,745,998 B2 | 6/2004 | Doyle |
| 6,811,139 B2 | 11/2004 | Hishikawa |
| 6,871,838 B2 | 3/2005 | Raines et al. |
| 6,890,291 B2 | 5/2005 | Robinson et al. |
| 6,958,809 B2 | 10/2005 | Sterling et al. |
| 6,964,406 B2 | 11/2005 | Doyle |
| 6,989,891 B2 | 1/2006 | Braig et al. |
| 7,037,302 B2 | 5/2006 | Vaillancourt |
| 7,040,598 B2 | 5/2006 | Raybuck |
| 7,061,593 B2 | 6/2006 | Braig et al. |
| 7,080,672 B2 | 7/2006 | Fournie et al. |
| 7,153,296 B2 | 12/2006 | Mitchell |
| 7,182,753 B2 | 2/2007 | Matsumoto |
| 7,244,249 B2 | 7/2007 | Leinsing et al. |
| 7,306,199 B2 | 12/2007 | Leinsing et al. |
| 7,316,777 B2 | 1/2008 | Loy, Jr. |
| 7,329,249 B2 | 2/2008 | Bonaldo |
| 7,350,764 B2 | 4/2008 | Raybuck |
| 7,500,949 B2 | 3/2009 | Gottlieb et al. |
| 7,531,098 B2 | 5/2009 | Robinson et al. |
| 7,608,042 B2 | 10/2009 | Goldberger et al. |
| 7,972,296 B2 | 7/2011 | Braig |
| 8,412,293 B2 | 4/2013 | Rule |
| 8,417,311 B2 | 4/2013 | Rule |
| 8,731,638 B2 | 5/2014 | Butler et al. |
| 8,731,639 B2 | 5/2014 | Callicoat et al. |
| 9,326,717 B2 | 5/2016 | Butler et al. |

(56) References Cited

U.S. PATENT DOCUMENTS

| | | |
|---|---|---|
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0199803 A1 | 10/2003 | Robinson et al. |
| 2003/0208165 A1 | 11/2003 | Christensen et al. |
| 2004/0068239 A1 | 4/2004 | Utterberg |
| 2004/0147034 A1 | 7/2004 | Gore et al. |
| 2004/0171993 A1 | 9/2004 | Bonaldo |
| 2004/0199126 A1 | 10/2004 | Harding et al. |
| 2004/0241736 A1 | 12/2004 | Hendee et al. |
| 2004/0249308 A1 | 12/2004 | Forssell |
| 2005/0059958 A1 | 3/2005 | Lessard et al. |
| 2005/0090764 A1 | 4/2005 | Wang |
| 2005/0137614 A1 | 6/2005 | Porter et al. |
| 2005/0151105 A1 | 7/2005 | Ryan et al. |
| 2005/0203360 A1 | 9/2005 | Brauker et al. |
| 2005/0256460 A1 | 11/2005 | Rome et al. |
| 2006/0009727 A1 | 1/2006 | O'Mahony et al. |
| 2006/0064159 A1 | 3/2006 | Porter |
| 2006/0079809 A1 | 4/2006 | Goldberger et al. |
| 2006/0157984 A1 | 7/2006 | Rome et al. |
| 2006/0161115 A1 | 7/2006 | Fangrow |
| 2006/0169628 A1 | 8/2006 | Loy, Jr. |
| 2006/0189926 A1 | 8/2006 | Hall et al. |
| 2006/0200070 A1 | 9/2006 | Callicoat et al. |
| 2006/0200071 A1 | 9/2006 | Sterling et al. |
| 2006/0229531 A1 | 10/2006 | Goldberger et al. |
| 2006/0276749 A1 | 12/2006 | Selmon |
| 2007/0060872 A1 | 3/2007 | Hall et al. |
| 2007/0142720 A1 | 6/2007 | Ridder et al. |
| 2007/0224865 A1 | 9/2007 | Fangrow |
| 2007/0225675 A1 | 9/2007 | Robinson et al. |
| 2007/0239096 A1 | 10/2007 | Keenan |
| 2007/0258083 A1 | 11/2007 | Heppell |
| 2008/0014601 A1 | 1/2008 | Goldberger et al. |
| 2008/0072663 A1 | 3/2008 | Keenan |
| 2008/0161723 A1 | 7/2008 | Keenan |
| 2008/0284167 A1 | 11/2008 | Lim et al. |
| 2008/0319344 A1 | 12/2008 | Reymond et al. |
| 2009/0032111 A1 | 2/2009 | Tong |
| 2009/0036764 A1 | 2/2009 | Rivas |
| 2009/0043171 A1 | 2/2009 | Rule |
| 2009/0131861 A1 | 5/2009 | Braig |
| 2009/0156911 A1 | 6/2009 | Rule |
| 2009/0157430 A1 | 6/2009 | Rule |
| 2009/0160656 A1 | 6/2009 | Seetharaman |
| 2009/0270815 A1 | 10/2009 | Stamp |
| 2010/0063481 A1 | 3/2010 | Hoffman et al. |
| 2010/0121170 A1 | 5/2010 | Rule |
| 2010/0145175 A1 | 6/2010 | Soldo |
| 2010/0273738 A1 | 10/2010 | Valcke et al. |
| 2010/0274112 A1 | 10/2010 | Hoss et al. |
| 2010/0281990 A1 | 11/2010 | Gravesen et al. |
| 2010/0317952 A1 | 12/2010 | Budiman et al. |
| 2011/0092784 A1 | 4/2011 | Butler |
| 2011/0190662 A1 | 8/2011 | McWeeney |
| 2011/0264071 A1 | 10/2011 | Braig |
| 2011/0306856 A1 | 12/2011 | Rule |
| 2011/0313317 A1 | 12/2011 | Callicoat |
| 2011/0313318 A1 | 12/2011 | Rule |
| 2012/0203089 A1 | 8/2012 | Rule |
| 2014/0236047 A1 | 8/2014 | Butler et al. |

FOREIGN PATENT DOCUMENTS

| | | |
|---|---|---|
| WO | WO 02/43866 | 6/2002 |
| WO | WO 03/016882 | 2/2003 |
| WO | WO 03/039362 | 5/2003 |
| WO | WO 2004/092715 A1 | 10/2004 |
| WO | WO 2005/110601 A1 | 11/2005 |
| WO | WO 2006/088771 | 8/2006 |
| WO | WO 2010/007254 | 1/2010 |
| WO | WO 2010/128399 | 11/2010 |

OTHER PUBLICATIONS

Davidson, Paul C., et al., A computer-directed intravenous insulin system shown to be safe, simple, and effective in 120,618 h of operation, *Diabetes Care*, vol. 28, No. 10, Oct. 2005, pp. 2418-2423.

Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.

Davidson, Paul C., et al., *Glucommander: A Computer-Directed IV Insulin System Shown to be Safe, Simple, and Effective in 120,618 Hours of Operation*, Atlanta Diabetes Associates presentation.

"Glucon Critical Care Blood Glucose Monitor", Glucon Inc., published no later than May 8, 2006 and possibly published as early as Oct. 9, 2001.

Berger, "An Enhanced Algorithm for Linear Multivariate Calibration," Analytical Chemistry, vol. 70, No. 3, pp. 623-627, Feb. 1, 1998.

Finkielman et al., "Agreement Between Bedside Blood and Plasma Glucose Measurement in the ICU Setting"; retrieved from http://www.chestjournal.org; CHEST/127/5/May 2005.

Widness et al., "Clinical Performance on an In-Line Point-of-Care Monitor in Neonates"; Pediatrics, vol. 106, No. 3, pp. 497-504, Sep. 2000.

International Search Report dated Nov. 19, 2010 in PCT/US2010/042664.

International Search Report dated Feb. 9, 2012 in PCT/US2011/034977.

Van Den Berghe, Greet, M.D., Ph.D., et al., Intensive Insulin Therapy in Critically Ill Patients, *The New England Journal of Medicine*, vol. 345, No. 19, Nov. 8, 2001, pp. 1359-1367.

European Search Report dated Sep. 9, 2014 in corresponding European Application No. 11778160.9.

European Search Report dated Sep. 9, 2014 in Application No. 10802810.1.

Office Action dated Aug. 6, 2015 in European Application No. 10802810.1.

Office Action dated Aug. 21, 2015 in European Application No. 11778160.9.

Office Action dated Apr. 11, 2016 in European Application No. 11778160.9.

\* cited by examiner

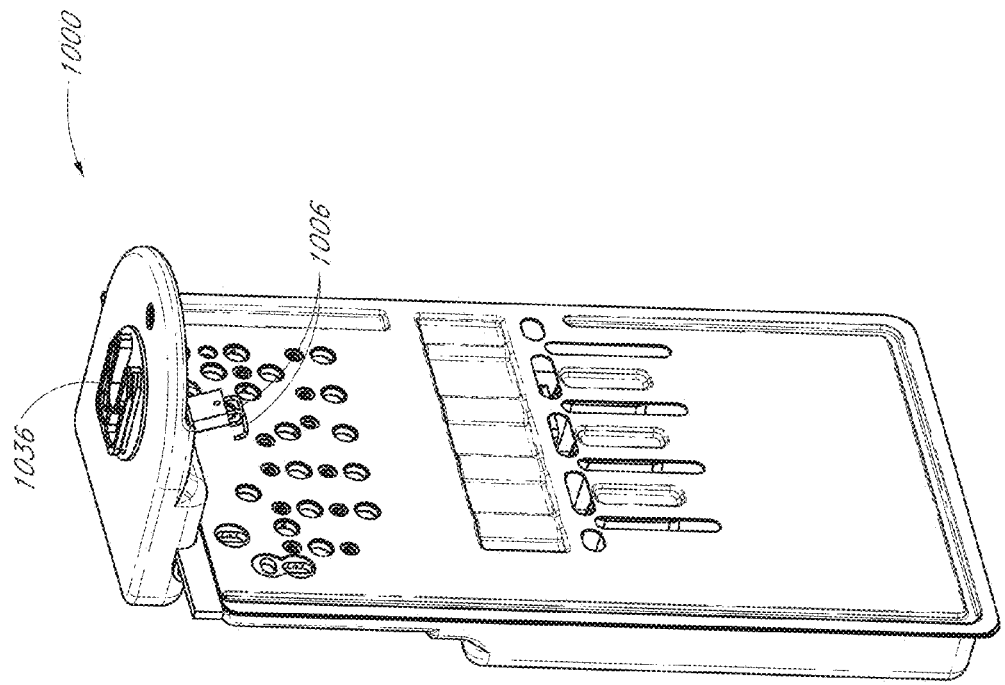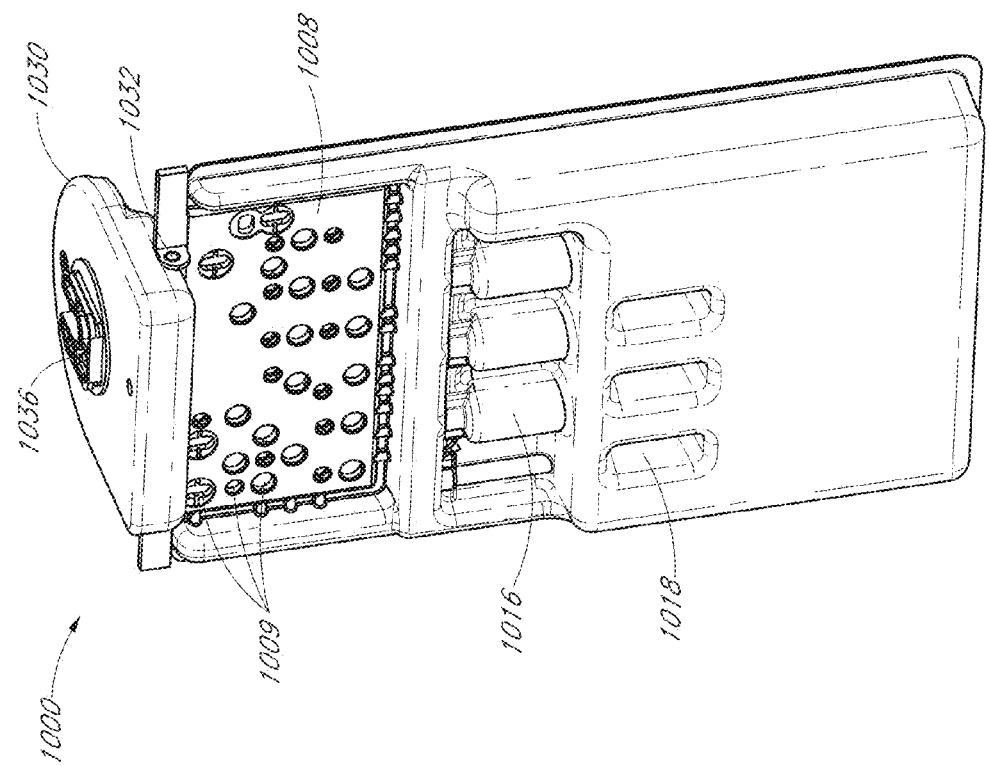
FIG. 10

2801

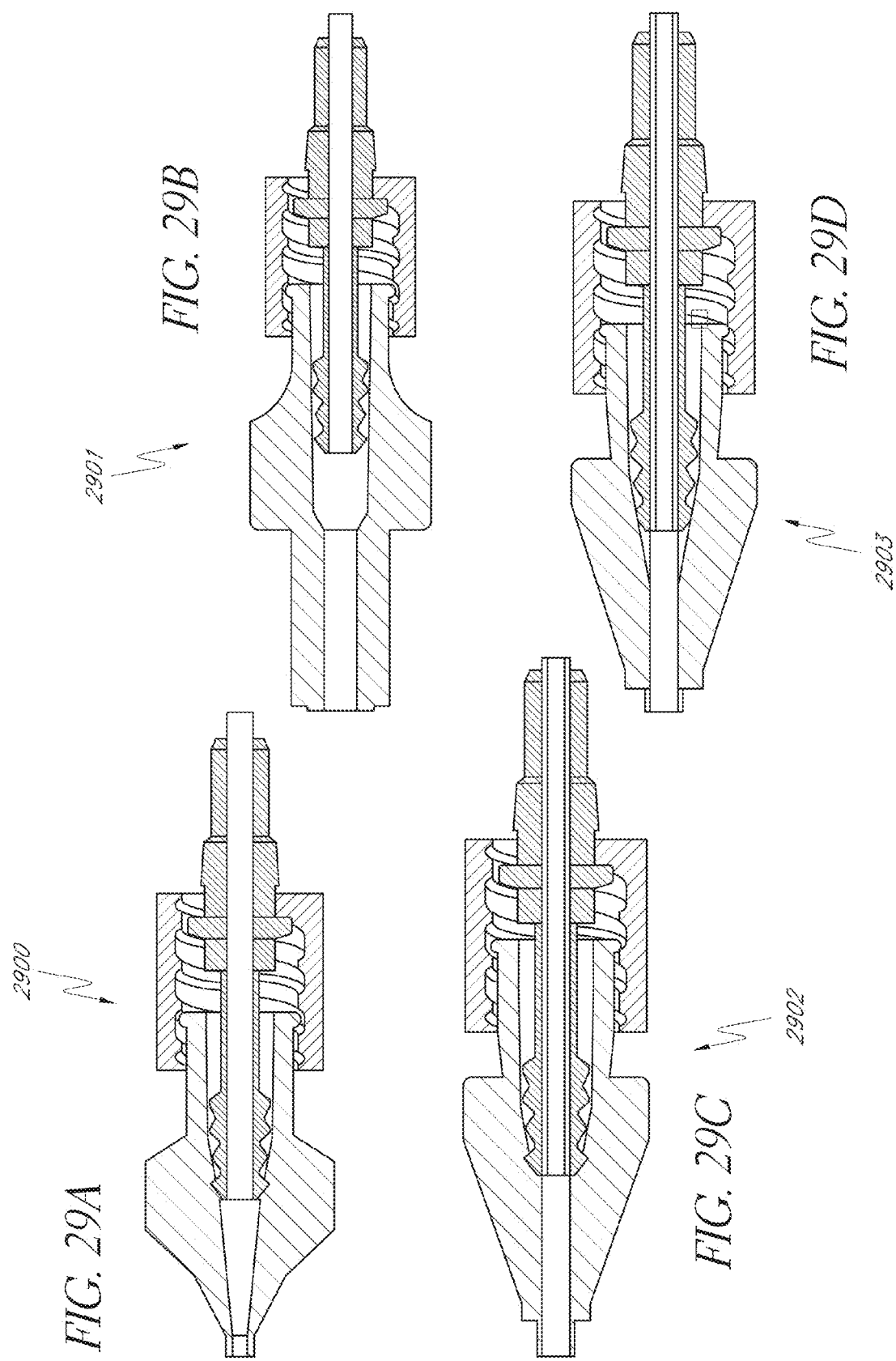

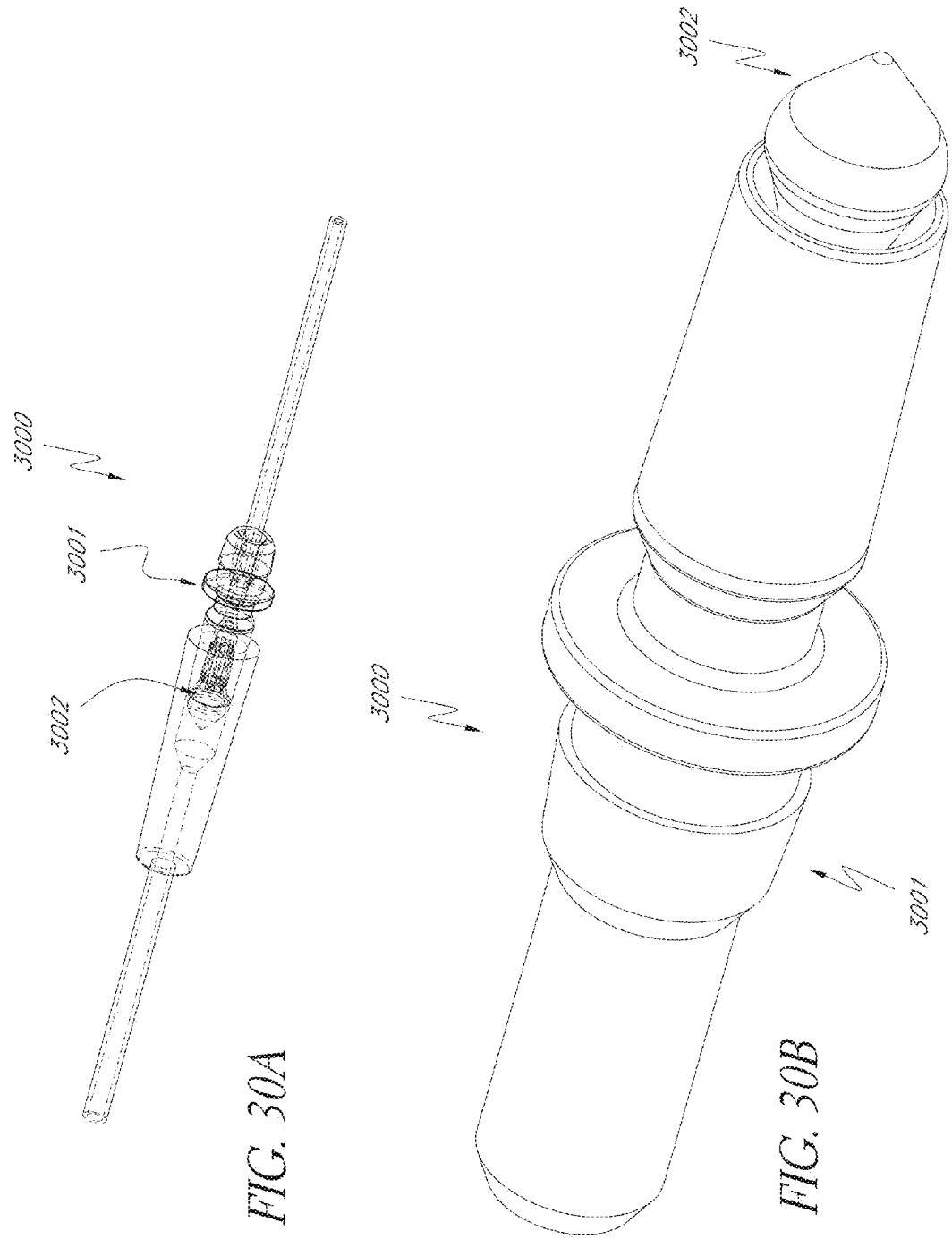

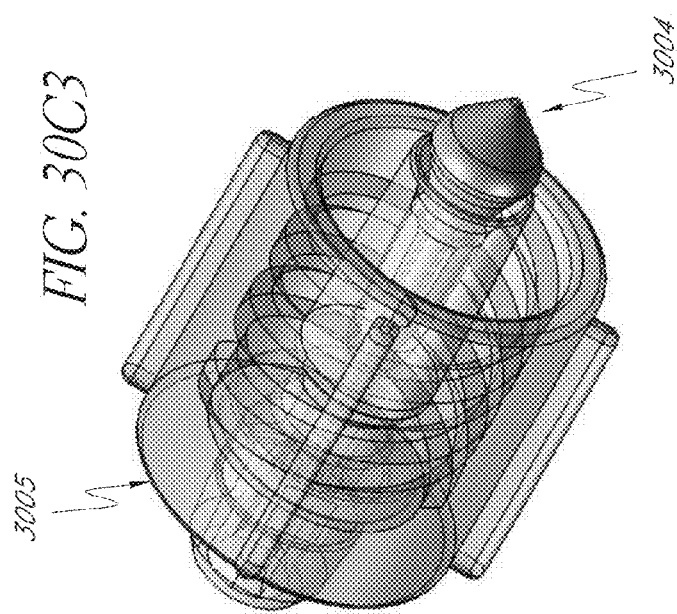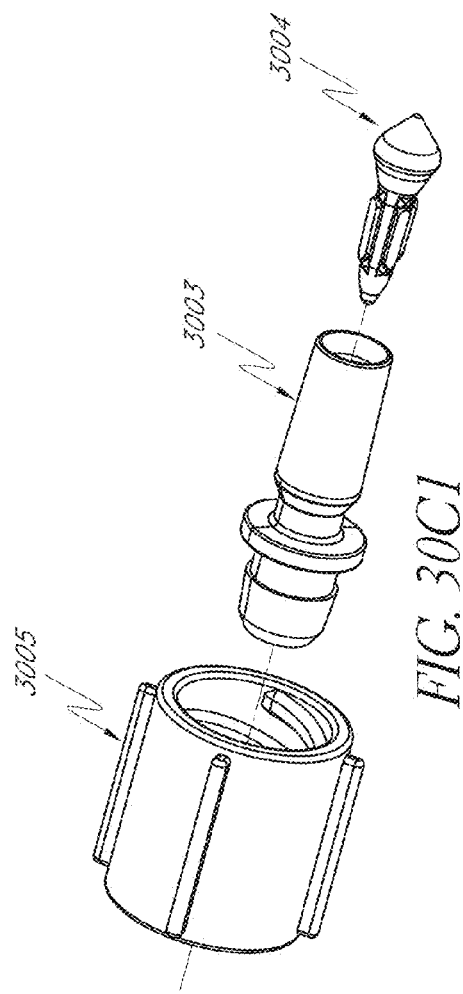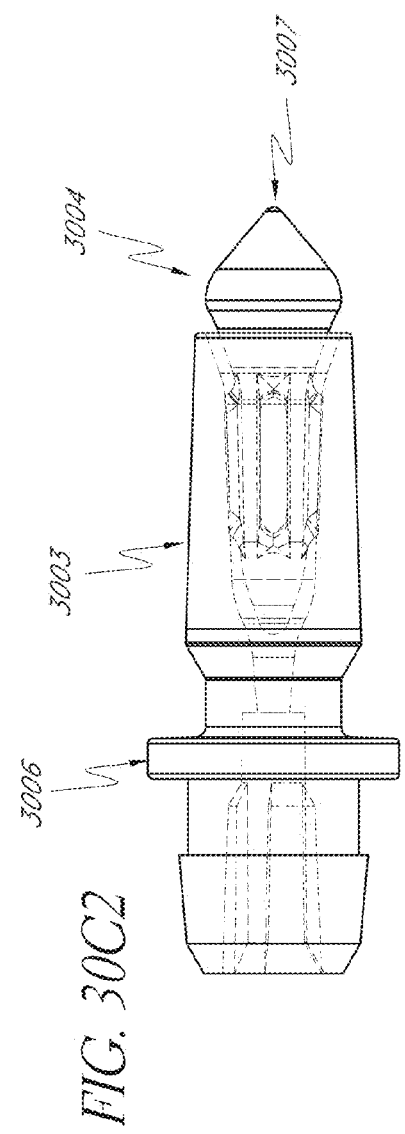

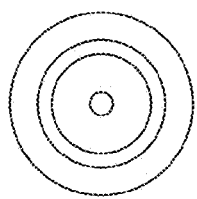
FIG. 30D4
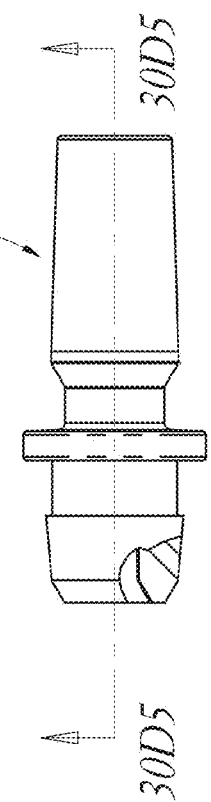
FIG. 30D1
FIG. 30D2
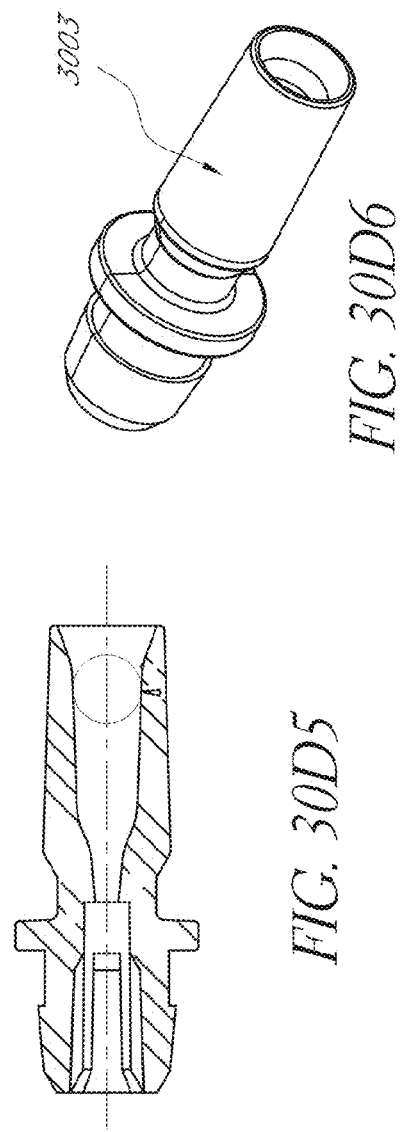
FIG. 30D6
FIG. 30D5
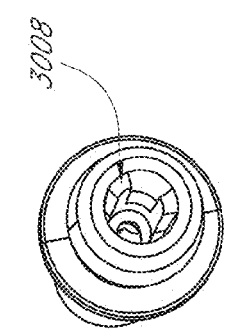
FIG. 30D3

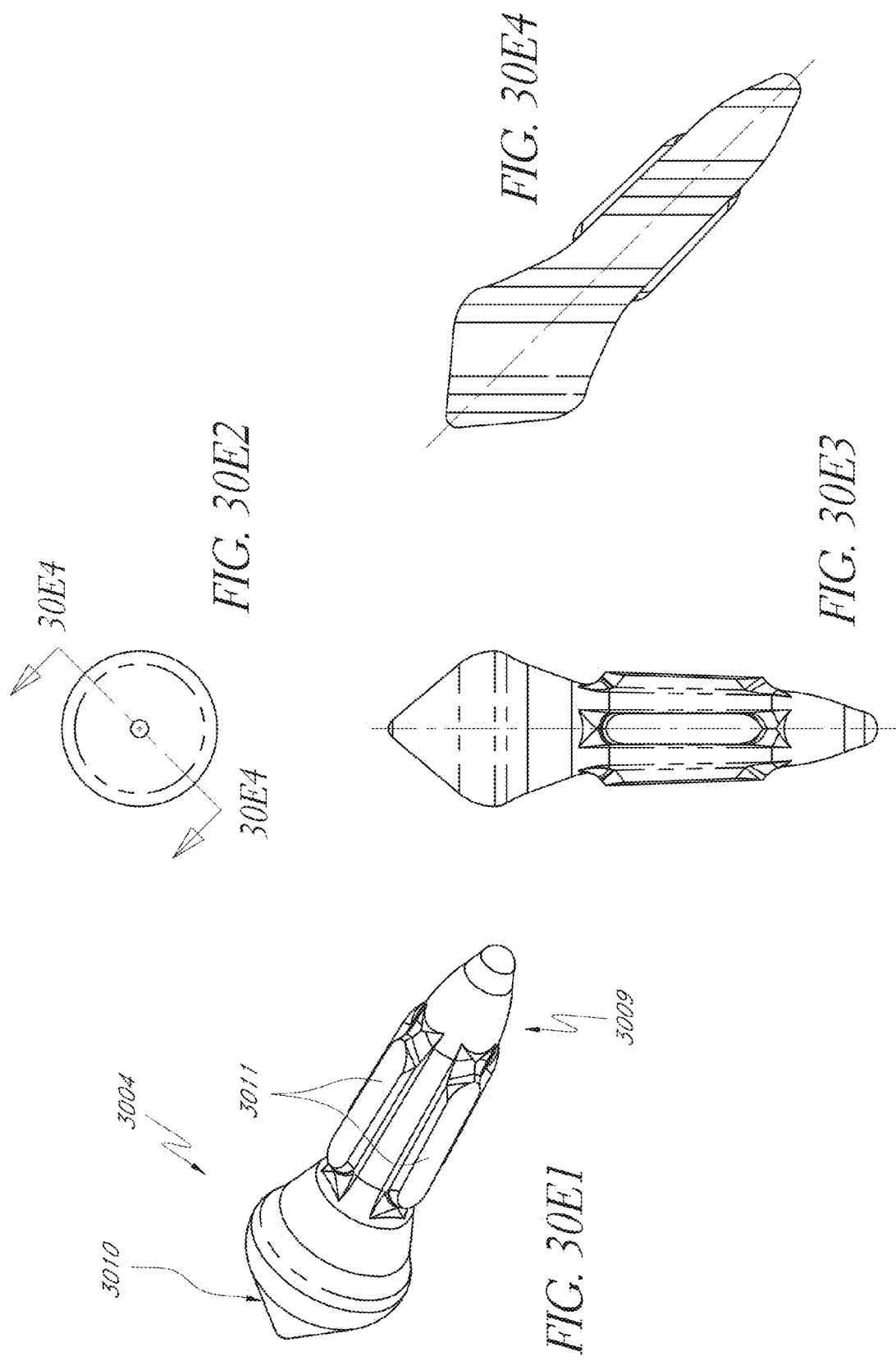

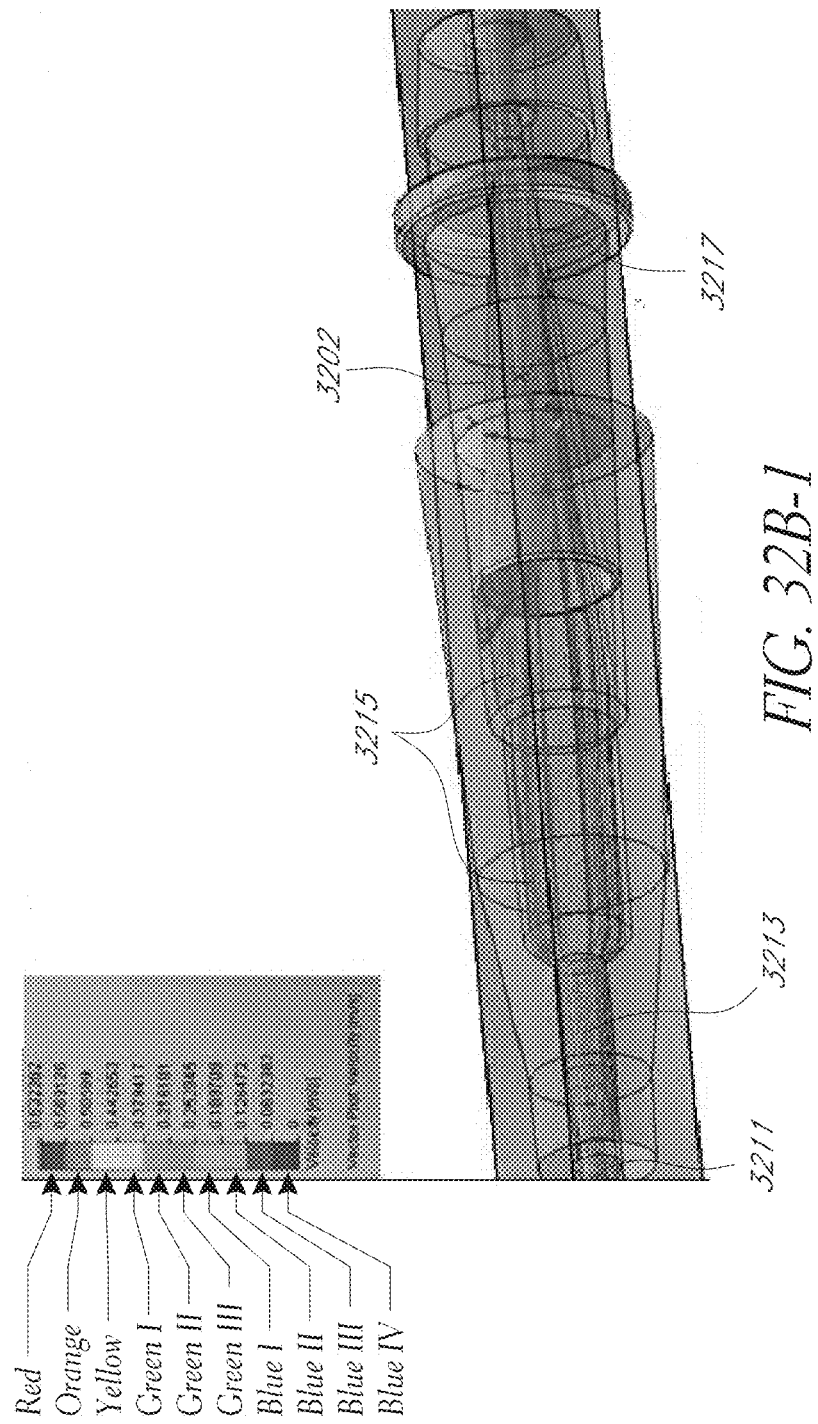

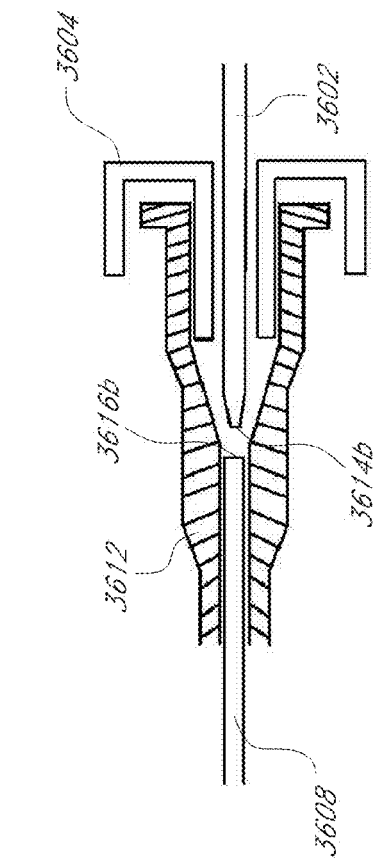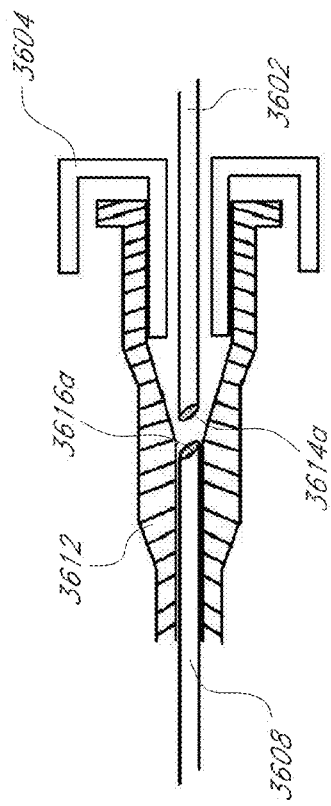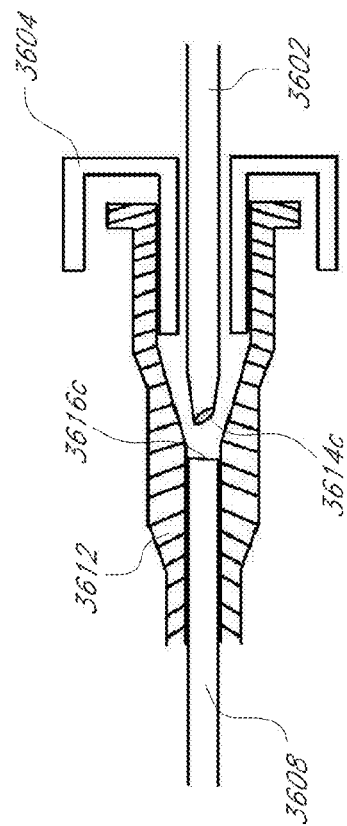
FIG. 36C
FIG. 36D
FIG. 36E

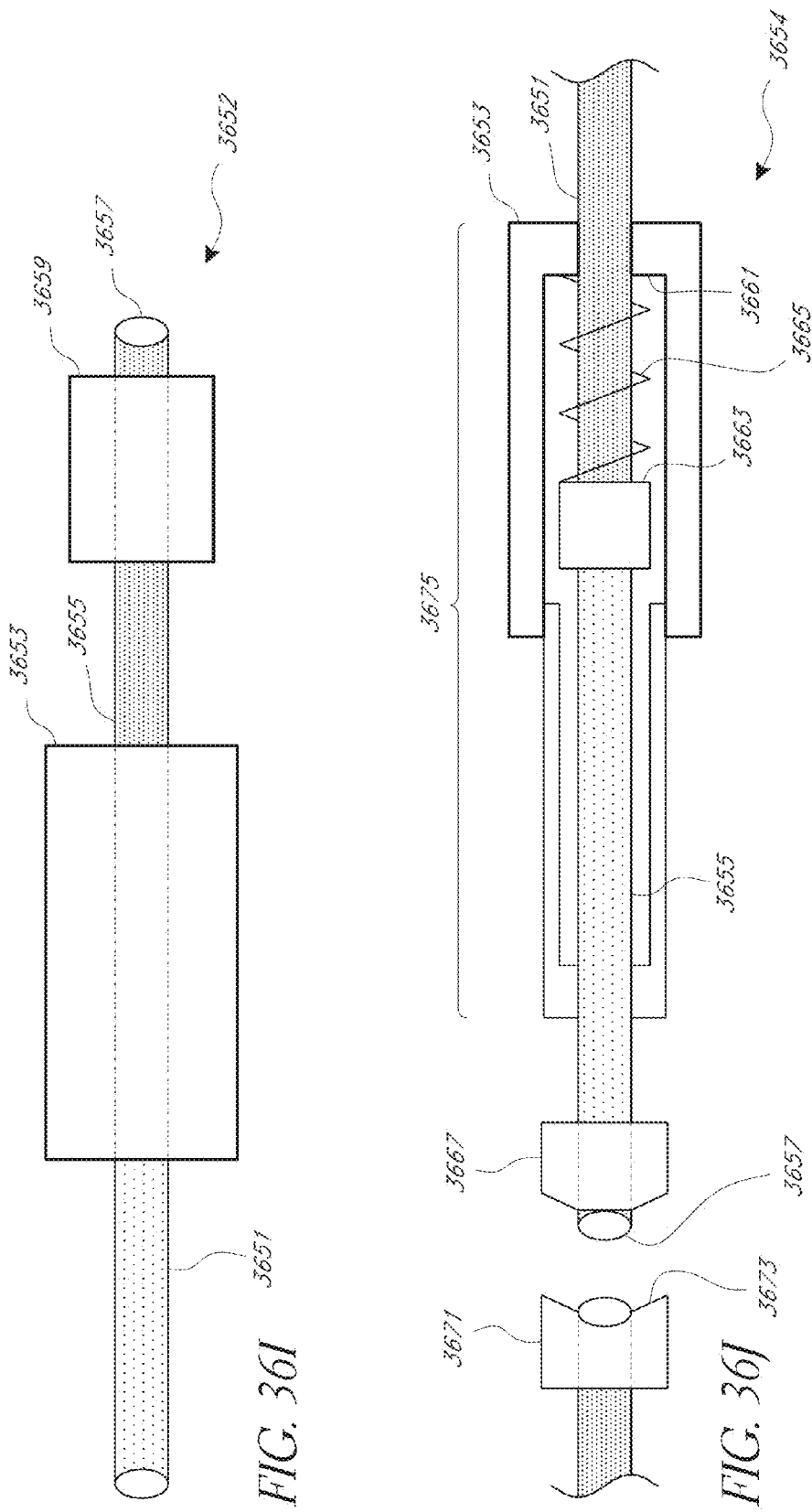

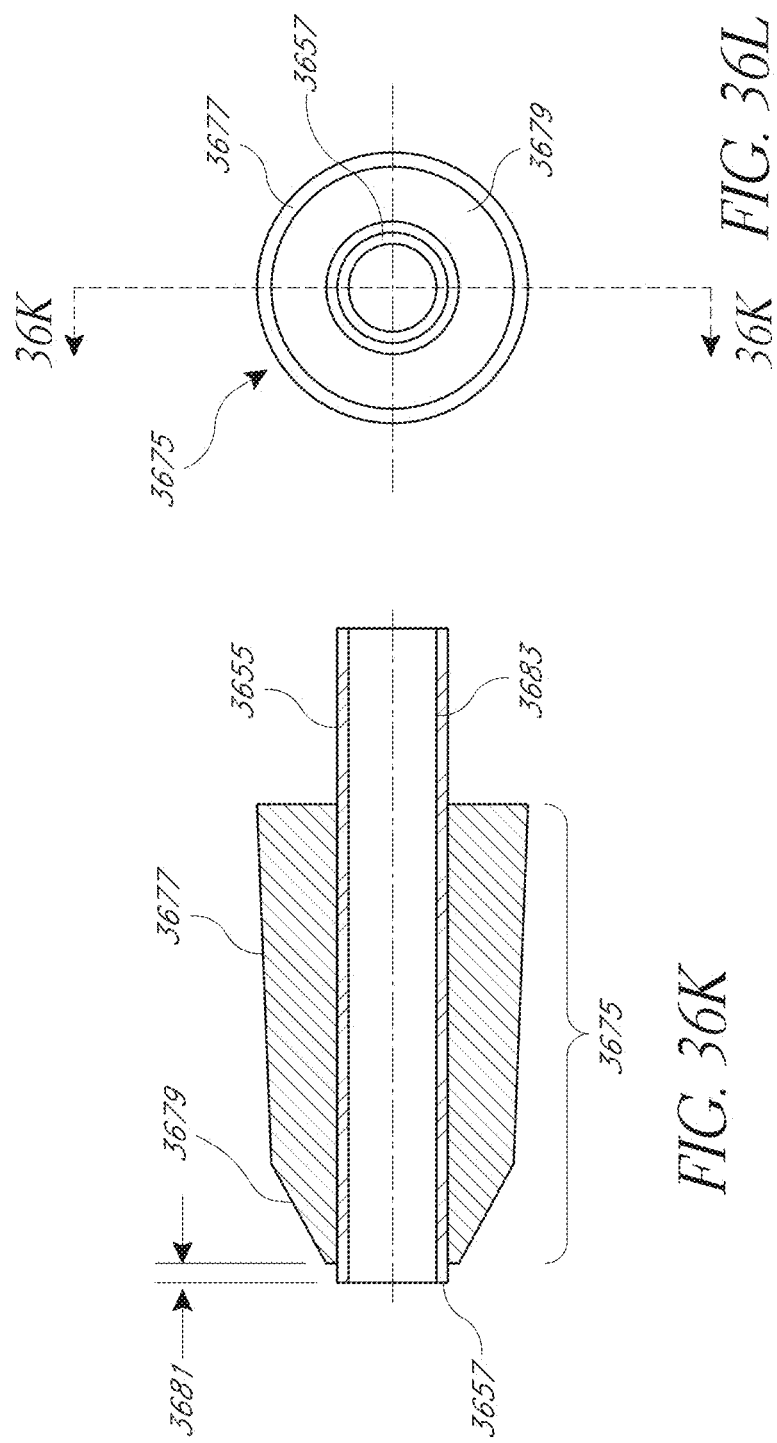

ADJUSTABLE CONNECTOR, IMPROVED FLUID FLOW AND REDUCED CLOTTING RISK

This application is a continuation of U.S. patent application Ser. No. 13/068,121, titled "Adjustable Connector, Improved Fluid Flow and Reduced Clotting Risk," filed on May 3, 2011, which claimed benefit under 35 U.S.C. § 119(e) of U.S. Provisional Application No. 61/330,812, titled "Adjustable Connector and Dead Space Reduction," filed on May 3, 2010, and was also a continuation-in-part of, and claimed benefit under 35 U.S.C. § 120 of U.S. application Ser. No. 12/804,336, titled "Adjustable Connector and Dead Space Reduction," filed on Jul. 20, 2010, which in turn claimed benefit under 35 U.S.C. § 119(e) of U.S. Provisional Application No. 61/227,040, titled "Analyte Detection System with a Flow Director," filed on Jul. 20, 2009. The entire disclosures of each of the above-identified applications are hereby incorporated by reference herein and made part of this specification.

This application also incorporates by reference herein in its entirety the disclosure of U.S. patent application Ser. No. 12/122,009, titled "Low-Volume Fittings," filed on May 16, 2008, which published as U.S. Publication No. 2008/0284167 on Nov. 20, 2008. This application also incorporates by reference herein in its entirety the disclosure of U.S. patent application Ser. No. 12/123,422, titled "Fluid Injection and Safety System," filed on May 19, 2008, which published as U.S. Publication No. 2009/0036764 on Feb. 5, 2009.

BACKGROUND

Field

Some embodiments of the disclosure relate generally to methods and devices for determining a concentration of an analyte in a sample, such as an analyte in a sample of bodily fluid, as well as methods and devices which can be used to support the making of such determinations. Various embodiments of the disclosure also relate to patient connectors that are configured to prevent or substantially reduce separated flow of fluids. In various embodiments, the patient connector can generally prevent accumulation of fluid during a flushing operation.

Description of Related Art

It is advantageous to measure the levels of certain analytes, such as glucose, in a bodily fluid, such as blood. This can be done, for example, in a hospital or clinical setting when there is a risk that the levels of certain analytes may move outside a desired range, which in turn can jeopardize the health of a patient. Systems for analyte monitoring in a hospital or clinical setting may suffer from various drawbacks. For example, fluid flow in the tubes and channels of systems can occur in a non-laminar manner such that fluid is separated or becomes stagnant in some places and turbulent in others. These discontinuities can lead to fluid accumulation or clogging of tubes and patient connectors. Systems and methods described herein can mitigate and/or overcome these drawbacks, both in the context of fluid connections for analyte monitors and for fluid connections and flow paths in other contexts.

SUMMARY

Example embodiments described herein have several features, no single one of which is indispensible or solely responsible for their desirable attributes. Without limiting the scope of the claims, some of the advantageous features will now be summarized.

Various embodiments disclosed herein can comprise a first inlet/outlet, a second inlet/outlet configured to connect to a mating connector, a fluid path between the first inlet/outlet and the second inlet/outlet which allows bidirectional fluid flow, an adjustable tip on the second inlet/outlet configured to adjustably accommodate and firmly abut the mating connector such that the fluid path in the accommodating connector communicates immediately with a corresponding fluid path in the mating connector and dead space between the fluid path and the corresponding fluid path is reduced, and a coating designed to improve fluid flow and reduce blood clotting which is applied to an inner portion of the fluid path and therefore positioned for contact with the fluid. The coating can be applied to a surface near the interface between the second inlet/outlet and the mating connector. The coating may be a drug-eluting coating, a heparin coating, or a lubricious coating. The coating may be applied to all portions of the accommodating connector that may come into contact with fluid in the fluid path. The accommodating connector can also have a sealing mass positioned near the interface of the second inlet/outlet and the mating connector, which is designed to reduce dead space at the connection. If the accommodating connector has such a sealing mass, the coating may be applied to the mass. The sealing mass can have a shape configured to generally approximates the shape of an opening in the mating connector even when the accommodating connector is not mating with the mating connector. The sealing mass can have a frustoconical shape. The sealing mass can be made of a resilient or compressible material, or it can be made of silicone.

In some embodiments, an accommodating connector is described which comprises a first inlet/outlet; a second inlet/outlet configured to connect to a mating connector; a fluid path between the first inlet/outlet and the second inlet/outlet; an adjustable tip on the second inlet/outlet configured to adjustably accommodate and firmly abut a mating connector such that a passage from the accommodating connector communicates immediately with a corresponding fluid path in the mating connector and dead space between the fluid path and the corresponding fluid path is reduced; and a coating designed to improve fluid flow and reduce blood clotting which is applied to at least a portion of the fluid path. The fluid path in the connector can be a tube, and the coating can be applied to a portion of the inner walls of this tube. The coating can be applied to a surface that is near the interface between the second inlet/outlet and the mating connector. The coating can be a drug-eluting coating, a heparin coating, or a lubricious coating. The coating may be applied to all portions of the accommodating connector that may come into contact with fluid in the fluid path.

In some embodiments, an accommodating connector is described which comprises a first inlet/outlet; a second inlet/outlet configured to connect to a mating connector; a fluid path between the first inlet/outlet and the second inlet/outlet; an adjustable tip on the second inlet/outlet configured to adjustably accommodate and firmly abut a mating connector such that a passage from the accommodating connector communicates immediately with a corresponding fluid path in the mating connector and dead space between the fluid path and the corresponding fluid path is reduced; and a sealing mass that is positioned at or near an interface between the second inlet/outlet and the mating connector and that has a shape configured to correspond with a shape of the mating connector when it is mating with the accommodating connector in order to reduce dead space at the interface between the second inlet/outlet and the mating connector. The sealing mass can have a shape configured to generally approximate the shape of an opening in the mating connector even when the accommodating connector is not mating with the mating connector. The sealing mass can have a frustoconical shape. The sealing mass can be made of a resilient or compressible material, or it can be made of silicone. The sealing mass may be able to form a fluid-tight seal around the fluid path when the accommodating connector is attached to a mating connector. The mating connector may be a standard connector. The mating connector may be a standard female connector. The sealing mass may have a radially symmetric shape, in order to create a better seal with the mating connector. The connector can have a coating designed to improve fluid flow and reduce blood clotting applied to a portion of the fluid path. This coating may also be applied to a portion of the sealing mass.

In some embodiments, an accommodating connector is described which comprises a first inlet/outlet; a second inlet/outlet configured to connect to a mating connector such that the second inlet/outlet protrudes from the accommodating connector in order to set the second inlet/outlet near an inner portion of the mating connector; a fluid path between the first inlet/outlet and the second inlet/outlet; a coating designed to improve fluid flow and reduce blood clotting which is applied to at least a portion of the fluid path; and a sealing mass that is positioned at or near an interface between the second inlet/outlet and the mating connector and that has a shape configured to correspond with a shape of the mating connector when it is mating with the accommodating connector in order to reduce dead space at the interface between the second inlet/outlet and the mating connector. The sealing mass can have a shape configured to generally approximate the shape of an opening in the mating connector even when the accommodating connector is not mating with the mating connector. The sealing mass can have a frustoconical shape. The sealing mass can be made of a resilient or compressible material, or it can be made of silicone. The coating may be applied to the sealing mass. The coating can be applied to a surface that is near the interface between the second inlet/outlet and the mating connector. The coating can be a drug-eluting coating, a heparin coating, or a lubricious coating.

In some embodiments, a patient connector is described which comprises a first inlet/outlet, a second inlet/outlet configured to connect to a standard mating connector, a fluid path between the first inlet/outlet and the second inlet/outlet, and a sealing mass that is positioned at or near an interface between the second inlet/outlet and the standard mating connector and that has a shape configured to correspond with a shape of the standard mating connector when it is mating with the patient connector in order to form at least a partial seal and to reduce dead space at the interface between the second inlet/outlet and the standard mating connector. The standard mating connector may be a standard female connector. The sealing mass may be made from a resilient or compressible material, or may be made from silicone. The patient connector may have a coating designed to improve fluid flow and reduce blood clotting which is applied to at least a portion of the fluid path. This coating may be applied to at least a portion of the sealing mass.

In some embodiments, a patient connector is described which comprises a first inlet/outlet, a second inlet/outlet configured to connect to a mating connector, a fluid path between the first inlet/outlet and the second inlet/outlet that is designed to minimize turbulence in the fluid path in order to improve fluid flow and reduce blood clotting, and a lubricious coating which is applied to at least a portion of the fluid path that may come into contact with a fluid flow at least partly comprised of blood, where the lubricious coating is designed to reduce friction and improve fluid flow and reduce turbulence and blood clotting. The lubricious coating may be applied to all portions of the patient connector that may come into contact with fluid in the fluid path.

In some embodiments, a system for extending the length of time a medical device connector can be used for repeated blood withdrawal is described. The system comprises a fluid draw apparatus having a fluid passageway configured for blood withdrawal and fluid infusion through the same passageway, and a medical device connector configured to connect the passageway of the fluid draw apparatus to a patient catheter for access to a blood vessel. The medical device connector comprises: a housing configured to firmly connect to the patient catheter, and a tube having a tube passageway and a tip, the tube generally positioned within the housing and configured to firmly connect and align its tube passageway with the fluid passageway. The medical connector further comprises one or more of the following: with the fluid passageway firmly connected to one end of the tube, the tube is configured to resiliently move with respect to the housing such that the tube is urged toward the patient catheter to resiliently and forcefully abut that catheter, minimize leaks or other dead space, and align an inner passageway of that catheter with the tube passageway when the housing is firmly connected to the patient catheter, thereby minimizing clot formation; the tube is configured to protrude toward the patient catheter and comprises a sealing mass adhered to or formed as part of the tip, the sealing mass generally surrounding the tube and configured to resiliently and forcefully abut the catheter and minimize leaks or other dead space when the housing is firmly connected to the patient catheter, thereby minimizing clot formation; and a lubricious coating in and/or around the tube passageway, the coating configured to lubricate blood-contacting surfaces to reduce friction and turbulence, thereby minimizing clot formation. The medical device connector is thereby configured to allow at least 12 hours of repeated blood draws into the fluid passageway without clot formation.

In some embodiments, a connector configured for use with a blood withdrawal system is described. The connector comprises: a housing configured to firmly connect to a vessel access device; and a tube having a tube passageway and a tip, the tube generally positioned within the housing and configured to firmly connect and align its tube passageway with a fluid passageway of the blood withdrawal system. The connector is further configured for at least 12 hours of periodic, repeated blood withdrawal using at least one of the following: with the fluid passageway firmly connected to one end of the tube, the tube is configured to resiliently move with respect to the housing such that the tube is urged toward the vessel access device to resiliently and forcefully abut that vessel access device, minimize leaks or other dead space, and align an inner passageway of that vessel access device with the tube passageway when the housing is firmly connected to the vessel access device, thereby minimizing clot formation; the tube is configured to protrude toward the vessel access device and comprises a sealing mass adhered to or formed as part of the tip, the sealing mass generally surrounding the tube and configured to resiliently and forcefully abut the vessel access device and minimize leaks or other dead space when the housing is firmly connected to the vessel access device, thereby minimizing clot formation; and a lubricious coating in and/or around the tube passageway, the coating configured to lubricate blood-contacting surfaces to reduce friction and turbulence, thereby minimizing clot formation.

In some embodiments, a connector configured to resist clot formation for at least 12 hours of periodic blood withdrawals is described. The connector resists clot formation for this time by incorporating at least one of the following three structures: a protruding inner tube configured to resiliently press against a patient catheter to provide a contiguous blood flow path and minimize gaps at a junction between the patient catheter and the protruding inner tube; a protruding inner tube comprising a sealing mass adhered to or formed as part of the tube, the sealing mass generally surrounding the tube and configured to resiliently and forcefully abut the patient catheter and minimize gaps surrounding the junction between the patient catheter and the protruding inner tube when the connector is connected to the patient catheter; and a protruding inner tube having a lubricious coating in and/or around the tube, the coating configured to lubricate blood-contacting surfaces to reduce friction and turbulence, thereby minimizing clot formation.

Various embodiments disclosed herein can comprise an analyte monitoring system further comprising a fluidic system in fluid communication with a source of bodily fluid, the fluidic system being configured to obtain a sample of bodily fluid from the source; a spectroscopic sample cell in fluid communication with the fluidic system and configured to receive the sample of bodily fluid; an analyte detection system coupled to the spectroscopic sample cell through a transparent window, the analyte detection system spectroscopically analyzing the sample of bodily fluid or a component of the sample of bodily fluid; and a fluid infusion system. In various embodiments, the analyte detection system is configured to estimate the concentration of an analyte in the sample of the bodily fluid or a component of the sample of the bodily fluid. In various embodiments, the fluidic system is fluidically connected to the source of bodily fluid through a patient connector which includes a spring loaded self adjusting extender tube and is configured to provide a continuous flow path.

In some embodiments, a system for eliminating dead space and improving fluid flow through medical connectors is described. The system comprises an outer portion comprising at least one standard-facing end (e.g. a Luer male or female connector); an inner portion comprising an extended flow passageway; and an actuating member that is situated between the outer and the inner portion and configured to move the inner portion toward or away from the outer portion thereby causing the extended flow passageway to approach an inner portion of any of a variety of standard connectors (e.g. standard Luer connectors) having different depths.

In some embodiments an extendable medical connector for reducing dead space and improving fluid flow is described. The connector comprises a standard-facing end (e.g. a Luer male or female connector) comprising a standard-facing outer portion; and a standard-facing inner portion comprising an extended flow passageway. The connector further includes an opposite end comprising an opposite outer portion comprising a first pushing surface; and a receiving opening configured to receive a regular flow passageway. In various embodiments, the standard-facing outer portion and the opposite outer portion together can comprising an outer housing. In various embodiments, the connector may include a second pushing surface facing the first pushing surface. In various embodiments, the extended flow passageway configured to connect to the regular flow passageway to form a combined flow passageway configured to move with the second pushing surface. The connector may also include a force exerting member is situated between the first and second pushing surfaces and configured to simultaneously exert a force against both of these pushing surfaces to thereby urge the first pushing surface (along with the outer housing) away from the second pushing surface (along with the combined inner portion), thereby causing the extended flow passageway to approach—and the inner portion of the standard-facing end to more firmly seat against—an inner portion of any of a variety of standard connectors having different depths.

In some embodiments, a penetrating connector configured to be positioned along a fluid line between a medical device and a source of body fluid to allow fluid flow while reducing leaks is described. The connector can include first and second openings at either end of the connector, the openings configured to allow fluid communication—through the connector—between the medical device and the source of body fluid; and cooperate with openings of other connecting devices to assist in forming mating complexes at either side end of the connector, at least one of the mating complexes having an enlarged space. The connector can also include an extender tube having a first cross-sectional width, the extender tube configured to convey the fluid along a fluid pathway that extends at least part of the way between the first and second openings; penetrate through at least one of the mating complexes while bypassing the enlarged space, which has a cross sectional width that is wider than the first cross-sectional width; confine fluid within its walls to prevent the fluid from flowing out into the enlarged space of the mating complex; and abut an opening of one of the other connecting devices such that fluid flows directly between the extender tube and the opening of the other connecting device. The connector can further include a force-exerting structure that uses a resilient property to improve a seal where the extender tube abuts the opening of the other connecting device.

In various embodiments, an accommodating connector configured to reduce leaks and improve fluid flow between a medical device and a source of body fluid, the accommodating connector comprising a first inlet/outlet; a second inlet/outlet; and a force-exerting structure having a stiffness. The accommodating connector is configured to connect to a mating connector that is attached to a source of bodily fluid; and the force-exerting structure is configured to exert a force on an inner portion of the mating connector in a contact region and firmly seat the first or second inlet/outlet against the inner portion of the mating connector such that a dead space between the first or second inlet/outlet and the inner portion of the mating connector is reduced.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings and the associated descriptions are provided to illustrate embodiments of the present disclosure and do not limit the scope of the claims.

FIG. 10 illustrates an embodiment of a removable cartridge that can interface with a monitoring device.

FIG. 29A-29D illustrates various embodiments of Luer connectors.

FIG. 30A schematically illustrates a patient connector including a flow director.

FIG. 30B schematically illustrates another embodiment of a patient connector assembly including a flow director.

FIGS. 30C1-30C3 schematically illustrate different views of a patient connector assembly including a flow director.

FIGS. 30D1-30D6 schematically illustrate different views of a patient connector assembly.

FIGS. 30E1-30E4 schematically illustrate different views of a flow director.

FIG. 32A-1 is a color version of FIG. 32A.

FIG. 32B-1 is a color version of FIG. 32B.

FIGS. 32C-1-32E-1 are color versions of FIGS. 32C-32E.

FIGS. 36C-36J are generalized illustrations of self-adjusting connectors.

FIGS. 36K-36L are generalized illustrations of a sealing mass.

FIGS. 37A-37H illustrate a self-adjusting patient connector connected to central venous catheters and peripherally inserted central catheters having different diameters.

Figure 1:
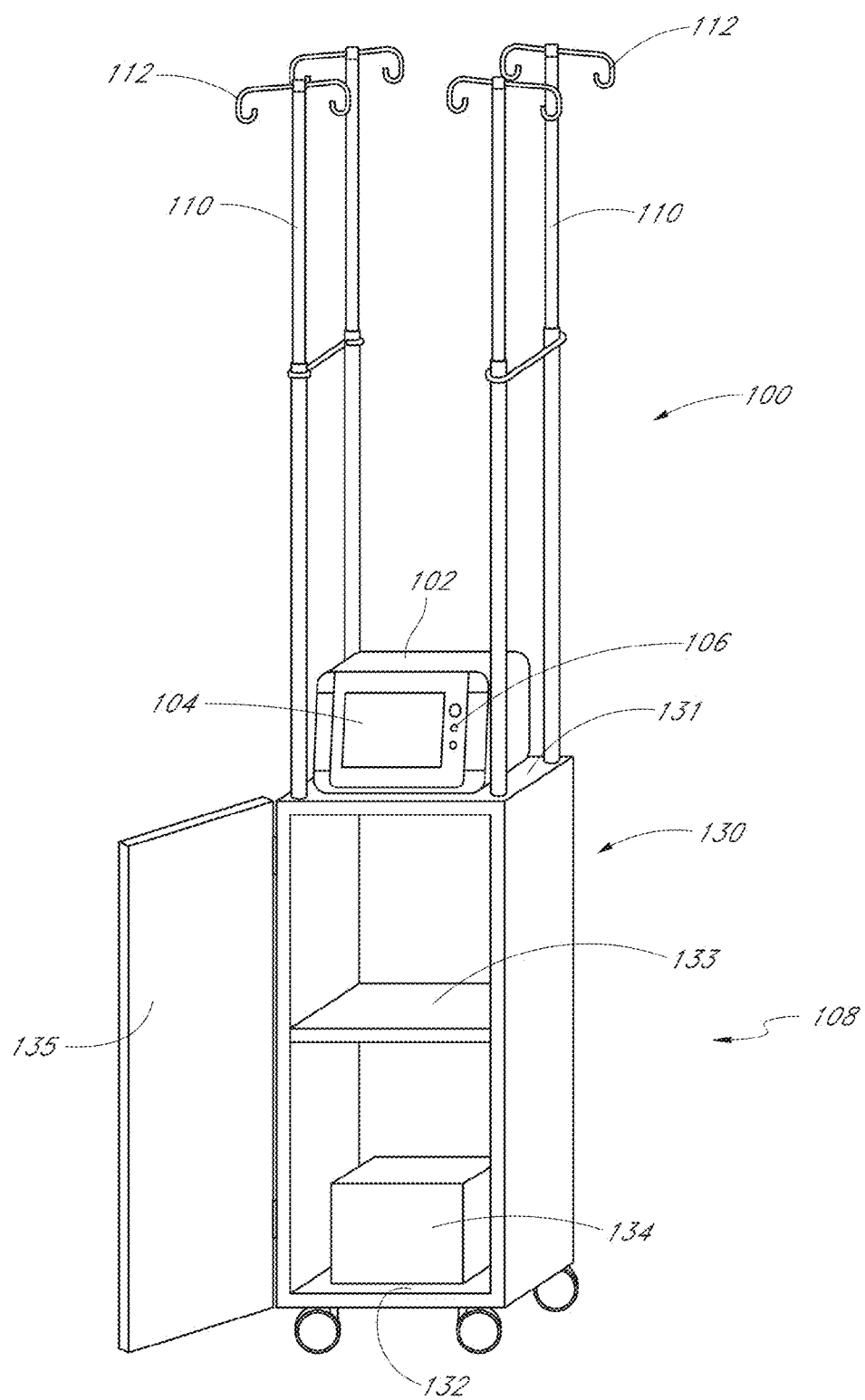
FIG. 1 shows an embodiment of an apparatus for withdrawing and analyzing fluid samples.

These and other features will now be described with reference to the drawings summarized above. The drawings and the associated descriptions are provided to illustrate embodiments and not to limit the scope of the disclosure or claims. Throughout the drawings, reference numbers may be reused to indicate correspondence between referenced elements. In addition, where applicable, the first one or two digits of a reference numeral for an element can frequently indicate the figure number in which the element first appears.

DETAILED DESCRIPTION OF PREFERRED EMBODIMENTS

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The systems and methods discussed herein can be used anywhere, including, for example, in laboratories, hospitals, healthcare facilities, intensive care units (ICUs), or residences. Moreover, the systems and methods discussed herein can be used for invasive techniques, as well as non-invasive techniques or techniques that do not involve a body or a patient such as, for example, in vitro techniques.

Analyte Monitoring Apparatus

FIG. 1 shows an embodiment of an apparatus 100 for withdrawing and analyzing fluid samples. The apparatus 100 includes a monitoring device 102. In some embodiments, the monitoring device 102 can be an OPTISCANNER™ monitor available from OptiScan Biomedical Corporation of Hayward, Calif. In some embodiments, the device 102 can measure one or more physiological parameters, such as the concentration of one or more substance(s) in a sample fluid. The sample fluid can be, for example, whole blood from a patient 302 (see, e.g., FIG. 3) and/or a component of whole blood such as, e.g., blood plasma. In some embodiments, the device 100 can also deliver an infusion fluid to a patient.

In the illustrated embodiment, the monitoring device 102 includes a display 104 such as, for example, a touch-sensitive liquid crystal display. The display 104 can provide an interface that includes alerts, indicators, charts, and/or soft buttons. The device 102 also can include one or more inputs and/or outputs 106 that provide connectivity and/or permit user interactivity.

In the embodiment shown in FIG. 1, the device 102 is mounted on a stand 108. The stand 108 may comprise a cart such as, for example, a wheeled cart 130 as shown in FIG. 1. In some embodiments, the stand 108 is configured to roll on a wheeled pedestal 240 (shown in FIG. 2). The stand 108 advantageously can be easily moved and includes one or more poles 110 and/or hooks 112. The poles 110 and hooks 112 can be configured to accommodate other medical devices and/or implements, including, for example, infusion pumps, saline bags, arterial pressure sensors, other monitors and medical devices, and so forth. Some stands or carts may become unstable if intravenous (IV) bags, IV pumps, and other medical devices are hung too high on the stand or cart. In some embodiments, the apparatus 100 can be configured to have a low center of gravity, which may overcome possible instability. For example, the stand 108 can be weighted at the bottom to at least partially offset the weight of IV bags, IV pumps and medical devices that may be attached to the hooks 112 that are placed above the monitoring device 102. Adding weight toward the bottom (e.g., near the wheels) may help prevent the apparatus 100 from tipping over.

In some embodiments, the apparatus 100 includes the cart 130, which has an upper shelf 131 on which the monitoring device 102 may be placed (or attached) and a bottom shelf 132 on which a battery 134 may be placed (or attached). The battery 134 may be used as a main or backup power supply for the monitoring device 102 (which may additionally or alternatively accept electrical power from a wall socket). Two or more batteries are used in certain embodiments. The apparatus 100 may be configured so that the upper and lower shelves 131, 132 are close to ground level, and the battery provides counterweight. Other types of counterweights may be used. For example, in some embodiments, portions of the cart 130 near the floor (e.g., a lower shelf) are weighted, formed from a substantial quantity of material (e.g., thick sheets of metal), and/or formed from a relatively high-density metal (e.g., lead). In some embodiments the bottom shelf 132 is approximately 6 inches to 1 foot above ground level, and the upper shelf 131 is approximately 2 feet to 4 feet above ground level. In some embodiments the upper shelf 131 may be configured to support approximately 40 pounds (lbs), and the bottom shelf 132 may be configured to support approximately 20 lbs. One possible advantage of embodiments having such a configuration is that IV pumps, bags containing saline, blood and/or drugs, and other medical equipment weighing approximately 60 lbs, collectively, can be hung on the hooks 112 above the shelves without making the apparatus 100 unstable. The apparatus 100 may be moved by applying a horizontal force on the apparatus 100, for example, by pushing and/or pulling the poles 110. In many cases, a user may exert force on an upper portion of the apparatus 100, for example, close to shoulder-height. By counterbalancing the weight as described above, the apparatus 100 may be moved in a reasonably stable manner.

In the illustrated embodiment, the cart 130 includes the bottom shelf 132 and an intermediate shelf 133, which are enclosed on three sides by walls and on a fourth side by a door 135. The door 135 can be opened (as shown in FIG. 1) to provide access to the shelves 132, 133. In other embodiments, the fourth side is not enclosed (e.g., the door 135 is not used). Many cart variations are possible. In some embodiments the battery 134 can be placed on the bottom shelf 134 or the intermediate shelf 133.

Figure 2:
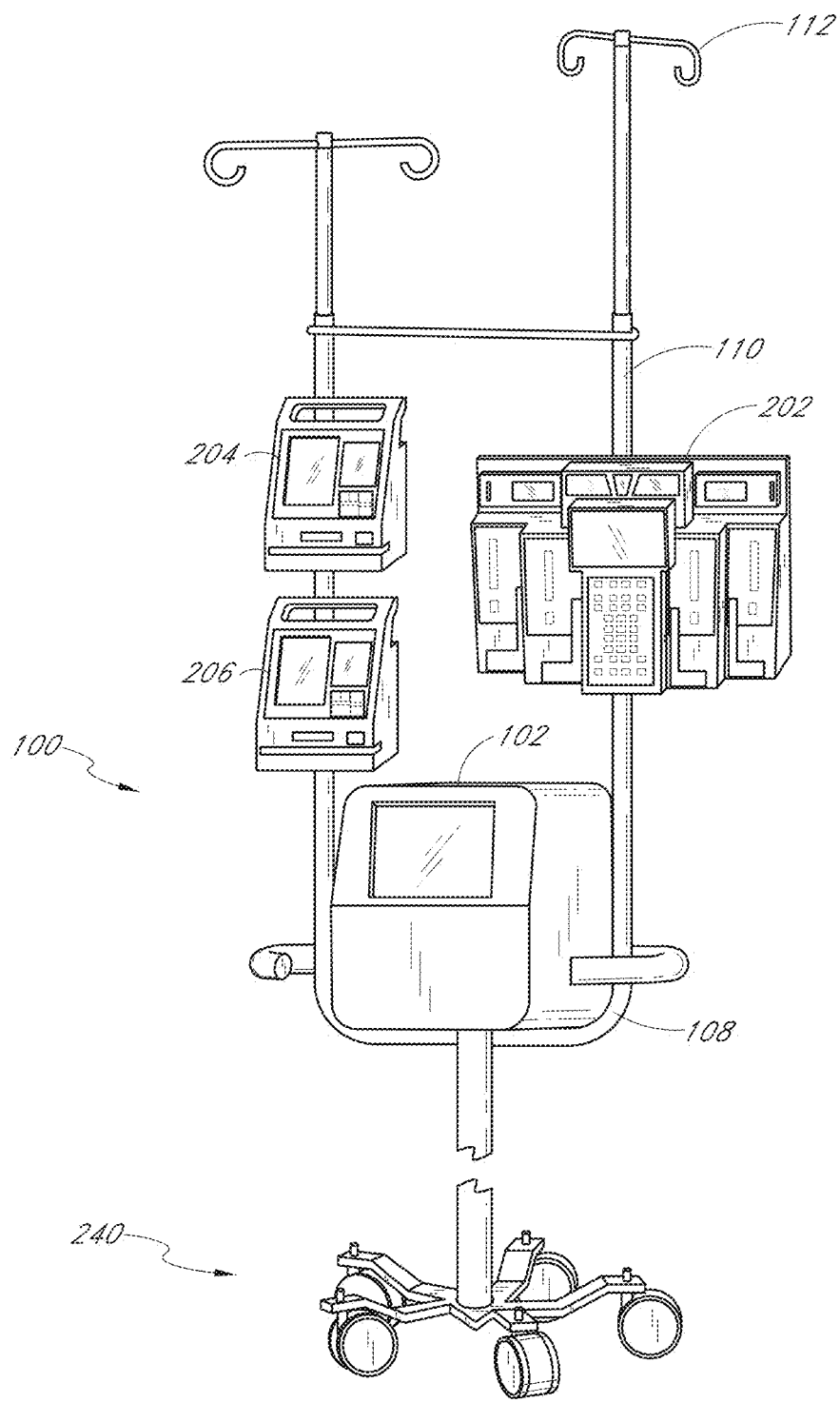
FIG. 2 illustrates how various other devices can be supported on or near an embodiment of apparatus illustrated in FIG. 1.

FIG. 2 illustrates how various other devices can be supported on or near the apparatus 100 illustrated in FIG. 1. For example, the poles 110 of the stand 108 can be configured (e.g., of sufficient size and strength) to accommodate multiple devices 202, 204, 206. In some embodiments, one or more COLLEAGUE® volumetric infusion pumps available from Baxter International Inc. of Deerfield, Ill. can be accommodated. In some embodiments, one or more Alaris® PC units available from Cardinal Health, Inc. of Dublin, Ohio can be accommodated. Furthermore, various other medical devices (including the two examples mentioned here), can be integrated with the disclosed monitoring device 102 such that multiple devices function in concert for the benefit of one or multiple patients without the devices interfering with each other.

Figure 3:
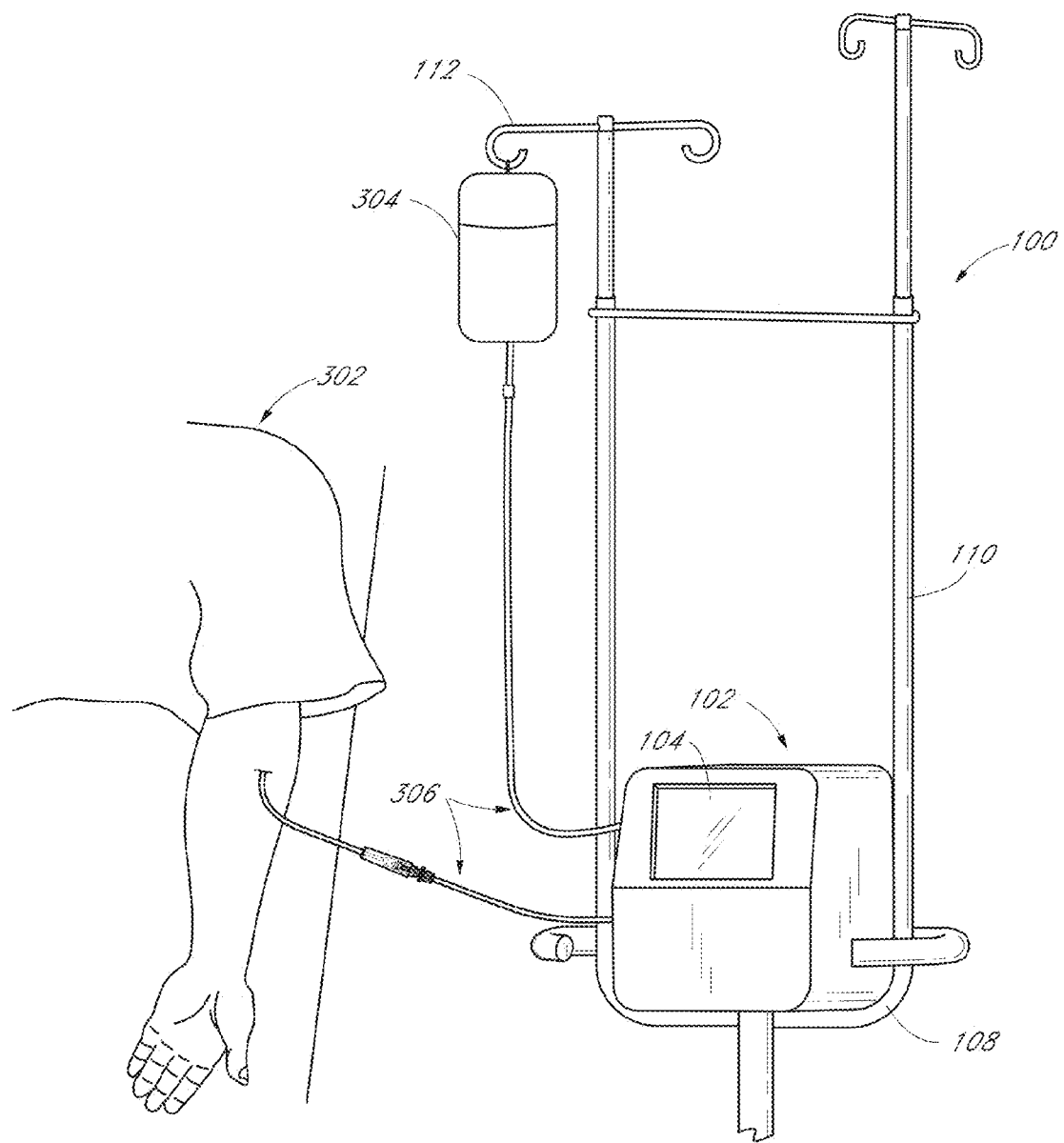
FIG. 3 illustrates an embodiment of the apparatus in FIG. 1 configured to be connected to a patient.
Figure 3A:
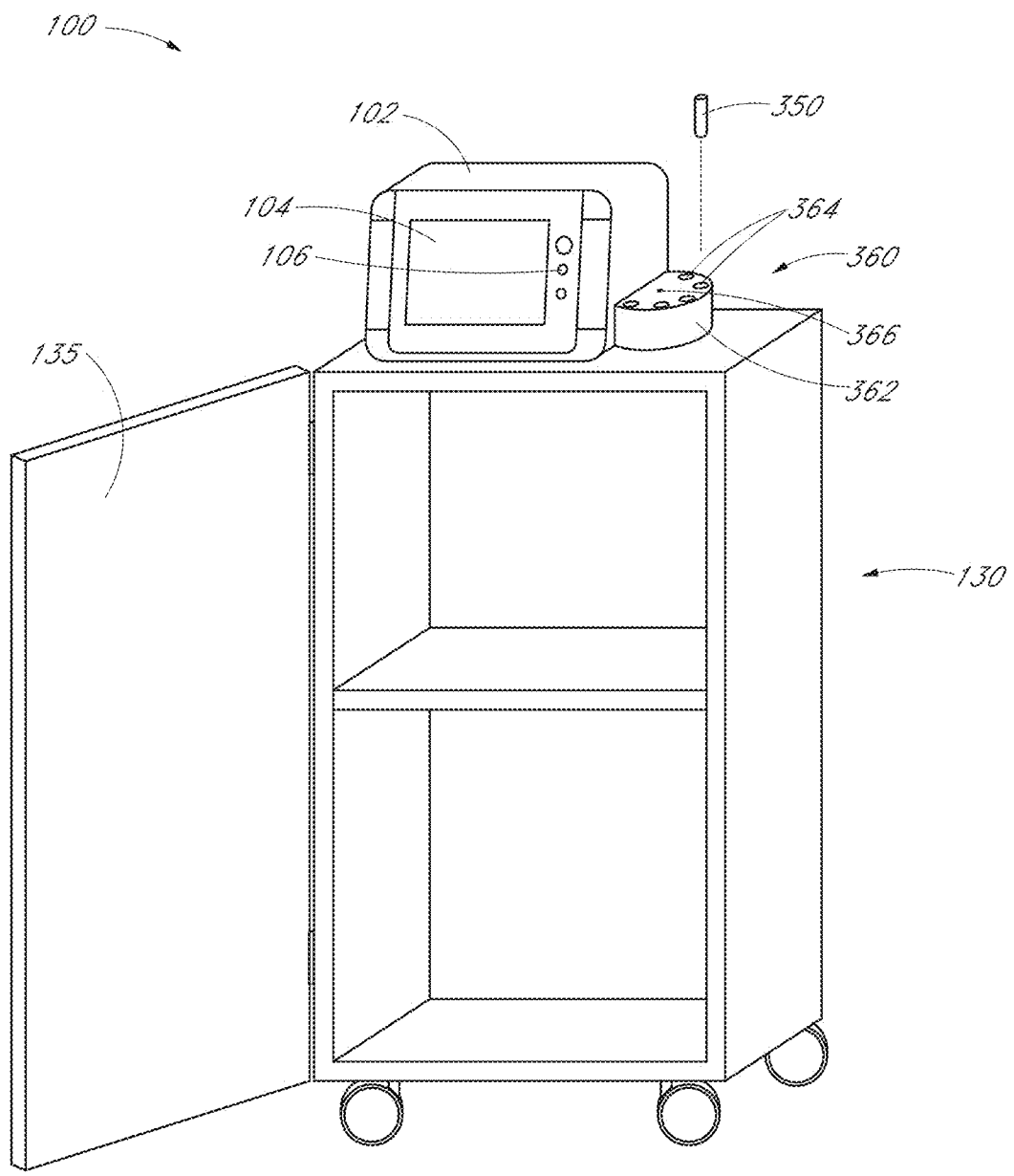
FIG. 3A illustrates an embodiment of the apparatus in FIG. 1 that is not configured to be connected to a patient but which receives a fluid sample from an extracorporeal fluid container such as, for example, a test tube. This embodiment of the apparatus advantageously provides in vitro analysis of a fluid sample.

FIG. 3 illustrates the apparatus 100 of FIG. 1 as it can be connected to a patient 302. The monitoring device 102 can be used to determine the concentration of one or more substances in a sample fluid. The sample fluid can come can come from the patient 302, as illustrated in FIG. 3, or the sample fluid can come from a fluid container, as illustrated in FIG. 3A. In some preferred embodiments, the sample fluid is whole blood.

In some embodiments (see, e.g., FIG. 3), the monitoring device 102 can also deliver an infusion fluid to the patient 302. An infusion fluid container 304 (e.g., a saline bag), which can contain infusion fluid (e.g., saline and/or medication), can be supported by the hook 112. The monitoring device 102 can be in fluid communication with both the container 304 and the sample fluid source (e.g., the patient 302), through tubes 306. The infusion fluid can comprise any combination of fluids and/or chemicals. Some advantageous examples include (but are not limited to): water, saline, dextrose, lactated Ringer's solution, drugs, and insulin.

The example monitoring device 102 schematically illustrated in FIG. 3 allows the infusion fluid to pass to the patient 302 and/or uses the infusion fluid itself (e.g., as a flushing fluid or a standard with known optical properties, as discussed further below). In some embodiments, the monitoring device 102 may not employ infusion fluid. The monitoring device 102 may thus draw samples without delivering any additional fluid to the patient 302. The monitoring device 102 can include, but is not limited to, fluid handling and analysis apparatuses, connectors, passageways, catheters, tubing, fluid control elements, valves, pumps, fluid sensors, pressure sensors, temperature sensors, hematocrit sensors, hemoglobin sensors, colorimetric sensors, gas (e.g., "bubble") sensors, fluid conditioning elements, gas injectors, gas filters, blood plasma separators, and/or communication devices (e.g., wireless devices) to permit the transfer of information within the monitoring device 102 or between the monitoring device 102 and a network.

In some embodiments, the apparatus 100 is not connected to a patient and may receive fluid samples from a container such as a decanter, flask, beaker, tube, cartridge, test strip, etc., or any other extracorporeal fluid source. The container may include a biological fluid sample such as, e.g., a body fluid sample. For example, FIG. 3A schematically illustrates an embodiment of the monitoring device 102 that is configured to receive a fluid sample from one or more test tubes 350. This embodiment of the monitoring device 102 is configured to perform in vitro analysis of a fluid (or a fluid component) in the test tube 350. The test tube 350 may comprise a tube, vial, bottle, or other suitable container or vessel. The test tube 350 may include an opening disposed at one end of the tube through which the fluid sample may be added prior to delivery of the test tube to the monitoring device 102. In some embodiments, the test tubes 350 may also include a cover adapted to seal the opening of the tube. The cover may include an aperture configured to permit a tube, nozzle, needle, pipette, or syringe to dispense the fluid sample into the test tube 350. The test tubes 350 may comprise a material such as, for example, glass, polyethylene, or polymeric compounds. In various embodiments, the test tubes 350 may be re-usable units or may be disposable, single-use units. In certain embodiments, the test tubes 350 may comprise commercially available low pressure/vacuum sample bottles, test bottles, or test tubes.

In the embodiment shown in FIG. 3A, the monitoring device 102 comprises a fluid delivery system 360 configured to receive a container (e.g., the test tube 350) containing a fluid sample and deliver the fluid sample to a fluid handling system (such as, e.g., fluid handling system 404 described below). In some embodiments, the fluid handling system delivers a portion of the fluid sample to an analyte detection system for in vitro measurement of one or more physiological parameters (e.g., an analyte concentration). Prior to measurement, the fluid handling system may, in some embodiments, separate the fluid sample into components, and a measurement may be performed on one or more of the components. For example, the fluid sample in the test tube 350 may comprise whole blood, and the fluid handling system may separate blood plasma from the sample (e.g., by filtering and/or centrifuging).

In the embodiment illustrated in FIG. 3A, the fluid delivery system 360 comprises a carousel 362 having one or more openings 364 adapted to receive the test tube 350. The carousel 362 may comprise one, two, four, six, twelve, or more openings 364. In the illustrated embodiment, the carousel 362 is configured to rotate around a central axis or spindle 366 so that a test tube 350 inserted into one of the openings 364 is delivered to the monitoring device 102. In certain embodiments, the fluid handling system of the monitoring device 102 comprises a sampling probe that is configured to collect a portion of the fluid sample from the test tube 350 (e.g., by suction or aspiration). The collected portion may then be transported in the device 102 as further described below (see, e.g., FIGS. 4-7). For example, in one embodiment suitable for use with whole blood, the collected portion of the whole blood sample is transported to a centrifuge for separation into blood plasma, a portion of the blood plasma is transported to an infrared spectroscope for measurement of one or more analytes (e.g., glucose), and the measured blood plasma is then transported to a waste container for disposal.

In other embodiments of the apparatus 100 shown in FIG. 3A, the fluid delivery system 360 may comprise a turntable, rack, or caddy adapted to receive the test tube 350. In yet other embodiments, the monitoring device 102 may comprise an inlet port adapted to receive the test tube 350. Additionally, in other embodiments, the fluid sample may be delivered to the apparatus 100 using a test cartridge, a test strip, or other suitable container. Many variations are possible.

In some embodiments, one or more components of the apparatus 100 can be located at another facility, room, or other suitable remote location. One or more components of the monitoring device 102 can communicate with one or more other components of the monitoring device 102 (or with other devices) by communication interface(s) such as, but not limited to, optical interfaces, electrical interfaces, and/or wireless interfaces. These interfaces can be part of a local network, internet, wireless network, or other suitable networks.

System Overview

Figure 4:
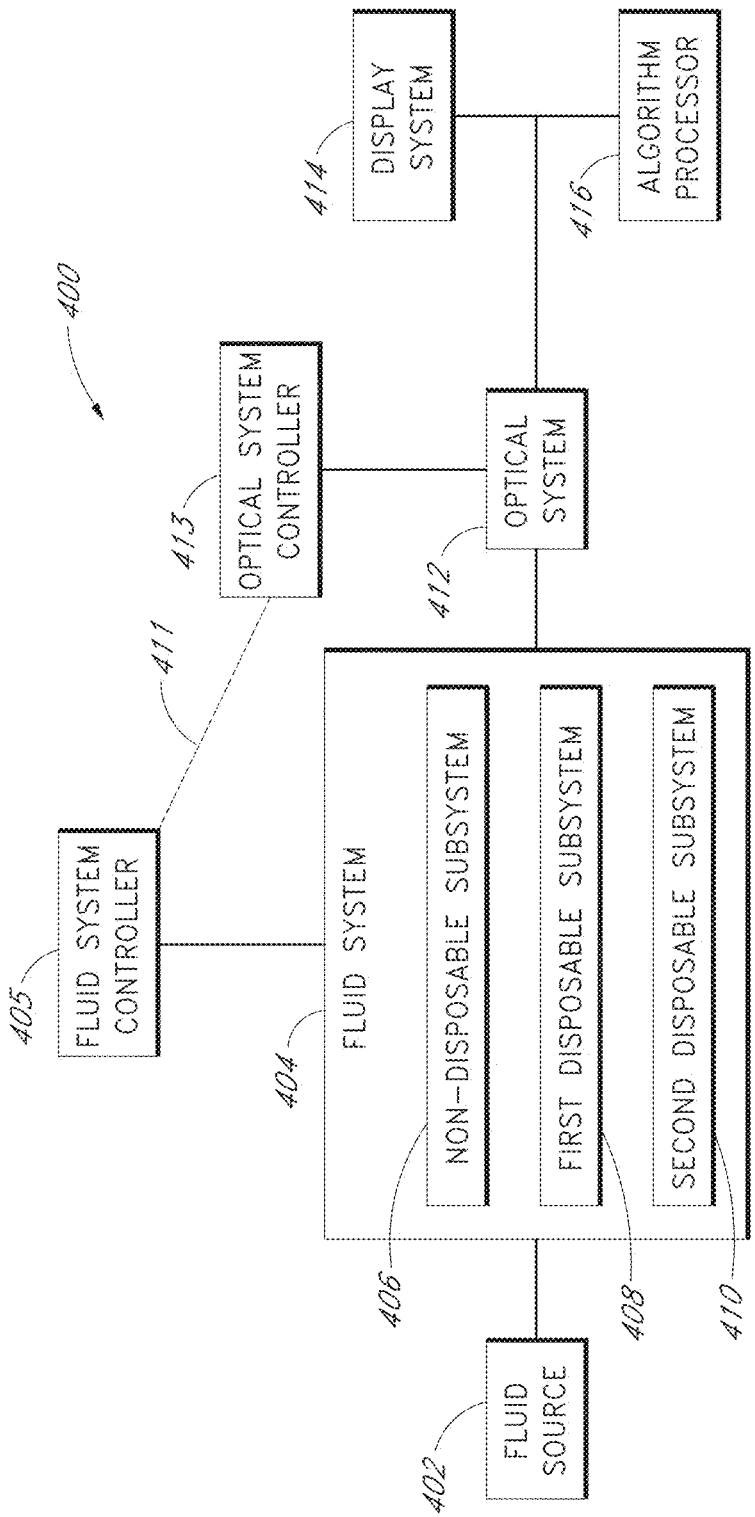
FIG. 4 is a block diagram of an embodiment of a system for withdrawing and analyzing fluid samples.

FIG. 4 is a block diagram of a system 400 for sampling and analyzing fluid samples. The monitoring device 102 can comprise such a system. The system 400 can include a fluid source 402 connected to a fluid-handling system 404. The fluid-handling system 404 includes fluid passageways and other components that direct fluid samples. Samples can be withdrawn from the fluid source 402 and analyzed by an optical system 412. The fluid-handling system 404 can be controlled by a fluid system controller 405, and the optical system 412 can be controlled by an optical system controller 413. The sampling and analysis system 400 can also include a display system 414 and an algorithm processor 416 that assist in fluid sample analysis and presentation of data.

In some embodiments, the sampling and analysis system 400 is a mobile point-of-care apparatus that monitors physiological parameters such as, for example, blood glucose concentration. Components within the system 400 that may contact fluid and/or a patient, such as tubes and connectors, can be coated with an antibacterial coating to reduce the risk of infection. Connectors between at least some components of the system 400 can include a self-sealing valve, such as a spring valve, in order to reduce the risk of contact between port openings and fluids, and to guard against fluid escaping from the system. Other components can also be included in a system for sampling and analyzing fluid in accordance with the described embodiments.

The sampling and analysis system 400 can include a fluid source 402 (or more than one fluid source) that contain(s) fluid to be sampled. The fluid-handling system 404 of the sampling and analysis system 400 is connected to, and can draw fluid from, the fluid source 402. The fluid source 402 can be, for example, a blood vessel such as a vein or an artery, a container such as a decanter, flask, beaker, tube, cartridge, test strip, etc., or any other corporeal or extracorporeal fluid source. For example, in some embodiments, the fluid source 402 may be a vein or artery in the patient 302 (see, e.g., FIG. 3). In other embodiments, the fluid source 402 may comprise an extracorporeal container 350 of fluid delivered to the system 400 for analysis (see, e.g., FIG. 3B). The fluid to be sampled can be, for example, blood, plasma, interstitial fluid, lymphatic fluid, or another fluid. In some embodiments, more than one fluid source can be present, and more than one fluid and/or type of fluid can be provided.

In some embodiments, the fluid-handling system 404 withdraws a sample of fluid from the fluid source 402 for analysis, centrifuges at least a portion of the sample, and prepares at least a portion of the sample for analysis by an optical sensor such as a spectrophotometer (which can be part of an optical system 412, for example). These functions can be controlled by a fluid system controller 405, which can also be integrated into the fluid-handling system 404. The fluid system controller 405 can also control the additional functions described below. In some embodiments, the sample can be withdrawn continuously or substantially continuously at certain time intervals with a given period. The time intervals at which the sample is withdrawn can be periodic or aperiodic and range from approximately 1 minute to approximately 15 minutes (e.g., the sample can be withdrawn at time intervals of 1 minute, 5 minutes, 10 minutes or 15 minutes). In some embodiments, the sample can be withdrawn at discrete time intervals (e.g., once every 30 minutes, once every 45 minutes or once every hour).

The duration of time over which the sample of fluid is withdrawn, referred to as "draw period", may be set to avoid clinical drawbacks, and/or it can be varied according to a health-care provider's wishes. For example, in some embodiments, fluid may be continuously withdrawn into the sampling and analysis system 400 over a draw period lasting approximately 10 seconds to approximately 5 minutes.

In some embodiments, the amount of sample withdrawn from the fluid source 402 can be small. For example, in some embodiments, the volume of sample withdrawn from the fluid source can be between approximately 1.0 ml and approximately 10.0 ml in a draw period (e.g. 2.0 ml-6.0 ml of sample can be withdrawn in a draw period of approximately 1 minute). In some embodiments, the amount of sample withdrawn can be in the range of approximately 20 ml/day to approximately 500 ml/day. In some embodiments, the amount of sample withdrawn can be outside this range.

In some embodiments, at least a portion of the sample is returned to the fluid source 402. At least some of the sample, such as portions of the sample that are mixed with other materials or portions that are otherwise altered during the sampling and analysis process, or portions that, for any reason, are not to be returned to the fluid source 402, can also be placed in a waste bladder (not shown in FIG. 4). The waste bladder can be integrated into the fluid-handling system 404 or supplied by a user of the system 400. The fluid-handling system 404 can also be connected to a saline source, a detergent source, and/or an anticoagulant source, each of which can be supplied by a user, attached to the fluid-handling system 404 as additional fluid sources, and/or integrated into the fluid-handling system 404.

Components of the fluid-handling system 404 can be modularized into one or more non-disposable, disposable, and/or replaceable subsystems. In the embodiment shown in FIG. 4, components of the fluid-handling system 404 are separated into a non-disposable subsystem 406, a first disposable subsystem 408, and a second disposable subsystem 410.

The non-disposable subsystem 406 can include components that, while they may be replaceable or adjustable, do not generally require regular replacement during the useful lifetime of the system 400. In some embodiments, the non-disposable subsystem 406 of the fluid-handling system 404 includes one or more reusable valves and sensors. For example, the non-disposable subsystem 406 can include one or more valves (or non-disposable portions thereof), (e.g., pinch-valves, rotary valves, etc.), sensors (e.g., ultrasonic bubble sensors, non-contact pressure sensors, optical blood dilution sensors, etc). The non-disposable subsystem 406 can also include one or more pumps (or non-disposable portions thereof). For example, some embodiments can include pumps available from Hospira. In some embodiments, the components of the non-disposable subsystem 406 are not directly exposed to fluids and/or are not readily susceptible to contamination.

The first and second disposable subsystems 408, 410 can include components that are regularly replaced under certain circumstances in order to facilitate the operation of the system 400. For example, the first disposable subsystem 408 can be replaced after a certain period of use, such as a few days, has elapsed. Replacement may be necessary, for example, when a bladder within the first disposable subsystem 408 is filled to capacity. Such replacement may mitigate fluid system performance degradation associated with and/ or contamination wear on system components.

In some embodiments, the first disposable subsystem 408 includes components that may contact fluids such as patient blood, saline, flushing solutions, anticoagulants, and/or detergent solutions. For example, the first disposable subsystem 408 can include one or more tubes, fittings, cleaner pouches and/or waste bladders. The components of the first disposable subsystem 408 can be sterilized in order to decrease the risk of infection and can be configured to be easily replaceable.

In some embodiments, the second disposable subsystem 410 can be designed to be replaced under certain circumstances. For example, the second disposable subsystem 410 can be replaced when the patient being monitored by the system 400 is changed. The components of the second disposable subsystem 410 may not need replacement at the same intervals as the components of the first disposable subsystem 408. For example, the second disposable subsystem 410 can include a sample holder and/or at least some components of a centrifuge, components that may not become filled or quickly worn during operation of the system 400. Replacement of the second disposable subsystem 410 can decrease or eliminate the risk of transferring fluids from one patient to another during operation of the system 400, enhance the measurement performance of system 400, and/or reduce the risk of contamination or infection.

In some embodiments, the sample holder of the second disposable subsystem 410 receives the sample obtained from the fluid source 402 via fluid passageways of the first disposable subsystem 408. The sample holder is a container that can hold fluid for the centrifuge and can include a window to the sample for analysis by a spectrometer. In some embodiments, the sample holder includes windows that are made of a material that is substantially transparent to electromagnetic radiation in the mid-infrared range of the spectrum. For example, the sample holder windows can be made of calcium fluoride.

An injector can provide a fluid connection between the first disposable subsystem 408 and the sample holder of the second disposable subsystem 410. In some embodiments, the injector can be removed from the sample holder to allow for free spinning of the sample holder during centrifugation.

In some embodiments, the components of the sample are separated by centrifuging for a period of time before measurements are performed by the optical system 412. For example, a fluid sample (e.g., a blood sample) can be centrifuged at a relatively high speed. The sample can be spun at a certain number of revolutions per minute (RPM) for a given length of time to separate blood plasma for spectral analysis. In some embodiments, the fluid sample is spun at about 7200 RPM. In some embodiments, the sample is spun at about 5000 RPM. In some embodiments, the fluid sample is spun at about 4500 RPM. In some embodiments, the fluid sample is spun at more than one rate for successive time periods. The length of time can be approximately 5 minutes. In some embodiments, the length of time is approximately 2 minutes. Separation of a sample into the components can permit measurement of solute (e.g., glucose) concentration in plasma, for example, without interference from other blood components. This kind of post-separation measurement, (sometimes referred to as a "direct measurement") has advantages over a solute measurement taken from whole blood because the proportions of plasma to other components need not be known or estimated in order to infer plasma glucose concentration. In some embodiments, the separated plasma can be analyzed electrically using one or more electrodes instead of, or in addition to, being analyzed optically. This analysis may occur within the same device, or within a different device. For example, in certain embodiments, an optical analysis device can separate blood into components, analyze the components, and then allow the components to be transported to another analysis device that can further analyze the components (e.g., using electrical and/or electrochemical measurements).

An anticoagulant, such as, for example, heparin can be added to the sample before centrifugation to prevent clotting. The fluid-handling system 404 can be used with a variety of anticoagulants, including anticoagulants supplied by a hospital or other user of the monitoring system 400. A detergent solution formed by mixing detergent powder from a pouch connected to the fluid-handling system 404 with saline can be used to periodically clean residual protein and other sample remnants from one or more components of the fluid-handling system 404, such as the sample holder. Sample fluid to which anticoagulant has been added and used detergent solution can be transferred into the waste bladder.

The system 400 shown in FIG. 4 includes an optical system 412 that can measure optical properties (e.g., transmission) of a fluid sample (or a portion thereof). In some embodiments, the optical system 412 measures transmission in the mid-infrared range of the spectrum. In some embodiments, the optical system 412 includes a spectrometer that measures the transmission of broadband infrared light through a portion of a sample holder filled with fluid. The spectrometer need not come into direct contact with the sample. As used herein, the term "sample holder" is a broad term that carries its ordinary meaning as an object that can provide a place for fluid. The fluid can enter the sample holder by flowing.

In some embodiments, the optical system 412 includes a filter wheel that contains one or more filters. In some embodiments, more than ten filters can be included, for example twelve or fifteen filters. In some embodiments, more than 20 filters (e.g., twenty-five filters) are mounted on the filter wheel. The optical system 412 includes a light source that passes light through a filter and the sample holder to a detector. In some embodiments, a stepper motor moves the filter wheel in order to position a selected filter in the path of the light. An optical encoder can also be used to finely position one or more filters. In some embodiments, one or more tunable filters may be used to filter light into multiple wavelengths. The one or more tunable filters may provide the multiple wavelengths of light at the same time or at different times (e.g., sequentially). The light source included in the optical system 412 may emit radiation in the ultraviolet, visible, near-infrared, mid-infrared, and/or far-infrared regions of the electromagnetic spectrum. In some embodiments, the light source can be a broadband source that emits radiation in a broad spectral region (e.g., from about 1500 nm to about 6000 nm). In other embodiments, the light source may emit radiation at certain specific wavelengths. The light source may comprise one or more light emitting diodes (LEDs) emitting radiation at one or more wavelengths in the radiation regions described herein. In other embodiments, the light source may comprise one or more laser modules emitting radiation at one or more wavelengths. The laser modules may comprise a solid state laser (e.g., a Nd:YAG laser), a semiconductor based laser (e.g., a GaAs and/or InGaAsP laser), and/or a gas laser (e.g., an Ar-ion laser). In some embodiments, the laser modules may comprise a fiber laser. The laser modules may emit radiation at certain fixed wavelengths. In some embodiments, the emission wavelength of the laser module(s) may be tunable over a wide spectral range (e.g., about 30 nm to about 100 nm). In some embodiments, the light source included in the optical system 412 may be a thermal infrared emitter. The light source can comprise a resistive heating element, which, in some embodiments, may be integrated on a thin dielectric membrane on a micromachined silicon structure. In one embodiment the light source is generally similar to the electrical modulated thermal infrared radiation source, IRSource™, available from the Axetris Microsystems division of Leister Technologies, LLC (Itasca, Ill.).

The optical system 412 can be controlled by an optical system controller 413. The optical system controller can, in some embodiments, be integrated into the optical system 412. In some embodiments, the fluid system controller 405 and the optical system controller 413 can communicate with each other as indicated by the line 411. In some embodiments, the function of these two controllers can be integrated and a single controller can control both the fluid-handling system 404 and the optical system 412. Such an integrated control can be advantageous because the two systems are preferably integrated, and the optical system 412 is preferably configured to analyze the very same fluid handled by the fluid-handling system 404. Indeed, portions of the fluid-handling system 404 (e.g., the sample holder described above with respect to the second disposable subsystem 410 and/or at least some components of a centrifuge) can also be components of the optical system 412. Accordingly, the fluid-handling system 404 can be controlled to obtain a fluid sample for analysis by optical system 412, when the fluid sample arrives, the optical system 412 can be controlled to analyze the sample, and when the analysis is complete (or before), the fluid-handling system 404 can be controlled to return some of the sample to the fluid source 402 and/or discard some of the sample, as appropriate.

Figure 24:
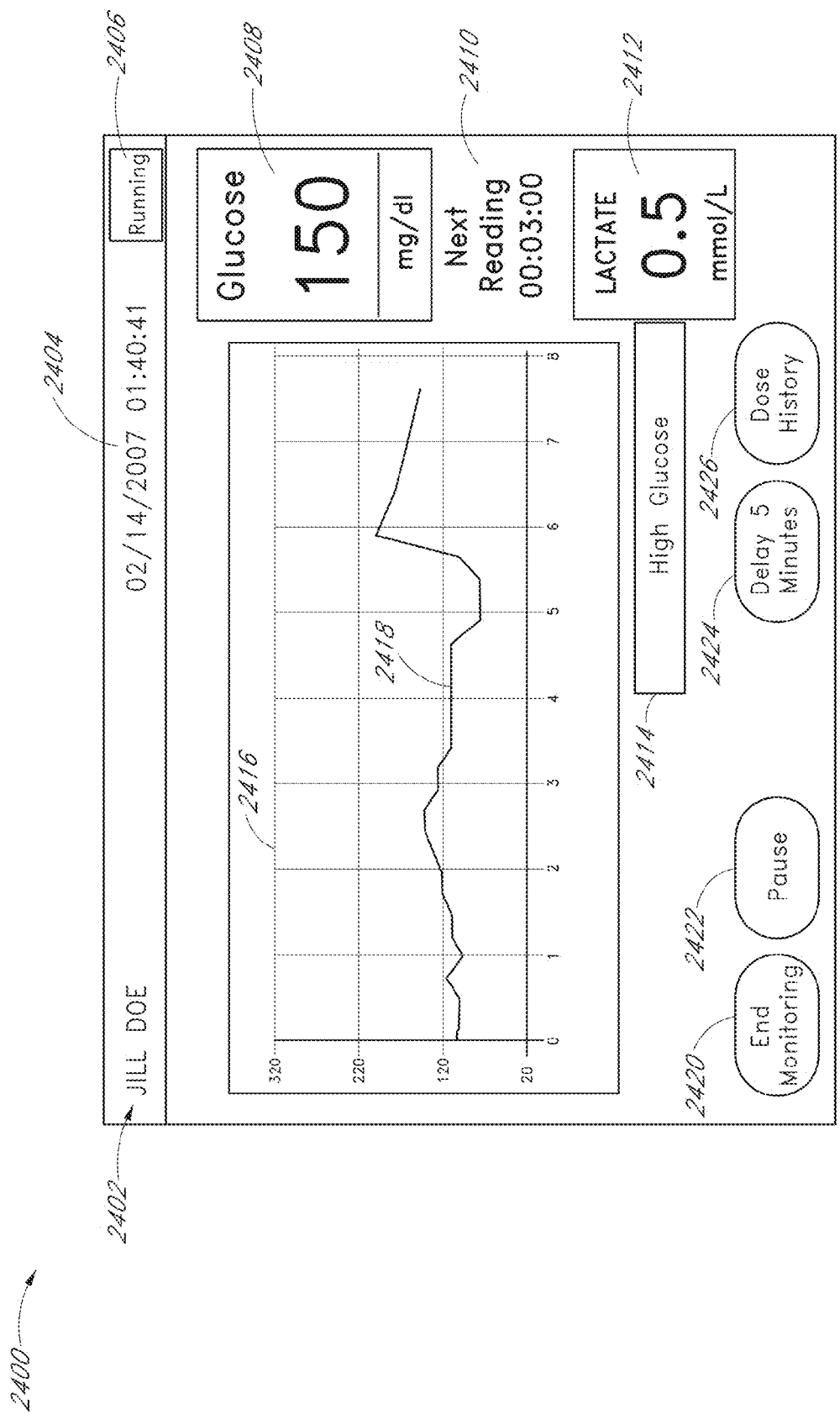
FIGS. 24 and 25 schematically illustrate the visual appearance of embodiments of a user interface for a system for withdrawing and analyzing fluid samples.
Figure 25:
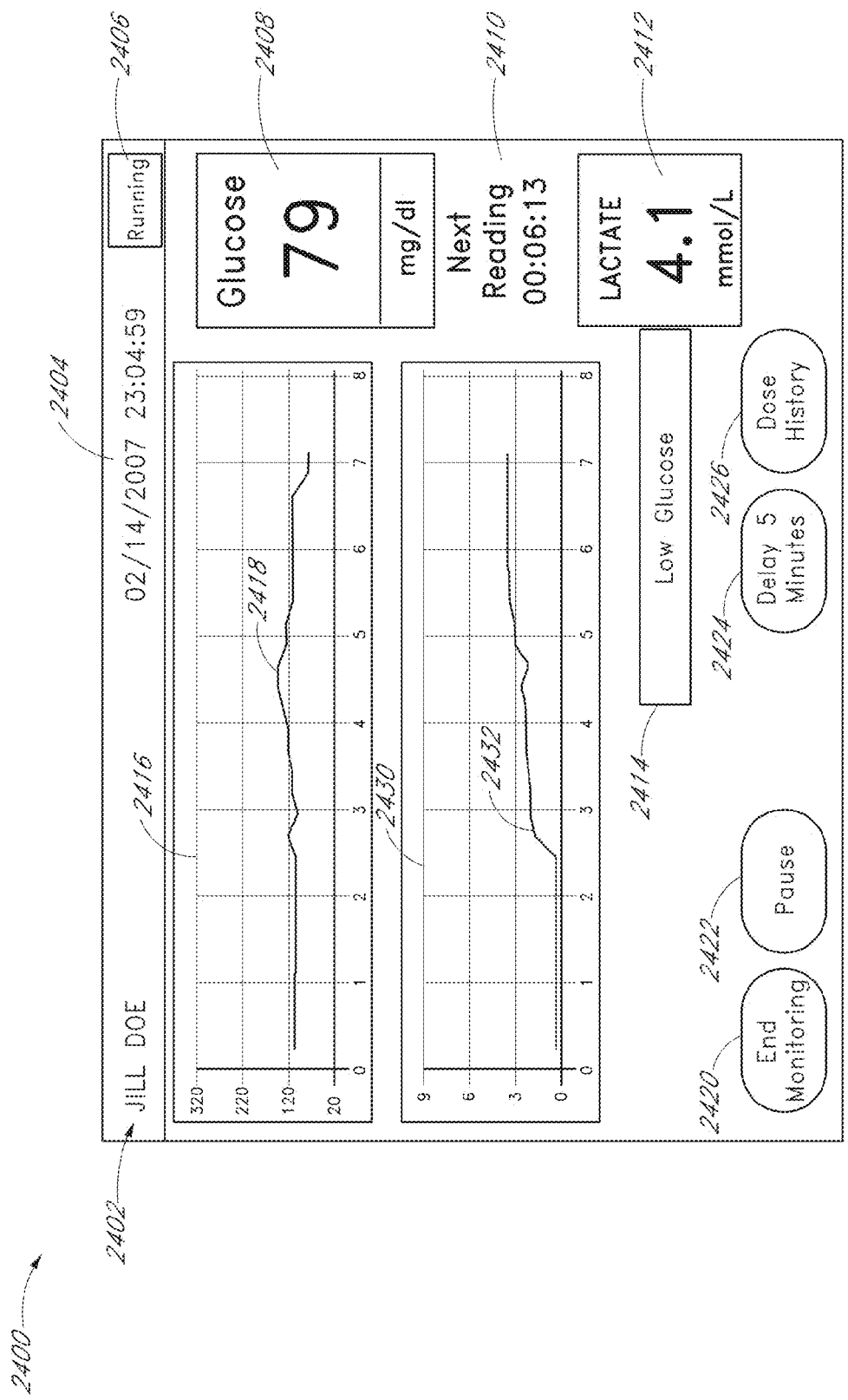

The system 400 shown in FIG. 4 includes a display system 414 that provides for communication of information to a user of the system 400. In some embodiments, the display 414 can be replaced by or supplemented with other communication devices that communicate in non-visual ways. The display system 414 can include a display processor that controls or produces an interface to communicate information to the user. The display system 414 can include a display screen. One or more parameters such as, for example, blood glucose concentration, system 400 operating parameters, and/or other operating parameters can be displayed on a monitor (not shown) associated with the system 400. An example of one way such information can be displayed is shown in FIGS. 24 and 25. In some embodiments, the display system 414 can communicate measured physiological parameters and/or operating parameters to a computer system over a communications connection.

The system 400 shown in FIG. 4 includes an algorithm processor 416 that can receive spectral information, such as optical density (OD) values (or other analog or digital optical data) from the optical system 412 and or the optical system controller 413. In some embodiments, the algorithm processor 416 calculates one or more physiological parameters and can analyze the spectral information. Thus, for example and without limitation, a model can be used that determines, based on the spectral information, physiological parameters of fluid from the fluid source 402. The algorithm processor 416, a controller that may be part of the display system 414, and any embedded controllers within the system 400 can be connected to one another with a communications bus.

Some embodiments of the systems described herein (e.g., the system 400), as well as some embodiments of each method described herein, can include a computer program accessible to and/or executable by a processing system, e.g., a one or more processors and memories that are part of an embedded system. Indeed, the controllers may comprise one or more computers and/or may use software. Thus, as will be appreciated by those skilled in the art, various embodiments may be embodied as a method, an apparatus such as a special purpose apparatus, an apparatus such as a data processing system, or a carrier medium, e.g., a computer program product. The carrier medium carries one or more computer readable code segments for controlling a processing system to implement a method. Accordingly, various embodiments may take the form of a method, an entirely hardware embodiment, an entirely software embodiment or an embodiment combining software and hardware aspects. Furthermore, any one or more of the disclosed methods (including but not limited to the disclosed methods of measurement analysis, interferent determination, and/or calibration constant generation) may be stored as one or more computer readable code segments or data compilations on a carrier medium. Any suitable computer readable carrier medium may be used including a magnetic storage device such as a diskette or a hard disk; a memory cartridge, module, card or chip (either alone or installed within a larger device); or an optical storage device such as a CD or DVD.

Fluid Handling System

Figure 5:
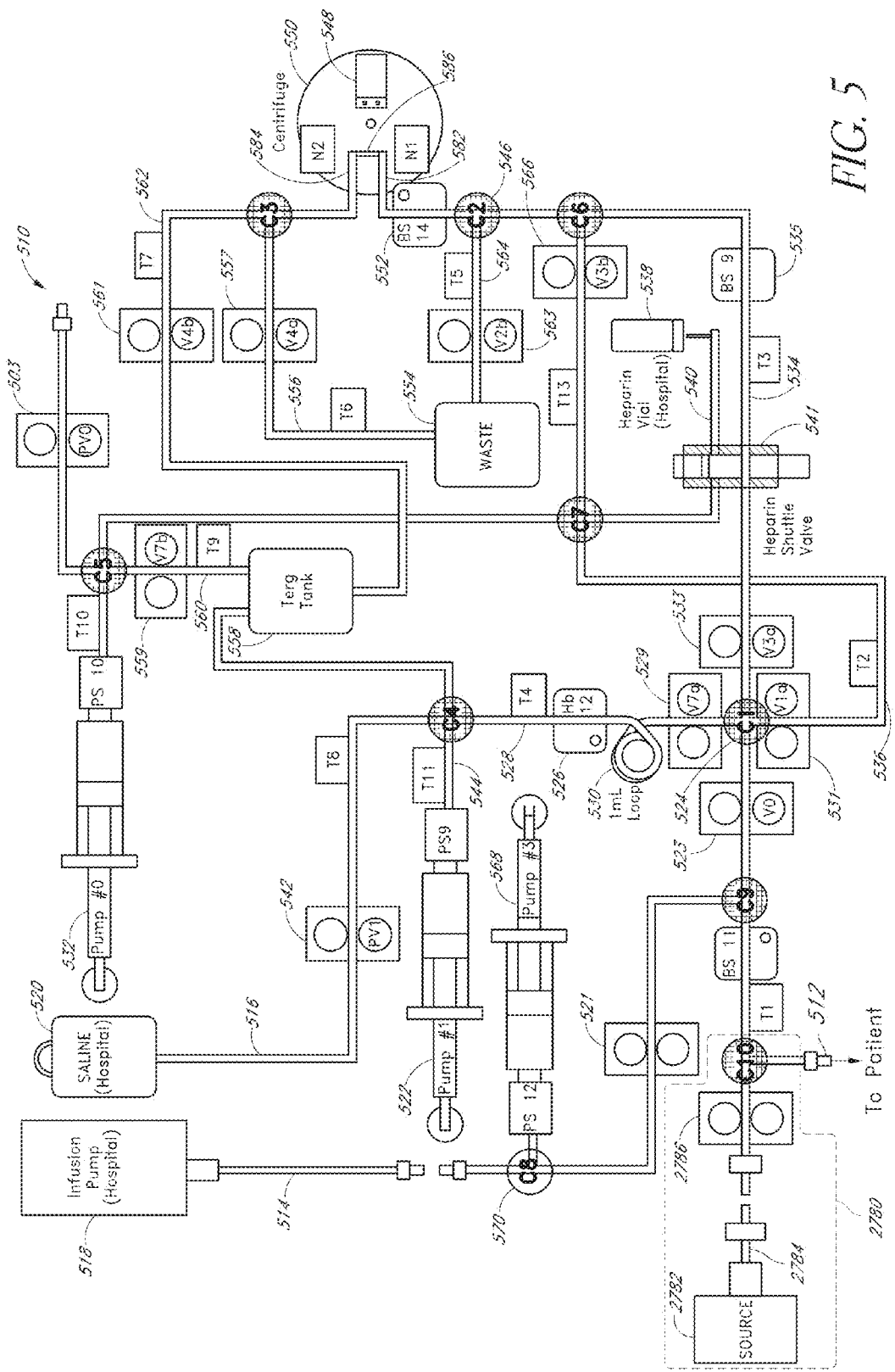
FIG. 5 schematically illustrates an embodiment of a fluid system that can be part of a system for withdrawing and analyzing fluid samples.

The generalized fluid-handling system 404 can have various configurations. In this context, FIG. 5 schematically illustrates the layout of an example embodiment of a fluid system 510. In this schematic representation, various components are depicted that may be part of a non-disposable subsystem 406, a first disposable subsystem 408, a second disposable subsystem 410, and/or an optical system 412. The fluid system 510 is described practically to show an example cycle as fluid is drawn and analyzed.

In addition to the reference numerals used below, the various portions of the illustrated fluid system 510 are labeled for convenience with letters to suggest their roles as follows: T# indicates a section of tubing. C# indicates a connector that joins multiple tubing sections. V# indicates a valve. BS# indicates a bubble sensor or ultrasonic air detector. N# indicates a needle (e.g., a needle that injects sample into a sample holder). PS# indicates a pressure sensor (e.g., a reusable pressure sensor). Pump# indicates a fluid pump (e.g., a syringe pump with a disposable body and reusable drive). "Hb 12" indicates a sensor for hemoglobin (e.g., a dilution sensor that can detect hemoglobin optically).

The term "valve" as used herein is a broad term and is used, in accordance with its ordinary meaning, to refer to any flow regulating device. For example, the term "valve" can include, without limitation, any device or system that can controllably allow, prevent, or inhibit the flow of fluid through a fluid passageway. The term "valve" can include some or all of the following, alone or in combination: pinch valves, rotary valves, stop cocks, pressure valves, shuttle valves, mechanical valves, electrical valves, electro-mechanical flow regulators, etc. In some embodiments, a valve can regulate flow using gravitational methods or by applying electrical voltages or by both.

The term "pump" as used herein is a broad term and is used, in accordance with its ordinary meaning, to refer to any device that can urge fluid flow. For example, the term "pump" can include any combination of the following: syringe pumps, peristaltic pumps, vacuum pumps, electrical pumps, mechanical pumps, hydraulic pumps, etc. Pumps and/or pump components that are suitable for use with some embodiments can be obtained, for example, from or through Hospira.

The function of the valves, pumps, actuators, drivers, motors (e.g., the centrifuge motor), etc. described below is controlled by one or more controllers (e.g., the fluid system controller 405, the optical system controller 413, etc.) The controllers can include software, computer memory, electrical and mechanical connections to the controlled components, etc.

At the start of a measurement cycle, most lines, including a patient tube 512 (T1), an Arrival sensor tube 528 (T4), an anticoagulant valve tube 534 (T3), and a sample cell 548 can be filled with saline that can be introduced into the system through the infusion tube 514 and the saline tube 516, and which can come from an infusion pump 518 and/or a saline bag 520. The infusion pump 518 and the saline bag 520 can be provided separately from the system 510. For example, a hospital can use existing saline bags and infusion pumps to interface with the described system. The infusion valve 521 can be open to allow saline to flow into the tube 512 (T1).

Before drawing a sample, the saline in part of the system 510 can be replaced with air. Thus, for example, the following valves can be closed: air valve 503 (PV0), the detergent tank valve 559 (V7b), 566 (V3b), 523 (V0), 529 (V7a), and 563 (V2b). At the same time, the following valves can be open: valves 531 (V1a), 533 (V3a) and 577 (V4a). Simultaneously, a second pump 532 (pump #0) pumps air through the system 510 (including tube 534 (T3), sample cell 548, and tube 556 (T6)), pushing saline through tube 534 (T3) and sample cell 548 into a waste bladder 554.

Next, a sample can be drawn. With the valves 542 (PV1), 559 (V7b), and 561 (V4b) closed, a first pump 522 (pump #1) is actuated to draw sample fluid to be analyzed (e.g. blood) from a fluid source (e.g., a laboratory sample container, a living patient, etc.) up into the patient tube 512 (T1), through the tube past the two flanking portions of the open pinch-valve 523 (V0), through the first connector 524 (C1), into the looped tube 530, past the arrival sensor 526 (Hb12), and into the arrival sensor tube 528 (T4). The arrival sensor 526 may be used to detect the presence of blood in the tube 528 (T4). For example in some embodiments, the arrival sensor 526 may comprise a hemoglobin sensor. In some other embodiments, the arrival sensor 526 may comprise a color sensor that detects the color of fluid flowing through the tube 528 (T4). During this process, the valve 529 (V7a) and 523 (V0) are open to fluid flow, and the valves 531 (V1a), 533 (V3a), 542 (PV1), 559 (V7b), and 561 (V4b) can be closed and therefore block (or substantially block) fluid flow by pinching the tube.

Before drawing the sample, the tubes 512 (T1) and 528 (T4) are filled with saline and the hemoglobin (Hb) level is zero. The tubes that are filled with saline are in fluid communication with the sample source (e.g., the fluid source 402). The sample source can be the vessels of a living human or a pool of liquid in a laboratory sample container, for example. When the saline is drawn toward the first pump 522, fluid to be analyzed is also drawn into the system because of the suction forces in the closed fluid system. Thus, the first pump 522 draws a relatively continuous column of fluid that first comprises generally nondiluted saline, then a mixture of saline and sample fluid (e.g., blood), and then eventually nondiluted sample fluid. In the example illustrated here, the sample fluid is blood.

The arrival sensor 526 (Hb12) can detect and/or verify the presence of blood in the tubes. For example, in some embodiments, the arrival sensor 526 can determine the color of the fluid in the tubes. In some embodiments, the arrival sensor 526 (Hb12) can detect the level of Hemoglobin in the sample fluid. As blood starts to arrive at the arrival sensor 526 (Hb12), the sensed hemoglobin level rises. A hemoglobin level can be selected, and the system can be pre-set to determine when that level is reached. A controller such as the fluid system controller 405 of FIG. 4 can be used to set and react to the pre-set value, for example. In some embodiments, when the sensed hemoglobin level reaches the pre-set value, substantially undiluted sample is present at the first connector 524 (C1). The preset value can depend, in part, on the length and diameter of any tubes and/or passages traversed by the sample. In some embodiments, the pre-set value can be reached after approximately 2 mL of fluid (e.g., blood) has been drawn from a fluid source. A nondiluted sample can be, for example, a blood sample that is not diluted with saline solution, but instead has the characteristics of the rest of the blood flowing through a patient's body. A loop of tubing 530 (e.g., a 1-mL loop) can be advantageously positioned as illustrated to help insure that undiluted fluid (e.g., undiluted blood) is present at the first connector 524 (C1) when the arrival sensor 526 registers that the preset Hb threshold is crossed. The loop of tubing 530 provides additional length to the Arrival sensor tube 528 (T4) to make it less likely that the portion of the fluid column in the tubing at the first connector 524 (C1) has advanced all the way past the mixture of saline and sample fluid, and the nondiluted blood portion of that fluid has reached the first connector 524 (C1).

In some embodiments, when nondiluted blood is present at the first connector 524 (C1), a sample is mixed with an anticoagulant and is directed toward the sample cell 548. An amount of anticoagulant (e.g., heparin) can be introduced into the tube 534 (T3), and then the undiluted blood is mixed with the anticoagulant. A heparin vial 538 (e.g., an insertable vial provided independently by the user of the system 510) can be connected to a tube 540. An anticoagulant valve 541 (which can be a shuttle valve, for example) can be configured to connect to both the tube 540 and the anticoagulant valve tube 534 (T3). The valve can open the tube 540 to a suction force (e.g., created by the pump 532), allowing heparin to be drawn from the vial 538 into the valve 541. Then, the anticoagulant valve 541 can slide the heparin over into fluid communication with the anticoagulant valve tube 534 (T3). The anticoagulant valve 541 can then return to its previous position. Thus, heparin can be shuttled from the tube 540 into the anticoagulant valve tube 534 (T3) to provide a controlled amount of heparin into the tube 534 (T3).

With the valves 542 (PV1), 559 (V7b), 561 (V4b), 523 (V0), 531 (V1a), 566 (V3b), and 563 (V2b) closed, and the valves 529 (V7a) and 533 (V3a) open, first pump 522 (pump #1) pushes the sample from tube 528 (T4) into tube 534 (T3), where the sample mixes with the heparin injected by the anticoagulant valve 541 as it flows through the system 510. As the sample proceeds through the tube 534 (T3), the air that was previously introduced into the tube 534 (T3) is displaced. The sample continues to flow until a bubble sensor 535 (BS9) indicates a change from air to a liquid, and thus the arrival of a sample at the bubble sensor. In some embodiments, the volume of tube 534 (T3) from connector 524 (C1) to bubble sensor 535 (BS9) is a known and/or engineered amount, and may be approximately 500 μL, 2000 μL or 100 μL, for example. In some embodiments, the volume of tube 534 (T3) from connector 524 (C1) to bubble sensor 535 (BS9) may be approximately less than 10 ml.

When bubble sensor 535 (BS9) indicates the presence of a sample, the remainder of the sampled blood can be returned to its source (e.g., the patient veins or arteries). The first pump 522 (pump #1) pushes the blood out of the Arrival sensor tube 528 (T4) and back to the patient by opening the valve 523 (V0), closing the valves 531 (V1a) and 533 (V3a), and keeping the valve 529 (V7a) open. The Arrival sensor tube 528 (T4) is preferably flushed with approximately 2 mL of saline. This can be accomplished by closing the valve 529 (V7a), opening the valve 542 (PV1), drawing saline from the saline source 520 into the tube 544, closing the valve 542 (PV1), opening the valve 529 (V7a), and forcing the saline down the Arrival sensor tube 528 (T4) with the pump 522. In some embodiments, less than two minutes elapse between the time that blood is drawn from the patient and the time that the blood is returned to the patient.

Following return of the unused patient blood sample, the sample is pushed up the anticoagulant valve tube 534 (T3), through the second connector 546 (C2), and into the sample cell 548, which can be located on the centrifuge rotor 550. This fluid movement is facilitated by the coordinated action (either pushing or drawing fluid) of the pump 522 (pump #1), the pump 532 (pump #0), and the various illustrated valves. In particular, valve 531 (V1a) can be opened, and valves 503 (PV0) and 559 (V7b) can be closed. Pump movement and valve position corresponding to each stage of fluid movement can be coordinated by one ore multiple controllers, such as the fluid system controller 405 of FIG. 4.

After the unused sample is returned to the patient, the sample can be divided into separate slugs before being delivered into the sample cell 548. Thus, for example, valve 533 (V3a) is opened, valves 566 (V3b), 523 (V0) and 529 (V7a) are closed, and the pump 532 (pump #0) uses air to push the sample toward sample cell 548. In some embodiments, the sample (for example, 200 µL or 100 µL) is divided into multiple (e.g., more than two, five, or four) "slugs" of sample, each separated by a small amount of air. As used herein, the term "slug" refers to a continuous column of fluid that can be relatively short. Slugs can be separated from one another by small amounts of air (or bubbles) that can be present at intervals in the tube. In some embodiments, the slugs are formed by injecting or drawing air into fluid in the first connector 546 (C2).

In some embodiments, when the leading edge of the sample reaches blood sensor 552 (BS14), a small amount of air (the first "bubble") is injected at a connector C6. This bubble helps define the first "slug" of liquid, which extends from the bubble sensor to the first bubble. In some embodiments, the valves 533 (V3a) and 566 (V3b) are alternately opened and closed to form a bubble at connector C6, and the sample is pushed toward the sample cell 548. Thus, for example, with pump 532 actuated, valve 566 V(3b) is briefly opened and valve 533 (V3a) is briefly closed to inject a first air bubble into the sample.

In some embodiments, the volume of the tube 534 (T3) from the connector 546 (C2) to the bubble sensor 552 (BS14) is less than the volume of tube 534 (T3) from the connector 524 (C1) to the bubble sensor 535 (BS9). Thus, for example and without limitation, the volume of the tube 534 (T3) from the connector 524 (C1) to the bubble sensor 535 (BS9) can be in the range of approximately 80 µL to approximately 120 µL, (e.g., 100 µL,) and the volume of the tube 534 (T3) from the connector 546 (C2) to the bubble sensor 552 (BS14) can be in the range of approximately 5 µL to approximately 25 µL (e.g., 15 µL). In some embodiments, multiple blood slugs are created. For example, more than two blood slugs can be created, each having a different volume. In some embodiments, five blood slugs are created, each having approximately the same volume of approximately 20 µL each. In some embodiments, three blood slugs are created, the first two having a volume of 100 µL and the last having a volume of 20 µL. In some embodiments, four blood slugs are created; the first three blood slugs can have a volume of approximately 15 µL and the fourth can have a volume of approximately 35 µL.

A second slug can be prepared by opening the valve 533 (V3a), closing the valve 566 (V3b), with pump 532 (pump #0) operating to push the first slug through a first sample cell holder interface tube 582 (N1), through the sample cell 548, through a second sample cell holder interface tube 584 (N2), and toward the waste bladder 554. When the first bubble reaches the bubble sensor 552 (BS 14), the open/closed configurations of valves 533 (V3a) and 566 (V3b) are reversed, and a second bubble is injected into the sample, as before. A third slug can be prepared in the same manner as the second (pushing the second bubble to bubble sensor 552 (BS 14) and injecting a third bubble). After the injection of the third air bubble, the sample can be pushed through system 510 until the end of the sample is detected by bubble sensor 552 (BS 14). The system can be designed such that when the end of the sample reaches this point, the last portion of the sample (a fourth slug) is within the sample cell 548, and the pump 532 can stop forcing the fluid column through the anticoagulant valve tube 534 (T3) so that the fourth slug remains within the sample cell 548. Thus, the first three blood slugs can serve to flush any residual saline out the sample cell 548. The three leading slugs can be deposited in the waste bladder 554 by passing through the tube 556 (T6) and past the tube-flanking portions of the open pinch valve 557 (V4a).

In some embodiments, the fourth blood slug is centrifuged for a given length of time (e.g., more than 1 minute, five minutes, or 2 minutes, to take three advantageous examples) at a relatively fast speed (e.g., 7200 RPM, 5000 RPM, or 4500 RPM, to take three examples). Thus, for example, the sample cell holder interface tubes 582 (N1) and 584 (N2) disconnect the sample cell 548 from the tubes 534 (T3) and 562 (T7), permitting the centrifuge rotor 550 and the sample cell 548 to spin together. Spinning separates a sample (e.g., blood) into its components, isolates the plasma, and positions the plasma in the sample cell 548 for measurement. The centrifuge 550 can be stopped with the sample cell 548 in a beam of radiation (not shown) for analysis. The radiation, a detector, and logic can be used to analyze a portion of the sample (e.g., the plasma) spectroscopically (e.g., for glucose, lactate, or other analyte concentration). In some embodiments, some or all of the separated components (e.g., the isolated plasma) may be transported to a different analysis chamber. For example, another analysis chamber can have one or more electrodes in electrical communication with the chamber's contents, and the separated components may be analyzed electrically. At any suitable point, one or more of the separated components can be transported to the waste bladder 554 when no longer needed. In some chemical analysis systems and apparatus, the separated components are analyzed electrically. Analysis devices may be connected serially, for example, so that the analyzed substance from an optical analysis system (e.g., an OPTISCANNER™ fluid analyzer) can be transferred to an independent analysis device (e.g., a chemical analysis device) for subsequent analysis. In certain embodiments, the analysis devices are integrated into a single system. Many variations are possible.

In some embodiments, portions of the system 510 that contain blood after the sample cell 548 has been provided with a sample are cleaned to prevent blood from clotting. Accordingly, the centrifuge rotor 550 can include two passageways for fluid that may be connected to the sample cell holder interface tubes 582 (N1) and 584 (N2). One passageway is sample cell 548, and a second passageway is a shunt 586. An embodiment of the shunt 586 is illustrated in more detail in FIG. 16 (see reference numeral 1586).

The shunt 586 can allow cleaner (e.g., a detergent such as tergazyme A) to flow through and clean the sample cell holder interface tubes without flowing through the sample cell 548. After the sample cell 548 is provided with a sample, the interface tubes 582 (N1) and 584 (N2) are disconnected from the sample cell 548, the centrifuge rotor 550 is rotated to align the shunt 586 with the interface tubes 582 (N1) and 584 (N2), and the interface tubes are connected with the shunt. With the shunt in place, the detergent tank 559 is pressurized by the second pump 532 (pump #0) with valves 561 (V4b) and 563 (V2b) open and valves 557 (V4a) and 533 (V3a) closed to flush the cleaning solution back through the interface tubes 582 (N1) and 584 (N2) and into the waste bladder 554. Subsequently, saline can be drawn from the saline bag 520 for a saline flush. This flush pushes saline through the Arrival sensor tube 528 (T4), the anticoagulant valve tube 534 (T3), the sample cell 548, and the waste tube 556 (T6). Thus, in some embodiments, the following valves are open for this flush: 529 (V7a), 533 (V3a), 557 (V4a), and the following valves are closed: 542 (PV1), 523 (V0), 531 (V1a), 566 (V3b), 563 (V2b), and 561 (V4b).

Following analysis, the second pump 532 (pump #0) flushes the sample cell 548 and sends the flushed contents to the waste bladder 554. This flush can be done with a cleaning solution from the detergent tank 558. In some embodiments, the detergent tank valve 559 (V7b) is open, providing fluid communication between the second pump 532 and the detergent tank 558. The second pump 532 forces cleaning solution from the detergent tank 558 between the tube-flanking portions of the open pinch valve 561 and through the tube 562 (T7). The cleaning flush can pass through the sample cell 548, through the second connector 546, through the tube 564 (T5) and the open valve 563 (V2b), and into the waste bladder 554.

Subsequently, the first pump 522 (pump #1) can flush the cleaning solution out of the sample cell 548 using saline in drawn from the saline bag 520. This flush pushes saline through the Arrival sensor tube 528 (T4), the anticoagulant valve tube 534 (T3), the sample cell 548, and the waste tube 556 (T6). Thus, in some embodiments, the following valves are open for this flush: 529 (V7a), 533 (V3a), 557 (V4a), and the following valves are closed: 542 (PV1), 523 (V0), 531 (V1a), 566 (V3b), 563 (V2b), and 561 (V4b).

When the fluid source is a living entity such as a patient, a low flow of saline (e.g., 1-5 mL/hr) is preferably moved through the patient tube 512 (T1) and into the patient to keep the patient's vessel open (e.g., to establish a keep vessel open, or "KVO" flow). This KVO flow can be temporarily interrupted when fluid is drawn into the fluid system 510. The source of this KVO flow can be the infusion pump 518, the third pump 568 (pump #3), or the first pump 522 (pump #1). In some embodiments, the infusion pump 518 can run continuously throughout the measurement cycle described above. This continuous flow can advantageously avoid any alarms that may be triggered if the infusion pump 518 senses that the flow has stopped or changed in some other way. In some embodiments, when the infusion valve 521 closes to allow pump 522 (pump #1) to withdraw fluid from a fluid source (e.g., a patient), the third pump 568 (pump #3) can withdraw fluid through the connector 570, thus allowing the infusion pump 518 to continue pumping normally as if the fluid path was not blocked by the infusion valve 521. If the measurement cycle is about two minutes long, this withdrawal by the third pump 568 can continue for approximately two minutes. Once the infusion valve 521 is open again, the third pump 568 (pump #3) can reverse and insert the saline back into the system at a low flow rate. Preferably, the time between measurement cycles is longer than the measurement cycle itself (for example, the time interval can be longer than ten minutes, shorter than ten minutes, shorter than five minutes, longer than two minutes, longer than one minute, etc.). Accordingly, the third pump 568 can insert fluid back into the system at a lower rate than it withdrew that fluid. This can help prevent an alarm by the infusion pump.

Figure 6:
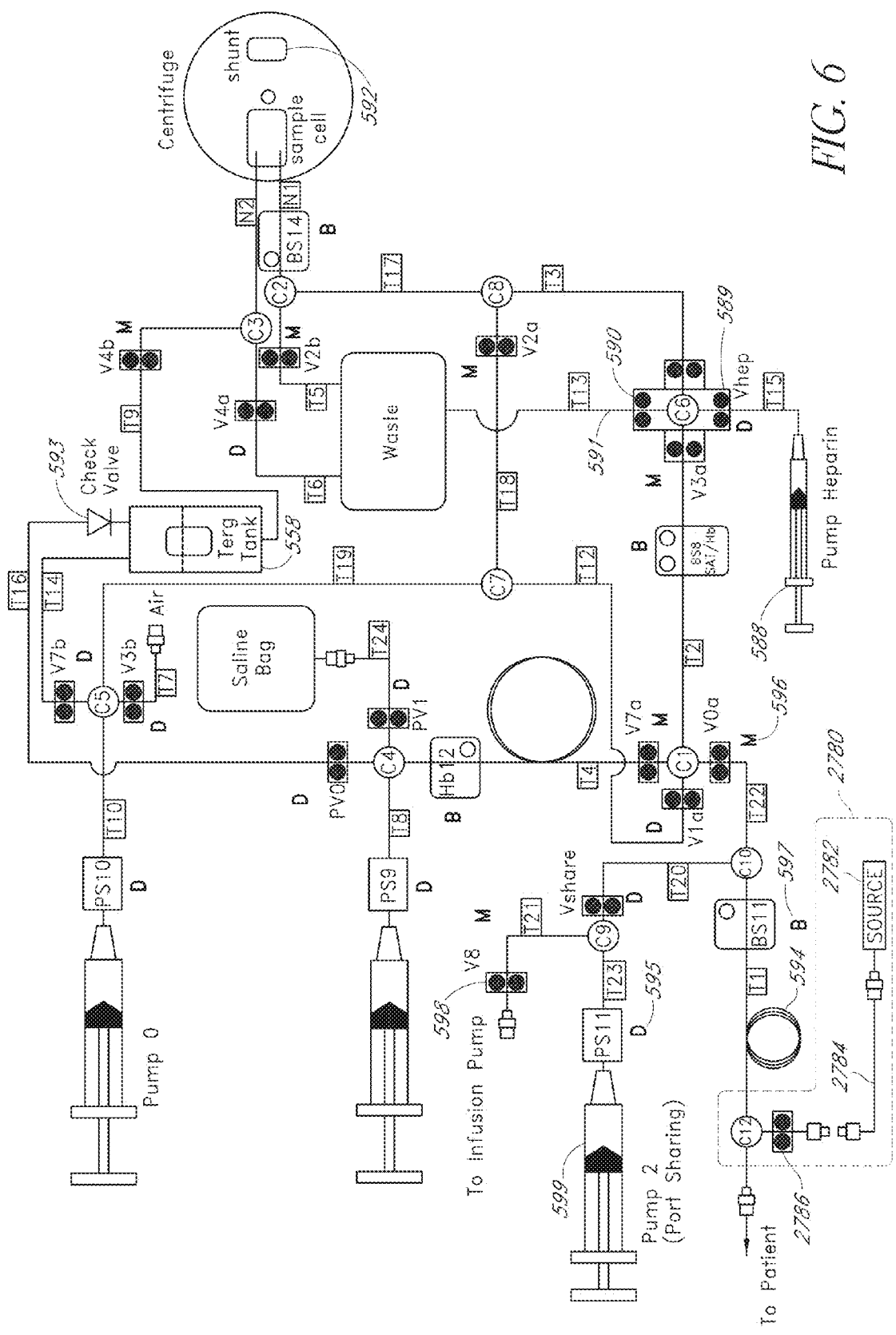
FIG. 6 schematically illustrates another embodiment of a fluid system that can be part of a system for withdrawing and analyzing fluid samples.

FIG. 6 schematically illustrates another embodiment of a fluid system that can be part of a system for withdrawing and analyzing fluid samples. In this embodiment, the anticoagulant valve 541 has been replaced with a syringe-style pump 588 (Pump Heparin) and a series of pinch valves around a junction between tubes. For example, a heparin pinch valve 589 (Vhep) can be closed to prevent flow from or to the pump 588, and a heparin waste pinch valve 590 can be closed to prevent flow from or to the waste container from this junction through the heparin waste tube 591. This embodiment also illustrates the shunt 592 schematically. Other differences from FIG. 5 include the check valve 593 located near the detergent tank 558 and the patient loop 594. The reference letters D, for example, the one indicated at 595, refer to components that are advantageously located on the door. The reference letters M, for example, the one indicated at 596, refer to components that are advantageously located on the monitor. The reference letters B, for example, the one indicated at 597, refer to components that can be advantageously located on both the door and the monitor.

In some embodiments, the system 400 (see FIG. 4), the apparatus 100 (see FIG. 1), or even the monitoring device 102 (see FIG. 1) itself can also actively function not only to monitor analyte levels (e.g., glucose), but also to change and/or control analyte levels. Thus, the monitoring device 102 can be both a monitoring and an infusing device. In some embodiments, the fluid handling system 510 can include an optional analyte control subsystem 2780 that will be further described below (see discussion of analyte control).

In certain embodiments, analyte levels in a patient can be adjusted directly (e.g., by infusing or extracting glucose) or indirectly (e.g., by infusing or extracting insulin). FIG. 6 illustrates one way of providing this function. The infusion pinch valve 598 (V8) can allow the port sharing pump 599 (compare to the third pump 568 (pump #3) in FIG. 5) to serve two roles. In the first role, it can serve as a "port sharing" pump. The port sharing function is described with respect to the third pump 568 (pump #3) of FIG. 5, where the third pump 568 (pump #3) can withdraw fluid through the connector 570, thus allowing the infusion pump 518 to continue pumping normally as if the fluid path was not blocked by the infusion valve 521. In the second role, the port sharing pump 599 can serve as an infusion pump. The infusion pump role allows the port sharing pump 599 to draw a substance (e.g., glucose, saline, etc.) from another source when the infusion pinch valve 598 is open, and then to infuse that substance into the system or the patient when the infusion pinch valve 598 is closed. This can occur, for example, in order to change the level of a substance in a patient in response to a reading by the monitor that the substance is too low. In some embodiments, one or more of the pumps may comprise a reversible infusion pump configured to interrupt the flow of the infusion fluid and draw a sample of blood for analysis.

Mechanical/Fluid System Interface

Figure 7:
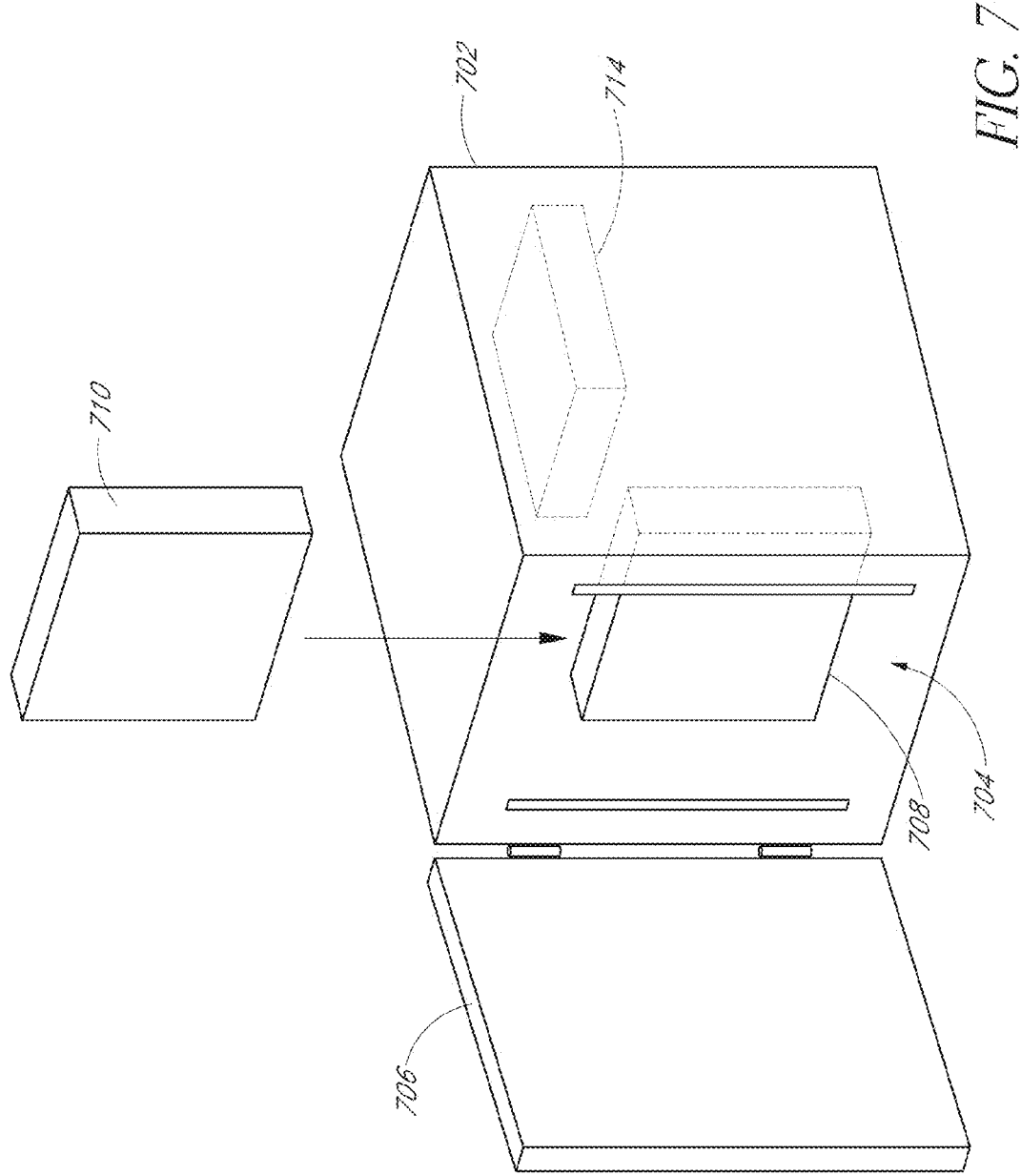
FIG. 7 is an oblique schematic depiction of an embodiment of a monitoring device.

FIG. 7 is an oblique schematic depiction of a modular monitoring device 700, which can correspond to the monitoring device 102. The modular monitoring device 700 includes a body portion 702 having a receptacle 704, which can be accessed by moving a movable portion 706. The receptacle 704 can include connectors (e.g., rails, slots, protrusions, resting surfaces, etc.) with which a removable portion 710 can interface. In some embodiments, portions of a fluidic system that directly contact fluid are incorporated into one or more removable portions (e.g., one or more disposable cassettes, sample holders, tubing cards, etc.). For example, a removable portion 710 can house at least a portion of the fluid system 510 described previously, including portions that contact sample fluids, saline, detergent solution, and/or anticoagulant.

In some embodiments, a non-disposable fluid-handling subsystem 708 is disposed within the body portion 702 of the monitoring device 700. The first removable portion 710 can include one or more openings that allow portions of the non-disposable fluid-handling subsystem 708 to interface with the removable portion 710. For example, the non-disposable fluid-handling subsystem 708 can include one or more pinch valves that are designed to extend through such openings to engage one or more sections of tubing. When the first removable portion 710 is present in a corresponding first receptacle 704, actuation of the pinch valves can selectively close sections of tubing within the removable portion. The non-disposable fluid-handling subsystem 708 can also include one or more sensors that interface with connectors, tubing sections, or pumps located within the first removable portion 710. The non-disposable fluid-handling subsystem 708 can also include one or more actuators (e.g., motors) that can actuate moveable portions (e.g., the plunger of a syringe) that may be located in the removable portion F10. A portion of the non-disposable fluid-handling subsystem 708 can be located on or in the moveable portion F06 (which can be a door having a slide or a hinge, a detachable face portion, etc.).

In the embodiment shown in FIG. 7, the monitoring device 700 includes an optical system 714 disposed within the body portion 702. The optical system 714 can include a light source and a detector that are adapted to perform measurements on fluids within a sample holder (not shown). The light source may comprise a fixed wavelength light source and/or a tunable light source. The light source may comprise one or more sources including, for example, broadband sources, LEDs, and lasers. In some embodiments, the sample holder comprises a removable portion, which can be associated with or disassociated from the removable portion F10. The sample holder can include an optical window through which the optical system 714 can emit radiation for measuring properties of a fluid in the sample holder. The optical system 714 can include other components such as, for example, a power supply, a centrifuge motor, a filter wheel, and/or a beam splitter.

In some embodiments, the removable portion 710 and the sample holder are adapted to be in fluid communication with each other. For example, the removable portion 710 can include a retractable injector that injects fluids into a sample holder. In some embodiments, the sample holder can comprise or be disposed in a second removable portion (not shown). In some embodiments, the injector can be retracted to allow the centrifuge to rotate the sample holder freely.

The body portion 702 of the monitoring device 700 can also include one or more connectors for an external battery (not shown). The external battery can serve as a backup emergency power source in the event that a primary emergency power source such as, for example, an internal battery (not shown) is exhausted.

FIG. 7 shows an embodiment of a system having subcomponents illustrated schematically. By way of a more detailed (but nevertheless non-limiting) example, FIG. 8 and FIG. 9 show more details of the shape and physical configuration of a sample embodiment.

Figure 8:
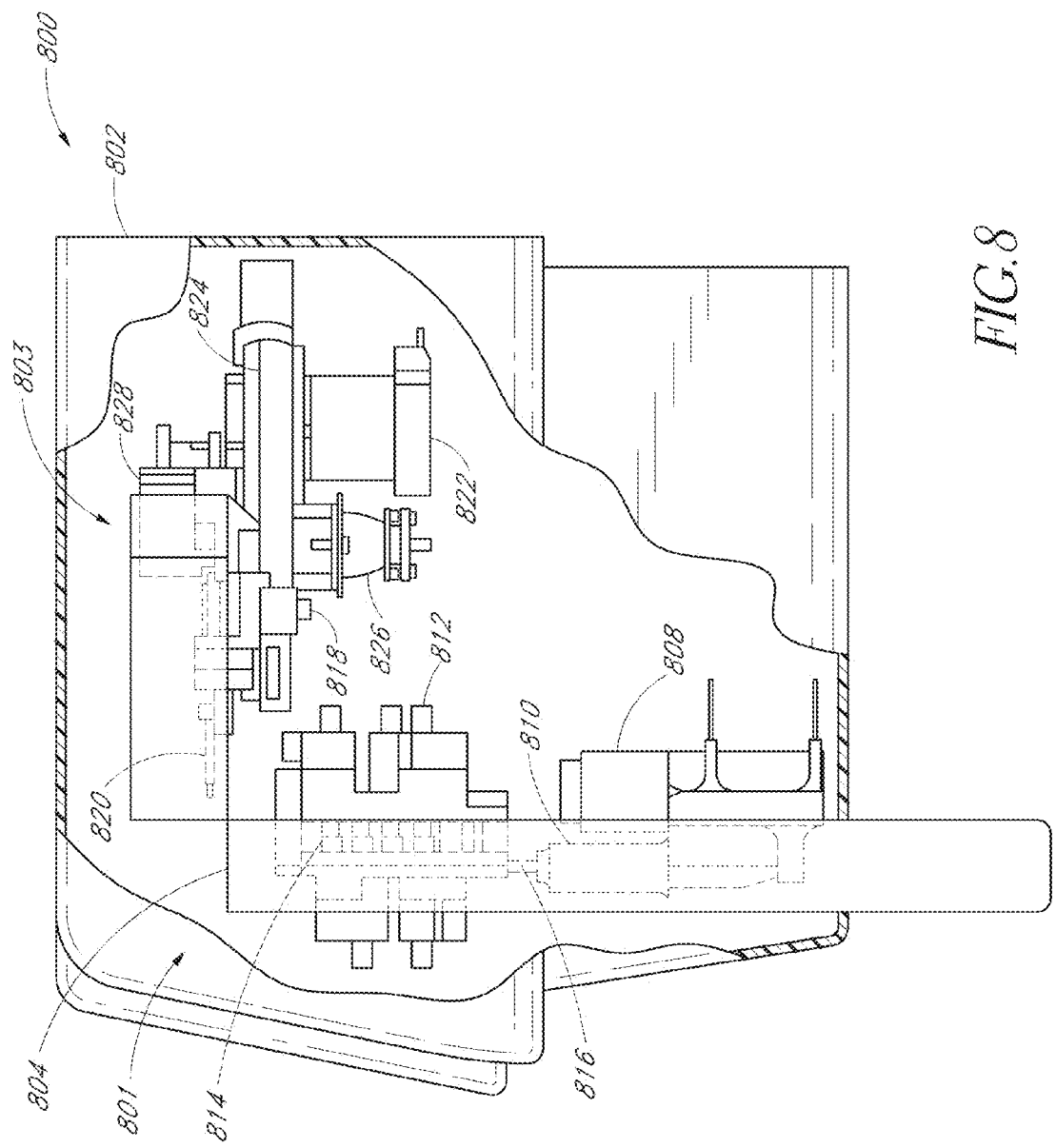
FIG. 8 shows a cut-away side view of an embodiment of a monitoring device.
Figure 9:
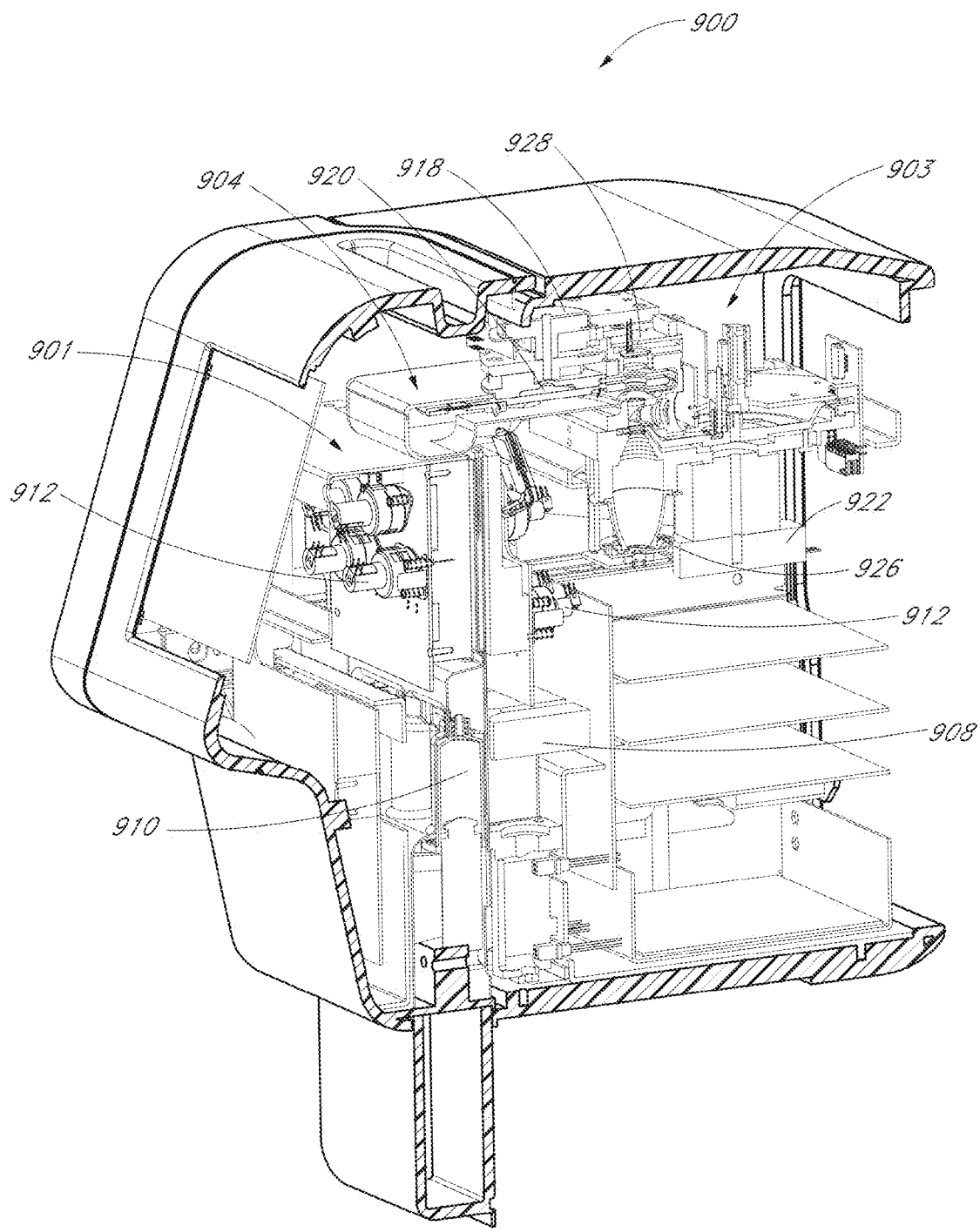
FIG. 9 shows a cut-away perspective view of an embodiment of a monitoring device.

FIG. 8 shows a cut-away side view of a monitoring device 800 (which can correspond, for example, to the device 102 shown in FIG. 1). The device 800 includes a casing 802. The monitoring device 800 can have a fluid system. For example, the fluid system can have subsystems, and a portion or portions thereof can be disposable, as schematically depicted in FIG. 4. As depicted in FIG. 8, the fluid system is generally located at the left-hand portion of the casing 802, as indicated by the reference 801. The monitoring device 800 can also have an optical system. In the illustrated embodiment, the optical system is generally located in the upper portion of the casing 802, as indicated by the reference 803. Advantageously, however, the fluid system 801 and the optical system 803 can both be integrated together such that fluid flows generally through a portion of the optical system 803, and such that radiation flows generally through a portion of the fluid system 801.

Depicted in FIG. 8 are examples of ways in which components of the device 800 mounted within the casing 802 can interface with components of the device 800 that comprise disposable portions. Not all components of the device 800 are shown in FIG. 8. A disposable portion 804 having a variety of components is shown in the casing 802. In some embodiments, one or more actuators 808 housed within the casing 802, operate syringe bodies 810 located within a disposable portion 804. The syringe bodies 810 are connected to sections of tubing 816 that move fluid among various components of the system. The movement of fluid is at least partially controlled by the action of one or more pinch valves 812 positioned within the casing 802. The pinch valves 812 have arms 814 that extend within the disposable portion 804. Movement of the arms 814 can constrict a section of tubing 816.

In some embodiments, a sample cell holder 820 can engage a centrifuge motor 818 mounted within the casing 802 of the device 800. A filter wheel motor 822 disposed within the housing 802 rotates a filter wheel 824, and in some embodiments, aligns one or more filters with an optical path. An optical path can originate at a source 826 within the housing 802 that can be configured to emit a beam of radiation (e.g., infrared radiation, visible radiation, ultraviolet radiation, etc.) through the filter and the sample cell holder 820 and to a detector 828. A detector 828 can measure the optical density of the light when it reaches the detector.

FIG. 9 shows a cut-away perspective view of an alternative embodiment of a monitoring device 900. Many features similar to those illustrated in FIG. 8 are depicted in this illustration of an alternative embodiment. A fluid system 901 can be partially seen. The disposable portion 904 is shown in an operative position within the device. One of the actuators 808 can be seen next to a syringe body 910 that is located within the disposable portion 904. Some pinch valves 912 are shown next to a fluid-handling portion of the disposable portion 904. In this figure, an optical system 903 can also be partially seen. The sample holder 920 is located underneath the centrifuge motor 918. The filter wheel motor 922 is positioned near the radiation source 926, and the detector 928 is also illustrated.

FIG. 10 illustrates two views of a cartridge 1000 that can interface with a fluid system such as the fluid system 510 of FIG. 5. The cartridge 1000 can be configured for insertion into a receptacle of the device 800 of FIG. 8 and/or the device 900 shown in FIG. 9. In some embodiments, the cartridge 1000 can comprise a portion that is disposable and a portion that is reusable. In some embodiments, the cartridge 1000 can be disposable. The cartridge 1000 can fill the role of the removable portion 710 of FIG. 7, for example. In some embodiments, the cartridge 1000 can be used for a system having only one disposable subsystem, making it a simple matter for a health care provider to replace and/or track usage time of the disposable portion. In some embodiments, the cartridge 1000 includes one or more features that facilitate insertion of the cartridge 1000 into a corresponding receptacle. For example, the cartridge 1000 can be shaped so as to promote insertion of the cartridge 1000 in the correct orientation. The cartridge 1000 can also include labeling or coloring affixed to or integrated with the cartridge's exterior casing that help a handler insert the cartridge 1000 into a receptacle properly.

The cartridge 1000 can include one or more ports for connecting to material sources or receptacles. Such ports can be provided to connect to, for example, a saline source, an infusion pump, a sample source, and/or a source of gas (e.g., air, nitrogen, etc.). The ports can be connected to sections of tubing within the cartridge 1000. In some embodiments, the sections of tubing are opaque or covered so that fluids within the tubing cannot be seen, and in some embodiments, sections of tubing are transparent to allow interior contents (e.g., fluid) to be seen from outside.

Figure 15:
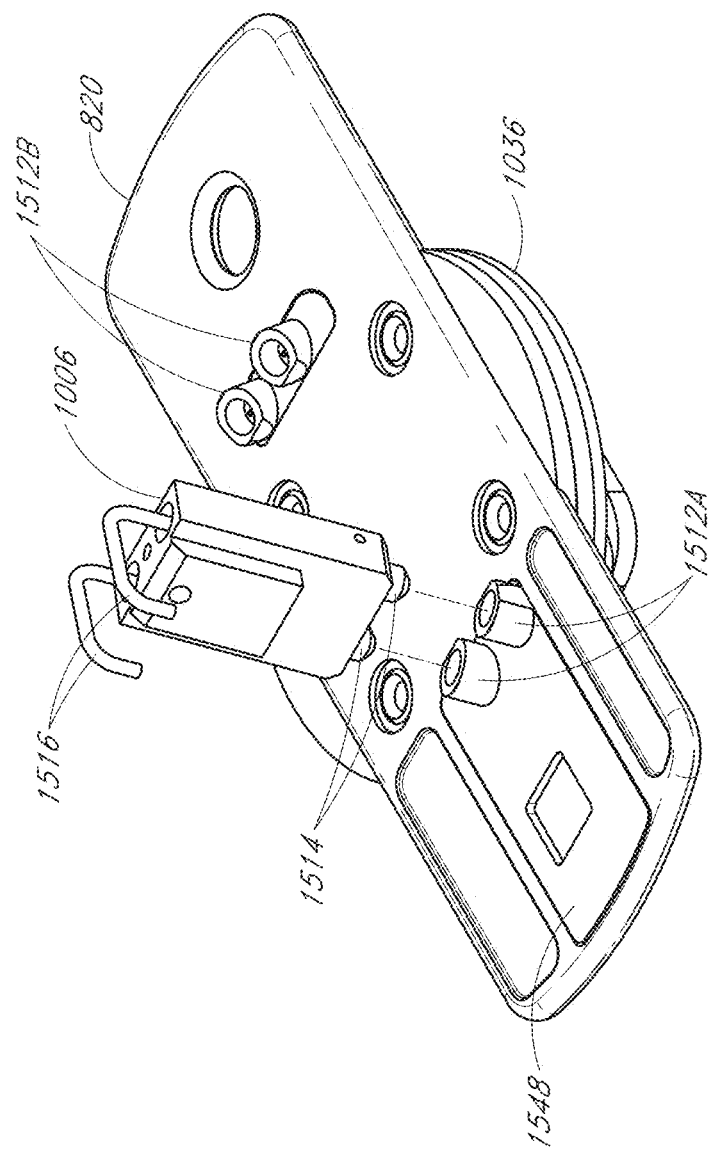
FIG. 15 shows an underneath perspective view of a sample cell holder attached to a centrifuge interface, with a view of an interface with a sample injector.

The cartridge 1000 shown in FIG. 10 can include a sample injector 1006. The sample injector 1006 can be configured to inject at least a portion of a sample into a sample holder (see, e.g., the sample cell 548), which can also be incorporated into the cartridge 1000. The sample injector 1006 can include, for example, the sample cell holder interface tubes 582 (N1) and 584 (N2) of FIG. 5, embodiments of which are also illustrated in FIG. 15.

The housing of the cartridge 1000 can include a tubing portion 1008 containing within it a card having one or more sections of tubing. In some embodiments, the body of the cartridge 1000 includes one or more apertures 1009 through which various components, such as, for example, pinch valves and sensors, can interface with the fluid-handling portion contained in the cartridge 1000. The sections of tubing found in the tubing portion 1008 can be aligned with the apertures 1009 in order to implement at least some of the functionality shown in the fluid system 510 of FIG. 5.

The cartridge 1000 can include a pouch space (not shown) that can comprise one or more components of the fluid system 510. For example, one or more pouches and/or bladders can be disposed in the pouch space (not shown). In some embodiments, a cleaner pouch and/or a waste bladder can be housed in a pouch space. The waste bladder can be placed under the cleaner pouch such that, as detergent is removed from the cleaner pouch, the waste bladder has more room to fill. The components placed in the pouch space (not shown) can also be placed side-by-side or in any other suitable configuration.

The cartridge 1000 can include one or more pumps 1016 that facilitate movement of fluid within the fluid system 510. Each of the pump housings 1016 can contain, for example, a syringe pump having a plunger. The plunger can be configured to interface with an actuator outside the cartridge 1000. For example, a portion of the pump that interfaces with an actuator can be exposed to the exterior of the cartridge 1000 housing by one or more apertures 1018 in the housing.

The cartridge 1000 can have an optical interface portion 1030 that is configured to interface with (or comprise a portion of) an optical system. In the illustrated embodiment, the optical interface portion 1030 can pivot around a pivot structure 1032. The optical interface portion 1030 can house a sample holder (not shown) in a chamber that can allow the sample holder to rotate. The sample holder can be held by a centrifuge interface 1036 that can be configured to engage a centrifuge motor (not shown). When the cartridge 1000 is being inserted into a system, the orientation of the optical interface portion 1030 can be different than when it is functioning within the system.

In some embodiments, the cartridge 1000 is designed for single patient use. The cartridge 1000 may also be disposable and/or designed for replacement after a period of operation. For example, in some embodiments, if the cartridge 1000 is installed in a continuously operating monitoring device that performs four measurements per hour, the waste bladder may become filled or the detergent in the cleaner pouch depleted after about three days. The cartridge 1000 can be replaced before the detergent and waste bladder are exhausted. In some embodiments, a portion of the cartridge 1000 can be disposable while another portion of the cartridge 1000 is disposable, but lasts longer before being discarded. In some embodiments, a portion of the cartridge 1000 may not be disposable at all. For example, a portion thereof may be configured to be cleaned thoroughly and reused for different patients. Various combinations of disposable and less- or non-disposable portions are possible.

The cartridge 1000 can be configured for easy replacement. For example, in some embodiments, the cartridge 1000 is designed to have an installation time of only minutes. For example, the cartridge can be designed to be installed in less than about five minutes, or less than two minutes. During installation, various fluid lines contained in the cartridge 1000 can be primed by automatically filling the fluid lines with saline. The saline can be mixed with detergent powder from the cleaner pouch in order to create a cleaning solution.

The cartridge 1000 can also be designed to have a relatively brief shut down time. For example, the shut down process can be configured to take less than about fifteen minutes, or less than about ten minutes, or less than about five minutes. The shut down process can include flushing the patient line; sealing off the insulin pump connection, the saline source connection, and the sample source connection; and taking other steps to decrease the risk that fluids within the used cartridge 1000 will leak after disconnection from the monitoring device.

Some embodiments of the cartridge 1000 can comprise a flat package to facilitate packaging, shipping, sterilizing, etc. Advantageously, however, some embodiments can further comprise a hinge or other pivot structure. Thus, as illustrated, an optical interface portion 1030 can be pivoted around a pivot structure 1032 to generally align with the other portions of the cartridge 1000. The cartridge can be provided to a medical provider sealed in a removable wrapper, for example.

In some embodiments, the cartridge 1000 is designed to fit within standard waste containers found in a hospital, such as a standard biohazard container. For example, the cartridge 1000 can be less than one foot long, less than one foot wide, and less than two inches thick. In some embodiments, the cartridge 1000 is designed to withstand a substantial impact, such as that caused by hitting the ground after a four foot drop, without damage to the housing or internal components. In some embodiments, the cartridge 1000 is designed to withstand significant clamping force applied to its casing. For example, the cartridge 1000 can be built to withstand five pounds per square inch of force without damage. In some embodiments, the cartridge 1000 can be designed to be less sturdy and more biodegradable. In some embodiments, the cartridge 1000 can be formed and configured to withstand more or less than five pounds of force per square inch without damage. In some embodiments, the cartridge 1000 is non pyrogenic and/or latex free.

Figure 11:
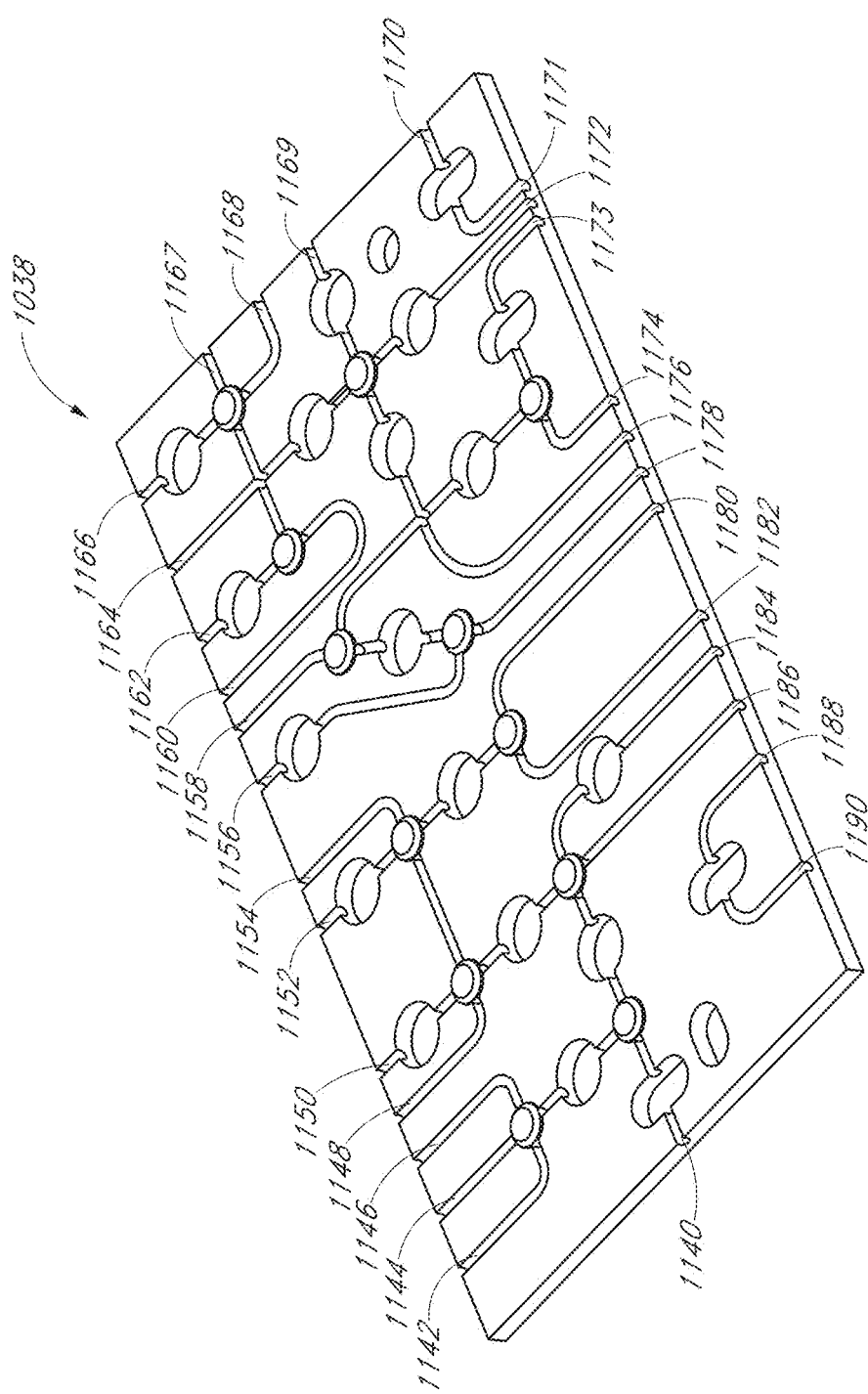
FIG. 11 illustrates an embodiment of a fluid routing card that can be part of the removable cartridge of FIG. 10.

FIG. 11 illustrates an embodiment of a fluid-routing card 1038 that can be part of the removable cartridge of FIG. 10. For example, the fluid-routing card 1038 can be located generally within the tubing portion 1008 of the cartridge 1000. The fluid-routing card 1038 can contain various passages and/or tubes through which fluid can flow as described with respect to FIG. 5 and/or FIG. 6, for example. Thus, the illustrated tube opening openings can be in fluid communication with the following fluidic components, for example:

| Tube Opening Reference Numeral | Can Be In Fluid Communication With |
| --- | --- |
| 1142 | third pump 568 (pump #3) |
| 1144 | infusion pump 518 |
| 1146 | Presx |
| 1148 | air pump |
| 1150 | Vent |
| 1152 | detergent (e.g., tergazyme) source or waste tube |
| 1154 | Presx |
| 1156 | detergent (e.g., tergazyme) source or waste tube |
| 1158 | waste receptacle |
| 1160 | first pump 522 (pump #1) (e.g., a saline pump) |
| 1162 | saline source or waste tube |
| 1164 | anticoagulant (e.g., heparin) pump (see FIG. 6) and/or shuttle valve |
| 1166 | detergent (e.g., tergazyme) source or waste tube |
| 1167 | Presx |
| 1168 | Arrival sensor tube 528 (T4) |
| 1169 | tube 536 (T2) |
| 1170 | Arrival sensor tube 528 (T4) |
| 1171 | Arrival sensor tube 528 (T4) |
| 1172 | anticoagulant (e.g., heparin) pump |
| 1173 | T17 (see FIG. 6) |
| 1174 | Sample cell holder interface tube 582 (N1) |
| 1176 | anticoagulant valve tube 534 (T3) |
| 1178 | Sample cell holder interface tube 584 (N2) |
| 1180 | T17 (see FIG. 6) |
| 1182 | anticoagulant valve tube 534 (T3) |
| 1184 | Arrival sensor tube 528 (T4) |
| 1186 | tube 536 (T2) |
| 1188 | anticoagulant valve tube 534 (T3) |
| 1190 | anticoagulant valve tube 534 (T3) |

The depicted fluid-routing card 1038 can have additional openings that allow operative portions of actuators and/or valves to protrude through the fluid-routing card 1038 and interface with the tubes.

Figure 12:
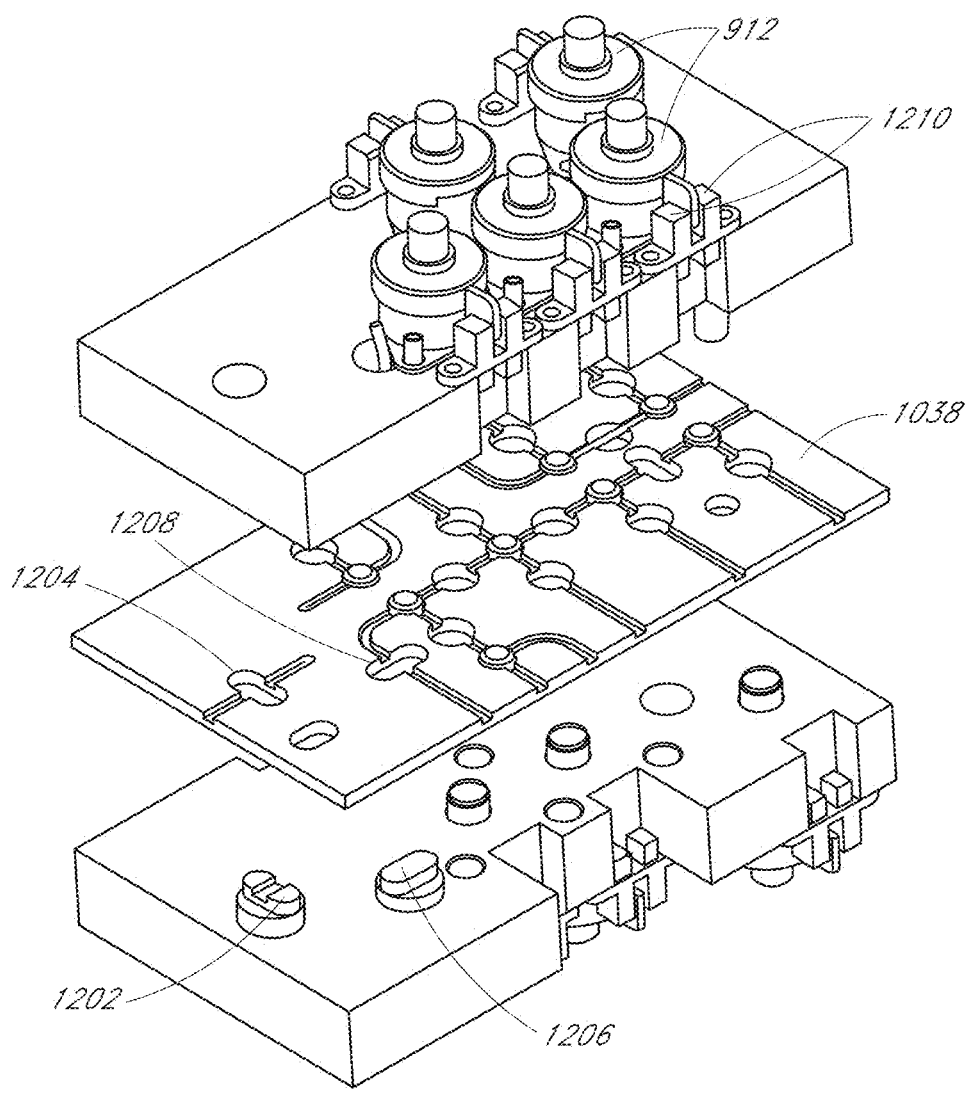
FIG. 12 illustrates how non-disposable actuators can interface with the fluid routing card of FIG. 11.

FIG. 12 illustrates how actuators, which can sandwich the fluid-routing card 1038 between them, can interface with the fluid-routing card 1038 of FIG. 11. Pinch valves 812 can have an actuator portion that protrudes away from the fluid-routing card 1038 containing a motor. Each motor can correspond to a pinch platen 1202, which can be inserted into a pinch platen receiving hole 1204. Similarly, sensors, such as a bubble sensor 1206 can be inserted into receiving holes (e.g., the bubble sensor receiving hole 1208). Movement of the pinch valves 812 can be detected by the position sensors 1210.

Figure 13:
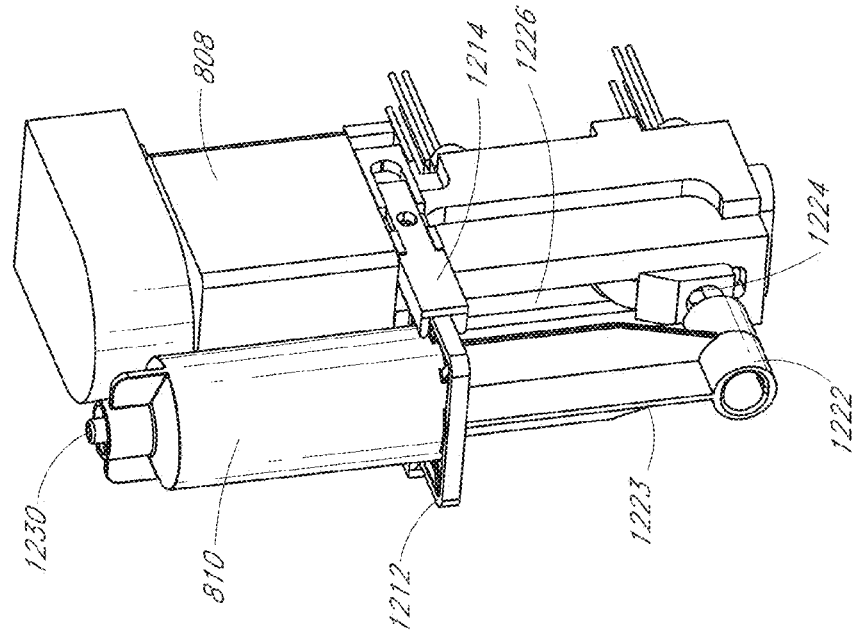
FIG. 13 illustrates a modular pump actuator connected to a syringe housing that can form a portion of a removable cartridge.

FIG. 13 illustrates an actuator 808 that is connected to a corresponding syringe body 810. The actuator 808 is an example of one of the actuators 808 that is illustrated in FIG. 8 and in FIG. 9, and the syringe body 810 is an example of one of the syringe bodies 810 that are visible in FIG. 8 and in FIG. 9. A ledge portion 1212 of the syringe body 810 can be engaged (e.g., slid into) a corresponding receiving portion 1214 in the actuator 808. In some embodiments, the receiving portion 1214 can slide outward to engage the stationary ledge portion 1212 after the disposable cartridge 804 is in place. Similarly, a receiving tube 1222 in the syringe plunger 1223 can be slide onto (or can receive) a protruding portion 1224 of the actuator 808. The protruding portion 1224 can slide along a track 1226 under the influence of a motor inside the actuator 808, thus actuating the syringe plunger 1223 and causing fluid to flow into or out of the syringe tip 1230.

Figure 14:
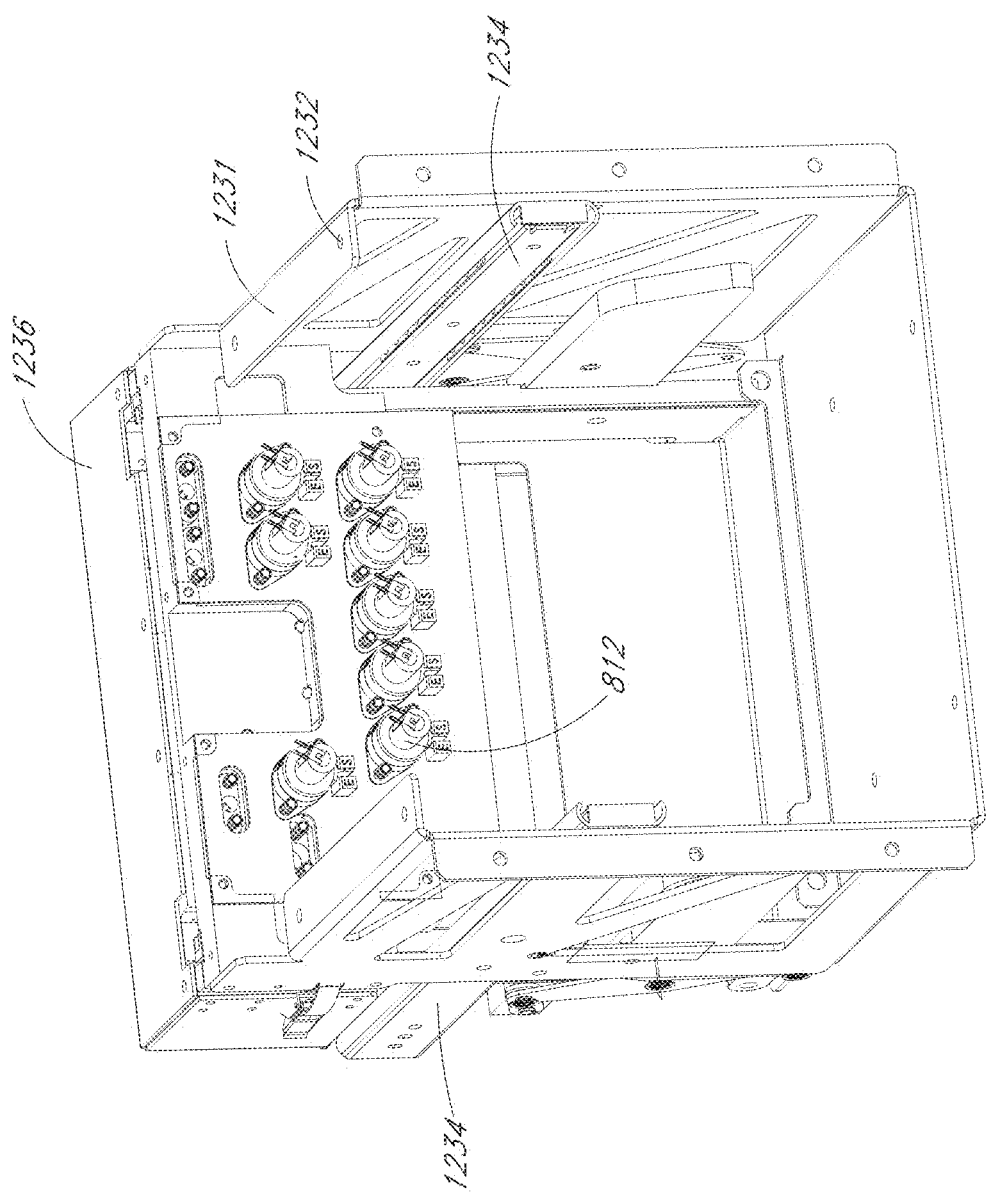
FIG. 14 shows a rear perspective view of internal scaffolding and some pinch valve pump bodies.

FIG. 14 shows a rear perspective view of internal scaffolding 1231 and the protruding bodies of some pinch valves 812. The internal scaffolding 1231 can be formed from metal and can provide structural rigidity and support for other components. The scaffolding 1231 can have holes 1232 into which screws can be screwed or other connectors can be inserted. In some embodiments, a pair of sliding rails 1234 can allow relative movement between portions of an analyzer. For example, a slidable portion 1236 (which can correspond to the movable portion 706, for example) can be temporarily slid away from the scaffolding 1231 of a main unit in order to allow an insertable portion (e.g., the cartridge 804) to be inserted.

FIG. 15 shows an underneath perspective view of the sample cell holder 820, which is attached to the centrifuge interface 1036. The sample cell holder 820 can have an opposite side (see FIG. 17) that allows it to slide into a receiving portion of the centrifuge interface 1036. The sample cell holder 820 can also have receiving nubs 1512A that provide a pathway into a sample cell 1548 held by the sample cell holder 820. Receiving nubs 1512B can provide access to a shunt 1586 (see FIG. 16) inside the sample cell holder 820. The receiving nubs 1512A and 1512B can receive and or dock with fluid nipples 1514. The fluid nipples 1514 can protrude at an angle from the sample injector 1006, which can in turn protrude from the cartridge 1000 (see FIG. 10). The tubes 1516 shown protruding from the other end of the sample injector 1006 can be in fluid communication with the sample cell holder interface tubes 582 (N1) and 584 (N2) (see FIG. 5 and FIG. 6), as well as 1074 and 1078 (see FIG. 11).

Figure 16:
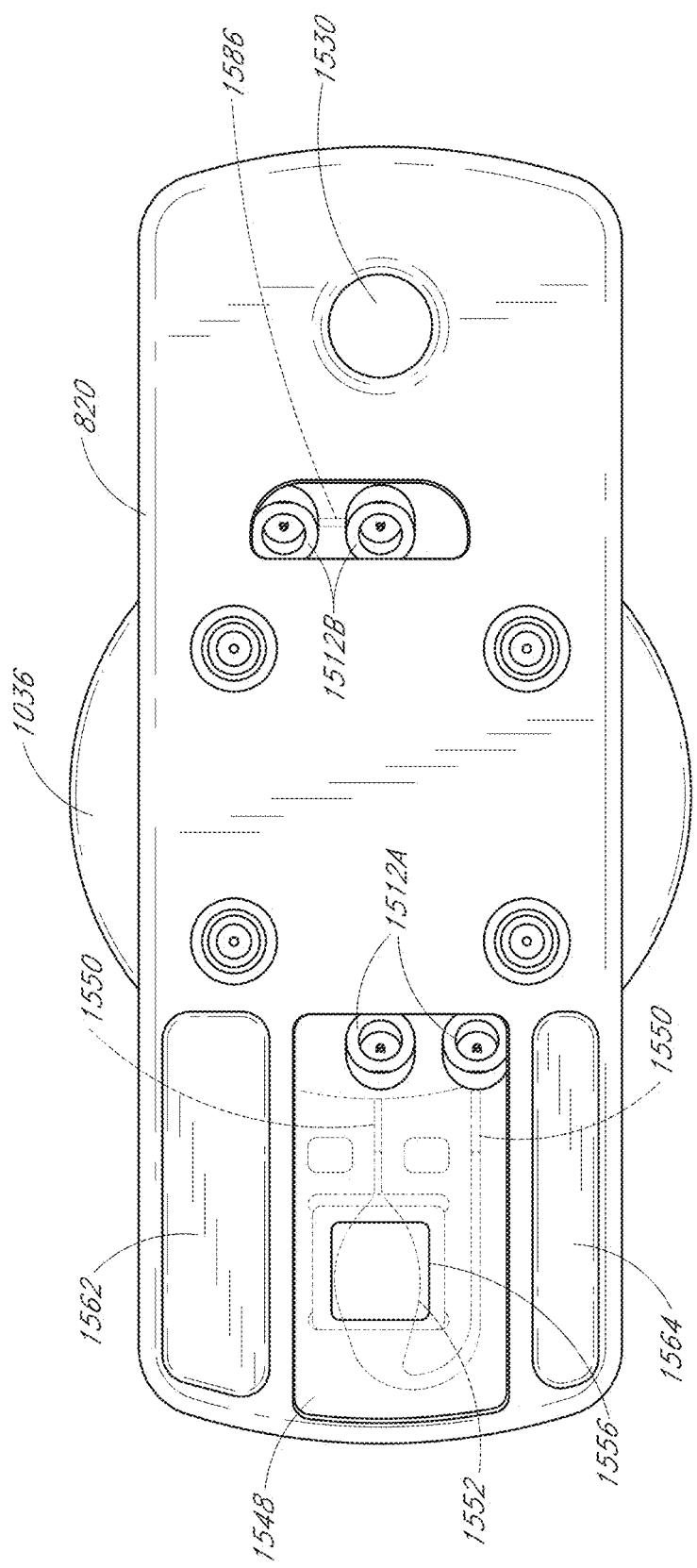
FIG. 16 shows a plan view of a sample cell holder with hidden and/or non-surface portions illustrated using dashed lines.

FIG. 16 shows a plan view of the sample cell holder 820 with hidden and/or non-surface portions illustrated using dashed lines. The receiving nubs 1512A communicate with passages 1550 inside the sample cell 1548 (which can correspond, for example to the sample cell 548 of FIG. 5). The passages widen out into a wider portion 1552 that corresponds to a window 1556. The window 1556 and the wider portion 1552 can be configured to house the sample when radiation is emitted along a pathlength that is generally non-parallel to the sample cell 1548. The window 1556 can allow calibration of the instrument with the sample cell 1548 in place, even before a sample has arrived in the wider portion 1552.

An opposite opening 1530 can provide an alternative optical pathway between a radiation source and a radiation detector (e.g., the radiation source 826 of FIG. 18) and may be used, for example, for obtaining a calibration measurement of the source and detector without an intervening window or sample. Thus, the opposite opening 1530 can be located generally at the same radial distance from the axis of rotation as the window 1556.

The receiving nubs 1512B communicate with a shunt passage 1586 inside the sample cell holder 820 (which can correspond, for example to the shunt 586 of FIG. 5).

Other features of the sample cell holder 820 can provide balancing properties for even rotation of the sample cell holder 820. For example, the wide trough 1562 and the narrower trough 1564 can be sized or otherwise configured so that the weight and/or mass of the sample cell holder 820 is evenly distributed from left to right in the view of FIG. 16, and/or from top to bottom in this view of FIG. 16.

Figure 17:
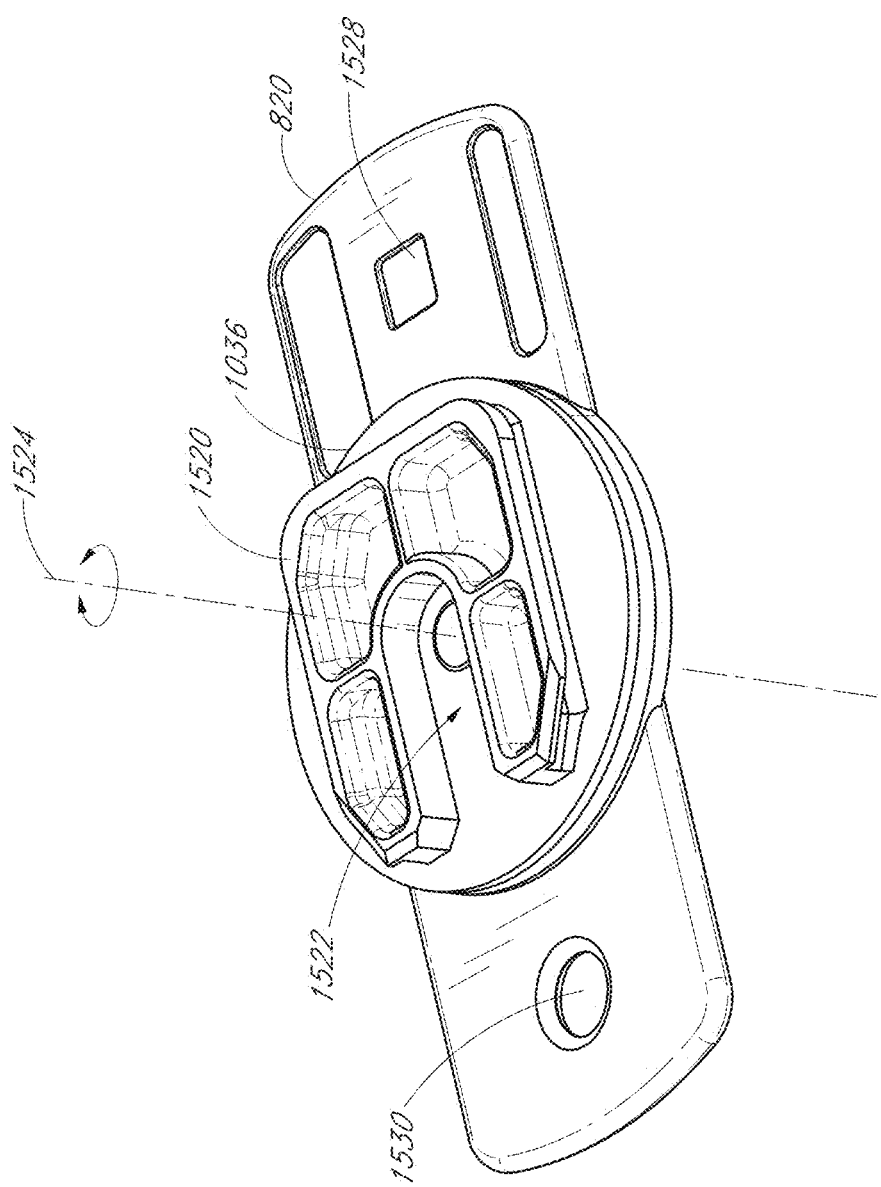
FIG. 17 shows a top perspective view of the centrifuge interface connected to the sample holder.

FIG. 17 shows a top perspective view of the centrifuge interface 1036 connected to the sample cell holder 820. The centrifuge interface 1036 can have a bulkhead 1520 with a rounded slot 1522 into which an actuating portion of a centrifuge can be slid from the side. The centrifuge interface 1036 can thus be spun about an axis 1524, along with the sample cell holder 820, causing fluid (e.g., whole blood) within the sample cell 1548 to separate into concentric strata, according to relative density of the fluid components (e.g., plasma, red blood cells, buffy coat, etc.), within the sample cell 1548. The sample cell holder 820 can be transparent, or it can at least have transparent portions (e.g., the window 1556 and/or the opposite opening 1530) through which radiation can pass, and which can be aligned with an optical pathway between a radiation source and a radiation detector (see, e.g., FIG. 20). In addition, a round opening 1530 through centrifuge rotor 1520 provides an optical pathway between the radiation source and radiation detector and may be used, for example, for obtaining a calibration measurement of the source and detector without an intervening window or sample.

Figure 18:
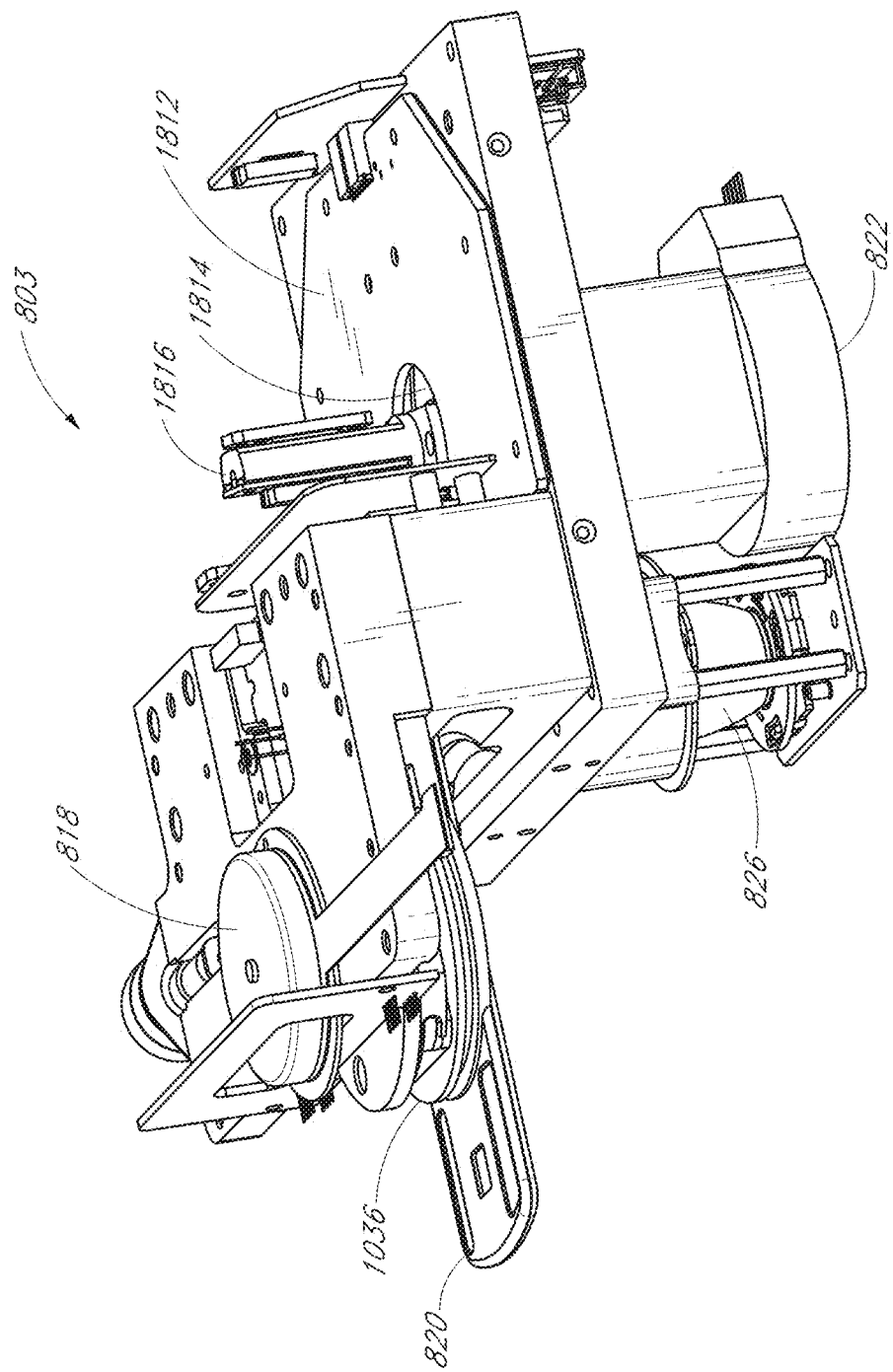
FIG. 18 shows a perspective view of an example optical system.

FIG. 18 shows a perspective view of an example optical system 803. Such a system can be integrated with other systems as shown in FIG. 9, for example. The optical system 803 can fill the role of the optical system 412, and it can be integrated with and/or adjacent to a fluid system (e.g., the fluid-handling system 404 or the fluid system 801). The sample cell holder 820 can be seen attached to the centrifuge interface 1036, which is in turn connected to, and rotatable by the centrifuge motor 818. A filter wheel housing 1812 is attached to the filter wheel motor 822 and encloses a filter wheel 1814. A protruding shaft assembly 1816 can be connected to the filter wheel 1814. The filter wheel 1814 can have multiple filters (see FIG. 19). The radiation source 826 is aligned to transmit radiation through a filter in the filter wheel 1814 and then through a portion of the sample cell holder 820. Transmitted and/or reflected and/or scattered radiation can then be detected by a radiation detector.

Figure 19:
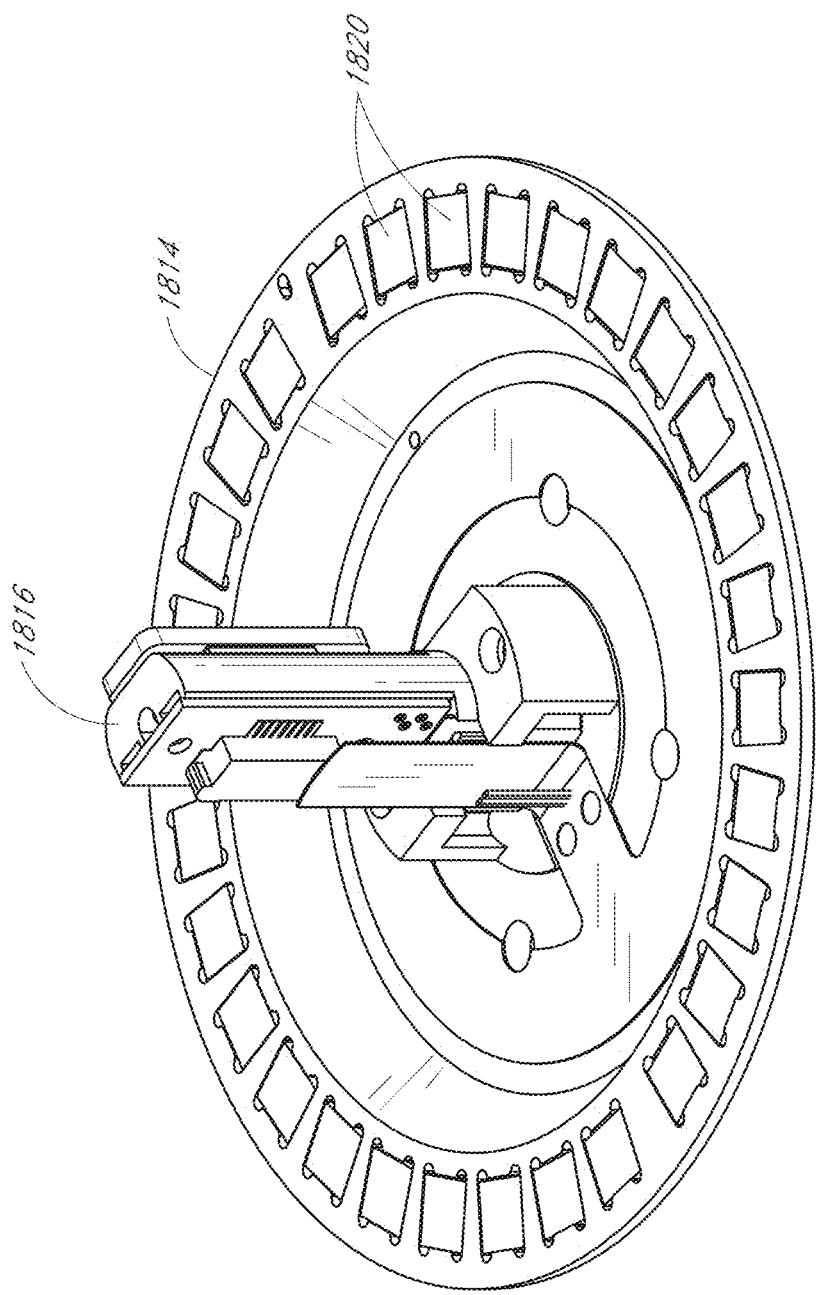
FIG. 19 shows a filter wheel that can be part of the optical system of FIG. 18.

FIG. 19 shows a view of the filter wheel 1814 when it is not located within the filter wheel housing 1812 of the optical system 803. Additional features of the protruding shaft assembly 1816 can be seen, along with multiple filters 1820. In some embodiments, the filters 1820 can be removably and/or replaceably inserted into the filter wheel 1814.

Spectroscopic System

As described above with reference to FIG. 4, the system 400 comprises the optical system 412 for analysis of a fluid sample. In various embodiments, the optical system 412 comprises one or more optical components including, for example, a spectrometer, a photometer, a reflectometer, or any other suitable device for measuring optical properties of the fluid sample. The optical system 412 may perform one or more optical measurements on the fluid sample including, for example, measurements of transmittance, absorbance, reflectance, scattering, and/or polarization. The optical measurements may be performed in one or more wavelength ranges including, for example, infrared (IR) and/or optical wavelengths. As described with reference to FIG. 4 (and further described below), the measurements from the optical system 412 are communicated to the algorithm processor 416 for analysis. For example, In some embodiments the algorithm processor 416 computes concentration of analyte(s) (and/or interferent(s)) of interest in the fluid sample. Analytes of interest include, e.g., glucose and lactate in whole blood or blood plasma.

Figure 20:
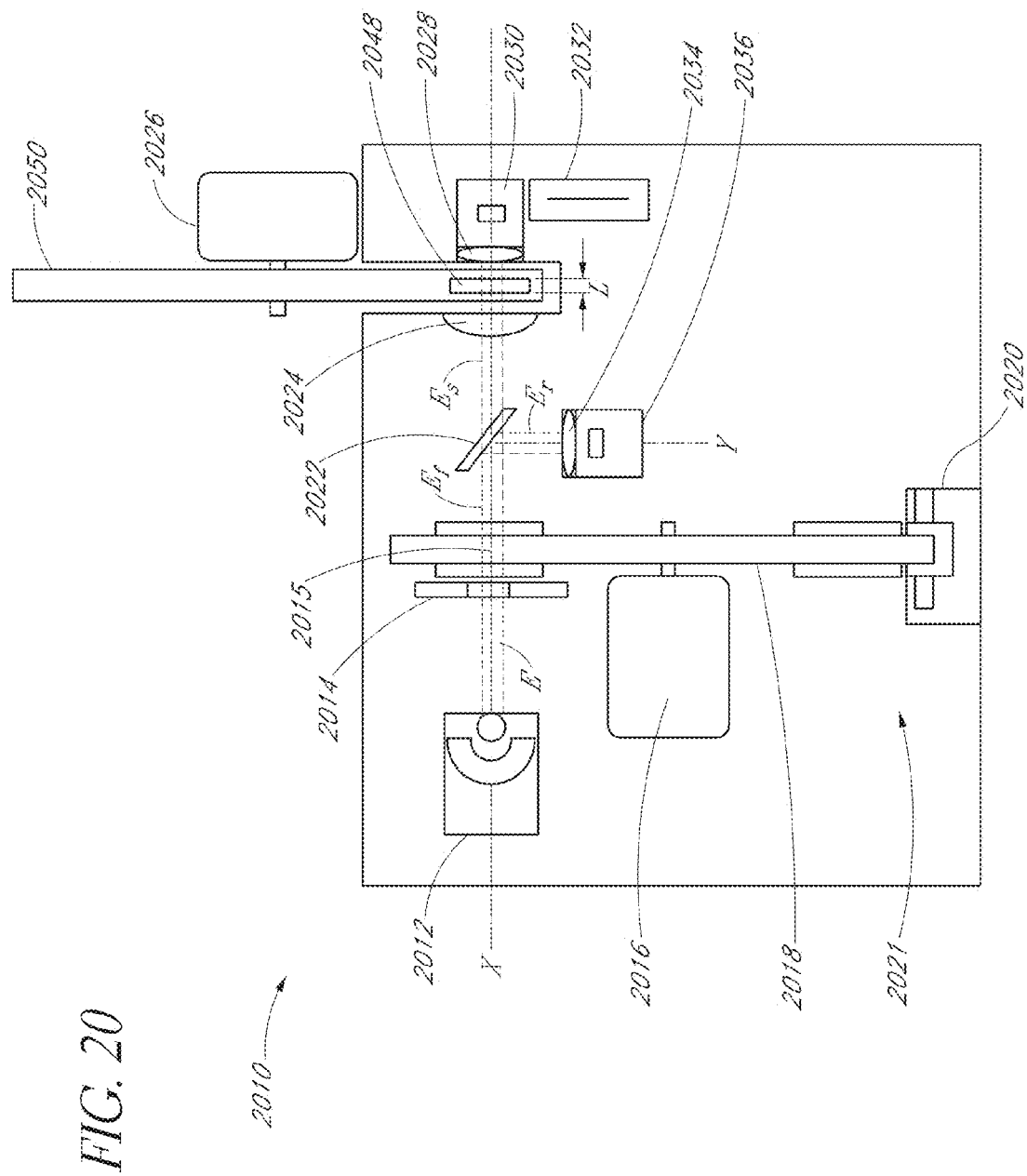
FIG. 20 schematically illustrates an embodiment of an optical system that comprises a spectroscopic analyzer adapted to measure spectra of a fluid sample.

FIG. 20 schematically illustrates an embodiment of the optical system 412 that comprises a spectroscopic analyzer 2010 adapted to measure spectra of a fluid sample such as, for example, blood or blood plasma. The analyzer 2010 comprises an energy source 2012 disposed along an optical axis X of the analyzer 2010. When activated, the energy source 2012 generates an electromagnetic energy beam E, which advances from the energy source 2012 along the optical axis X. In some embodiments, the energy source 2012 comprises an infrared energy source, and the energy beam E comprises an infrared beam. In some embodiments, the infrared energy beam E comprises a mid-infrared energy beam or a near-infrared energy beam. In some embodiments, the energy beam E can include optical and/or radio frequency wavelengths.

The energy source 2012 may comprise a broad-band and/or a narrow-band source of electromagnetic energy. In some embodiments, the energy source 2012 comprises optical elements such as, e.g., filters, collimators, lenses, mirrors, etc., that are adapted to produce a desired energy beam E. For example, in some embodiments, the energy beam E is an infrared beam in a wavelength range between about 2 µm and 20 µm. In some embodiments, the energy beam E comprises an infrared beam in a wavelength range between about 4 µm and 10 µm. In the infrared wavelength range, water generally is the main contributor to the total absorption together with features from absorption of other blood components, particularly in the 6 µm-10 µm range. The 4 µm to 10 µm wavelength band has been found to be advantageous for determining glucose concentration, because glucose has a strong absorption peak structure from about 8.5 µm to 10 µm, whereas most other blood components have a relatively low and flat absorption spectrum in the 8.5 µm to 10 µm range. Two exceptions are water and hemoglobin, which are interferents in this range.

The energy beam E may be temporally modulated to provide increased signal-to-noise ratio (S/N) of the measurements provided by the analyzer 2010 as further described below. For example, in some embodiments, the beam E is modulated at a frequency of about 10 Hz or in a range from about 1 Hz to about 30 Hz. A suitable energy source 2012 may be an electrically modulated thin-film thermoresistive element such as the HawkEye IR-50 available from Hawkeye Technologies of Milford, Conn.

As depicted in FIG. 20, the energy beam E propagates along the optical axis X and passes through an aperture 2014 and a filter 2015 thereby providing a filtered energy beam $E_f$. The aperture 2014 helps collimate the energy beam E and can include one or more filters adapted to reduce the filtering burden of the filter 2015. For example, the aperture 2014 may comprise a broadband filter that substantially attenuates beam energy outside a wavelength band between about 4 µm to about 10 µm. The filter 2015 may comprise a narrow-band filter that substantially attenuates beam energy having wavelengths outside of a filter passband (which may be tunable or user-selectable in some embodiments). The filter passband may be specified by a half-power bandwidth ("HPBW"). In some embodiments, the filter 2015 may have an HPBW in a range from about 0.1 µm to about 2 µm, or 0.01 µm to about 1 µm. In some embodiments, the bandwidths are in a range from about 0.2 µm to 0.5 µm, or 0.1 µm to 0.35 µm. Other filter bandwidths may be used. The filter 2015 may comprise a varying-passband filter, an electronically tunable filter, a liquid crystal filter, an interference filter, and/or a gradient filter. In some embodiments, the filter 2015 comprises one or a combination of a grating, a prism, a monochrometer, a Fabry-Perot etalon, and/or a polarizer. Other optical elements may be utilized as well.

In the embodiment shown in FIG. 20, the analyzer 2010 comprises a filter wheel assembly 2021 configured to dispose one or more filters 2015 along the optical axis X. The filter wheel assembly 2021 comprises a filter wheel 2018, a filter wheel motor 2016, and a position sensor 2020. The filter wheel 2018 may be substantially circular and have one or more filters 2015 or other optical elements (e.g., apertures, gratings, polarizers, minors, etc.) disposed around the circumference of the wheel 2018. In some embodiments, the number of filters 2015 in the filter wheel 2016 may be, for example, 1, 2, 5, 10, 15, 20, 25, or more. The motor 2016 is configured to rotate the filter wheel 2018 to dispose a desired filter 2015 (or other optical element) in the energy beam E so as to produce the filtered beam $E_f$. In some embodiments, the motor 2016 comprises a stepper motor. The position sensor 2020 determines the angular position of the filter wheel 2016, and communicates a corresponding filter wheel position signal to the algorithm processor 416, thereby indicating which filter 2015 is in position on the optical axis X. In various embodiments, the position sensor 2020 may be a mechanical, optical, and/or magnetic encoder. An alternative to the filter wheel 2018 is a linear filter translated by a motor. The linear filter can include an array of separate filters or a single filter with properties that change along a linear dimension.

The filter wheel motor 2016 rotates the filter wheel 2018 to position the filters 2015 in the energy beam E to sequentially vary the wavelengths or the wavelength bands used to analyze the fluid sample. In some embodiments, each individual filter 2015 is disposed in the energy beam E for a dwell time during which optical properties in the passband of the filter are measured for the sample. The filter wheel motor 2016 then rotates the filter wheel 2018 to position another filter 2015 in the beam E. In some embodiments, 25 narrow-band filters are used in the filter wheel 2018, and the dwell time is about 2 seconds for each filter 2015. A set of optical measurements for all the filters can be taken in about 2 minutes, including sampling time and filter wheel movement. In some embodiments, the dwell time may be different for different filters 2015, for example, to provide a substantially similar S/N ratio for each filter measurement. Accordingly, the filter wheel assembly 2021 functions as a varying-passband filter that allows optical properties of the sample to be analyzed at a number of wavelengths or wavelength bands in a sequential manner.

In some embodiments of the analyzer 2010, the filter wheel 2018 includes 25 finite-bandwidth infrared filters having a Gaussian transmission profile and full-width half-maximum (FWHM) bandwidth of 28 cm$^{-1}$ corresponding to a bandwidth that varies from 0.14 μm at 7.08 μm to 0.28 μm at 10 μm. The central wavelength of the filters are, in microns: 7.082, 7.158, 7.241, 7.331, 7.424, 7.513, 7.605, 7.704, 7.800, 7.905, 8.019, 8.150, 8.271, 8.598, 8.718, 8.834, 8.969, 9.099, 9.217, 9.346, 9.461, 9.579, 9.718, 9.862, and 9.990.

With further reference to FIG. 20, the filtered energy beam $E_f$ propagates to a beamsplitter 2022 disposed along the optical axis X. The beamsplitter 2022 separates the filtered energy beam $E_f$ into a sample beam $E_s$ and a reference beam $E_r$. The reference beam $E_r$ propagates along a minor optical axis Y, which in this embodiment is substantially orthogonal to the optical axis X. The energies in the sample beam $E_s$ and the reference beam $E_r$ may comprise any suitable fraction of the energy in the filtered beam $E_f$.

For example, in some embodiments, the sample beam $E_s$ comprises about 80%, and the reference beam $E_r$ comprises about 20%, of the filtered beam energy $E_f$. A reference detector 2036 is positioned along the minor optical axis Y. An optical element 2034, such as a lens, may be used to focus or collimate the reference beam $E_r$ onto the reference detector 2036. The reference detector 2036 provides a reference signal, which can be used to monitor fluctuations in the intensity of the energy beam E emitted by the source 2012. Such fluctuations may be due to drift effects, aging, wear, or other imperfections in the source 2012. The algorithm processor 416 may utilize the reference signal to identify changes in properties of the sample beam $E_s$ that are attributable to changes in the emission from the source 2012 and not to the properties of the fluid sample. By so doing, the analyzer 2010 may advantageously reduce possible sources of error in the calculated properties of the fluid sample (e.g., concentration). In other embodiments of the analyzer 2010, the beamsplitter 2022 is not used, and substantially all of the filtered energy beam $E_f$ propagates to the fluid sample.

As illustrated in FIG. 20, the sample beam $E_s$ propagates along the optical axis X, and a relay lens 2024 transmits the sample beam $E_s$ into a sample cell 2048 so that at least a fraction of the sample beam $E_s$ is transmitted through at least a portion of the fluid sample in the sample cell 2048. A sample detector 2030 is positioned along the optical axis X to measure the sample beam $E_s$ that has passed through the portion of the fluid sample. An optical element 2028, such as a lens, may be used to focus or collimate the sample beam $E_s$ onto the sample detector 2030. The sample detector 2030 provides a sample signal that can be used by the algorithm processor 416 as part of the sample analysis.

In the embodiment of the analyzer 2010 shown in FIG. 20, the sample cell 2048 is located toward the outer circumference of the centrifuge wheel 2050 (which can correspond, for example, to the sample cell holder 820 described herein). The sample cell 2048 preferably comprises windows that are substantially transmissive to energy in the sample beam $E_s$. For example, in implementations using mid-infrared energy, the windows may comprise calcium fluoride. As described herein with reference to FIG. 5, the sample cell 2048 is in fluid communication with an injector system that permits filling the sample cell 2048 with a fluid sample (e.g., whole blood) and flushing the sample cell 2048 (e.g., with saline or a detergent). The injector system may disconnect after filling the sample cell 2048 with the fluid sample to permit free spinning of the centrifuge wheel 2050.

The centrifuge wheel 2050 can be spun by a centrifuge motor 2026. In some embodiments of the analyzer 2010, the fluid sample (e.g., a whole blood sample) is spun at a certain number of revolutions per minute (RPM) for a given length of time to separate blood plasma for spectral analysis. In some embodiments, the fluid sample is spun at about 7200 RPM. In some embodiments, the fluid sample is spun at about 5000 RPM or 4500 RPM. In some embodiments, the fluid sample is spun at more than one rate for successive time periods. The length of time can be approximately 5 minutes. In some embodiments, the length of time is approximately 2 minutes. In some embodiments, an anti-clotting agent such as heparin may be added to the fluid sample before centrifuging to reduce clotting. With reference to FIG. 20, the centrifuge wheel 2050 is rotated to a position where the sample cell 2048 intercepts the sample beam $E_s$, allowing energy to pass through the sample cell 2048 to the sample detector 2030.

The embodiment of the analyzer 2010 illustrated in FIG. 20 advantageously permits direct measurement of the concentration of analytes in the plasma sample rather than by inference of the concentration from measurements of a whole blood sample. An additional advantage is that relatively small volumes of fluid may be spectroscopically analyzed. For example, in some embodiments the fluid sample volume is between about 1 µL and 80 µL and is about 25 µL in some embodiments. In some embodiments, the sample cell 2048 is disposable and is intended for use with a single patient or for a single measurement.

In some embodiments, the reference detector 2036 and the sample detector 2030 comprise broadband pyroelectric detectors. As known in the art, some pyroelectric detectors are sensitive to vibrations. Thus, for example, the output of a pyroelectric infrared detector is the sum of the exposure to infrared radiation and to vibrations of the detector. The sensitivity to vibrations, also known as "microphonics," can introduce a noise component to the measurement of the reference and sample energy beams $E_r$, $E_s$ using some pyroelectric infrared detectors. Because it may be desirable for the analyzer 2010 to provide high signal-to-noise ratio measurements, such as, e.g., S/N in excess of 100 dB, some embodiments of the analyzer 2010 utilize one or more vibrational noise reduction apparatus or methods. For example, the analyzer 2010 may be mechanically isolated so that high S/N spectroscopic measurements can be obtained for vibrations below an acceleration of about 1.5 G.

In some embodiments of the analyzer 2010, vibrational noise can be reduced by using a temporally modulated energy source 2012 combined with an output filter. In some embodiments, the energy source 2012 is modulated at a known source frequency, and measurements made by the detectors 2036 and 2030 are filtered using a narrowband filter centered at the source frequency. For example, in some embodiments, the energy output of the source 2012 is sinusoidally modulated at 10 Hz, and outputs of the detectors 2036 and 2030 are filtered using a narrow bandpass filter of less than about 1 Hz centered at 10 Hz. Accordingly, microphonic signals that are not at 10 Hz are significantly attenuated. In some embodiments, the modulation depth of the energy beam E may be greater than 50% such as, for example, 80%. The duty cycle of the beam may be between about 30% and 70%. The temporal modulation may be sinusoidal or any other waveform. In embodiments utilizing temporally modulated energy sources, detector output may be filtered using a synchronous demodulator and digital filter. The demodulator and filter are software components that may be digitally implemented in a processor such as the algorithm processor 416. Synchronous demodulators, coupled with low pass filters, are often referred to as "lock in amplifiers."

The analyzer 2010 may also include a vibration sensor 2032 (e.g., one or more accelerometers) disposed near one (or both) of the detectors 2036 and 2030. The output of the vibration sensor 2032 is monitored, and suitable actions are taken if the measured vibration exceeds a vibration threshold. For example, in some embodiments, if the vibration sensor 2032 detects above-threshold vibrations, the system discards any ongoing measurement and "holds off" on performing further measurements until the vibrations drop below the threshold. Discarded measurements may be repeated after the vibrations drop below the vibration threshold. In some embodiments, if the duration of the "hold off" is sufficiently long, the fluid in the sample cell 2030 is flushed, and a new fluid sample is delivered to the cell 2030 for measurement. The vibration threshold may be selected so that the error in analyte measurement is at an acceptable level for vibrations below the threshold. In some embodiments, the threshold corresponds to an error in glucose concentration of 5 mg/dL. The vibration threshold may be determined individually for each filter 2015.

Certain embodiments of the analyzer 2010 include a temperature system (not shown in FIG. 20) for monitoring and/or regulating the temperature of system components (such as the detectors 2036, 2030) and/or the fluid sample. Such a temperature system can include temperature sensors, thermoelectrical heat pumps (e.g., a Peltier device), and/or thermistors, as well as a control system for monitoring and/or regulating temperature. In some embodiments, the control system comprises a proportional-plus-integral-plus-derivative (PID) control. For example, in some embodiments, the temperature system is used to regulate the temperature of the detectors 2030, 2036 to a desired operating temperature, such as 35 degrees Celsius.

Optical Measurement

The analyzer 2010 illustrated in FIG. 20 can be used to determine optical properties of a substance in the sample cell 2048. The substance can include whole blood, plasma, saline, water, air or other substances. In some embodiments, the optical properties include measurements of an absorbance, transmittance, and/or optical density in the wavelength passbands of some or all of the filters 2015 disposed in the filter wheel 2018. As described above, a measurement cycle comprises disposing one or more filters 2015 in the energy beam E for a dwell time and measuring a reference signal with the reference detector 2036 and a sample signal with the sample detector 2030. The number of filters 2015 used in the measurement cycle will be denoted by N, and each filter 2015 passes energy in a passband around a center wavelength $\lambda_i$, where i is an index ranging over the number of filters (e.g., from 1 to N). The set of optical measurements from the sample detector 2036 in the passbands of the N filters 2015 provide a wavelength-dependent spectrum of the substance in the sample cell 2048. The spectrum will be denoted by $C_s(\lambda_i)$, where $C_s$ may be a transmittance, absorbance, optical density, or some other measure of an optical property of the substance. In some embodiments, the spectrum is normalized with respect to one or more of the reference signals measured by the reference detector 2030 and/or with respect to spectra of a reference substance (e.g., air or saline). The measured spectra are communicated to the algorithm processor 416 for calculation of the concentration of the analyte(s) of interest in the fluid sample.

In some embodiments, the analyzer 2010 performs spectroscopic measurements on the fluid sample (known as a "wet" reading) and on one or more reference samples. For example, an "air" reading occurs when the sample detector 2036 measures the sample signal without the sample cell 2048 in place along the optical axis X. (This can occur, for example, when the opposite opening 1530 is aligned with the optical axis X). A "water" or "saline" reading occurs when the sample cell 2048 is filled with water or saline, respectively. The algorithm processor 416 may be programmed to calculate analyte concentration using a combination of these spectral measurements.

In some embodiments, a pathlength corrected spectrum is calculated using wet, air, and reference readings. For example, the transmittance at wavelength denoted by $T_i$, may be calculated according to $T_i=(S_i(\text{wet})/R_i(\text{wet}))/(S_i(\text{air})/R_i(\text{air}))$, where $S_i$ denotes the sample signal from the sample detector 2036 and $R_i$ denotes the corresponding reference signal from the reference detector 2030. In some embodiments, the algorithm processor 416 calculates the optical density, $OD_i$, as a logarithm of the transmittance, e.g., according to $OD_i=-\text{Log}(T_i)$. In one implementation, the analyzer 2010 takes a set of wet readings in each of the N filter passbands and then takes a set of air readings in each of the N filter passbands. In other embodiments, the analyzer 2010 may take an air reading before (or after) the corresponding wet reading.

The optical density $OD_i$ is the product of the absorption coefficient at wavelength $\lambda_i$, $\alpha_i$, times the pathlength L over which the sample energy beam $E_s$ interacts with the substance in the sample cell 2048, e.g., $OD_i=\alpha_i L$. The absorption coefficient $\alpha_i$ of a substance may be written as the product of an absorptivity per mole times a molar concentration of the substance. FIG. 20 schematically illustrates the pathlength L of the sample cell 2048. The pathlength L may be determined from spectral measurements made when the sample cell 2048 is filled with a reference substance. For example, because the absorption coefficient for water (or saline) is known, one or more water (or saline) readings can be used to determine the pathlength L from measurements of the transmittance (or optical density) through the cell 2048. In some embodiments, several readings are taken in different wavelength passbands, and a curve-fitting procedure is used to estimate a best-fit pathlength L. The pathlength L may be estimated using other methods including, for example, measuring interference fringes of light passing through an empty sample cell 2048.

The pathlength L may be used to determine the absorption coefficients of the fluid sample at each wavelength. Molar concentration of an analyte of interest can be determined from the absorption coefficient and the known molar absorptivity of the analyte. In some embodiments, a sample measurement cycle comprises a saline reading (at one or more wavelengths), a set of N wet readings (taken, for example, through a sample cell 2048 containing saline solution), followed by a set of N air readings (taken, for example, through the opposite opening 1530). As discussed above, the sample measurement cycle can be performed in a given length of time that may depend, at least in part, on filter dwell times. For example, the measurement cycle may take five minutes when the filter dwell times are about five seconds. In some embodiments, the measurement cycle may take about two minutes when the filter dwell times are about two seconds. After the sample measurement cycle is completed, a detergent cleaner may be flushed through the sample cell 2048 to reduce buildup of organic matter (e.g., proteins) on the windows of the sample cell 2048. The detergent is then flushed to a waste bladder.

In some embodiments, the system stores information related to the spectral measurements so that the information is readily available for recall by a user. The stored information can include wavelength-dependent spectral measurements (including fluid sample, air, and/or saline readings), computed analyte values, system temperatures and electrical properties (e.g., voltages and currents), and any other data related to use of the system (e.g., system alerts, vibration readings, S/N ratios, etc.). The stored information may be retained in the system for a time period such as, for example, 30 days. After this time period, the stored information may be communicated to an archival data storage system and then deleted from the system. In some embodiments, the stored information is communicated to the archival data storage system via wired or wireless methods, e.g., over a hospital information system (HIS).

Analyte Analysis

The algorithm processor 416 (FIG. 4) (or any other suitable processor or processors) may be configured to receive from the analyzer 2010 the wavelength-dependent optical measurements $Cs(\lambda_i)$ of the fluid sample. In some embodiments, the optical measurements comprise spectra such as, for example, optical densities $OD_i$ measured in each of the N filter passbands centered around wavelengths $\lambda_i$. The optical measurements $Cs(\lambda_i)$ are communicated to the processor 416, which analyzes the optical measurements to detect and quantify one or more analytes in the presence of interferents. In some embodiments, one or more poor quality optical measurements $Cs(\lambda_i)$ are rejected (e.g., as having a S/N ratio that is too low), and the analysis performed on the remaining, sufficiently high-quality measurements. In another embodiment, additional optical measurements of the fluid sample are taken by the analyzer 2010 to replace one or more of the poor quality measurements.

Interferents can comprise components of a material sample being analyzed for an analyte, where the presence of the interferent affects the quantification of the analyte. Thus, for example, in the spectroscopic analysis of a sample to determine an analyte concentration, an interferent could be a compound having spectroscopic features that overlap with those of the analyte, in at least a portion of the wavelength range of the measurements. The presence of such an interferent can introduce errors in the quantification of the analyte. More specifically, the presence of one or more interferents can affect the sensitivity of a measurement technique to the concentration of analytes of interest in a material sample, especially when the system is calibrated in the absence of, or with an unknown amount of, the interferent.

Independently of or in combination with the attributes of interferents described above, interferents can be classified as being endogenous (i.e., originating within the body) or exogenous (i.e., introduced from or produced outside the body). As an example of these classes of interferents, consider the analysis of a blood sample (or a blood component sample or a blood plasma sample) for the analyte glucose. Endogenous interferents include those blood components having origins within the body that affect the quantification of glucose, and can include water, hemoglobin, blood cells, and any other component that naturally occurs in blood. Exogenous interferents include those blood components having origins outside of the body that affect the quantification of glucose, and can include items administered to a person, such as medicaments, drugs, foods or herbs, whether administered orally, intravenously, topically, etc.

Independently of or in combination with the attributes of interferents described above, interferents can comprise components which are possibly, but not necessarily, present in the sample type under analysis. In the example of analyzing samples of blood or blood plasma drawn from patients who are receiving medical treatment, a medicament such as acetaminophen is possibly, but not necessarily, present in this sample type. In contrast, water is necessarily present in such blood or plasma samples.

Certain disclosed analysis methods are particularly effective if each analyte and interferent has a characteristic signature in the measurement (e.g., a characteristic spectroscopic feature), and if the measurement is approximately affine (e.g., includes a linear term and an offset) with respect to the concentration of each analyte and interferent. In such methods, a calibration process is used to determine a set of one or more calibration coefficients and a set of one or more optional offset values that permit the quantitative estimation of an analyte. For example, the calibration coefficients and the offsets may be used to calculate an analyte concentration from spectroscopic measurements of a material sample (e.g., the concentration of glucose in blood plasma). In some of these methods, the concentration of the analyte is estimated by multiplying the calibration coefficient by a measurement value (e.g., an optical density) to estimate the concentration of the analyte. Both the calibration coefficient and measurement can comprise arrays of numbers. For example, in some embodiments, the measurement comprises spectra $C_s(\lambda_i)$ measured at the wavelengths $\lambda_i$, and the calibration coefficient and optional offset comprise an array of values corresponding to each wavelength $\lambda_i$. In some embodiments, as further described below, a hybrid linear analysis (HLA) technique is used to estimate analyte concentration in the presence of a set of interferents, while retaining a high degree of sensitivity to the desired analyte. The data used to accommodate the set of possible interferents can include (a) signatures of each of the members of the family of potential additional substances and (b) a typical quantitative level at which each additional substance, if present, is likely to appear. In some embodiments, the calibration coefficient (and optional offset) are adjusted to minimize or reduce the sensitivity of the calibration to the presence of interferents that are identified as possibly being present in the fluid sample.

In some embodiments, the analyte analysis method uses a set of training spectra each having known analyte concentration and produces a calibration that minimizes the variation in estimated analyte concentration with interferent concentration. The resulting calibration coefficient indicates sensitivity of the measurement to analyte concentration. The training spectra need not include a spectrum from the individual whose analyte concentration is to be determined. That is, the term "training" when used in reference to the disclosed methods does not require training using measurements from the individual whose analyte concentration will be estimated (e.g., by analyzing a bodily fluid sample drawn from the individual).

Several terms are used herein to describe the analyte analysis process. The term "Sample Population" is a broad term and includes, without limitation, a large number of samples having measurements that are used in the computation of calibration values (e.g., calibration coefficients and optional offsets). In some embodiments, the term Sample Population comprises measurements (such as, e.g., spectra) from individuals and may comprise one or more analyte measurements determined from those same individuals. Additional demographic information may be available for the individuals whose sample measurements are included in the Sample Population. For an embodiment involving the spectroscopic determination of glucose concentration, the Sample Population measurements may include a spectrum (measurement) and a glucose concentration (analyte measurement).

Various embodiments of Sample Populations may be used in various embodiments of the systems and methods described herein. Several examples of Sample Populations will now be described. These examples are intended to illustrate certain aspects of possible Sample Population embodiments but are not intended to limit the types of Sample Populations that may be generated. In certain embodiments, a Sample Population may include samples from one or more of the example Sample Populations described below.

In some embodiments of the systems and methods described herein, one or more Sample Populations are included in a "Population Database." The Population Database may be implemented and/or stored on a computer-readable medium. In certain embodiments, the systems and methods may access the Population Database using wired and/or wireless techniques. Certain embodiments may utilize several different Population Databases that are accessible locally and/or remotely. In some embodiments, the Population Database includes one or more of the example Sample Populations described below. In some embodiments, two or more databases can be combined into a single database, and in other embodiments, any one database can be divided into multiple databases.

An example Sample Population may comprise samples from individuals belonging to one or more demographic groups including, for example, ethnicity, nationality, gender, age, etc. Demographic groups may be established for any suitable set of one or more distinctive factors for the group including, for example, medical, cultural, behavioral, biological, geographical, religious, and genealogical traits. For example, in certain embodiments, a Sample Population includes samples from individuals from a specific ethnic group (e.g., Caucasians, Hispanics, Asians, African Americans, etc.). In another embodiment, a Sample Population includes samples from individuals of a specific gender or a specific race. In some embodiments, a Sample Population includes samples from individuals belonging to more than one demographic group (e.g., samples from Caucasian women).

Another example Sample Population can comprise samples from individuals having one or more medical conditions. For example, a Sample Population may include samples from individuals who are healthy and unmedicated (sometimes referred to as a Normal Population). In some embodiments, the Sample Population includes samples from individuals having one or more health conditions (e.g., diabetes). In some embodiments, the Sample Population includes samples from individuals taking one or more medications. In certain embodiments, Sample Population includes samples from individuals diagnosed to have a certain medical condition or from individuals being treated for certain medical conditions or some combination thereof. The Sample Population may include samples from individuals such as, for example, ICU patients, maternity patients, and so forth.

An example Sample Population may comprise samples that have the same interferent or the same type of interferents. In some embodiments, a Sample Population can comprise multiple samples, all lacking an interferent or a type of interferent. For example, a Sample Population may comprise samples that have no exogenous interferents, that have one or more exogenous interferents of either known or unknown concentration, and so forth. The number of interferents in a sample depends on the measurement and analyte(s) of interest, and may number, in general, from zero to a very large number (e.g., greater than 300). All of the interferents typically are not expected to be present in a particular material sample, and in many cases, a smaller number of interferents (e.g., 0, 1, 2, 5, 10, 15, 20, or 25) may be used in an analysis. In certain embodiments, the number of interferents used in the analysis is less than or equal to the number of wavelength-dependent measurements N in the spectrum $Cs(\lambda_i)$.

Certain embodiments of the systems and methods described herein are capable of analyzing a material sample using one or more Sample Populations (e.g., accessed from the Population Database). Certain such embodiments may use information regarding some or all of the interferents which may or may not be present in the material sample. In some embodiments, a list of one or more possible interferents, referred to herein as forming a "Library of Interferents," can be compiled. Each interferent in the Library can be referred to as a "Library Interferent." The Library Interferents may include exogenous interferents and endogenous interferents that may be present in a material sample. For example, an interferent may be present due to a medical condition causing abnormally high concentrations of the exogenous and endogenous interferents. In some embodiments, the Library of Interferents may not include one or more interferents that are known to be present in all samples. Thus, for example, water, which is a glucose interferent for many spectroscopic measurements, may not be included in the Library of Interferents. In certain embodiments, the systems and methods use samples in the Sample Population to train calibration methods.

The material sample being measured, for example a fluid sample in the sample cell 2048, may also include one or more Library Interferents which may include, but is not limited to, an exogenous interferent or an endogenous interferent. Examples of exogenous interferent can include medications, and examples of endogenous interferents can include urea in persons suffering from renal failure. In addition to components naturally found in the blood, the ingestion or injection of some medicines or illicit drugs can result in very high and rapidly changing concentrations of exogenous interferents.

In some embodiments, measurements of a material sample (e.g., a bodily fluid sample), samples in a Sample Population, and the Library Interferents comprise spectra (e.g., infrared spectra). The spectra obtained from a sample and/or an interferent may be temperature dependent. In some embodiments, it may be beneficial to calibrate for temperatures of the individual samples in the Sample Population or the interferents in the Library of Interferents. In some embodiments, a temperature calibration procedure is used to generate a temperature calibration factor that substantially accounts for the sample temperature. For example, the sample temperature can be measured, and the temperature calibration factor can be applied to the Sample Population and/or the Library Interferent spectral data. In some embodiments, a water or saline spectrum is subtracted from the sample spectrum to account for temperature effects of water in the sample.

In other embodiments, temperature calibration may not be used. For example, if Library Interferent spectra, Sample Population spectra, and sample spectra are obtained at approximately the same temperature, an error in a predicted analyte concentration may be within an acceptable tolerance. If the temperature at which a material sample spectrum is measured is within, or near, a temperature range (e.g., several degrees Celsius) at which the plurality of Sample Population spectra are obtained, then some analysis methods may be relatively insensitive to temperature variations. Temperature calibration may optionally be used in such analysis methods.

Figure 21:
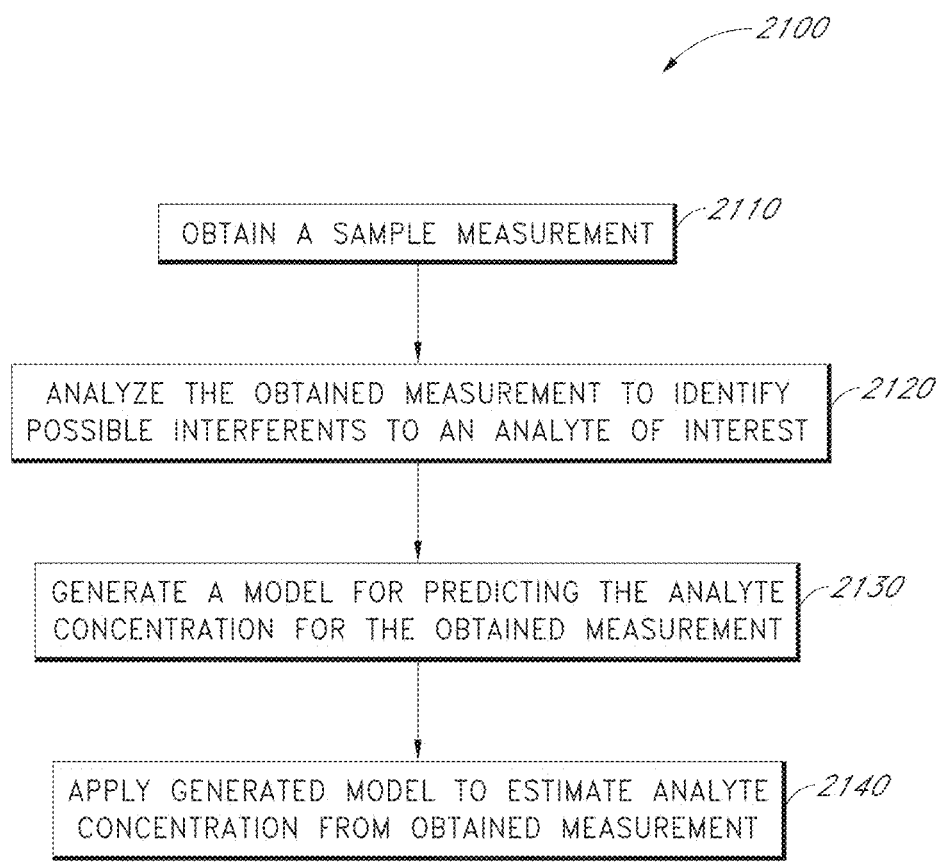
FIG. 21 is a flowchart that schematically illustrates an embodiment of a method for estimating the concentration of an analyte in the presence of interferents.

Systems and Methods for Estimating Analyte Concentration in the Presence of Interferents FIG. 21 is a flowchart that schematically illustrates an embodiment of a method 2100 for estimating the concentration of an analyte in the presence of interferents. In block 2110, a measurement of a sample is obtained, and in block 2120 data relating to the obtained measurement is analyzed to identify possible interferents to the analyte. In block 2130, a model is generated for predicting the analyte concentration in the presence of the identified possible interferents, and in block 2140 the model is used to estimate the analyte concentration in the sample from the measurement. In certain embodiments of the method 2100, the model generated in block 2130 is selected to reduce or minimize the effect of identified interferents that are not present in a general population of which the sample is a member.

An example embodiment of the method 2100 of FIG. 21 for the determination of an analyte (e.g., glucose) in a blood sample will now be described. This example embodiment is intended to illustrate various aspects of the method 2100 but is not intended as a limitation on the scope of the method 2100 or on the range of possible analytes. In this example, the sample measurement in block 2110 is an absorption spectrum, $Cs(\lambda_i)$, of a measurement sample S that has, in general, one analyte of interest, glucose, and one or more interferents.

In block 2120, a statistical comparison of the absorption spectrum of the sample S with a spectrum of the Sample Population and combinations of individual Library Interferent spectra is performed. The statistical comparison provides a list of Library Interferents that are possibly contained in sample S and can include either no Library Interferents or one or more Library Interferents. In this example, in block 2130, one or more sets of spectra are generated from spectra of the Sample Population and their respective known analyte concentrations and known spectra of the Library Interferents identified in block 2120. In block 2130, the generated spectra are used to calculate a model for predicting the analyte concentration from the obtained measurement. In some embodiments, the model comprises one or more calibration coefficients $\kappa(\lambda_i)$ that can be used with the sample measurements $Cs(\lambda_i)$ to provide an estimate of the analyte concentration, $g_{est}$. In block 2140, the estimated analyte concentration is determined form the model generated in block 2130. For example, in some embodiments of HLA, the estimated analyte concentration is calculated according to a linear formula: $g_{est} = \kappa(\lambda_i) \cdot C_s(\lambda_i)$. Because the absorption measurements and calibration coefficients may represent arrays of numbers, the multiplication operation indicated in the preceding formula may comprise a sum of the products of the measurements and coefficients (e.g., an inner product or a matrix product). In some embodiments, the calibration coefficient is determined so as to have reduced or minimal sensitivity to the presence of the identified Library Interferents.

Figure 22:
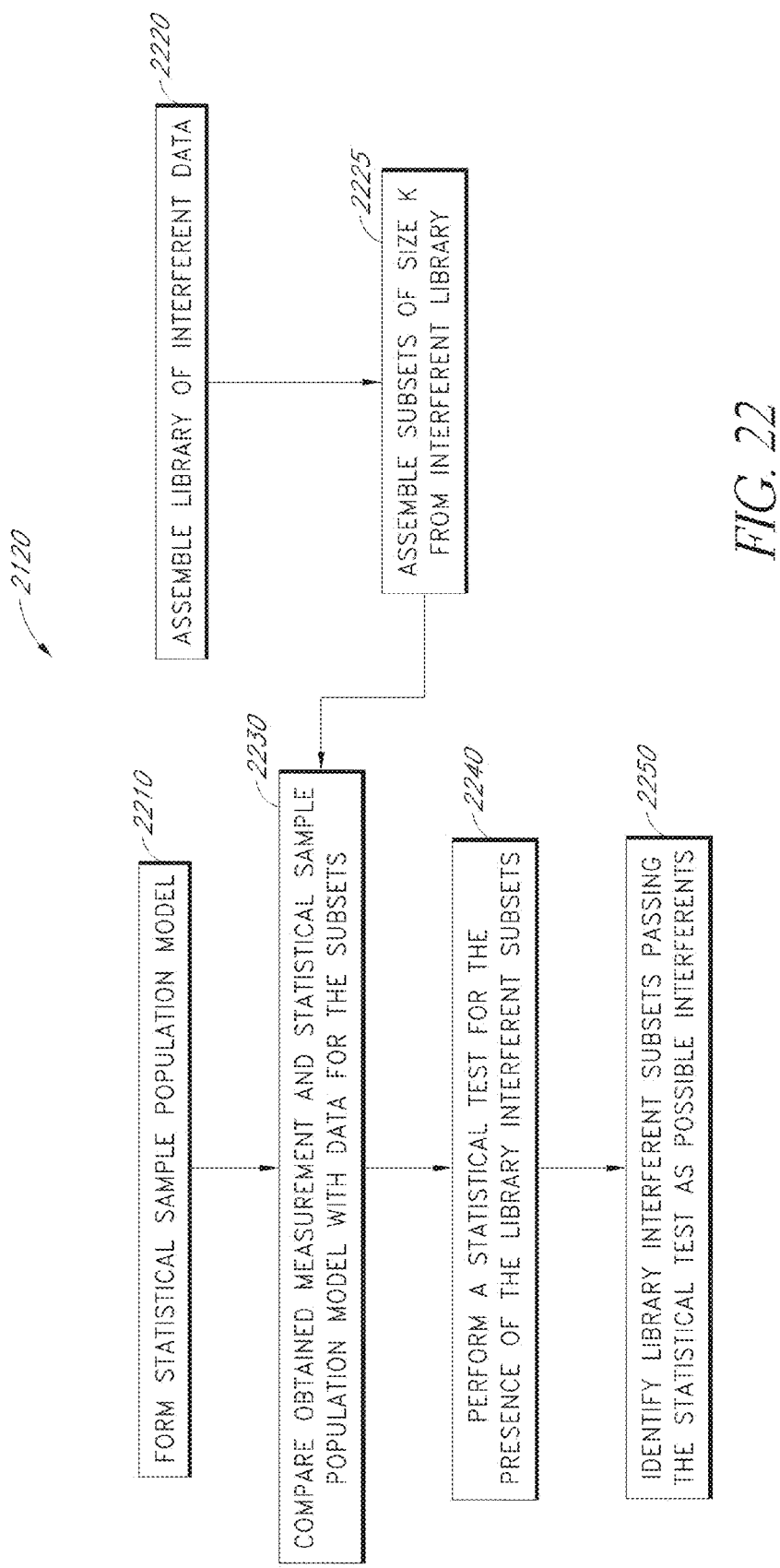
FIG. 22 is a flowchart that schematically illustrates an embodiment of a method for performing a statistical comparison of the absorption spectrum of a sample with the spectrum of a sample population and combinations of individual library interferent spectra.

An example embodiment of block 2120 of the method 2100 will now be described with reference to FIG. 22. In this example, block 2120 includes forming a statistical Sample Population model (block 2210), assembling a library of interferent data (block 2220), assembling all subsets of size K of the library interferents (block 2225), comparing the obtained measurement and statistical Sample Population model with data for each set of interferents from an interferent library (block 2230), performing a statistical test for the presence of each interferent from the interferent library (block 2240), and identifying possible interferents that pass the statistical test (block 2250). The size K of the subsets may be an integer such as, for example, 1, 2, 3, 4, 5, 6, 10, 16, or more. The acts of block 2220 can be performed once or can be updated as necessary. In certain embodiments, the acts of blocks 2230, 2240, and 2250 are performed sequentially for all subsets of Library Interferents that pass the statistical test (block 2240). In this example, in block 2210, a Sample Population Database is formed that includes a statistically large Sample Population of individual spectra taken over the same wavelength range as the sample spectrum, $C_s(\lambda_i)$. The Database also includes an analyte concentration corresponding to each spectrum. For example, if there are P Sample Population spectra, then the spectra in the Database can be represented as $C = \{C_1, C_2, \ldots, C_P\}$, and the analyte concentration corresponding to each spectrum can be represented as $g=\{g_1, g_2, \ldots, g_P\}$. In some embodiments, the Sample Population does not have any of the Library Interferents present, and the material sample has interferents contained in the Sample Population and one or more of the Library Interferents.

In some embodiments of block 2210, the statistical sample model comprises a mean spectrum and a covariance matrix calculated for the Sample Population. For example, if each spectrum measured at N wavelengths $\lambda_i$ is represented by an N×1 array, C, then the mean spectrum, $\mu$, is an N×1 array having values at each wavelength averaged over the range of spectra in the Sample Population. The covariance matrix, V, is calculated as the expected value of the deviation between C and $\mu$ and can be written as $V=(C-\mu)(-\mu)^T)$ where E(•) represents the expected value and the superscript T denotes transpose. In other embodiments, additional statistical parameters may be included in the statistical model of the Sample Population spectra.

Additionally, a Library of Interferents may be assembled in block 2220. A number of possible interferents can be identified, for example, as a list of possible medications or foods that might be ingested by the population of patients at issue. Spectra of these interferents can be obtained, and a range of expected interferent concentrations in the blood, or other expected sample material, can be estimated. In certain embodiments, the Library of Interferents includes, for each of "M" interferents, the absorption spectrum normalized to unit interferent concentration of each interferent, $IF=\{IF_1, IF_2, \ldots IF_M\}$, and a range of concentrations for each interferent from $T_{max}=\{Tmax_1, Tmax_2, \ldots, Tmax_M\}$ to $Tmin=\{T min_1, Tmin_2, \ldots, Tmin_M\}$. Information in the Library may be assembled once and accessed as needed. For example, the Library and the statistical model of the Sample Population may be stored in a storage device associated with the algorithm processor 416 (see, FIG. 4).

Continuing in block 2225, the algorithm processor 416 assembles one or more subsets comprising a number K of spectra taken from the Library of Interferents. The number K may be an integer such as, for example, 1, 2, 3, 4, 5, 6, 10, 16, or more. In some embodiments, the subsets comprise all combinations of the M Library spectra taken K at a time. In these embodiments, the number of subsets having K spectra is $M!/(K!(M-K)!)$, where ! represents the factorial function.

Continuing in block 2230, the obtained measurement data (e.g., the sample spectrum) and the statistical Sample Population model (e.g., the mean spectrum and the covariance matrix) are compared with data for each subset of interferents determined in block 2225 in order to determine the presence of possible interferents in the sample (block 2240). In some embodiments, the statistical test for the presence of an interferent subset in block 2240 comprises determining the concentrations of each subset of interferences that minimize a statistical measure of "distance" between a modified spectrum of the material sample and the statistical model of the Sample Population (e.g., the mean $\mu$ and the covariance V). The term "concentration" used in this context refers to a computed value, and, in some embodiments, that computed value may not correspond to an actual concentration. The concentrations may be calculated numerically. In some embodiments, the concentrations are calculated by algebraically solving a set of linear equations. The statistical measure of distance may comprise the well-known Mahalanobis distance (or square of the Mahalanobis distance) and/or some other suitable statistical distance metric (e.g., Hotelling's T-square statistic). In certain implementations, the modified spectrum is given by $C'_s(T)=C_s-IF \cdot T$ where $T=(T_1, T_2, \ldots T_K)^T$ is a K-dimensional column vector of interferent concentrations and $IF=\{IF_1, IF_2, \ldots IF_K\}$ represents the K interferent absorption spectra of the subset. In some embodiments, concentration of the $i^{th}$ interferent is assumed to be in a range from a minimum value, $T min_i$, to a maximum value, $Tmax_i$. The value of $Tmin_i$ may be zero, or may be a value between zero and $Tmax_i$, such as a fraction of $Tmax_i$, or may be a negative value. Negative values represent interferent concentrations that are smaller than baseline interferent values in the Sample Population.

In block 2250, a list of a number $N_s$ of possible interferent subsets may be identified as the particular subsets that pass one or more statistical tests (in block 2240) for being present in the material sample. One or more statistical tests may be used, alone or in combination, to identify the possible interferents. For example, if a statistical test indicates that an $i^{th}$ interferent is present in a concentration outside the range $Tmin_i$ to $Tmax_i$, then this result may be used to exclude the $i^{th}$ interferent from the list of possible interferents. In some embodiments, only the single most probable interferent subset is included on the list, for example, the subset having the smallest statistical distance (e.g., Mahalanobis distance). In an embodiment, the list includes the subsets $\xi$ having statistical distances smaller than a threshold value. In certain embodiments, the list includes a number $N_S$ of subsets having the smallest statistical distances, e.g., the list comprises the "best" candidate subsets. The number $N_S$ may be any suitable integer such as 10, 20, 50, 100, 200, or more. An advantage of selecting the "best" $N_S$ subsets is reduced computational burden on the algorithm processor 416. In some embodiments, the list includes all the Library Interferents. In certain such embodiments, the list is selected to comprise combinations of the $N_S$ subsets taken L at a time. For example, in some embodiments, pairs of subsets are taken (e.g., L=2). An advantage of selecting pairs of subsets is that pairing captures the most likely combinations of interferents and the "best" candidates are included multiple times in the list of possible interferents. In embodiments in which combinations of L subsets are selected, the number of combinations of subsets in the list of possible interferent subsets is $N_s!/(L!(N_S-L)!)$.

In other embodiments, the list of possible interferent subsets $\xi$ is determined using a combination of some or all of the above criteria. In another embodiment, the list of possible interferent subsets $\xi$ includes each of the subsets assembled in block 2225. Many selection criteria are possible for the list of possible interferent subsets $\xi$.

Figure 23:
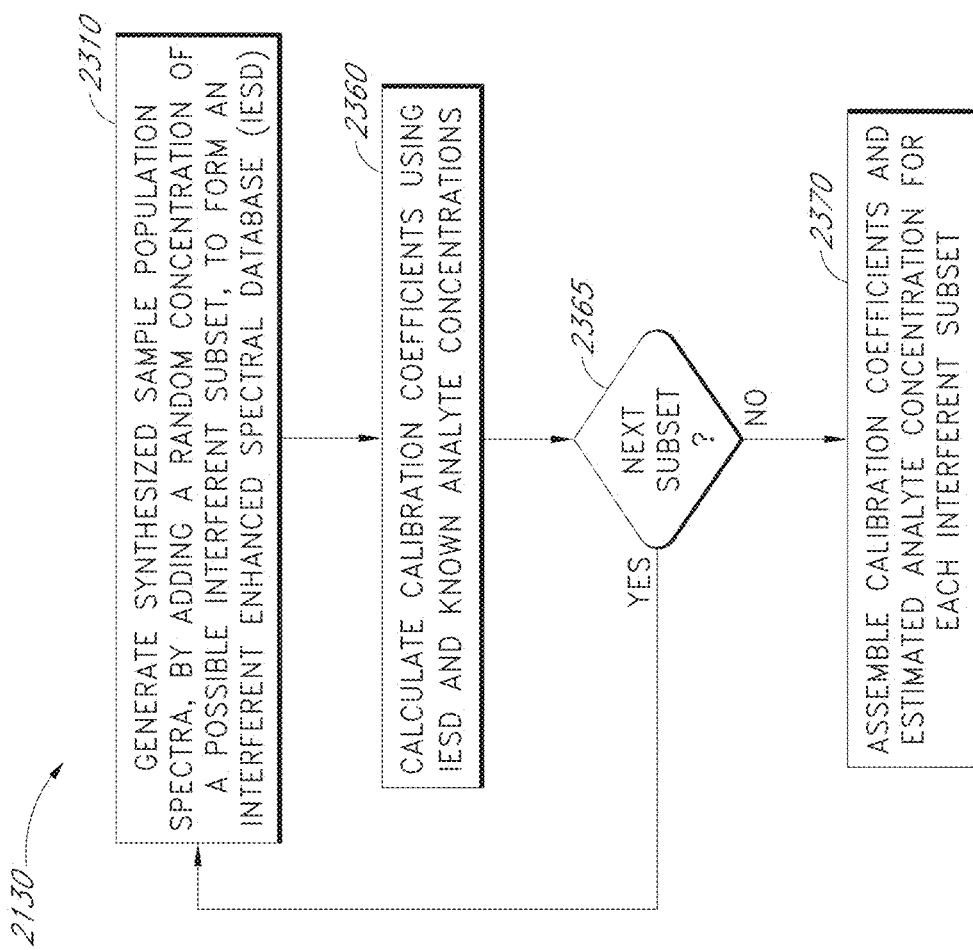
FIG. 23 is a flowchart that schematically illustrates an example embodiment of a method for estimating analyte concentration in the presence of the possible interferents.

Returning to FIG. 21, the method 2100 continues in block 2130 where analyte concentration is estimated in the presence of the possible interferent subsets $\xi$ determined in block 2250. FIG. 23 is a flowchart that schematically illustrates an example embodiment of the acts of block 2130. In block 2310, synthesized Sample Population measurements are generated to form an Interferent Enhanced Spectral Database (IESD). In block 2360, the IESD and known analyte concentrations are used to generate calibration coefficients for the selected interferent subset. As indicated in block 2365, blocks 2310 and 2360 may be repeated for each interferent subset $\xi$ identified in the list of possible interferent subsets (e.g., in block 2250 of FIG. 22). In this example embodiment, when all the interferent subsets $\xi$ have been processed, the method continues in block 2370, wherein an average calibration coefficient is applied to the measured spectra to determine a set of analyte concentrations.

In one example embodiment for block 2310, synthesized Sample Population spectra are generated by adding random concentrations of each interferent in one of the possible interferent subsets $\xi$. These spectra are referred to herein as an Interferent-Enhanced Spectral Database or IESD. In one example method, the IESD is formed as follows. A plurality of Randomly-Scaled Single Interferent Spectra (RSIS) are formed for each interferent in the interferent subset $\xi$. Each RSIS is formed by combinations of the interferent having spectrum IF multiplied by the maximum concentration Tmax, which is scaled by a random factor between zero and one. In certain embodiments, the scaling places the maximum concentration at the $95^{th}$ percentile of a log-normal distribution in order to generate a wide range of concentrations. In some embodiments, the log-normal distribution has a standard deviation equal to half of its mean value.

In this example method, individual RSIS are then combined independently and in random combinations to form a large family of Combination Interferent Spectra (CIS), with each spectrum in the CIS comprising a random combination of RSIS, selected from the full set of identified Library Interferents. An advantage of this method of selecting the CIS is that it produces adequate variability with respect to each interferent, independently across separate interferents.

The CIS and replicates of the Sample Population spectra are combined to form the IESD. Since the interferent spectra and the Sample Population spectra may have been obtained from measurements having different optical pathlengths, the CIS may be scaled to the same pathlength as the Sample Population spectra. The Sample Population Database is then replicated R times, where R depends on factors including the size of the Database and the number of interferents. The IESD includes R copies of each of the Sample Population spectra, where one copy is the original Sample Population Data, and the remaining R-1 copies each have one randomly chosen CIS spectra added. Accordingly, each of the IESD spectra has an associated analyte concentration from the Sample Population spectra used to form the particular IESD spectrum. In some embodiments, a 10-fold replication of the Sample Population Database is used for 130 Sample Population spectra obtained from 58 different individuals and 18 Library Interferents. A smaller replication factor may be used if there is greater spectral variety among the Library Interferent spectra, and a larger replication factor may be used if there is a greater number of Library Interferents.

After the IESD is generated in block 2310, in block 2360, the IESD spectra and the known, random concentrations of the subset interferents are used to generate a calibration coefficient for estimating the analyte concentration from a sample measurement. The calibration coefficient is calculated in some embodiments using a hybrid linear analysis (HLA) technique. In certain embodiments, the HLA technique uses a reference analyte spectrum to construct a set of spectra that are free of the desired analyte, projecting the analyte's spectrum orthogonally away from the space spanned by the analyte-free calibration spectra, and normalizing the result to produce a unit response. Further description of embodiments of HLA techniques may be found in, for example, "Measurement of Analytes in Human Serum and Whole Blood Samples by Near-Infrared Raman Spectroscopy," Chapter 4, Andrew J. Berger, Ph. D. thesis, Massachusetts Institute of Technology, 1998, and "An Enhanced Algorithm for Linear Multivariate Calibration," by Andrew J. Berger, et al., Analytical Chemistry, Vol. 70, No. 3, Feb. 1, 1998, pp. 623-627, the entirety of each of which is hereby incorporated by reference herein. In other embodiments, the calibration coefficients may be calculated using other techniques including, for example, regression techniques such as, for example, ordinary least squares (OLS), partial least squares (PLS), and/or principal component analysis.

In block 2365, the processor 416 determines whether additional interferent subsets remain in the list of possible interferent subsets. If another subset is present in the list, the acts in blocks 2310-2360 are repeated for the next subset of interferents using different random concentrations. In some embodiments, blocks 2310-2360 are performed for only the most probable subset on the list.

The calibration coefficient determined in block 2360 corresponds to a single interferent subset $\xi$ from the list of possible interferent subsets and is denoted herein as a single-interferent-subset calibration coefficient $\kappa_{avg}(\xi)$ In this example method, after all subsets $\xi$ have been processed, the method continues in block 2370, in which the single-interferent-subset calibration coefficient is applied to the measured spectra $C_s$ to determine an estimated, single-interferent-subset analyte concentration, $g(\xi)=\kappa_{avg}(\xi) \cdot C_s$, for the interferent subset $\xi$. The set of the estimated, single-interferent-subset analyte concentrations $g(\xi)$ for all subsets in the list may be assembled into an array of single-interferent-subset concentrations. As noted above, in some embodiments the blocks 2310-2370 are performed once for the most probable single-interferent-subset on the list (e.g., the array of single-interferent analyte concentrations has a single member).

Returning to block 2140 of FIG. 21, the array of single-interferent-subset concentrations, $g(\xi)$, is combined to determine an estimated analyte concentration, $g_{est}$, for the material sample. In certain embodiments, a weighting function $p(\xi)$ is determined for each of the interferent subsets $\xi$ on the list of possible interferent subsets. The weighting functions may be normalized such that $\Sigma p(\xi)=1$, where the sum is over all subsets $\xi$ that have been processed from the list of possible interferent subsets. In some embodiments, the weighting functions can be related to the minimum Mahalanobis distance or an optimal concentration. In certain embodiments, the weighting function $p(\xi)$, for each subset $\xi$, is selected to be a constant, e.g., $1/N_S$ where $N_S$ is the number of subsets processed from the list of possible interferent subsets. In other embodiments, other weighting functions $p(\xi)$ can be selected.

In certain embodiments, the estimated analyte concentration, $g_{est}$, is determined (in block 2140) by combining the single-interferent-subset estimates, $g(\xi)$, and the weighting functions, $p(\xi)$, to generate an average analyte concentration. The average concentration may be computed according to $g_{est}=\Sigma g(\xi) p(\xi)$, where the sum is over the interferent subsets processed from the list of possible interferent subsets. In some embodiments, the weighting function $p(\xi)$ is a constant value for each subset (e.g., a standard arithmetic average is used for determining average analyte concentration). By testing the above described example method on simulated data, it has been found that the average analyte concentration advantageously has errors that may be reduced in comparison to other methods (e.g., methods using only a single most probable interferent).

Although the flowchart in FIG. 21 schematically illustrates an embodiment of the method 2100 performed with reference to the blocks 2110-2140 described herein, in other embodiments, the method 2100 can be performed differently. For example, some or all of the blocks 2110-2140 can be combined, performed in a different order than shown, and/or the functions of particular blocks may be reallocated to other blocks and/or to different blocks. Embodiments of the method 2100 may utilize different blocks than are shown in FIG. 21.

For example, in some embodiments of the method 2100, the calibration coefficient is computed without synthesizing spectra and/or partitioning the data into calibration sets and test sets. Such embodiments are referred to herein as "Parameter-Free Interferent Rejection" (PFIR) methods. In one example embodiment using PFIR, for each of the possible interferent subsets $\xi$, the following calculations may be performed to compute an estimate of a calibration coefficient for each subset $\xi$. An average concentration may be estimated according to $g_{est}=\Sigma g(\xi) p(\xi)$, where the sum is over the interferent subsets processed from the list of possible interferent subsets.

An example of an alternative embodiment of block 2130 includes the following steps and calculations.

Step 1: For a subset's $N_{IF}$ interferents, form a scaled interferent spectra matrix. In certain embodiments, the scaled interferent spectra matrix is the product of an interferent spectral matrix, IF, multiplied by an interferent concentration matrix, $T_{max}$, and can be written as: IF $T_{max}$. In certain such embodiments, the interferent concentration matrix $T_{max}$ is a diagonal matrix having entries given by the maximum plasma concentrations for the various interferents.

Step 2: Calculate a covariance for the interferent component. If X denotes the IESD, the covariance of X, cov(X), is defined as the expectation $E((X-mean(X))(X-mean(X))^T)$ and is $$cov(X) \approx XX^T/(N-1) - mean(X)mean(X)^T.$$

As described above, the IESD (e.g., X) is obtained as a combination of Sample Population Spectra, C, with Combination Interferent Spectra (CIS): $X_j = C_j + IF_j \xi_j$, therefore the covariance is:

$$cov(X) \approx CC^T/(N-1) + IF \Xi \Xi^T IF^T/(N-1) - mean(X)mean(X)^T,$$

which can be written as, $$cov(X) \approx cov(C) + IF cov(\Xi) IF^T.$$

If the weights in the weighting matrix $\Xi$ are independent and identically distributed, the covariance of $\Xi$, cov($\Xi$), is a diagonal matrix having along the diagonal the variance, v, of the samples in $\Xi$. The last equation may be written as $$cov(X) \approx V_0 + v\Phi,$$

where $V_0$ is the covariance of the original sample population and $\Phi$ is the covariance of the IF spectral set.

Step 3: The group's covariance may be at least partially corrected for the presence of a single replicate of the Sample Population spectra with the IESD as formed from $N_{IF}$ replicates of the Sample Population Spectra with Combined Interferent Spectra. This partial correction may be achieved by multiplying the second term in the covariance formula given above by a correction factor $\rho$:

$$V = V_0 + \rho v \Phi,$$

where $\rho$ is a scalar weighting function that depends on the number of interferents in the group. In some embodiments, the scalar weighting function is $\rho = N_{IF}/(N_{IF}+1)$. In certain embodiments, the variance v of the weights is assumed to be the variance of a log-normal random variable having a 95th percentile at a value of 1.0, and a standard deviation equal to half of the mean value.

Step 4: The eigenvectors and the corresponding eigenvalues of the covariance matrix V are determined using any suitable linear algebraic methods. The number of eigenvectors (and eigenvalues) is equal to the number of wavelengths L in the spectral measurements. The eigenvectors may be sorted based on decreasing order of their corresponding eigenvalues.

Step 5: The matrix of eigenvectors is decomposed so as to provide an orthogonal matrix Q. For example, in some embodiments, a QR-decomposition is performed, thereby yielding the matrix Q having orthonormal columns and rows.

Step 6: The following matrix operations are performed on the orthogonal matrix Q. For n=2 to L-1, the product $P^{\parallel}_n = Q(:,1:n) Q(:,1:n)^T$ is calculated, where Q(:,1:n) denotes the submatrix comprising the first n columns of the full matrix Q. The orthogonal projection, $P^{\perp}_n$, away from the space spanned by Q(:,1:n) is determined by subtracting $P^{\parallel}_n$ from the L×L identity matrix I. The $n^{th}$ calibration vector is then determined from $\kappa_n = P^{\perp}_n \alpha_X / \alpha_X^T P^{\perp}_n \alpha_X$, and the $n^{th}$ error variance $E_n$ is determined as the projection of the full covariance V onto the subspace spanned by $\kappa_n$ as follows: $E_n = \kappa_n^T V \kappa_n$.

The steps 4-6 of this example are an embodiment of the HLA technique.

In some embodiments, the calibration coefficient $\kappa$ is selected as the calibration vector corresponding to the minimum error variance $E_n$. Thus, for example, the average group calibration coefficient $\kappa$ may be found by searching among all the error variances for the error variance $E_n$ that has the minimum value. The calibration coefficient is then selected as the $n^{th}$ calibration vector $\kappa_n$ corresponding to the minimum error variance $E_n$. In other embodiments, the calibration coefficient is determined by averaging some or all of the calibration vectors $\kappa_n$.

Examples of Algorithm Results and Effects of Sample Population

Embodiments of the above-described methods have been used to estimate blood plasma glucose concentrations in humans. Four example experiments will now be described. The population of individuals from whom samples were obtained for analysis (estimation of glucose concentration) will be referred to as the "target population." Infrared spectra obtained from the target population will be referred to as the "target spectra." In the four example experiments, the target population included 41 intensive care unit (ICU) patients. Fifty-five samples were obtained from the target population.

Example Experiment 1

In this example experiment, a partial least squares (PLS) regression method was applied to the infrared target spectra of the target patients' blood plasma to obtain the glucose estimates. In example experiment 1, estimated glucose concentration was not corrected for effects of interferents. The Sample Population used for the analysis included infrared spectra and independently measured glucose concentrations for 92 individuals selected from the general population. This Sample Population will be referred to as a "Normal Population."

Example Experiment 2

In example experiment 2, an embodiment of the Parameter-Free Interferent Rejection (PFIR) method was used to estimate glucose concentration for the same target population of patients in example experiment 1. The Sample Population was the Normal Population. In this example, calibration for Library Interferents was applied to the measured target spectra. The Library of Interferents included spectra of the 59 substances listed below:

Acetylsalicylic Acid
Ampicillin Sulbactam
Azithromycin
Aztreonam
Bacitracin
Benzyl Alcohol
Calcium Chloride
Calcium Gluconate
Cefazolin
Cefoparazone
Cefotaxime Sodium
Ceftazidime
Ceftriaxone
D_Sorbitol
Dextran
Ertapenem
Ethanol
Ethosuximide
Glycerol
Heparin
Hetastarch
Human Albumin
Hydroxy Butyric Acid
Imipenem Cilastatin
Iohexol
L_Arginine
Lactate Sodium
Magnesium Sulfate
Maltose
Mannitol
Meropenem
Oxylate Potassium
Phenytoin
Phosphates Potassium
Piperacillin
Piperacillin Tazobactam
PlasmaLyteA
Procaine HCl
Propylene Glycol
Pyrazinamide
Pyruvate Sodium
Pyruvic Acid
Salicylate Sodium
Sodium Acetate
Sodium Bicarbonate
Sodium Chloride
Sodium Citrate
Sodium Thiosulfate
Sulfadiazine
Urea
Uric Acid
Voriconazole
Xylitol
Xylose
PC 1 of Saline covariance
PC 2 of Saline covariance
PC 3 of Saline covariance
PC 4 of Saline covariance
ICU/Normal difference spectrum In some embodiments, the calibration data set is determined according to two criteria: the calibration method itself (e.g., HLA, PLS, OLS, PFIR) and the intended application of the method. The calibration data set may comprise spectra and corresponding analyte levels derived from a set of plasma samples from the Sample Population. In some embodiments, e.g., those where an HLA calibration method is used, the calibration data set may also include spectra of the analyte of interest.

In the example experiments 1 and 2, the Sample Population was the Normal Population. Thus, samples were drawn from a population of normal individuals who did not have identifiable medical conditions that might affect the spectra of their plasma samples. For example, the sample plasma spectra typically did not show effects of high levels of medications or other substances (e.g., ethanol), or effects of chemicals that are indicative of kidney or liver malfunction.

In some embodiments, an analysis method may calibrate for deviations from the distribution defined by the calibration plasma spectra by identifying a "base" set of interferent spectra likely to be responsible for the deviation. The analysis method may then recalibrate with respect to an enhanced spectral data set. In some embodiments, the enhancement can be achieved by including the identified interferent spectra into the calibration plasma spectra. When it is anticipated that the target population may have been administered significant amounts of substances not present in the samples of the calibration set, or when the target population have many distinct interferents, estimation of the interferents present in the target spectrum may be subject to a large degree of uncertainty. In some cases, this may cause analyte estimation to be subject to errors.

Accordingly, in certain embodiments, the calibration data set may be enhanced beyond the base of "normal" samples to include a population of samples intended to be more representative of the target population. The enhancement of the calibration set may be generated, in some embodiments, by including samples from a sufficiently diverse range of individuals in order to represent the range of likely interferents (both in type and in concentration) and/or the normal variability in underlying plasma characteristics. The enhancement may, additionally or alternatively, be generated by synthesizing interferent spectra having a range of concentrations as described above (see, e.g., discussion of block 2310 in FIG. 23). Using the enhanced calibration set may reduce the error in estimating the analyte concentration in the target spectra.

Example Experiments 3 and 4

Example experiments 3 and 4 use the analysis methods of example experiments 1 and 2, respectively (PLS without interferent correction and PFIR with interferent correction). However, example experiments 3 and 4 use a Sample Population having blood plasma spectral characteristics different from the Normal Population used in example experiments 1 and 2. In example experiments 3 and 4, the Sample Population was modified to include spectra of both the Normal Population and spectra of an additional population of 55 ICU patients. These spectra will be referred to as the "Normal+Target Spectra." In experiments 3 and 4, the ICU patients included Surgical ICU patients, Medical ICU patients as well as victims of severe trauma, including a large proportion of patients who had suffered major blood loss. Major blood loss may necessitate replacement of the patient's total blood volume multiple times during a single day and subsequent treatment of the patient via electrolyte and/or fluid replacement therapies. Major blood loss may also require administration of plasma-expanding medications. Major blood loss may lead to significant deviations from the blood plasma spectra representative of a Normal Population. The population of 55 ICU patients (who provided the Target Spectra) has some similarities to the individuals for whom the analyses in experiments 1-4 were performed (e.g., all were ICU patients), but in these experiments, target spectra from individuals in the target population were not included in the Target Spectra.

Results of example experiments 1-4 are shown in the following table. The glucose concentrations estimated from the analysis method were compared to independently determined glucose measurements to provide an average prediction error and a standard deviation of the average prediction error. The table demonstrates that independent of the Sample Population used (e.g., either the Normal Population or the Normal+Target Population), calibrating for interferents reduces both the average prediction error and the standard deviation (e.g., compare the results for experiment 2 to the results for experiment 1 and compare the results for experiment 4 to the results for experiment 3). The table further demonstrates that independent of the analysis method used (e.g., either PLS or PFIR), using a Sample Population with more similarity to the target population (e.g., the Normal+Target Population) reduces both the average prediction error and the standard deviation (e.g., compare the results for experiment 3 to the results for experiment 1 and compare the results for experiment 4 to the results for experiment 2).

| Example Experiment No. | Interferent Calibration | Sample Population | Average Prediction Error (mg/dL) | Standard Deviation (mg/dL) |
| --- | --- | --- | --- | --- |
| 1 | NO  | Normal | 126 | 164 |
| 2 | YES | Normal | −6.8 | 23.2 |
| 3 | NO  | Normal + Target | 8.2 | 16.9 |
| 4 | YES | Normal + Target | 1.32 | 12.6 |

Accordingly, embodiments of analysis methods that use a Sample Population that includes both normal spectra and spectra from individuals similar to those of the target population and that calibrate for possible interferents provide a good match between the estimated glucose concentration and the measured glucose concentration. As discussed above, a suitable Sample Population may be assembled from the Population Database in order to include normal spectra plus suitable target spectra from individuals that match a desired target population including, for example, ICU patients, trauma patients, a particular demographic group, a group having a common medical condition (e.g., diabetes), and so forth.

User Interface

The system 400 can include a display system 414, for example, as depicted in FIG. 4. The display system 414 may comprise an input device including, for example, a keypad or a keyboard, a mouse, a touchscreen display, and/or any other suitable device for inputting commands and/or information. The display system 414 may also include an output device including, for example, an LCD monitor, a CRT monitor, a touchscreen display, a printer, and/or any other suitable device for outputting text, graphics, images, videos, etc. In some embodiments, a touchscreen display is advantageously used for both input and output.

The display system 414 can include a user interface 2400 by which users can conveniently and efficiently interact with the system 400. The user interface 2400 may be displayed on the output device of the system 400 (e.g., the touchscreen display). In some embodiments, the user interface 2400 is implemented and/or stored as one or more code modules, which may be embodied in hardware, firmware, and/or software.

FIGS. 24 and 25 schematically illustrate the visual appearance of embodiments of the user interface 2400. The user interface 2400 may show patient identification information 2402, which can include patient name and/or a patient ID number. The user interface 2400 also can include the current date and time 2404. An operating graphic 2406 shows the operating status of the system 400. For example, as shown in FIGS. 24 and 25, the operating status is "Running," which indicates that the system 400 is fluidly connected to the patient ("Jill Doe") and performing normal system functions such as infusing fluid and/or drawing blood. The user interface 2400 can include one or more analyte concentration graphics 2408, 2412, which may show the name of the analyte and its last measured concentration. For example, the graphic 2408 in FIG. 24 shows "Glucose" concentration of 150 mg/dL, while the graphic 2412 shows "Lactate" concentration of 0.5 mmol/L. The particular analytes displayed and their measurement units (e.g., mg/dL, mmol/L, or other suitable unit) may be selected by the user. The size of the graphics 2408, 2412 may be selected to be easily readable out to a distance such as, e.g., 30 feet. The user interface 2400 may also include a next-reading graphic 2410 that indicates the time until the next analyte measurement is to be taken. In FIG. 24, the time until next reading is 3 minutes, whereas in FIG. 25, the time is 6 minutes, 13 seconds.

The user interface 2400 can include an analyte concentration status graphic 2414 that indicates status of the patient's current analyte concentration compared with a reference standard. For example, the analyte may be glucose, and the reference standard may be a hospital ICU's tight glycemic control (TGC). In FIG. 24, the status graphic 2414 displays "High Glucose," because the glucose concentration (150 mg/dL) exceeds the maximum value of the reference standard. In FIG. 25, the status graphic 2414 displays "Low Glucose," because the current glucose concentration (79 mg/dL) is below the minimum reference standard. If the analyte concentration is within bounds of the reference standard, the status graphic 2414 may indicate normal (e.g., "Normal Glucose"), or it may not be displayed at all. The status graphic 2414 may have a background color (e.g., red) when the analyte concentration exceeds the acceptable bounds of the reference standard.

The user interface 2400 can include one or more trend indicators 2416 that provide a graphic indicating the time history of the concentration of an analyte of interest. In FIGS. 24 and 25, the trend indicator 2416 comprises a graph of the glucose concentration (in mg/dL) versus elapsed time (in hours) since the measurements started. The graph includes a trend line 2418 indicating the time-dependent glucose concentration. In other embodiments, the trend line 2418 can include measurement error bars and may be displayed as a series of individual data points. In FIG. 25, the glucose trend indicator 2416 is shown as well as a trend indicator 2430 and trend line 2432 for the lactate concentration. In some embodiments, a user may select whether none, one, or both trend indicators 2416, 2418 are displayed. In some embodiments, one or both of the trend indicators 2416, 2418 may appear only when the corresponding analyte is in a range of interest such as, for example, above or below the bounds of a reference standard.

The user interface 2400 can include one or more buttons 2420-2426 that can be actuated by a user to provide additional functionality or to bring up suitable context-sensitive menus and/or screens. For example, in the embodiments shown in FIG. 24 and FIG. 25, four buttons 2420-2426 are shown, although fewer or more buttons are used in other embodiments. The button 2420 ("End Monitoring") may be pressed when one or more removable portions (see, e.g., 710 of FIG. 7) are to be removed. In many embodiments, because the removable portions 710, 712 are not reusable, a confirmation window appears when the button 2420 is pressed. If the user is certain that monitoring should stop, the user can confirm this by actuating an affirmative button in the confirmation window. If the button 2420 were pushed by mistake, the user can select a negative button in the confirmation window. If "End Monitoring" is confirmed, the system 400 performs appropriate actions to cease fluid infusion and blood draw and to permit ejection of a removable portion (e.g., the removable portion 710).

The button 2422 ("Pause") may be actuated by the user if patient monitoring is to be interrupted but is not intended to end. For example, the "Pause" button 2422 may be actuated if the patient is to be temporarily disconnected from the system 400 (e.g., by disconnecting the tubes 306). After the patient is reconnected, the button 2422 may be pressed again to resume monitoring. In some embodiments, after the "Pause" button 2422 has been pressed, the button 2422 displays "Resume."

The button 2424 ("Delay 5 Minutes") causes the system 400 to delay the next measurement by a delay time period (e.g., 5 minutes in the depicted embodiments). Actuating the delay button 2424 may be advantageous if taking a reading would be temporarily inconvenient, for example, because a health care professional is attending to other needs of the patient. The delay button 2424 may be pressed repeatedly to provide longer delays. In some embodiments, pressing the delay button 2424 is ineffective if the accumulated delay exceeds a maximum threshold. The next-reading graphic 2410 automatically increases the displayed time until the next reading for every actuation of the delay button 2424 (up to the maximum delay).

The button 2426 ("Dose History") may be actuated to bring up a dosing history window that displays patient dosing history for an analyte or medicament of interest. For example, in some embodiments, the dosing history window displays insulin dosing history of the patient and/or appropriate hospital dosing protocols. A nurse attending the patient can actuate the dosing history button 2426 to determine the time when the patient last received an insulin dose, the last dosage amount, and/or the time and amount of the next dosage. The system 400 may receive the patient dosing history via wired or wireless communications from a hospital information system.

In other embodiments, the user interface 2400 can include additional and/or different buttons, menus, screens, graphics, etc. that are used to implement additional and/or different functionalities.

Related Components

Figure 26:
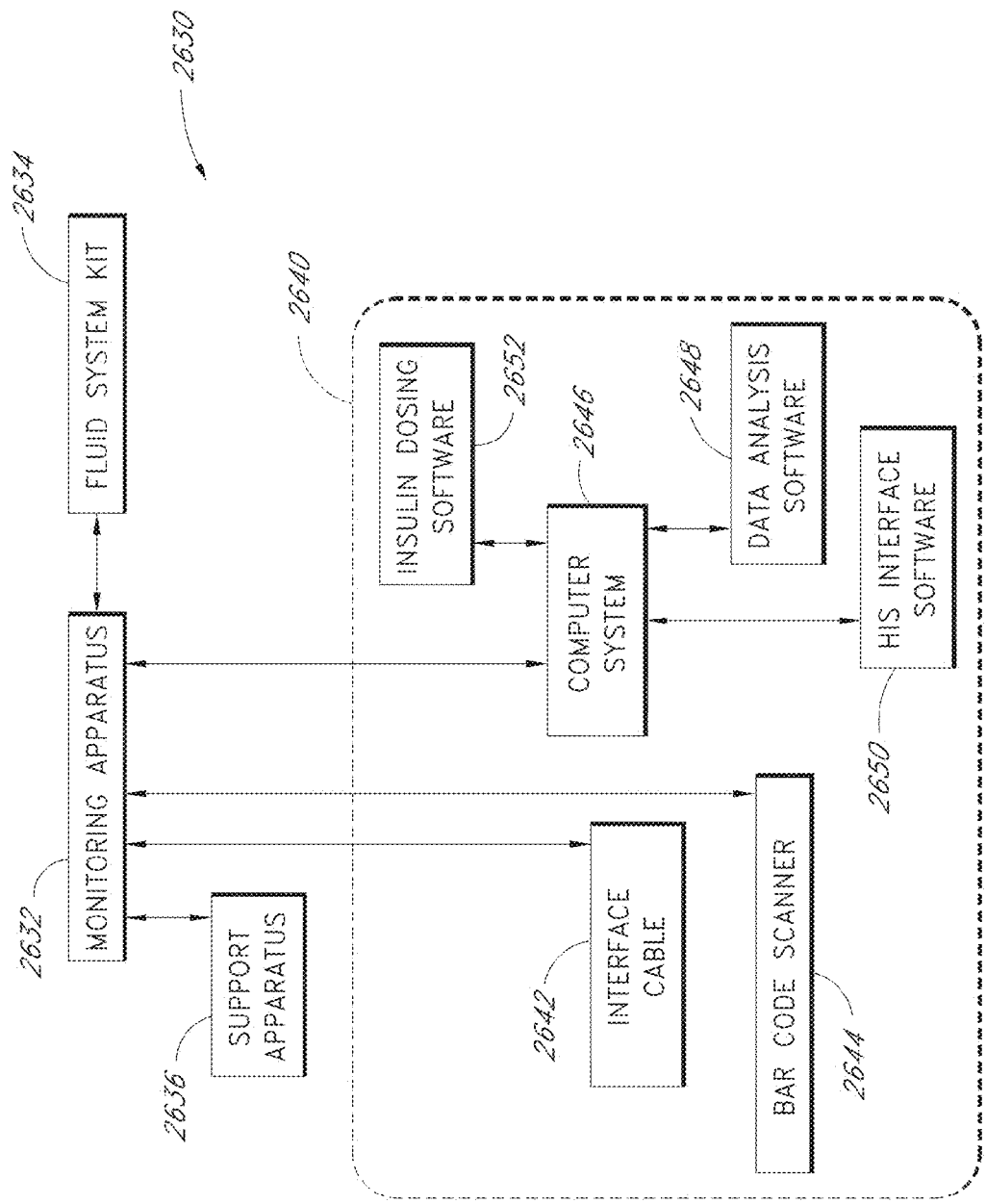
FIG. 26 schematically depicts various components and/or aspects of a patient monitoring system and the relationships among the components and/or aspects.

FIG. 26 schematically depicts various components and/or aspects of a patient monitoring system 2630 and how those components and/or aspects relate to each other. In some embodiments, the monitoring system 2630 can be the apparatus 100 for withdrawing and analyzing fluid samples. Some of the depicted components can be included in a kit containing a plurality of components. Some of the depicted components, including, for example, the components represented within the dashed rounded rectangle 2640 of FIG. 26, are optional and/or can be sold separately from other components.

The patient monitoring system 2630 shown in FIG. 26 includes a monitoring apparatus 2632. The monitoring apparatus 2632 can be the monitoring device 102, shown in FIG. 1 and/or the system 400 of FIG. 4. The monitoring apparatus 2632 can provide monitoring of physiological parameters of a patient. In some embodiments, the monitoring apparatus 2632 measures glucose and/or lactate concentrations in the patient's blood. In some embodiments, the measurement of such physiological parameters is substantially continuous. The monitoring apparatus 2632 may also measure other physiological parameters of the patient. In some embodiments, the monitoring apparatus 2632 is used in an intensive care unit (ICU) environment. In some embodiments, one monitoring apparatus 2632 is allocated to each patient room in an ICU.

The patient monitoring system 2630 can include an optional interface cable 2642. In some embodiments, the interface cable 2642 connects the monitoring apparatus 2632 to a patient monitor (not shown). The interface cable 2642 can be used to transfer data from the monitoring apparatus 2632 to the patient monitor for display. In some embodiments, the patient monitor is a bedside cardiac monitor having a display that is located in the patient room (see, e.g., the user interface 2400 shown in FIG. 24 and FIG. 25.) In some embodiments, the interface cable 2642 transfers data from the monitoring apparatus 2632 to a central station monitor and/or to a hospital information system (HIS). The ability to transfer data to a central station monitor and/or to a HIS may depend on the capabilities of the patient monitor system.

In the embodiment shown in FIG. 26, an optional bar code scanner 2644 is connected to the monitoring apparatus 2632. In some embodiments, the bar code scanner 2644 is used to enter patient identification codes, nurse identification codes, and/or other identifiers into the monitoring apparatus 2632. In some embodiments, the bar code scanner 2644 contains no moving parts. The bar code scanner 2644 can be operated by manually sweeping the scanner 2644 across a printed bar code or by any other suitable means. In some embodiments, the bar code scanner 2644 includes an elongated housing in the shape of a wand.

The patient monitoring system 2630 includes a fluid system kit 2634 connected to the monitoring apparatus 2632. In some embodiments, the fluid system kit 2634 includes fluidic tubes that connect a fluid source to an analytic subsystem. For example, the fluidic tubes can facilitate fluid communication between a blood source or a saline source and an assembly including a sample holder and/or a centrifuge. In some embodiments, the fluid system kit 2634 includes many of the components that enable operation of the monitoring apparatus 2632. In some embodiments, the fluid system kit 2634 can be used with anti-clotting agents (such as heparin), saline, a saline infusion set, a patient catheter, a port sharing IV infusion pump, and/or an infusion set for an IV infusion pump, any or all of which may be made by a variety of manufacturers. In some embodiments, the fluid system kit 2634 includes a monolithic housing that is sterile and disposable. In some embodiments, at least a portion of the fluid system kit 2634 is designed for single patient use. For example, the fluid system kit 2634 can be constructed such that it can be economically discarded and replaced with a new fluid system kit 2634 for every new patient to which the patient monitoring system 2630 is connected. In addition, at least a portion of the fluid system kit 2634 can be designed to be discarded after a certain period of use, such as a day, several days, several hours, three days, a combination of hours and days such as, for example, three days and two hours, or some other period of time. Limiting the period of use of the fluid system kit 2634 may decrease the risk of malfunction, infection, or other conditions that can result from use of a medical apparatus for an extended period of time.

In some embodiments, the fluid system kit 2634 includes a connector with a luer fitting for connection to a saline source. The connector may be, for example, a three-inch pigtail connector. In some embodiments, the fluid system kit 2634 can be used with a variety of spikes and/or IV sets used to connect to a saline bag. In some embodiments, the fluid system kit 2634 also includes a three-inch pigtail connector with a luer fitting for connection to one or more IV pumps. In some embodiments, the fluid system kit 2634 can be used with one or more IV sets made by a variety of manufacturers, including IV sets obtained by a user of the fluid system kit 2634 for use with an infusion pump. In some embodiments, the fluid system kit 2634 includes a tube with a low dead volume luer connector for attachment to a patient vascular access point. For example, the tube can be approximately seven feet in length and can be configured to connect to a proximal port of a cardiovascular catheter. In some embodiments, the fluid system kit 2634 can be used with a variety of cardiovascular catheters, which can be supplied, for example, by a user of the fluid system kit 2634.

As shown in FIG. 26, the monitoring apparatus 2632 is connected to a support apparatus 2636, such as an IV pole. The support apparatus 2636 can be customized for use with the monitoring apparatus 2632. A vendor of the monitoring apparatus 2632 may choose to bundle the monitoring apparatus 2632 with a custom support apparatus 2636. In some embodiments, the support apparatus 2636 includes a mounting platform for the monitoring apparatus 2632. The mounting platform can include mounts that are adapted to engage threaded inserts in the monitoring apparatus 2632. The support apparatus 2636 can also include one or more cylindrical sections having a diameter of a standard IV pole, for example, so that other medical devices, such as IV pumps, can be mounted to the support apparatus. The support apparatus 2636 can also include a clamp adapted to secure the apparatus to a hospital bed, an ICU bed, or another variety of patient conveyance device.

In the embodiment shown in FIG. 26, the monitoring apparatus 2632 is electrically connected to an optional computer system 2646. The computer system 2646 can comprise one or multiple computers, and it can be used to communicate with one or more monitoring devices. In an ICU environment, the computer system 2646 can be connected to at least some of the monitoring devices in the ICU. The computer system 2646 can be used to control configurations and settings for multiple monitoring devices (for example, the system can be used to keep configurations and settings of a group of monitoring devices common). The computer system 2646 can also run optional software, such as data analysis software 2648, HIS interface software 2650, and insulin dosing software 2652.

In some embodiments, the computer system 2646 runs optional data analysis software 2648 that organizes and presents information obtained from one or more monitoring devices. In some embodiments, the data analysis software 2648 collects and analyzes data from the monitoring devices in an ICU. The data analysis software 2648 can also present charts, graphs, and statistics to a user of the computer system 2646.

In some embodiments, the computer system 2646 runs optional hospital information system (HIS) interface software 2650 that provides an interface point between one or more monitoring devices and an HIS. The HIS interface software 2650 may also be capable of communicating data between one or more monitoring devices and a laboratory information system (LIS).

In some embodiments, the computer system 2646 runs optional insulin dosing software 2652 that provides a platform for implementation of an insulin dosing regimen. In some embodiments, the hospital tight glycemic control protocol is included in the software. The protocol allows computation of proper insulin doses for a patient connected to a monitoring device 2646. The insulin dosing software 2652 can communicate with the monitoring device 2646 to ensure that proper insulin doses are calculated.

Analyte Control and Monitoring

In some embodiments, it may be advantageous to control a level of an analyte (e.g., glucose) in a patient using an embodiment of an analyte detection system described herein. Although certain examples of glucose control are described below, embodiments of the systems and methods disclosed herein may be used to monitor and/or control other analytes (e.g., lactate).

For example, diabetic individuals control their glucose levels by administration of insulin. If a diabetic patient is admitted to a hospital or ICU, the patient may be in a condition in which he or she cannot self-administer insulin. Advantageously, embodiments of the analyte detection systems disclosed herein may be used to control the level of glucose in the patient. Additionally, it has been found that a majority of patients admitted to the ICU exhibit hyperglycemia without having diabetes. In such patients it may be beneficial to monitor and control their blood glucose level to be within a particular range of values. Further, it has been shown that tightly controlling blood glucose levels to be within a stringent range may be beneficial to patients undergoing surgical procedures.

A patient admitted to the ICU or undergoing surgery may be administered a variety of drugs and fluids such as Hetastarch, intravenous antibiotics, intravenous glucose, intravenous insulin, intravenous fluids such as saline, etc., which may act as interferents and make it difficult to determine the blood glucose level. Moreover, the presence of additional drugs and fluids in the blood stream may require different methods for measuring and controlling blood glucose level. Also, the patient may exhibit significant changes in hematocrit levels due to blood loss or internal hemorrhage, and there can be unexpected changes in the blood gas level or a rise in the level of bilirubin and ammonia levels in the event of an organ failure. Embodiments of the systems and methods disclosed herein advantageously may be used to monitor and control blood glucose (and/or other analytes) in the presence of possible interferents to estimation of glucose and for patients experiencing health problems.

In some environments, Tight Glycemic Control (TGC) can include: (1) substantially continuous monitoring (which can include periodic monitoring, at relatively frequent intervals of every 1, 5, 15, 30, 45, and/or 60 minutes, for example) of glucose levels; (2) determination of substances that tend to increase glucose levels (e.g., sugars such as dextrose) and/or decrease glucose levels (e.g., insulin); and/or (3) responsive delivery of one or more of such substances, if appropriate under the controlling TGC protocol. For example, one possible TGC protocol can be achieved by controlling glucose within a relatively narrow range (for example between 70 mg/dL to 110 mg/dL). As will be further described, in some embodiments, TGC may be achieved by using an analyte monitoring system to make continuous and/or periodic but frequent measurements of glucose levels.

In some embodiments, the analyte detection system schematically illustrated in FIGS. 4, 5, and 6 may be used to regulate the concentration of one or more analytes in the sample in addition to determining and monitoring the concentration of the one or more analytes. In some cases, the analyte detection system may be used in an ICU to monitor (and/or control) analytes that may be present in patients experiencing trauma. In some implementations, the concentration of the analytes is regulated to be within a certain range. The range may be predetermined (e.g., according to a hospital protocol or a physician's recommendation), or the range may be adjusted as conditions change.

In an example of glycemic control, a system can be used to determine and monitor the concentration of glucose in the sample. If the concentration of glucose falls below a lower threshold, glucose from an external source can be supplied. If the concentration of glucose increases above an upper threshold, insulin from an external source can be supplied. In some embodiments, glucose or insulin may be infused in a patient continuously over a certain time interval or may be injected in a large quantity at once (referred to as "bolus injection").

In some embodiments, a glycemic control system may be capable of delivering glucose, dextrose, glycogen, and/or glucagon from an external source relatively quickly in the event of hypoglycemia. As discussed, embodiments of the glycemic control system may be capable of delivering insulin from an external source relatively quickly in the event of hyperglycemia.

Returning to FIGS. 5 and 6, these figures schematically illustrate embodiments of a fluid handling system that comprise optional analyte control subsystems 2780. The analyte control subsystem 2780 may be used for providing control of an analyte such as, e.g., glucose, and may provide delivery of the analyte and/or related substances (e.g., dextrose solution and/or insulin in the case of glucose). The analyte control subsystem 2780 comprises a source 2782 such as, for example, the analyte (or a suitable compound related to the analyte) dissolved in water or saline. For example, if the analyte is glucose, the source 2782 may comprise a bag of dextrose solution (e.g., Dextrose or Dextrose 50%). The source 2782 can be coupled to an infusion pump (not shown). The source 2782 and the infusion pump can be provided separately from the analyte control subsystem 2780. For example, a hospital advantageously can use existing dextrose bags and infusion pumps with the subsystem 2780.

As schematically illustrated in FIGS. 5 and 6, the source 2782 is in fluid communication with the patient tube 512 via a tube 2784 and suitable connectors. A pinch valve 2786 may be disposed adjacent the tube 2784 to regulate the flow of fluid from the source 2782. A patient injection port can be located at a short distance from the proximal port of the central venous catheter or some other catheter connected to the patient.

In an example implementation for glycemic control, if the analyte detection system determines that the level of glucose has fallen below a lower threshold value (e.g., the patient is hypoglycemic), a control system (e.g., the fluid system controller 405 in some embodiments) controlling an infusion delivery system may close the pinch valves 521 and/or 542 to prevent infusion of insulin and/or saline into the patient. The control system may open the pinch valve 2786 and dextrose solution from the source 2782 can be infused (or alternatively injected as a bolus) into the patient. After a suitable amount of dextrose solution has been infused to the patient, the pinch valve 2786 can be closed, and the pinch valves 521 and/or 542 can be opened to allow flow of insulin and/or saline. In some systems, the amount of dextrose solution for infusion (or bolus injection) may be calculated based on one or more detected concentration levels of glucose. The source 2782 advantageously may be located at a short enough fluidic distance from the patient such that dextrose can be delivered to the patient within a time period of about one to about ten minutes. In other embodiments, the source 2782 can be located at the site where the patient tube 512 interfaces with the patient so that dextrose can be delivered within about one minute.

If the analyte detection system determines that the level of glucose has increased above an upper threshold value (e.g., the patient is hyperglycemic), the control system may close the pinch valves 542 and/or 2786 to prevent infusion of saline and/or dextrose into the patient. The control system may open the pinch valve 521, and insulin can be infused (or alternatively injected as a bolus) into the patient. After a suitable amount of insulin has been infused (or bolus injected) to the patient, the control system can close the pinch valve 521 and open the pinch valves 542 and/or 2786 to allow flow of saline and/or glucose. The suitable amount of insulin may be calculated based on one or more detected concentration levels of glucose in the patient. The insulin source 518 advantageously may be located at a short enough fluidic distance from the patient such that insulin can be delivered to the patient within about one to about ten minutes. In other embodiments, the insulin source 518 may be located at the site where the patient tube 512 interfaces with the patient so that insulin can be delivered to the patient within about one minute.

In some embodiments, sampling bodily fluid from a patient and providing medication to the patient may be achieved through the same lines of the fluid handling system. For example, in some embodiments, a port to a patient can be shared by alternately drawing samples and medicating through the same line. In some embodiments, a bolus can be provided to the patient at regular intervals (in the same or different lines). For example, a bolus of insulin can be provided to a patient after meals. In another embodiment comprising a shared line, a bolus of medication can be delivered when returning part of a body fluid sample back to the patient. In some implementations, the bolus of medication is delivered midway between samples (e.g., every 7.5 minutes if samples are drawn every 15 minutes). In other embodiment, a dual lumen tube can be used, wherein one lumen is used for the sample and the other lumen to medicate. In yet another embodiment, an analyte detection system (e.g., an OPTISCANNER™ monitor) may provide suitable commands to a separate insulin pump (on a shared port or different line).

Example Method for Glycemic Control

Figure 27:
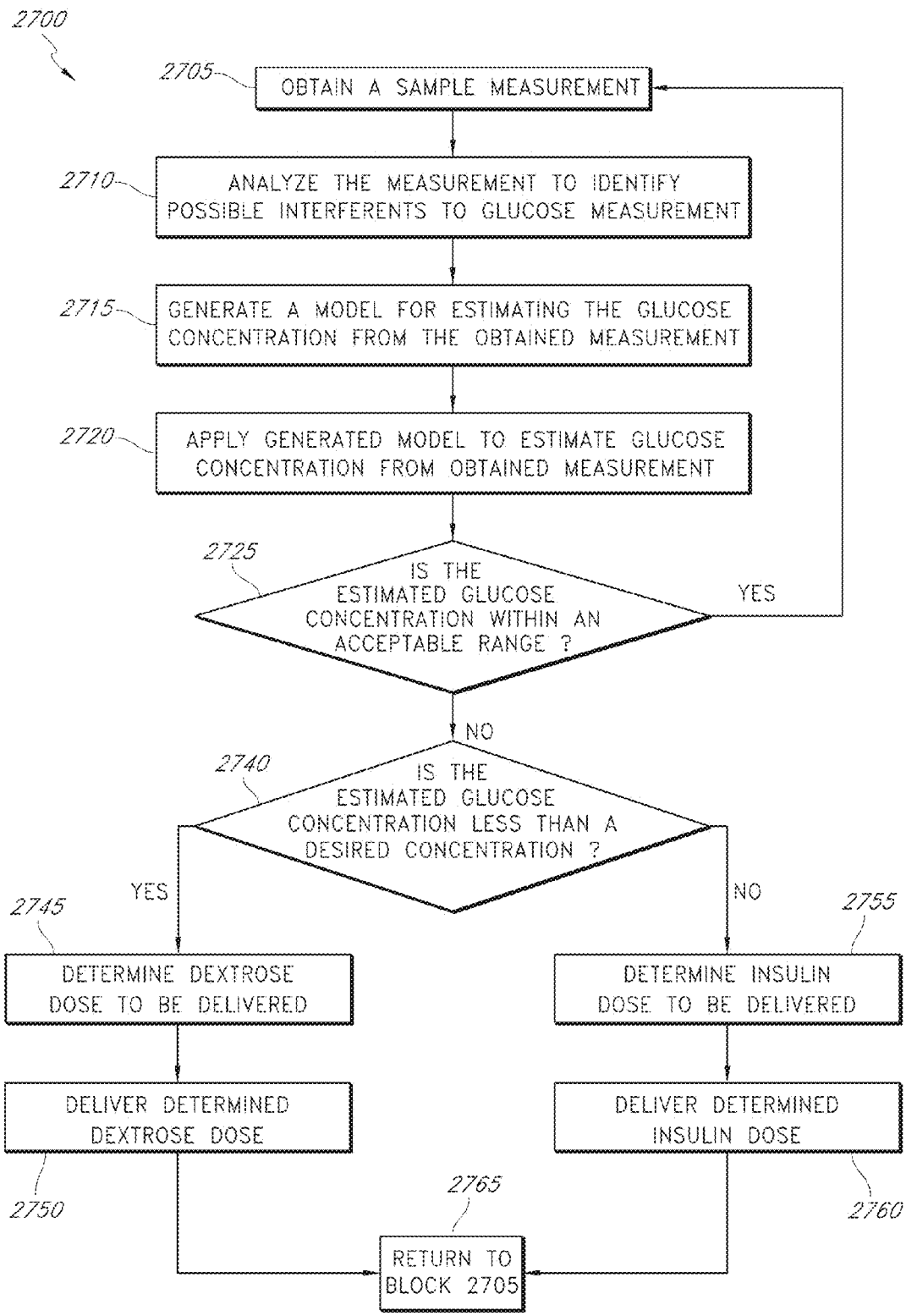
FIG. 27 is a flowchart that schematically illustrates an embodiment of a method of providing glycemic control.

FIG. 27 is a flowchart that schematically illustrates an example embodiment of a method 2700 of providing analyte control. The example embodiment is directed toward one possible implementation for glycemic control (including but not limited to tight glycemic control) and is intended to illustrate certain aspects of the method 2700 and is not intended to limit the scope of possible analyte control methods. In block 2705, a glucose monitoring apparatus (e.g., the monitoring apparatus 2632 of FIG. 26) draws a sample (e.g., a blood or blood plasma sample) from a sample source (e.g., a patient) and obtains a measurement from the sample (e.g., a portion of the drawn sample). The measurement may comprise an optical measurement such as, for example, an infrared spectrum of the sample. In block 2710, the measurement sample is analyzed to identify possible interferents to an estimation of the glucose concentration in the measurement sample. In block 2715, a model is generated for estimating the glucose concentration from the obtained measurement. In some embodiments, models developed from the algorithms describe above with reference to FIGS. 21-23 are used. The generated model may reduce or minimize effects of the identified interferents on the estimated glucose concentration, in certain embodiments. In block 2720, an estimated glucose concentration is determined from the model and the obtained measurement. In block 2725, the estimated glucose concentration in the sample is compared to an acceptable range of concentrations. The acceptable range may be determined according to a suitable glycemic control protocol such as, for example, a TGC protocol. For example, in certain TGC protocols the acceptable range may be a glucose concentration in a range from about 70 mg/dL to about 110 mg/dL. If the estimated glucose concentration lies within the acceptable range, the method 2700 returns to block 2705 to obtain the next sample measurement, which may be made within about one to about thirty minutes (e.g., every fifteen minutes).

In block 2725, if the estimated glucose concentration is outside the acceptable range of concentrations, then the method 2700 proceeds to block 2740 in which the estimated glucose concentration is compared with a desired glucose concentration. The desired glucose concentration may be based on, for example, the acceptable range of glucose concentrations, the parameters of the particular glycemic protocol, the patient's estimated glucose concentration, and so forth. If the estimated glucose concentration is below the desired concentration (e.g., the patient is hypoglycemic), a dose of dextrose to be delivered to the patient is calculated in block 2745. This calculation may take into account various factors including, for example, one or more estimated glucose concentrations, presence of additional drugs in the patient's system, time taken for dextrose to be assimilated by the patient, and the delivery method (e.g., continuous infusion or bolus injection). In block 2750, a fluid delivery system (e.g., a system such as the optional subsystem 2780 shown in FIGS. 5 and 6) delivers the calculated dose of dextrose to the patient.

In block 2740, if the estimated glucose concentration is greater than the desired concentration (e.g., the patient is hyperglycemic), a dose of insulin to be delivered is calculated in block 2755. The dose of insulin may depend on various factors including, for example, one or more estimated glucose concentrations in the patient, presence of other drugs, type of insulin used, time taken for insulin to be assimilated by the patient, method of delivery (e.g., continuous infusion or bolus injection), etc. In block 2750, a fluid delivery system (e.g., the optional subsystem 2780 shown in FIGS. 5 and 6) delivers the calculated dose of insulin to the patient.

In block 2765, the method 2700 returns to block 2705 to await the start of the next measurement cycle, which may be within about one to about thirty minutes (e.g., every fifteen minutes). In some embodiments, the next measurement cycle begins at a different time than normally scheduled in cases in which the estimated glucose concentration lies outside the acceptable range of concentrations under the glycemic protocol. Such embodiments advantageously allow the system to monitor response of the patient to the delivered dose of dextrose (or insulin). In some such embodiments, the time between measurement cycles is reduced so the system can more accurately monitor analyte levels in the patient.

Examples of Some Possible Additional or Alternative Analytes

Although examples of control and/or monitoring has been described in the illustrative context of glycemic control, embodiments of the systems and methods can be configured for control and/or monitoring of one or more of many possible analytes, in addition to or instead of glucose. Monitor and/or control of analytes may be particularly helpful in ICUs, which receive patients experiencing trauma. For example, another parameter that can be monitored is level of Hemoglobin (Hb). If the Hb level of a patient goes down without an apparent external reason, the patient could be suffering from internal bleeding. Indeed, many ICU patients (some estimate as many as 10%) suffer from what appears to be spontaneous internal bleeding that may not be otherwise detectable until the consequences are too drastic to easily overcome. In some embodiments, level of Hb can be measured indirectly, because its relationship to oxygen in the veins and arteries (at different points in the vasculature with respect to the heart and lungs) is understood. In some embodiments, the apparatus, systems and methods described herein can be useful for measuring a level of Hb.

Another parameter that can be monitored is lactate level, which can be related to sepsis or toxic shock. Indeed, high levels and/or rapid rise in lactate levels can be correlated to organ failure and oxygenation problems in the blood and organs. However, other direct measures of the biological effects related to lactate level problems can be difficult to measure, for example, only becoming measurable with a delay (e.g., 2-6 hours later). Thus, measurement of lactate level can help provide a valuable early warning of other medical problems. Indeed, if a problem with lactate levels is detected, a nurse or doctor may be able to prevent the correlated problems by providing more fluids.

Another parameter that can be monitored is central venous oxygen saturation (ScvO2). It can be advantageous to try to maintain a ScvO2 of 65-70% or greater in ICU patients (to help avoid sepsis, for example). In some embodiments, the apparatus, systems, and methods described herein can be useful for measuring a level of ScvO2.

Levels of lactate and ScvO2 in a patient can be used together to provide information and/or warnings to a health care provider, which can be especially useful in an ICU setting. For example, if lactate and ScvO2 are both high, a warning can be provided (e.g., automatically using an alarm). If lactate is high, but ScvO2 is low, a patient may benefit from additional fluids. If ScvO2 is high, but lactate is low, a cardiac problem may be indicated. Thus, a system that provides information about both lactate and ScvO2 can be very beneficial to a patient, especially, for example, in the ICU environment. Although lactate and ScvO2 have been used as an illustrative example, in other embodiments different combinations of analytes may be monitored and used to provide information and/or warnings to a health care provider.

An analyte monitoring apparatus can be usefully configured to draw blood from the body and analyze a portion of that blood. One useful assumption to make is that the drawn and analyzed blood is representative of the other blood that remains in the body and is not analyzed. This can be a valid assumption in many cases because blood flow in the body is a turbulent process, with the heart urging the blood through vessels and organs and tissue having various diameters and various levels of flow resistance. Indeed, there can be a great amount of variation in the flow rate of blood as it passes through the many regions of the body. This turbulence and variation of flow rates will tend to mix blood within the body, which will prevent blood in one part of the body from having a substantially different composition than blood in other parts of the body.

An analyte monitoring apparatus can also be usefully configured to be inserted into the body, and, for example, into the blood stream. This can have the advantage of eliminating any need to transport the blood out of the body; it can also introduce other potential risks. However, even if a monitoring device is inserted into the body, at any given time the device is likely only capable of measuring an analyte in a limited portion of the blood—for example, the blood that is in contact with (or within the view of) a sensor in the device. Thus, even in this case it is useful to assume that this limited portion of the blood is representative of the other blood in the body.

Some systems do not measure over a fixed amount of blood, but instead assume a constant relationship between the analyte in local blood and the amount of blood overall in the body. Such a constant relationship can be referred to as a stoichiometric relationship. If this assumption is inaccurate, results of the analysis can be inaccurate. This potential problem can be amplified when measurements are taken, for example, in a portion of the blood flow that has a varying rate of the analyte (e.g., for physiological reasons). For example, measurement of oxygen in the blood inside the lungs can be difficult over time because the lungs introduce blood into the oxygen periodically but at relatively short intervals. An indwelling system that is constantly measuring the glucose level of the blood that flows by and/or through its sensors may provide a reading that is too local and not provide a consistently useful overview of the amount of analyte generally present in the body as a whole. One way to avoid inaccuracies due to failures of this assumption is to measure an amount of analyte in a fixed amount of blood, drawn from a portion of the bloodstream that is physiologically likely to maintain a relatively constant level of the analyte in question. In many cases, the larger the blood sample, the less likely it will be to reflect misleading and/or temporary local distortions in an analyte level. Accordingly, ex-vivo systems that withdraw blood can have some advantages over systems with sensors that are inserted into the body notwithstanding the potential difficulties of repeatedly withdrawing blood out of the body and reducing clot risk in ex-vivo fluid systems.

Patient Connector Configured to Reduce Flow Separation

In systems and devices including fluid flow through a tube or a channel, the fluid can flow at different speeds and have different flow patterns at different positions across the width of the tube. For example, the layer of fluid flowing close to the inner walls of the tube or channel, also referred to as the boundary layer, can exhibit either laminar flow or turbulent flow. In various embodiments, when the boundary layer travels far enough against an opposing pressure gradient, the speed of the boundary layer can fall almost to zero. The fluid flow can become detached from the surface of the object and can form eddies and vortices. Flow separation can also occur in systems and devices including fluid flow across a junction (e.g. at a junction of two tubes or fluid channels having different internal diameters, or at a junction across two connectors). The speed of the flow will generally transition smoothly from a first speed to a second speed if the junction has a substantially smooth transition. In systems where the speed of the flow transitions smoothly from a first speed to a second speed across a junction, the flow can be generally along the internal walls of the connectors and tubes included in the junction. However, if the junction has an abrupt or a substantially unsmooth transition, then the fluid flow can also exhibit an abrupt or a substantially unsmooth transition from a first speed to a second speed. In systems where the speed of the flow transitions abruptly or substantially not smoothly from a first speed to a second speed across a junction, the flow can be disrupted and need not generally be along the internal walls of the connectors and tubes included in the junction. In various embodiments of the analyte monitoring system described herein, it is advantageous to prevent or substantially reduce separated fluid flow within various tubes and channels and across the various fluidic junctions. As discussed above, when fluid flow in the fluidic channels and tubes or across various fluidic junctions separates, the speed of the fluid within the boundary layer can fall almost to zero and the fluid flow can stagnate. This stagnation of the fluid flow can result in accumulation of the fluid along the walls of the fluidic channels and tubes and/or at the various fluidic junctions. Accumulation of fluid can result in clogging of the fluidic channels and/or tubes and fluidic junctions especially when the fluid comprises a bodily fluid such as blood that can coagulate. Thus, in various embodiments, preventing or reducing separated flow across the various fluidic junctions during withdrawing the sample from the patient and returning the unused sample back to the patient can substantially increase the time over which the tubes and connectors in the analyte monitoring system can be used, since the tubes and connectors may not clog as frequently when separated flow is prevented or substantially reduced. For example, in various embodiments prevent the tubes and the connectors connecting the analyte monitoring system to the patient can be used for several days before they have to be changed and/or cleaned if separated flow is prevented or substantially reduced within the various tubes and channels and across the various fluidic junctions when withdrawing or returning a sample from or to the patient.

Various embodiments of the patient connector configured to prevent or substantially reduce separated flow can allow connection of the analyte monitoring system to different types of patient catheters, for example, central venous catheter (CVC), peripherally inserted central catheter (PICC), and/or peripheral IV catheters. Various embodiments of the patient connector described herein can also connect to other embodiments catheters not disclosed above. CVCs can be generally used when a substantially large amount of fluid is required and the vascular access is compromised or unavailable. For example, vascular access can be compromised if peripheral veins are either unavailable or not available in sufficient quantity. In various embodiments, the CVC may include multiple lumens (e.g. 2, 3 or 5). In various embodiments of the CVC, the diameter of the inlet can be approximately equal to the diameter of the outlet. In some embodiments, the analyte monitoring system described above can connect to the proximal port of the CVC. In various embodiments, the proximal port can be the port wherein the outlet of the infusate is the closest to the caregiver or medical practitioner. In some embodiments, the proximal port can be the port wherein the outlet of the infusate is farthest from the inserted tip of the catheter. In various embodiments, an advantage of using the proximal port of the CVC is that no other medications or drugs are infused through this port. Another advantage of using the proximal CVC port is that because the flow rate in the central cavity of the heart where the catheter is placed is substantially large, the downstream infusions (from the mid or the distal port) do not substantially mix with the blood in the area of the proximal port. Thus the withdrawn blood can be substantially undiluted and have substantially less number of interfering compounds thereby resulting in substantially accurate measurements. Generally, heath care practitioners can use the proximal port for drawing blood for analysis, but they may clamp the other ports of the CVC (e.g. distal or mid ports) while blood is being drawn from the proximal port. Various embodiments of the analyte monitoring system employ novel push/pull fluidics systems that allow the use of the proximal port of the CVC while other ports (e.g. mid or distal ports) are in use as well because the various embodiments of the analyte monitoring system described herein can withdraw the sample at a slower rate than a health care practitioner would.

PICCs can be threaded from the hand to the same chamber as the CVC. In various embodiments of the PICCs, the diameter of the inlet can be approximately equal to the diameter of the outlet. Various embodiments of the PICC lines can offer a lower risk for the patient in terms of hospital acquired infection. In various embodiments, it's easier to keep PICC lines free of infection. In some embodiments, the location of the PICC lines can reduce the risk of infection to a patient. Various embodiments of the PICC lines including single outlet or multiple outlets can be used with the various embodiments of the analyte monitoring system described above. For example, in some embodiments of the analyte monitoring system (e.g. the OptiScan® device) a two channel multiple outlet PICC can be used. The outlets of the two channel multiple outlet PICC can be spaced apart. Various embodiments of the analyte monitoring system described above can use a dedicated outlet port of the PICC line with no other medications or drugs flowing in or out of the PICC line. An advantage of having a dedicated outlet port is a reduced risk of contamination or dilution of the sample thereby substantially increasing the accuracy of the measurement. In various embodiments, the analyte monitoring system described above can use a single channel PICC having a single outlet that is dedicated to the analyte monitoring system.

Peripheral IV catheters (Peripherals) are short catheters (e.g. having a 1-2" tip on a conical shaped body) that are inserted directly into the peripheral vein of an arm or hand of the patient. In various embodiments of the analyte monitoring system including peripheral IV catheter, the peripheral IV catheter can be connected to the antecubital vein or the median cubital vein. Various embodiments of the analyte monitoring including the peripheral IV catheters can be used in an Emergency Room setting, a clinical setting, or an intermediary care setting where a central line access and/or professionals trained in the placement of CVCs or PICCs are unavailable. Various embodiments of the analyte monitoring including the peripheral IV catheters can also be used in ICU settings. Various embodiments of the analyte monitoring including the peripheral IV catheters can also be used to monitor and control the glucose and other analyte levels in patients who have undergone surgery such as Coronary Artery Bypass Grafting (CABG) surgery or some other surgery, which may make placing a CVC line difficult.

Various embodiments of the peripheral IV catheters can be substantially different in shape as compared to the CVCs or PICCs. Thus, the peripheral IV catheters can have different flow dynamics as compared to the CVCs or PICCs. For example, in some embodiments, the peripheral IV catheters can have a tapering body which narrows down to a tip that is constant and is substantially smaller in outer diameter than the largest circumference of the body of the Various embodiments of the analyte monitoring including the peripheral IV catheters can also be used in ICU settings. This shape of the peripheral IV catheters can cause a backpressure when a fluid is flushed through the peripheral IV catheter. The backpressure can cause a build up of the fluid along the inner walls of the peripheral IV catheter which can result in clogging of the catheter. The backpressure on the fluid is substantially reduced in catheters not having such a shape (e.g. a CVC or a PICC). As discussed, above a patient connector configured to prevent or substantially reduce separated fluid flow when connected to the peripheral IV catheter can reduce the fluid buildup in the catheter and/or the connector and thus reduce the time over which the catheter and/or the connector will clog.

Figure 28A:
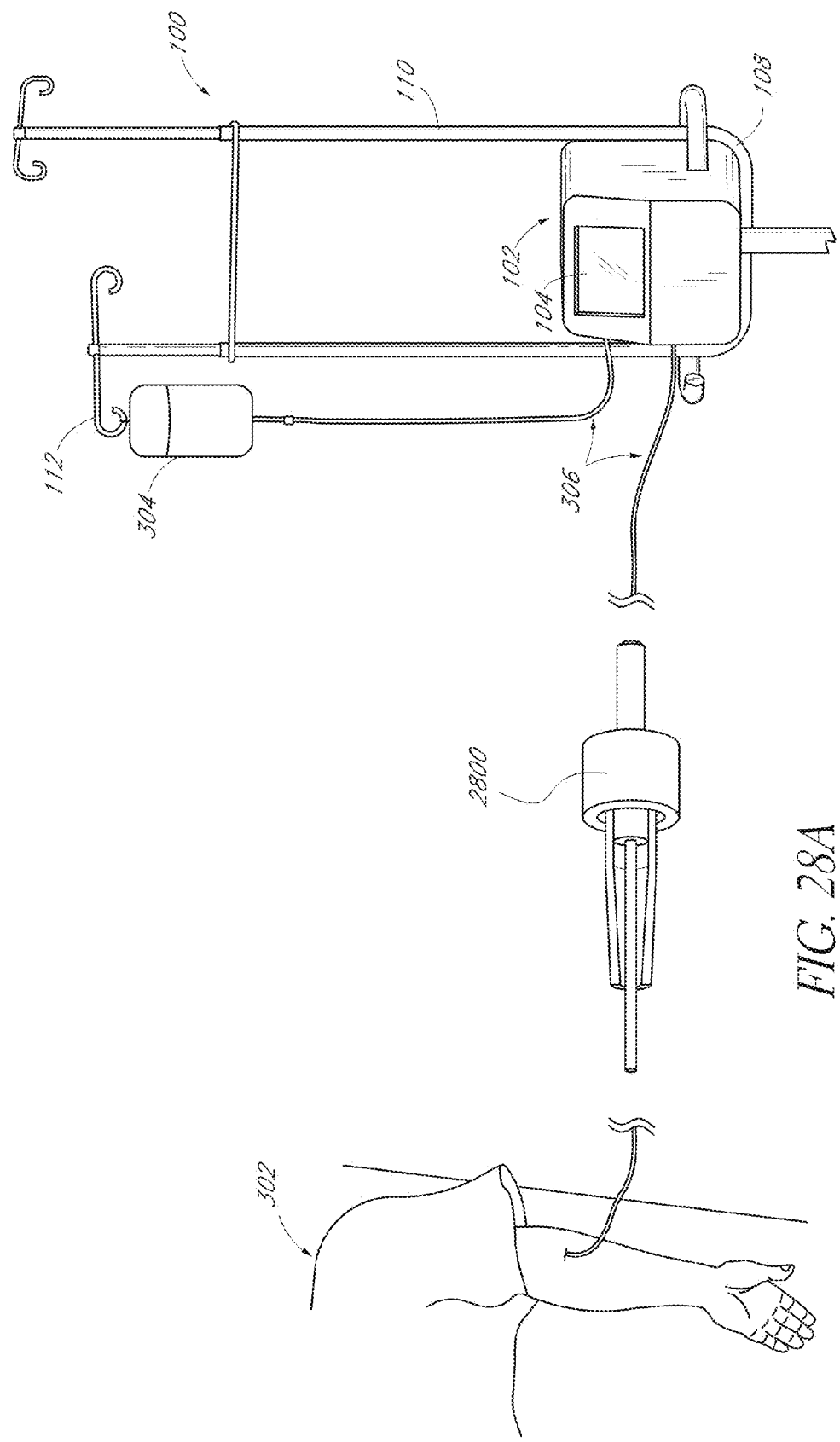
FIG. 28A illustrates a cross-section of a male Luer hub connector.
Figure 28B:
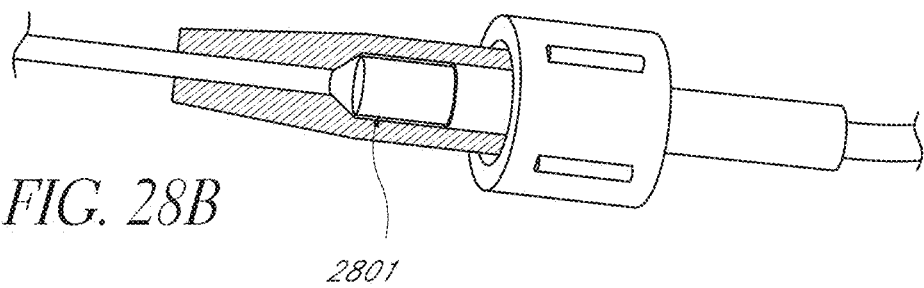
FIG. 28B illustrates a cross-section of a male Luer extended to take up volume in a catheter Luer.

FIG. 28A shows a cross-sectional view of a male Luer hub connector 2800 which conforms to the primary standards for dimensional and performance requirements (e.g. ISO 594). The connector 2800 can be used to connect the apparatus 100 of FIG. 1 to a patient 302 as shown in FIG. 28A. As discussed above with reference to FIG. 1 and FIG. 3, the monitoring device 102 can be used to determine the concentration of one or more substances in a sample fluid. The sample fluid can come from the patient 302, as illustrated in FIG. 28B. The male Luer hub connector may be manufactured by a variety of manufacturers (e.g. C.R. Bard International Ltd., Cook Medical, etc.). FIG. 28B shows a cross-sectional view of a standard male Luer hub connector including an extension region 2801. The extension region 2801 can reduce dead-space volume in the catheter. The advantages of including the extension region 2801 are discussed in U.S. patent application Ser. No. 12/122,009 filed on May 16, 2008 titled "LOW-VOLUME FITTINGS" (U.S. Publication No. 2008-0284167) which is incorporated by reference herein in its entirety. The shapes of various embodiments of the extension region 2801 and the materials used to form the extension regions are also discussed in detail in U.S. patent application Ser. No. 12/122,009 filed on May 16, 2008 titled "LOW-VOLUME FITTINGS" (U.S. Publication No. 2008-0284167) which is incorporated by reference herein in its entirety. FIGS. 29A-29D illustrate various embodiments of standard Luer connectors 2900, 2901, 2902 and 2903 (e.g. Bard, Cook and Arrow Luer connectors) conforming to ISO Luer standards that include an extension region 2901. The structure, materials and advantages of the different Luer connectors including an extension are discussed in detail in U.S. patent application Ser. No. 12/122,009 filed on May 16, 2008 titled "LOW-VOLUME FITTINGS" (U.S. Publication No. 2008-0284167) which is incorporated by reference herein in its entirety.

FIGS. 30A and 30B illustrate embodiments of a patient connector 3000 including a flow director configured to prevent or substantially reduce separated flow. In various embodiments, the patient connector 3000 can comprise a standard male Luer connector 3001 and a flow director 3002. In various embodiments, a spin lock ring may be provided to the standard male Luer connector which can partially overlap a standard female Luer connector that mates with the standard male Luer connector 3001. In various embodiments, the spin lock ring can be threaded.

FIGS. 30C1-30C3 schematically illustrate different views for an embodiment of a patient connector similar to the embodiments shown in FIGS. 30A and 30B. FIG. 30C1 shows a perspective view of an embodiment of the patient connector. The patient connector shown in FIG. 30C1 comprises three parts viz. a male Luer connector 3003, a flow director 3004 and a spin lock ring 3005. In various embodiments, the male Luer connector 3003 may conform to primary standards for dimensional and performance requirements (e.g. ISO 594). The male Luer connector 3003 is configured to connect with a matching female Luer connector which can have external threads. In various embodiments, the spin lock ring 3005 can surround the male Luer connector 3003. The spin lock ring 3005 can have internal threads 3006 that match with the external threads on the female Luer connector. The spin lock ring 3005 may facilitate a secure connection between the male and the female Luer connectors. The male Luer connector 3003 at its distal end is connected to the analyte monitoring system described herein. In various embodiments, the flow director 3004 is configured to fit into the male Luer connector 3003 as shown in FIG. 30C2 and FIG. 30C3. In various embodiments, the male Luer connector 3003 and the flow director 3004 may be fabricated from a clear polycarbonate material.

FIG. 30C2 shows the side-view of an assembled patient connector with the flow director 3004 fit into the male Luer connector 3003. As shown in FIG. 30C2, in various embodiments, the male Luer connector can include a flange 3006 and a Luer taper 3007. In various embodiments, the length of the Luer connector 3003 between the flange 3006 and the tip of the flow director 3007 can range from approximately 0.56 inches to approximately 0.58 inches. FIG. 30C3 shows a perspective view of the assembled patient connector.

FIGS. 30D1-30D6 show different views of the male Luer connector 3003. FIG. 30D1 is a side view of the male Luer connector 3003 comprising a flange 3006, a Luer taper 3007 and a cylindrical region 3008. FIG. 30D2 shows a view of the Luer connector 3003 through along the line A-A, while FIG. 30D3 shows the perspective of the Luer connector along the line A-A. As seen from FIGS. 30D2 and 30D3, the Luer connector 3003 has a generally circular cross-section in the plane perpendicular to the line A-A. In various embodiments, the Luer connector 3003 may include tubing support spars 3008 as shown in FIGS. 30D2 and 30D3. In various embodiments, the angular separation between two tubing support spars can be approximately 120 degrees. FIG. 30D4 shows another view of the Luer connector 3003 along the line A-A. FIG. 30D5 shows a cross-sectional view of the Luer connector shown in FIG. 30D1 while FIG. 30D6 shows a perspective view of the Luer connector shown in FIG. 30D1.

FIGS. 30E1-30E4 shows different views of the flow director 3004. FIG. 30E1 shows a perspective view of the flow director 3004. The flow director 3004 comprises an elongated region 3009 and a bulbous region 3010. In various embodiments, the bulbous region 3010 can be spherical, frusto-conical, cylindrical or can be enlarged in shape. The bulbous region 3010 can have other shapes as well. The elongated region 3009 is configured to fit in the interior of the male Luer connector 3003. The elongated region 3009 can have a plurality of weld areas 3011 which are configured to contact the internal walls of the male Luer connector 3003 and hold the flow director 3004 in place. The area between the weld areas 3011 which do not contact the internal walls of the male Luer connector 3003 form grooves or channels through which the fluid can flow. In various embodiments, the flow director can have two, three, four or more weld areas.

FIGS. 30E2 and 30E3 show alternate views of the flow director 3004. FIG. 30E4 shows a cross sectional view of the flow director 3004 through the line A-A of FIG. 30E2.

Figure 31:
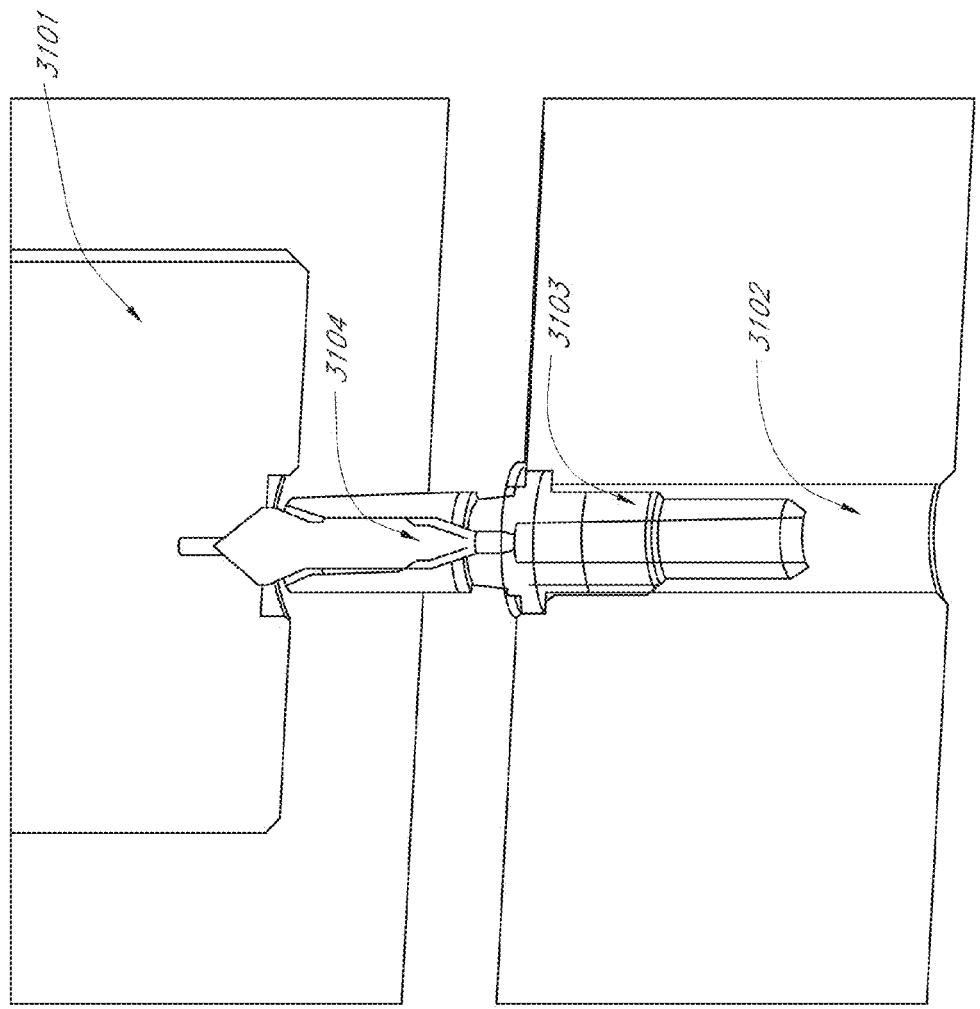
FIG. 31 schematically illustrates a method of bonding the flow director to a male Luer patient connector.

FIG. 31 shows an embodiment of a set-up that is used to attach (e.g. by welding, by joining, by bonding, etc.) the flow director to the internal walls of the Luer connector. The set-up includes an ultrasound device (e.g. an ultrasound horn) 3101 capable of providing ultrasound signals or energy. The set-up further includes a holder 3102 configured to support the male Luer connector 3103 during the attaching process. In various embodiments, the ultrasound device 3101 can be configured to support the flow director 3104 during the attaching process.

During the attaching process, the ultrasound device provides ultrasound energy to the flow director 3102 which causes the weld areas (e.g. 3011 of the flow director 3004) to heat and attach to the internal walls of the male Luer connector 3003. As discussed above, the area between the weld areas forms grooves or channels for allowing fluid flow.

Figure 32A:
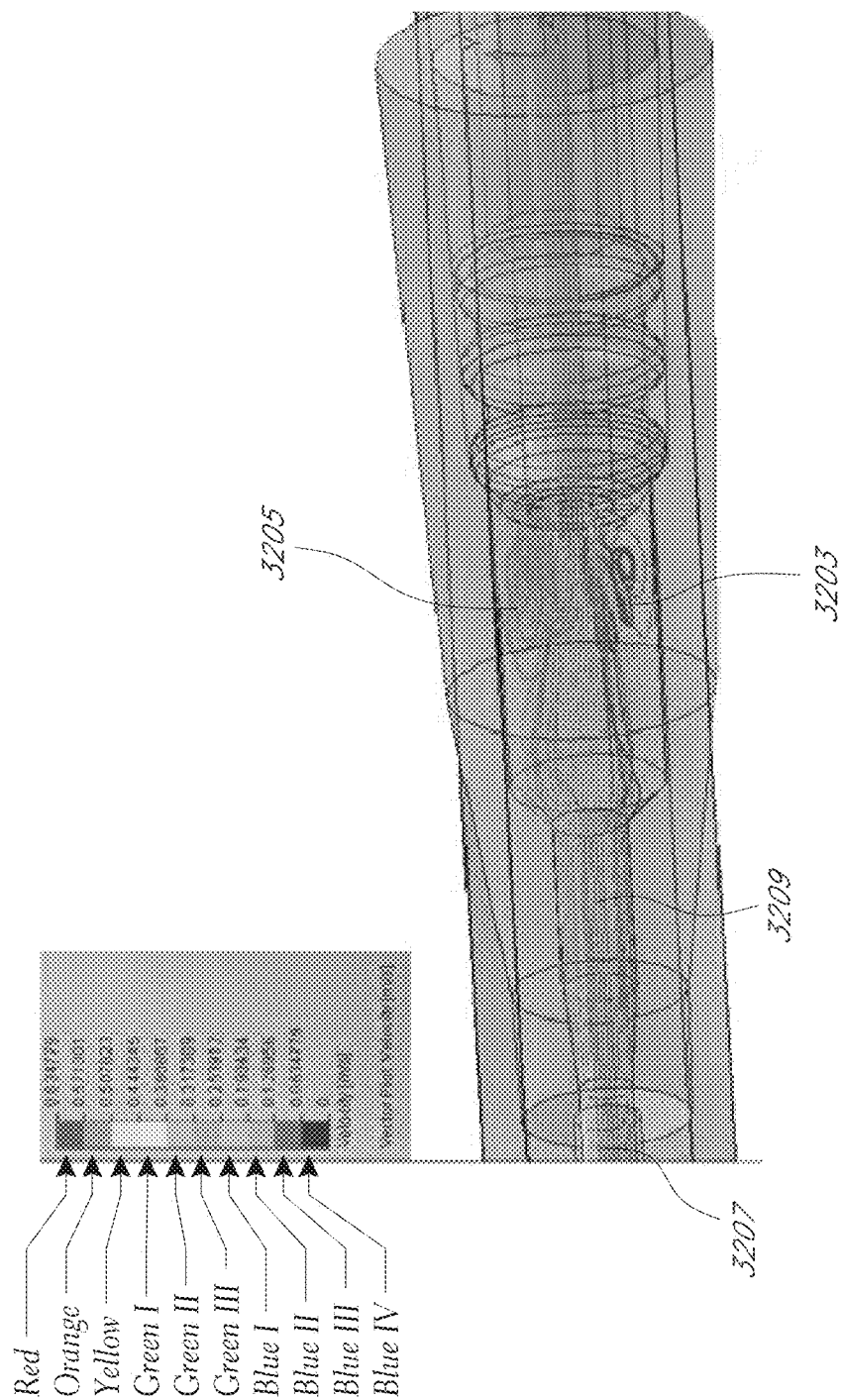
FIG. 32A illustrates a flow pattern in an embodiment of a patient connector.
Figures 1, 32A:
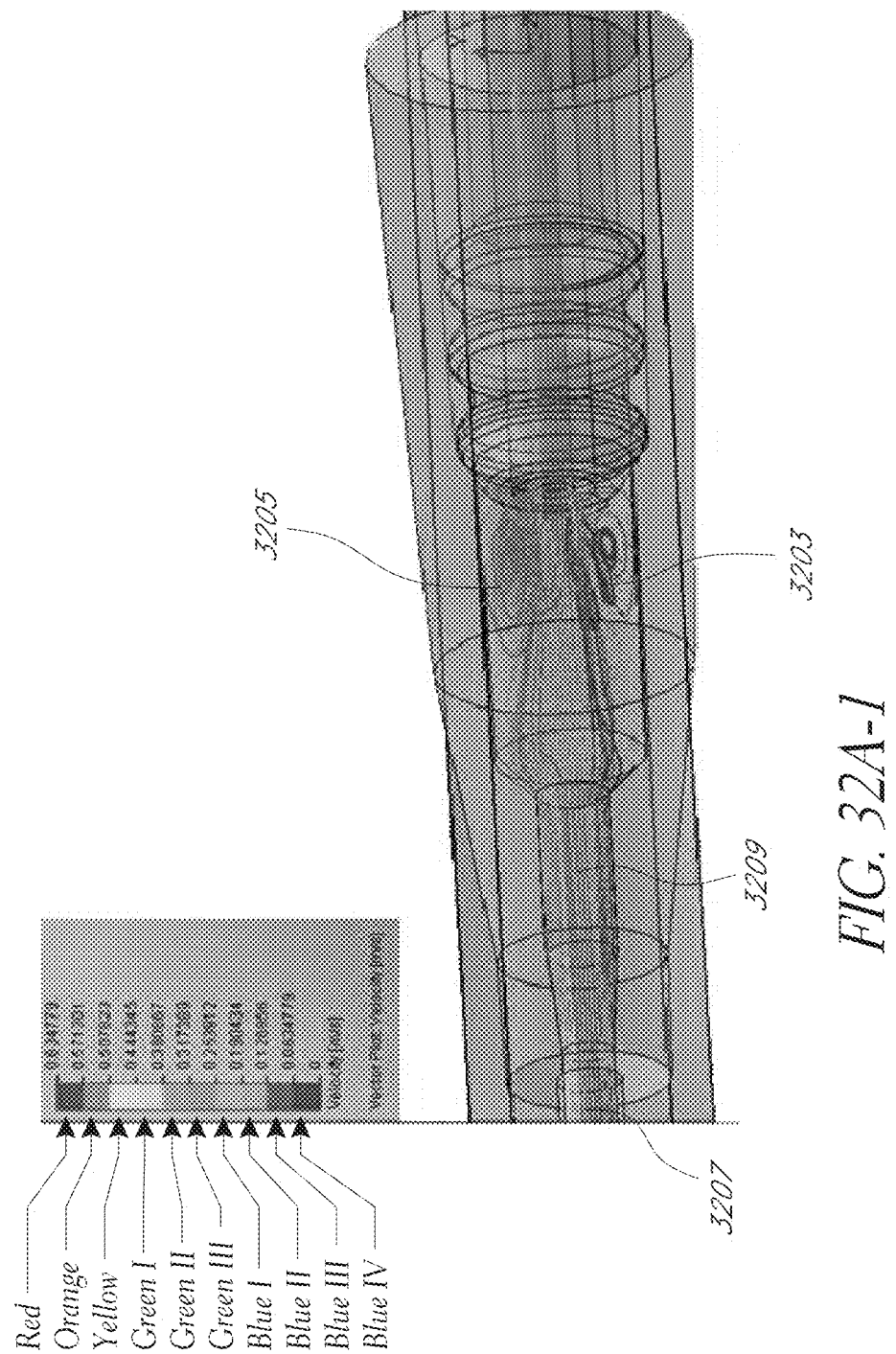
Figure 32B:
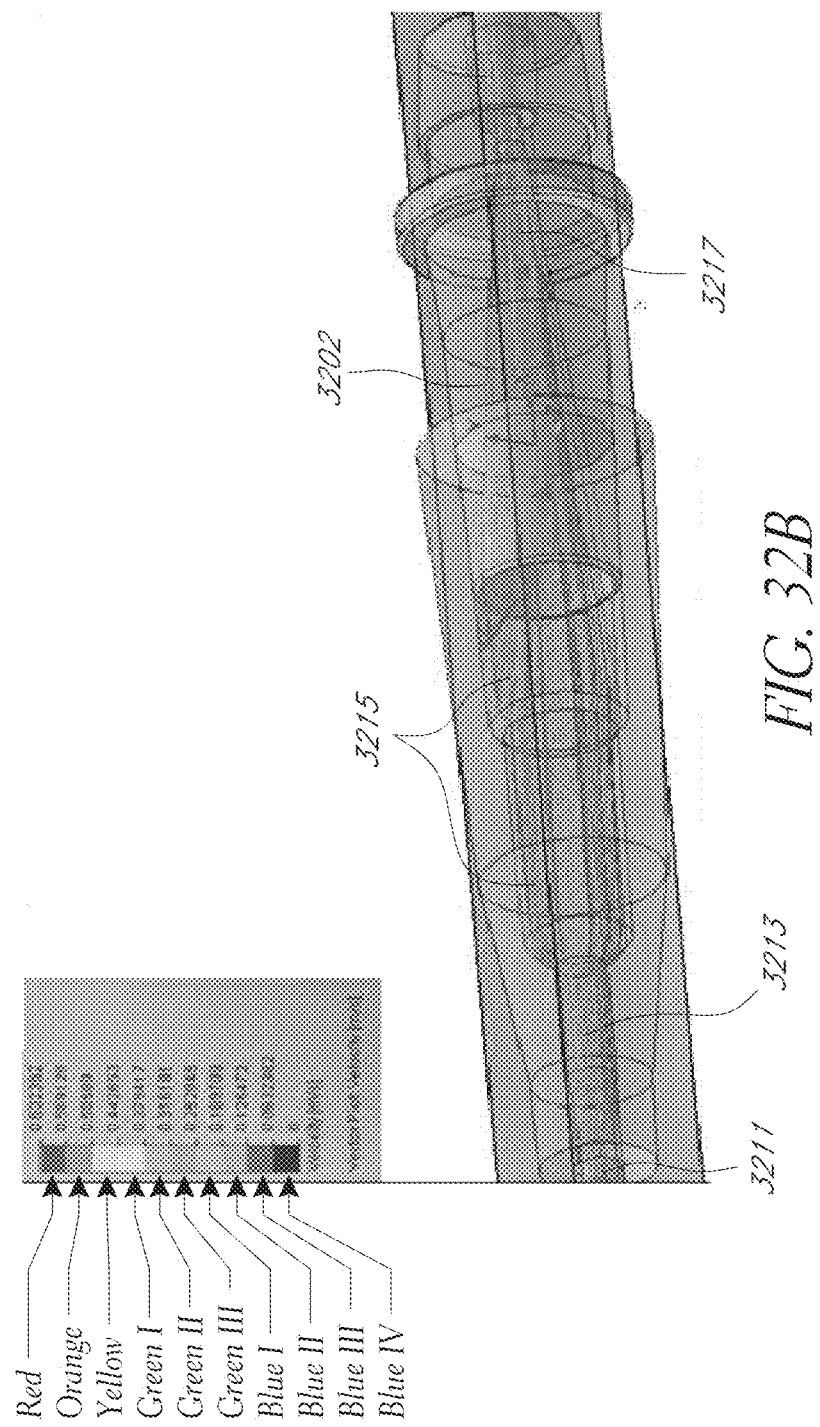
FIG. 32B illustrates a flow pattern in an embodiment of a patient connector including a tapered region.
Figure 32C:
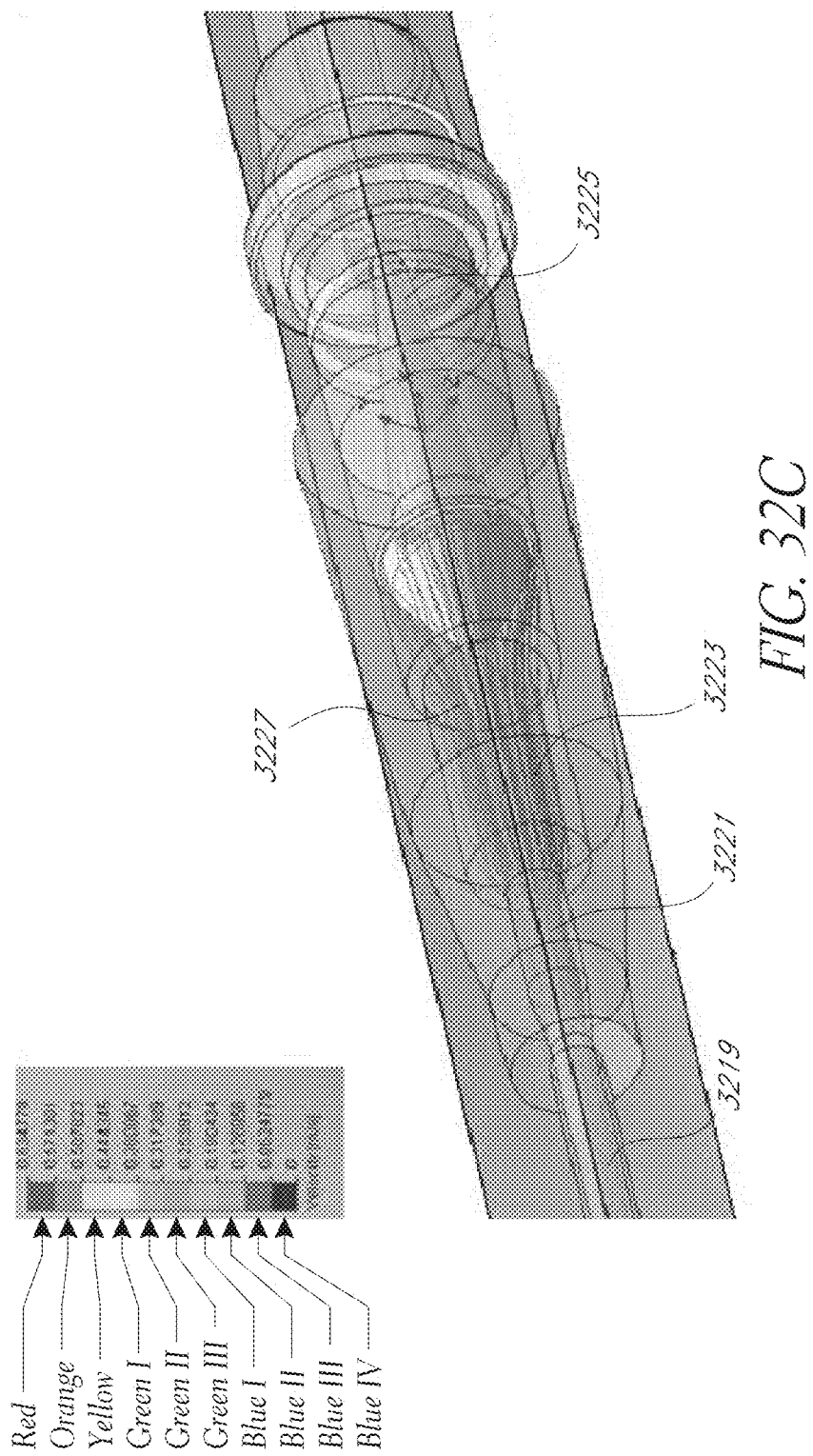
FIG. 32C-32E illustrates a flow pattern in various embodiments of a patient connector including a flow director.
Figures 1, 32C:
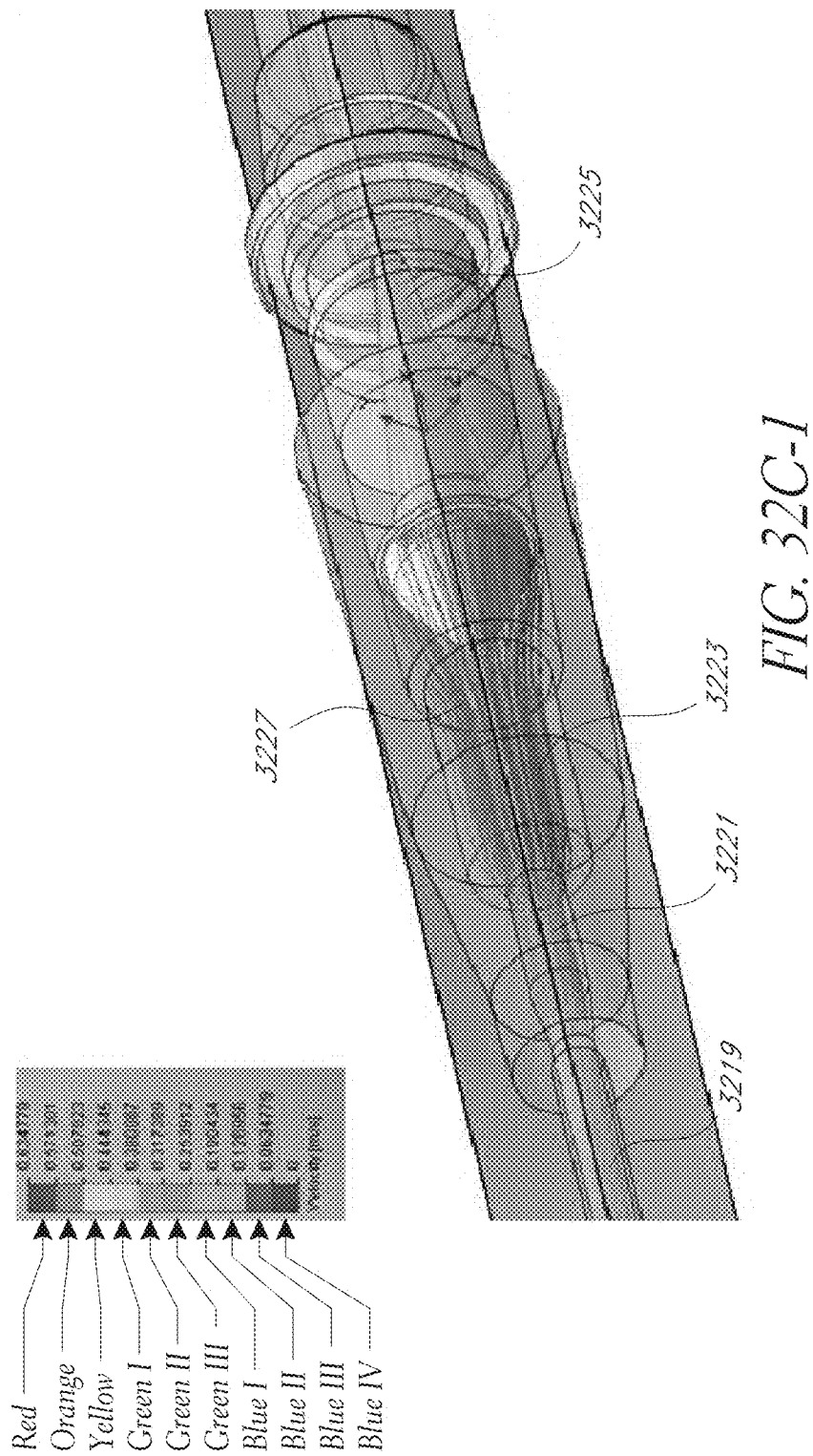
Figure 32D:
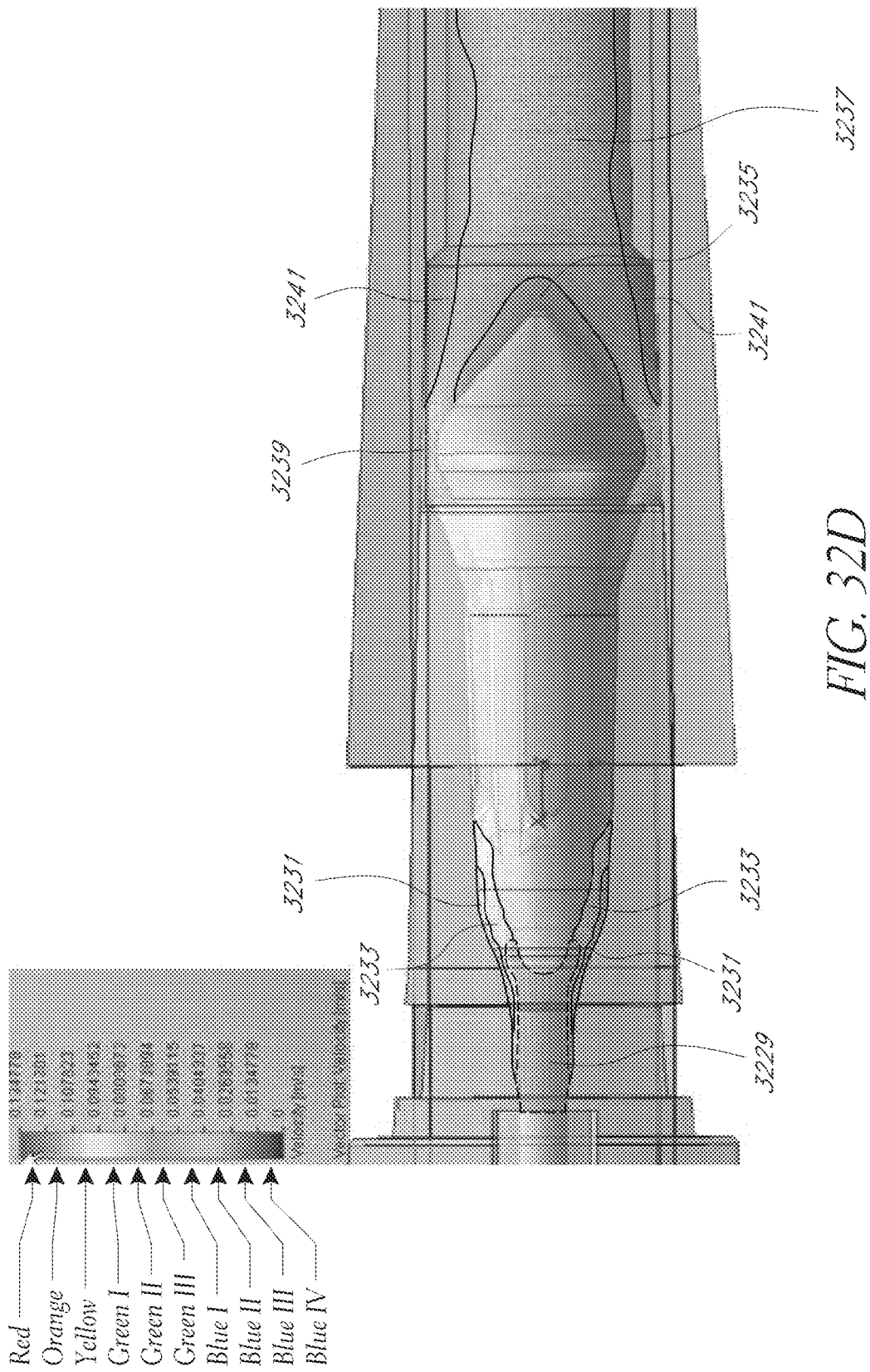
Figures 1, 32D:
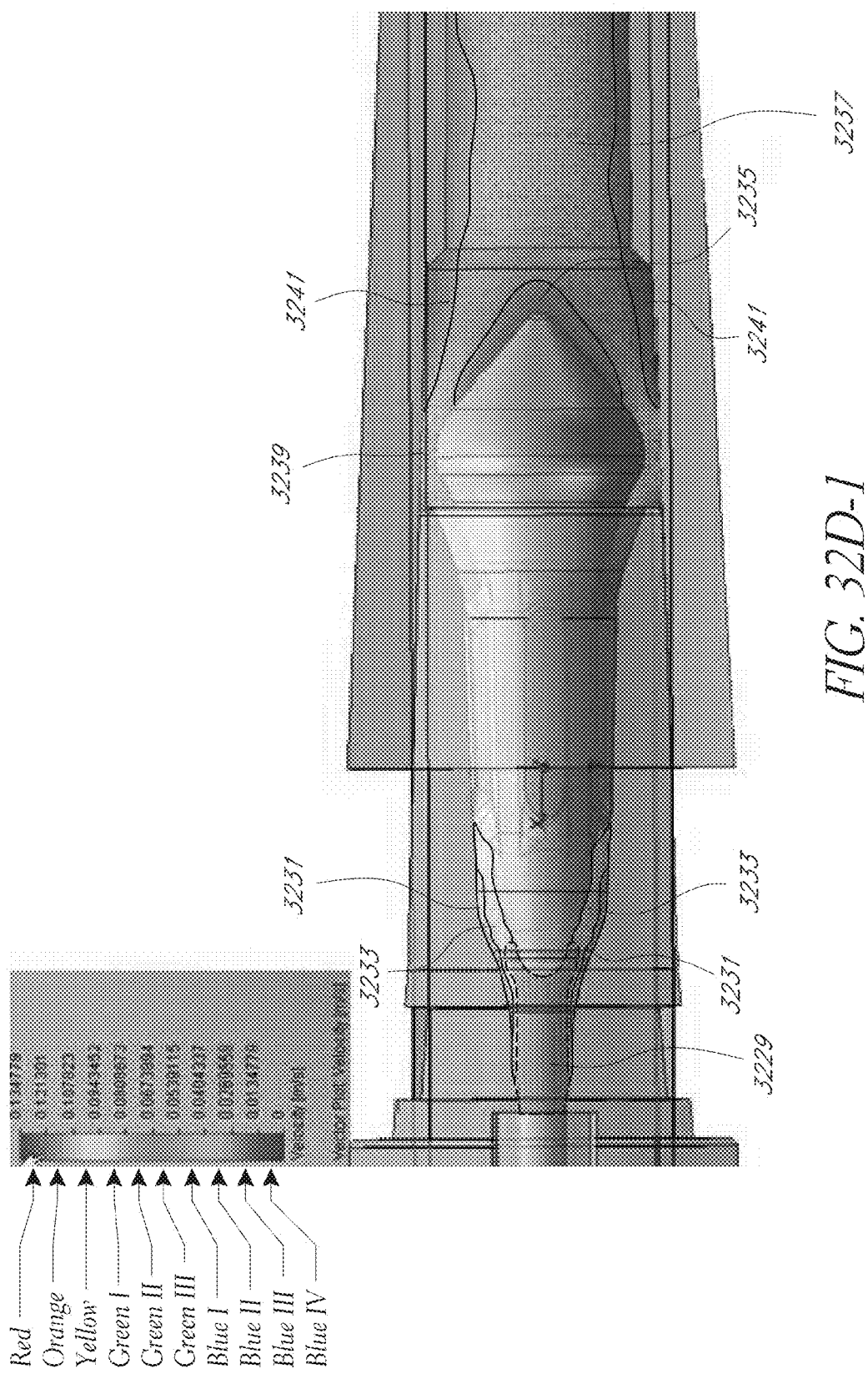
Figure 32E:
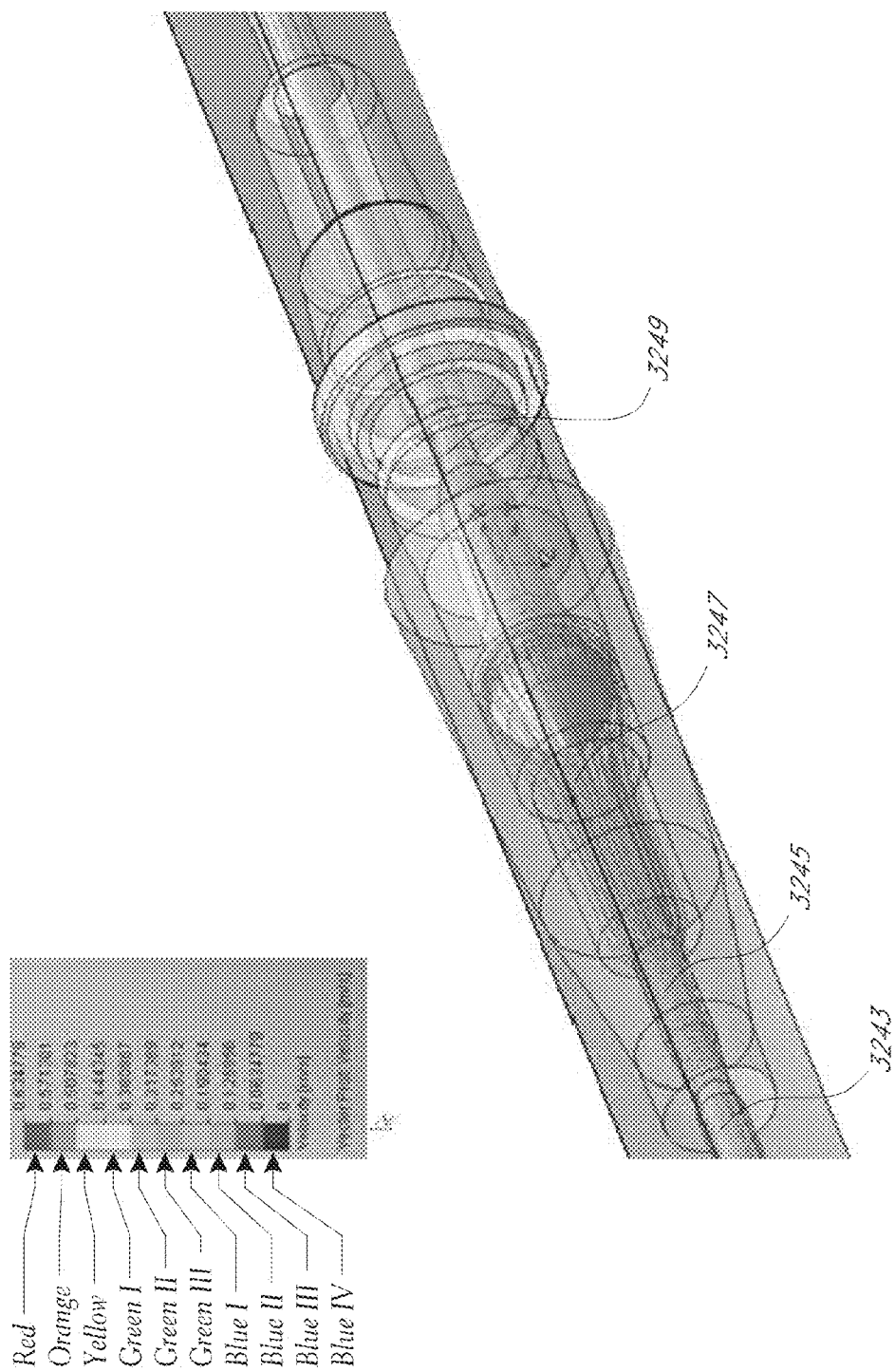
Figures 1, 32E:
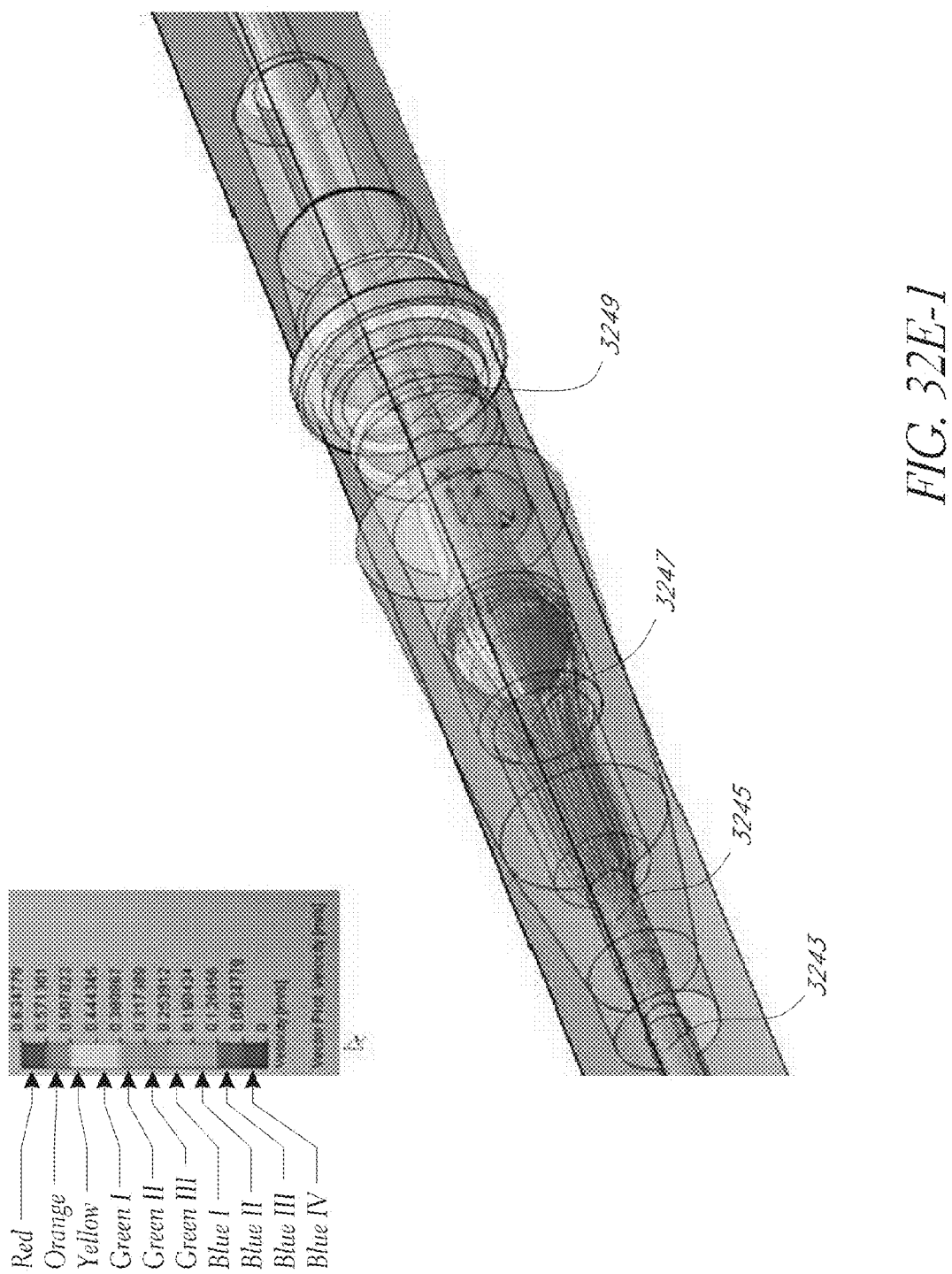

FIGS. 32A-32E show fluid flow patterns through various embodiments of a patient connector. The information provided in FIGS. 32A-32E are flow stream lines that are color coded to indicate the magnitudes of the velocity vector (e.g. speed). FIGS. 32A-1-32E-1 are color versions of FIGS. 32A-32E which illustrate the flow stream lines in color. FIG. 32A shows the flow of fluid through a patient connector that is attached to the various embodiments of the analyte monitoring system described above. The direction of fluid flow is from right to left. As seen from FIG. 32A, the fluid streamlines illustrate regions of substantially non-separated flow 3207 and 3209, wherein the fluid streamlines have magnitude of the velocity vector between approximately 0.38 m/s (shown by the color code Green II) and approximately 0.19 m/s (shown by color code Blue II). FIG. 32A also shows areas of separated flow 3205 and 3203, wherein the fluid streamlines have magnitude of the velocity vector between approximately 0.13 m/s (shown by color code Blue III) and approximately 0 m/s (shown by color code Blue IV). In other embodiments, the magnitudes of the velocity vector for the fluid streamlines can be different (e.g. higher or lower) from the values presented above.

FIG. 32B shows the flow of fluid through a patient connector that includes a standard female Luer connector and a male Luer connector having a tapered internal region 3202. The direction of fluid flow is from right to left. The fluid flow is substantially less separated in the embodiment shown in FIG. 32B as compared to the embodiment shown in FIG. 32A as can be observed from the fluid streamlines. As can be seen in FIG. 32B, the fluid streamlines illustrate regions of substantially non-separated flow 3211, 3213 and 3217, wherein the fluid streamlines have magnitude of the velocity vector between approximately 0.38 m/s (shown by the color code Green II) and approximately 0.13 m/s (shown by color code Blue II). FIG. 32B also shows regions of slow flowing fluid 3215, wherein the fluid streamlines have magnitude of the velocity vector between approximately 0.13 m/s (shown by color code Blue III) and approximately 0 m/s (shown by color code Blue IV). In other embodiments, the magnitudes of the velocity vector for the fluid streamlines can be different (e.g. higher or lower) from the values presented above.

FIGS. 32C-32E show the flow of fluid through a patient connector that includes a flow director as described above. The flow of fluid is from right to left in FIGS. 32C and 32E and from left to right in FIG. 32D. As can be observed from FIG. 32C, the fluid flow streamlines show regions 3219, 3221 and 3225 where the magnitude of the velocity vector of the fluid flow is between approximately 0.39 m/s (shown by color code Green II) and approximately 0.13 m/s (shown by color code Blue II). The regions 3223 and 3227 shown in FIG. 32C show areas where the magnitude of the velocity vector of the fluid flow streamline is between approximately 0.13 m/s (shown by color code Blue III) and approximately 0 m/s (shown by color code Blue IV).

FIG. 32D illustrates the fluid flow pattern in an embodiment of a patient connector including a flow director. These regions are depicted with boundaries shown as solid lines, to aid in the illustration and description. However, each region is not actually distinct or physically separated from any of the other regions. The general fluid velocities change within regions and across the illustrated boundaries in a smooth and non-abrupt manner. Moreover, each of these regions is three-dimensional and, because each depicts fluid flow velocities in a structure having general cylindrical symmetry, the regions of common flow velocities are generally cylindrically symmetrical. For ease of illustration, the regions are depicted in cross-section, while the flow director is shaded to indicate three-dimensional contours. In the region 3229 the magnitude of the velocity vector of the fluid flow streamline is between approximately 0.13 m/s (shown by color code Red) and approximately 0.11 m/s. In the region 3231 which is closer to the walls of the patient connector near the tapered end of the flow director, the magnitude of the velocity vector of the fluid flow streamline is between approximately 0.08 m/s (shown by color code Green I) and approximately 0.05 m/s (shown by color code Green III). In the region 3233 between the lateral edges of the flow director and the wall of the patient connector the magnitude of the velocity vector of the fluid flow streamline is between approximately 0.11 m/s (shown by color code Yellow) and approximately 0.08 m/s (shown by color code Green I). The fluid flow can smoothly transition from region 3229 to region 3233 without any abrupt changes in the flow direction or flow velocity. As can be seen from FIG. 32D, that the magnitude of the velocity vector of the fluid flow streamline in the region 3239, near the bulbous portion of the flow director is between approximately 0.08 m/s (shown by the color code Green I) and 0.05 m/s (shown by the color code Green III) and the magnitude of the velocity vector of the fluid flow streamlines in the regions 3235 near the tip of the bulbous portion of the flow director is between approximately 0.02 m/s (shown by the color code Blue II) and 0 m/s (shown by the color code Blue IV). The magnitude of the velocity vector of the fluid flow streamlines in areas 3241 and 3237 is between approximately 0.04 m/s (shown by the color code Blue I) and 0 m/s (shown by the color code Blue IV).

FIG. 32E shows regions 3243, 3245 and 3249 where the magnitude of the velocity vector of the fluid flow streamlines is between approximately 0.38 m/s (shown by color code Green I) and approximately 0.13 m/s (shown by color code Blue II). The magnitude of the velocity vector of the fluid flow streamlines near the bulbous portion of the flow director is between approximately 0.13 m/s (shown by color code Blue III) and approximately 0 m/s (shown by color code Blue IV).

Figure 33A:
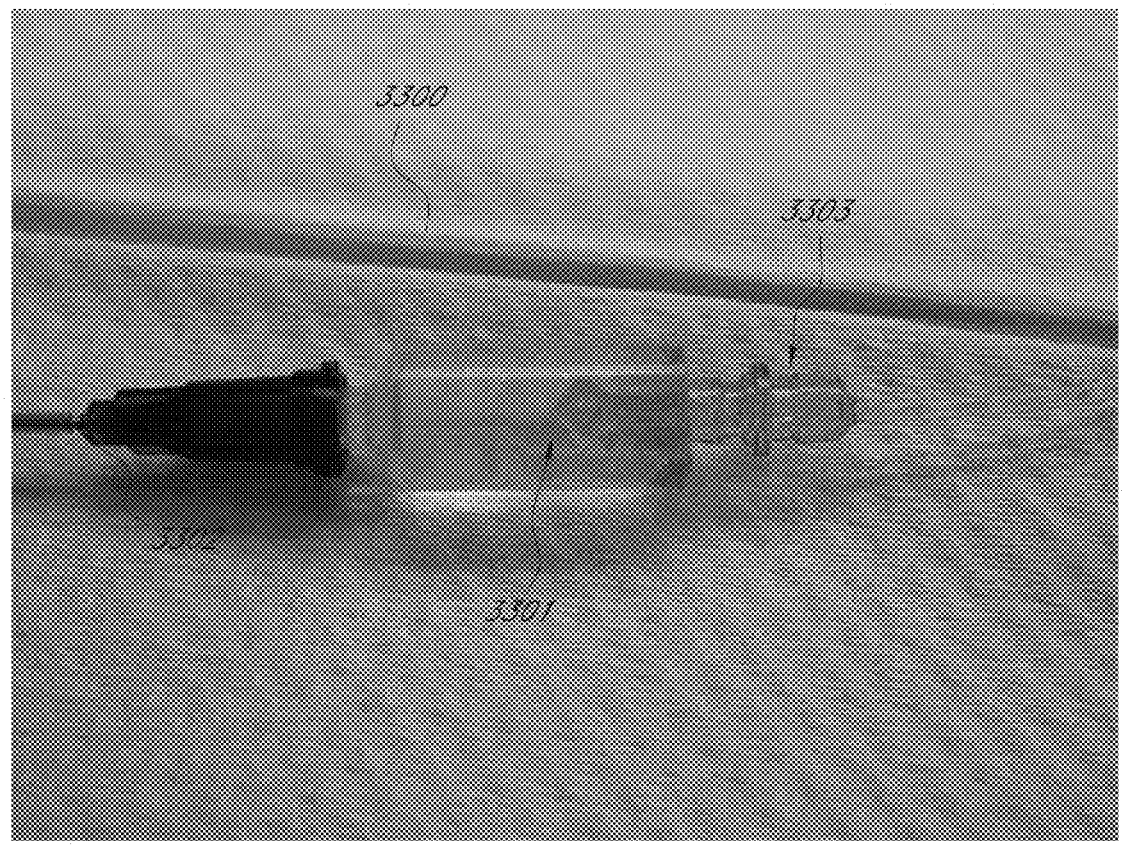
FIG. 33A illustrates an embodiment of a patient connector including a flow director.
Figure 33B:
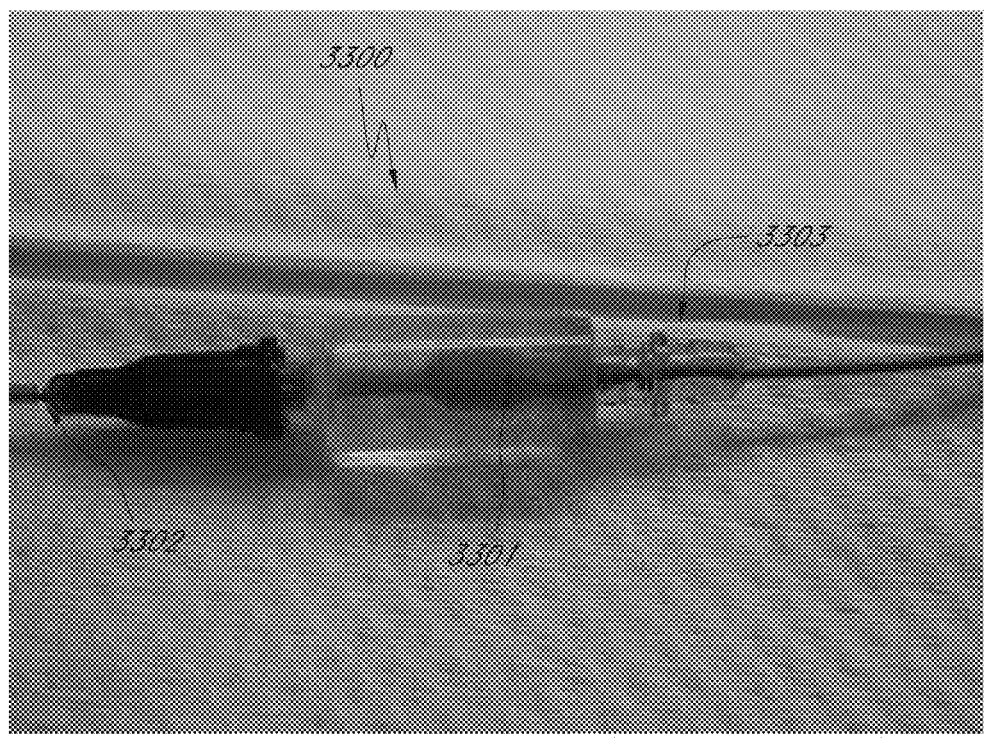
FIGS. 33B-33C illustrate the embodiment of a patient connector shown in FIG. 33A during use and after use.
Figure 33C:
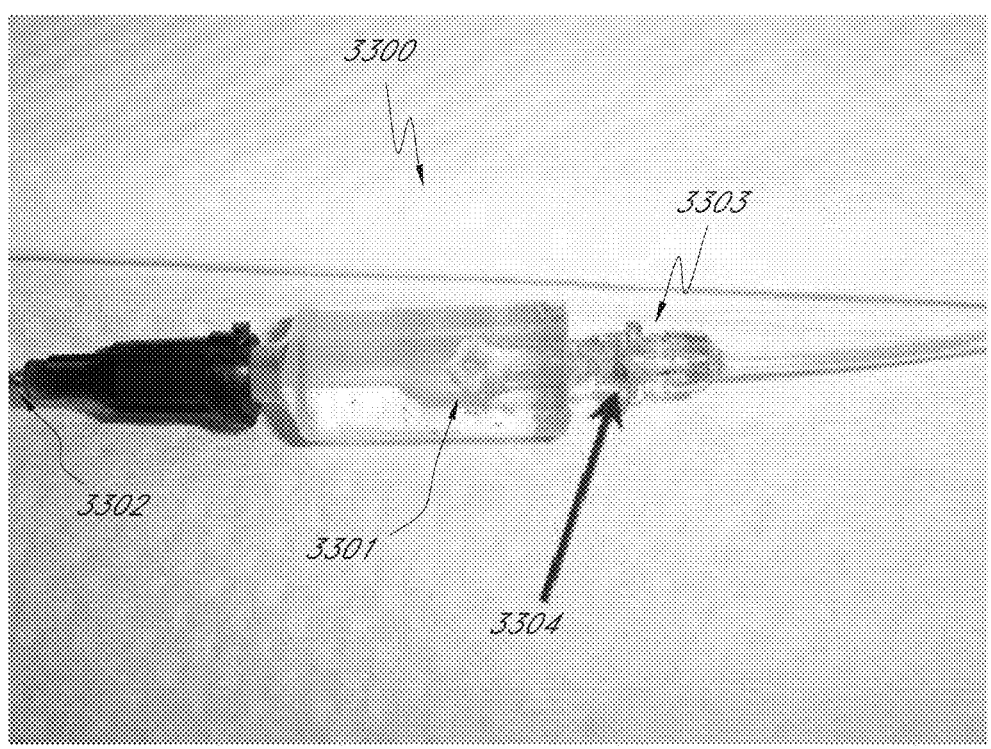

FIG. 33A shows an embodiment of a patient connector 3300 comprising a flow director 3301. The patient connector has a patient end 3302 which is proximal to the patient. In various embodiments, the patient end 3302 can comprise a standard female Luer connector. The analyte end 3303 which is farther from the patient end 3302 is connected to an analyte monitoring system. In various embodiments, the end 3303 can comprise a male Luer connector. In various embodiments, the flow director can be attached to the male Luer connector. FIG. 33B shows the flow of a fluid through the patient connector 3300 shown in FIG. 33A. FIG. 33C shows the patient connector 3300 after use for an extended period of time. In some embodiments, the patient connector including a flow director can be used without any significant accumulation for up to 6 hours. In various embodiments, the patient connector including a flow director can be used without any significant accumulation for up to 60 hours. It can be seen from FIG. 33C that there is some accumulation of fluid in the region 3304.

Figure 34A:
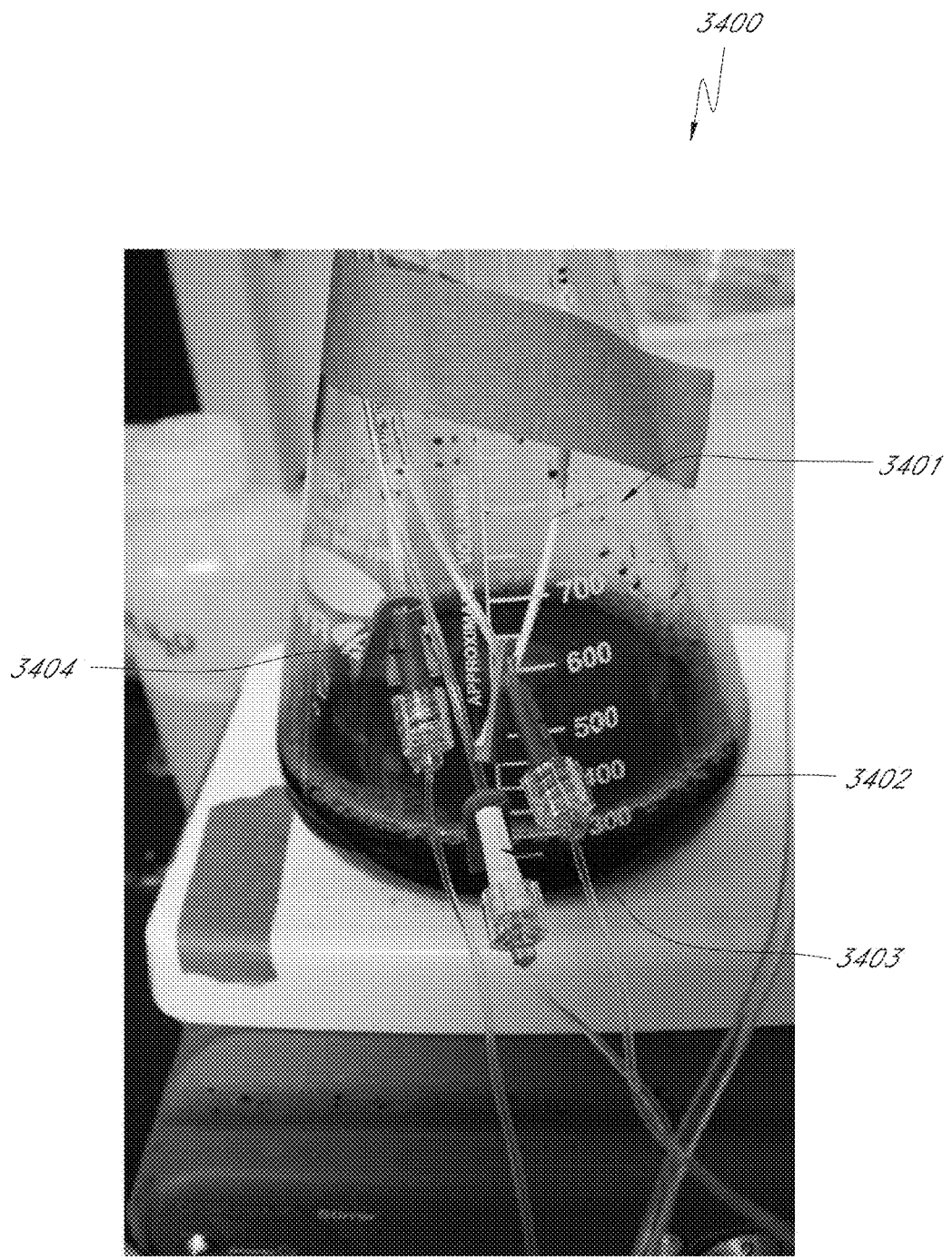
FIG. 34A illustrates an experimental setup used to test the flow directing ability of various embodiments of a patient connector including a flow director.
Figure 34B:
FIG. 34B shows an internal view of an embodiment of the patient connector used in the setup of FIG. 34A.

FIG. 34A shows an experimental set-up 3400 to test the ability of the patient connector including a flow director to prevent or substantially reduce separated flow. The set-up includes a source of bodily fluid (e.g. whole blood, plasma, heparinized blood, etc.) 3401. In some embodiments the source of bodily fluid 3401 may be a flask, a beaker, a human being or a part of a human being, an animal or a part of an animal. In the experimental set-up illustrated in FIG. 34A, bodily fluid is circulated substantially continuously from the source to an analyte monitoring system and back to the source 3401 through one or more patient connectors 3402, 3403 and 3404. FIG. 34B shows the internal view of one of the patient connectors 3402, 3403 and 3404 after re-circulating heparinized blood through it for approximately 60 hours. From FIG. 34B, it is apparent that there is no fluid accumulation in the interior of the patient connector.

Figure 35:
FIG. 35 shows an experimental setup to test the flow directing ability of the embodiment of a patient connector including a flow director.

The ability of the patient connector to prevent or substantially reduce separated flow was also tested using animal studies. In one embodiment of the study an animal (e.g. a sheep or a pig) or part of the animal was used as the source of bodily fluid. Bodily fluid was circulated from the animal or part of the animal to an analyte monitoring system and back to the animal or part of the animal through one or more patient connectors including a flow director. It was observed that even after approximately 6 hours of continuously circulating bodily fluid, the patient connectors showed no accumulation of bodily fluid or clots, thereby demonstrating the ability of the patient connector to prevent or substantially reduce separated flow. FIG. 35 shows the experimental setup for one such study performed wherein the source of bodily fluid was a vein in a pig's ear. In one embodiment, a catheter (e.g. 20 Ga. peripheral catheter) comprising a patient connector including a flow director was attached to a vein in the pig's ear. An analyte monitoring system substantially continuously withdrew bodily fluid from the vein through the catheter, analyzed the bodily fluid and returned the unused bodily fluid to the pig's ear. The patient connector showed no clots or clogged regions after approximately 6 hours of operation.

Self-Adjusting Patient Connector

In various embodiments, tubes or lines (e.g., the patient tube 512 of the monitoring device 102 illustrated in FIG. 5) may be joined to other tubes or lines (e.g. a central venous catheter (CVC) or a peripherally inserter central catheter (PICC) attached to the patient) via a standard connector (e.g. a standard Luer connector) that includes matching fittings on the ends of the tubes to be joined. The standard connectors may conform to standards that have been developed to permit compatibility and standardization of commonly-used medical devices. An example of specifications for fittings used for medical applications may be found, for example, in the International Standard ISO 594 titled "Conical fittings with 6% (Luer) Taper for syringes, needles and certain other medical equipment," and referred to herein as the "ISO Luer Standard." Fittings meeting the ISO Luer Standard are referred to herein as "Luer fittings."

While standards, such as the ISO Luer Standard, provide a framework for producing interchangeable and/or compatible connectors, the internal volume and/or shape of the internal volume within fittings may vary between interchangeable and compatible—but non-identical—fittings. This variation may present problems for low flow or low volume systems, or for systems benefitting when fluid within connectors is exposed to only smooth surfaces. In addition, dead space can sometimes be a problem in lines that are used to provide patients with medication. As used herein, the term "dead space" is a broad term and is used in accordance with its ordinary meaning to refer to any unwanted or unproductive areas that do not allow efficient and/or smooth fluid flow. For example, a widened portion, a peripheral opening or cavity that is located out of a main fluid flow path can be "dead space" because fluid can get caught in that space and either form eddy currents, turbulence, or stagnation. If a line with a connector having dead space is used to provide a patient with medication, some of the medication may remain trapped in the dead space. If the line is later flushed with saline, unknown and potentially dangerous amounts of the medication may be flushed from the dead space and infused into the patient. In an extreme case, this may ultimately be deadly.

For example, in medical systems and devices used in hospitals it can be useful to use anticoagulants (e.g. heparin) to help prevent deposits from building up in fluid systems, especially those that contain bodily fluids such as blood. In some medical devices connected to the vasculature of a patient, anticoagulants (e.g., heparin) can be used to prevent blood clotting in a patient and/or to keep the fluid lines open (e.g., by preventing fluids from coagulating in dead spaces of connectors). However, if excessive amounts of these anticoagulants are infused into a patient—for example, when the line is flushed—the patient may lose some clotting capability and Heparin Induced Thrombocytopenia (HIT) can result in many or all heparin-sensitive patients. HIT can be a very dangerous condition, and may lead to loss of vision, loss of a limb, or even death. Systems and methods of preventing accidental injection into the patient are described in U.S. patent application Ser. No. 12/123,422, the publication of which is incorporated by reference herein in its entirety. Another approach of preventing infusion of heparin into a patient is to avoid the use of anticoagulants (e.g. heparin) in portions of devices that may be connected to or in fluid communication with a patient's vasculature. However, not using anticoagulants can result in connectors attached to a patient's vasculature being blocked over time due to clotting and/or accumulation of deposits—e.g., in dead spaces and junctions of the connector.

For at least these reasons there is a need for connectors that can provide a continuous flow path between connecting tubes, through the connector, with minimized change in the cross-sectional area of various points along the flow path and with reduced dead space. Such connectors can promote smooth flow and reduce unwanted turbulence and stagnation in fluid systems, leading to reduced medical risk. Such connectors may have coatings on the inner or outer walls of the connecting tubes. The coatings can be designed to provide a clinical benefit (e.g., delivering therapeutic compounds to the fluid flowing through the connector); they can provide a mechanical benefit (e.g., reducing friction and improving fluid flow or protecting the sidewall materials from prolonged contact with the fluid flowing through the connector); and/or they can provide safety and efficiency benefits (e.g., decreasing the probability of blood clotting and lengthening the useful life of the connector and/or a fluid handling system such as may be included in a removable cartridge).

Various embodiments of Standard Luer connectors that are modified to have reduced internal volume were described in U.S. Publication No. 2008/0284167 which is incorporated by reference herein in its entirety. In certain embodiments described in U.S. Publication No. 2008/0284167, the coupled fittings present a nearly uniform flow diameter along for fluids within the fitting.

Figure 36A:
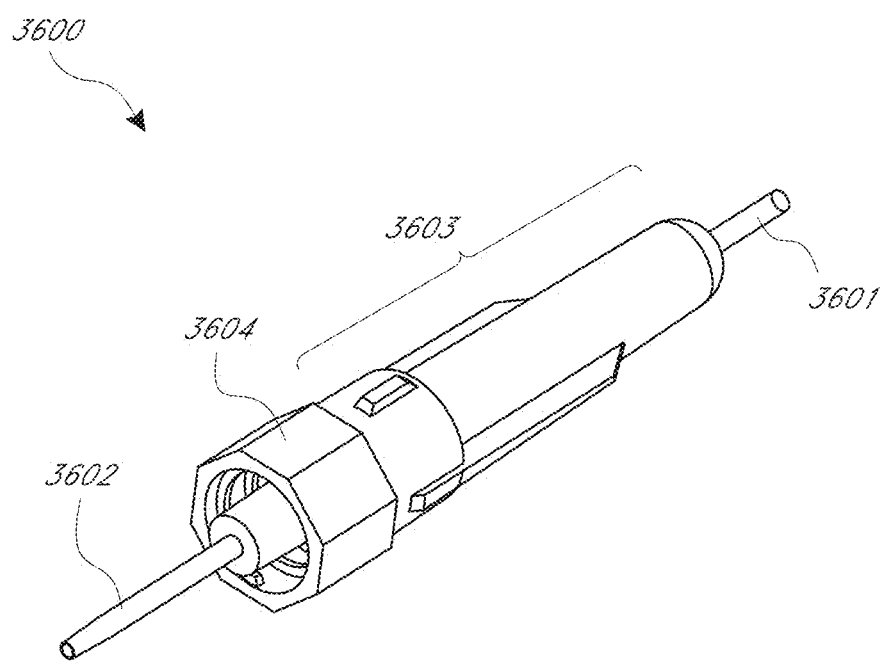
FIG. 36A illustrates an embodiment of a self-adjusting patient connector.
Figure 36B:
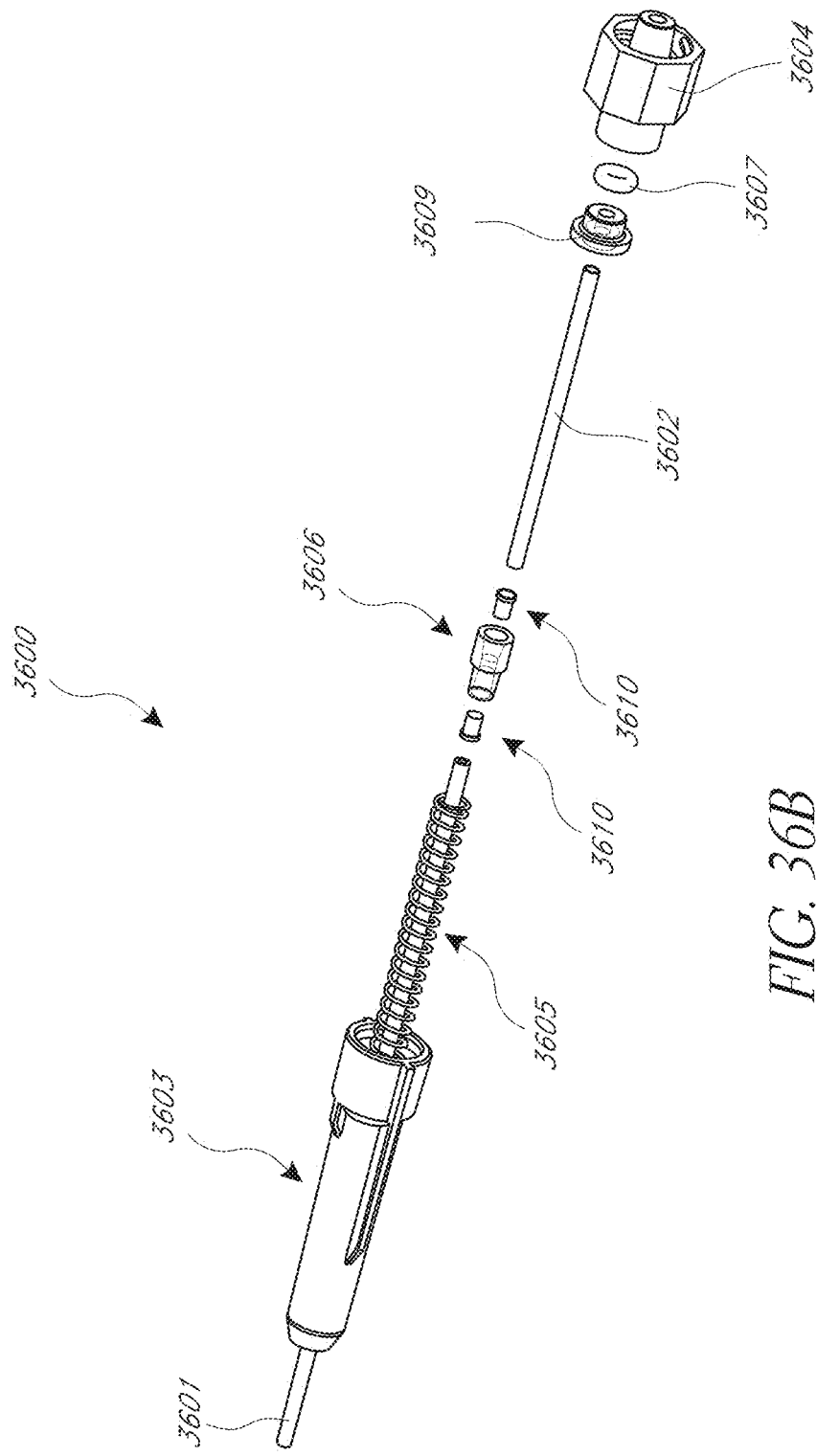
FIG. 36B illustrates an exploded view of the self-adjusting patient connector disclosed in FIG. 36A.

Some embodiments disclosed herein describe self-adjusting and/or universal patient connectors that have very little dead space volume and that can mate with the base of a catheter (e.g. a CVC or a PICC) hub. FIGS. 36A and 36B disclose examples of a self-adjusting and/or universal patient connector 3600 that comprise a spring loaded self-adjusting extending tip. As used herein, the term "universal" is a broad term and is used in accordance with its ordinary meaning to describe any device that is widely compatible with other devices or that can adjust or accommodate to various shapes and/or mate with various devices. Just because a device may not be configured to mate with every possible counterpart does not mean it is not "universal." The self-adjusting and/or universal patient connector 3600 is configured to connect a fluid line 3601 (which may come from a medical device or system such as a monitoring device 102, e.g., the OPTISCANNER™) to an extender tube 3602 which in turn can connect to a fluid line (e.g. a single lumen or a multi lumen CVC or a PICC line, not shown in FIG. 36A or 36B) attached to a patient. In some implementations, the connector can be reversed and be oriented in the opposite manner, such that the extender tube 3602 generally protrudes toward a medical device and away from a patient.

The extender tube 3602 can be configured and constructed in such a way as to withstand pressures of 20 psi. In some embodiments, the extender tube 3602 can be configured and constructed in such a way as to withstand pressures less than or greater than 20 psi. The thickness and construction of the material of the extender tube walls allow it to withstand pressure in the fluid lines. Moreover, a spring (discussed below) can urge the extender tube 3602 into position and that spring can also assist the extender tube to prevent leaks from internal pressure.

FIGS. 36C, 36D, and 36E show partial section views of embodiments having different tip characteristics, and how tips can approach and/or interface with portions of another connector. In various embodiments, the extender tube 3602 can end abruptly as if it were cleanly and perpendicularly sliced to form a flat or "square" tip. A square or flattened tip can provide a convenient shape to allow the extender tube 3602 to effectively abut another tube (e.g., if the other tube also has a square face 3616b tip as shown on the tubes 3608 in FIGS. 36D-36E). In some embodiments, the second end of the tube 3602 can gradually diminish in diameter to form a relatively long, sharp, or "tapered" tip (see the tubes 3602 in each of FIGS. 36C-36E for examples of tapered tips, either having frustoconical portions, beveled portions, or both). In some embodiments, the second end of the tube 3602 can be partly tapered but with a blunted or flattened extreme face 3614b as shown in FIG. 36D. In various embodiments the extender tube 3602 can be beveled at its edge to form a flat face 3614a, 3614c that may or may not be configured to conform to, insert into, directly abut, or otherwise interface with another tube 3608 as shown in FIGS. 36C and 36E. In some embodiments, the extender tube 3602 can comprise a conical tip for smooth insertion partially into another tube (see FIGS. 36D and 36E for examples of partly conical tips). The interface between tubes 3608 and 3602 can also be configured with one face convex and the other concave, and/or with one having a protrusion and the other having a complementary opening. Various combinations of tip shapes can be configured to form a good seal and allow smooth flow between adjacent tubes.

Figure 36F:
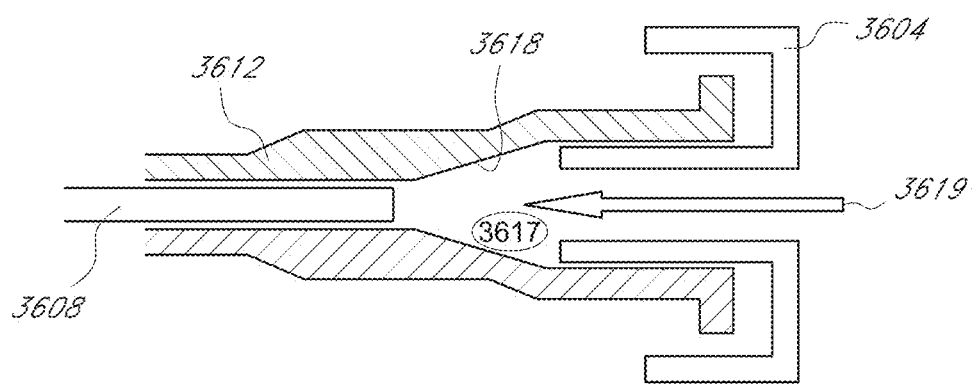

In some embodiments, a universal connector is designed to interface with various existing and commonly-used connectors. In FIGS. 36C-36F, for example, a mating connector 3612, a tube 3608, and a Luer base 3604 can together represent an existing device that is commonly used in medical settings, for example. Referring to FIG. 36F, these structures can be referred to together as a "standard" connector. But connecting two standard connectors together can have a drawback of allowing fluid to flow out of a tube 3608 and into a portion having a wider cross-section that may include side regions or "dead space" 3617. This dead space 3617 can inhibit smooth flow and allow unwanted pooling, stagnation, and when blood is involved, clotting.

Embodiments herein can provide a penetrating connector having an extender tube 3602 that can be positioned along a fluid line (e.g., the line comprising the tube 3608 and the fluid line 3601) between a medical device and a source of body fluid to allow fluid flow while reducing leaks. Reducing leaks can involve pressure containment such as, for example, preventing fluid from escaping when the internal fluid pressure is less than 20 psi. The penetrating connector can have openings at either end (see, e.g. the receiving opening 3634 discussed further below with respect to FIG. 36G, and the opening at the other end in the general vicinity of reference numeral 3626b of FIG. 36G) that cooperate with openings of other connecting devices and/or fluid lines to assist in forming mating complexes (e.g., the structures illustrated in FIGS. 36C-36E and/or FIGS. 37A-37H) at either end of the connector. The mating complexes can include an enlarged space (e.g. the dead space 3617 shown in FIG. 36F). The extender tube 3602 can penetrate into an opening in a standard connector or one of the mating complexes as suggested by arrow 3619, and it can bypass dead space 3617, thereby confining fluid within its walls to prevent the fluid from flowing out into the enlarged space (e.g., the dead space 3617) of the mating complex. The extender tube can physically contact either the side-walls 3618 of the mating connector 3612, or the tube 3608, or both. The penetration of the extender tube 3602 along the path of the arrow 3619 can be provided either by the force of a health care provider putting two connectors together or by a force-exerting structure (e.g. a spring) or other resilient mechanism. The force-exerting structure can use a resilient property to improve a seal between the extender tube and the opening in the standard connector or another medical device. The force-exerting structure can comprise one or more of the following: a spring 3605; a hub 3606; an extender tube 3602 with a stiff tip; an extender tube 3602 with a stiff body; a back-up ring 3609, an O-ring 3607; an inner portion of a mating connector 3612; a tube 360; a surface 3618 or some other portion of a mating connector 3612; or some combination of the above.

With further reference to FIG. 36F and with the understanding that an extender tube 3602 can be inserted as shown with arrow 3619, in order to achieve a good seal between an extender tube 3602 and the portion of the standard connector contacted by that extender tube 3602—thereby reducing leakage such as into a dead space 3617—the extender tube 3602 or a portion thereof can be relatively more or less resilient (or conversely relatively more or less stiff) than the material with which it is designed to come in contact. Moreover, the extender tube 3602 that can be inserted along the path of the arrow 3619 can have a complementary shape to improve the seal and the flow of fluid between the two tubes 3602 and 3608. Various embodiments of a universal connector can comprise a structure having stiffness that is sufficient to resist deformation when the universal connector is pushed or urged into position in order to connect to another connector (e.g. a standard connector having a fluid line such as the tube 3608 that may be attached to a patient) or tube. The presence of the stiff structure (combined with complementary properties of a material to be contacted) can also aid in forming a good seal with the other tube and allow smooth fluid flow across the junction between the universal connector and the other (e.g., a standard) connector. In some embodiments, if the connector (e.g. the surface 3618) or tube (e.g. the tube 3608) that is to mate with a universal connector is very stiff then the universal connector can include components (e.g. an O-ring, a spring, an extender tube, etc.) that are comparatively less stiff.

Without subscribing to any particular theory, generally resilience and/or stiffness of any structure are properties that can depend on the material, geometry of the structure and boundary conditions that exist when the structure is brought into contact with another structure. Accordingly, the stiffness-providing or resilience-providing structure of the universal connector can comprise a material having a sufficient modulus of rigidity (or elasticity) or having a shape that resists or allows deformation. In some embodiments of a universal connector, an extender tube 3602 can be formed from a relatively stiff material that can be urged into contact with a surface 3618 or a tube 3608 with a spring 3605 (see FIG. 36B). Stiffness and/or resiliency can be provided both by the materials and/or shape of a standard connector (see FIG. 36F), the materials and/or shape of an extender tube 3602; the materials and/or shape of a combination of the spring 3605 and the extender tube 3602, etc. The stiffness of the spring 3605 or the extender tube 3602 can also vary to account for the expected material and geometry of the mating connector 3612 or tube 3608. Useful materials include polyvinylchloride ("PVC"—less stiff) and polyimide (more stiff).

As an example, in some embodiments, the extender tube 3602 can be stiffer than the mating connector (e.g. mating connector 3612 shown in FIGS. 36C-36E) or the tube included within the mating connector (e.g. tube 3608 shown in FIGS. 36C-36E). As another example, the extender tube 3602 can be stiffer than the inner walls of the mating connector (e.g. inner wall 3618 shown in FIG. 36F). In some embodiments, the extender tube 3602 can comprise a material that is stiffer (and/or has a higher modulus of elasticity) than the material of the fluid line 3601, the material of the mating connector 3612 of FIGS. 36C-36E and/or the material of the tube 3608 of FIGS. 36C-36E. As an example, the extender tube can comprise a stiff material such as polyimide that can be stiffer than PVC. In some variations of the universal patient connector, the extender tube can comprise a stiffer material at its extremity while the remaining portion of the extender tube 3602 can comprise a less stiff material. In some embodiments, the portion of the extender tube 3602 that extends beyond the patient connector can comprise a stiffer material while the portion of the extender tube that is within the patient connector can comprise a less stiff material. In some embodiments, the extender tube 3602 can be stiffer or less resilient than the spring 3605. However, the spring 3605 can provide support to the extender 3602 and can assist the extender tube 3602 in pushing against the mating materials (e.g., the tube 3608, the mating connector 3612, etc.) Indeed, the spring 3605 can itself be relatively stiff, while still providing resiliency.

With further reference to FIG. 36A, a spring housing 3603 can surround a portion of the fluid line 3601 and connect to a standard Luer base 3604 that is configured to mate with standard Luer connections. The standard Luer base 3604 can thus provide a sturdy physical connection on the outside, while the spring housing can provide a frame against which an internal spring can push, urging the protruding end of the extender tube 3602 into a smoother and more immediate mating relationship with another connector. The extender tube 3602 can thus allow fluid to bypass any dead space that may otherwise exist in the Luer connection and flow directly into a downstream (or upstream) connector.

The connector 3600 (including the standard Luer base 3604 and the spring housing 3603, for example), can be configured and constructed in such a way as to withstand (e.g., contain while reducing or preventing leaks) pressure of 100 psi. The thickness and construction of the material of the connector walls can allow it to withstand pressure in the fluid lines. The line pressure at the connector can vary depending on back pressure (e.g., blood pressure) and the type of catheter to which the connector 3600 may be attaching. In a common implementation, the pressure within an assembled connector 3600 can be approximately 1.5 psi above the back pressure.

FIG. 36B illustrates an exploded view of the universal and/or self-adjusting patient connector 3600. The universal and/or self-adjusting patient connector comprises a spring housing 3603 which houses a spring 3605. In various embodiments, the fluid line 3601 is inserted through the spring housing 3603 and the spring 3605 and meets up with or connects to a first end of an extender tube 3602. A second end of the tube 3602 extends into a standard Luer base 3604. In various embodiments, an O-ring 3607 and a back-up ring 3609 can encircle the extender tube 3602 and be generally disposed between the spring housing 3603 and the Luer base 3604. In various embodiments, the first end of the extender tube 3602 can seat against a hub 3606 which intervenes between the fluid line 3601 and the extender tip 3602. The hub 3606 can have a passage that smoothly changes diameter, if warranted, between the inner diameter of the fluid line 3601 and the inner diameter of the extender tube 3602, thus providing a continuous flow path with minimal cross sectional area change and minimizing dead volume. The extender tube 3602 (which can be referred to as a spring loaded self-adjusting extender tube, for example) can also maintain relatively uniform velocity of the fluid across the patient connector. Maintaining uniform velocity across the connector can provide the following advantages: (a) rapid flushing fluid line 3601 and/or tube 3603; (ii) reducing or eliminating trapped bubbles; (iii) reducing or eliminating blood clotting that may otherwise occur in a patient connector.

Figure 36G:
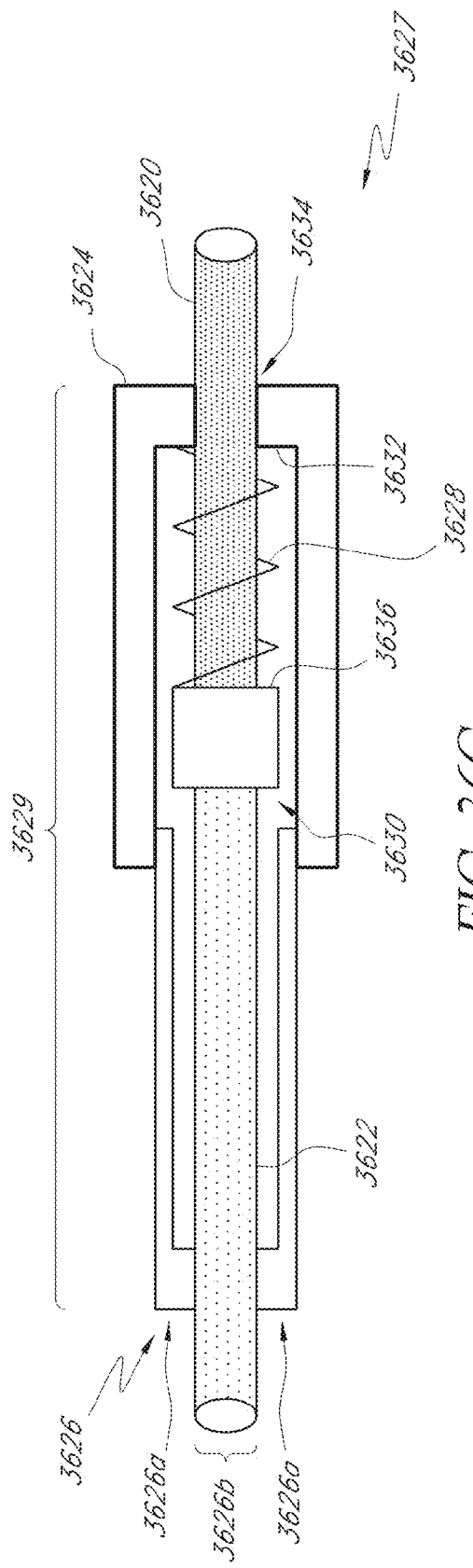

A universal and/or self-adjusting patient connector, in a generalized form, can be illustrated as shown in FIG. 36G. The connector can comprise a standard-facing end 3626 (e.g., an end configured to mate with a standard male or female Luer connector) that can include a standard-facing outer portion 3626a and a standard-facing inner portion 3626b that comprises an extended flow passageway 3622. The connector can further include an opposite end 3627 having an opposite outer portion 3624 comprising a first pushing surface 3632 and a receiving opening 3634 configured to receive a regular flow passageway 3620. In various embodiments, the standard-facing outer portion 3626a and the opposite outer portion 3624 together comprise an outer housing 3629. The connector further comprises a second pushing surface 3636 facing the first pushing surface 3632. The extended flow passageway 3622 is configured to connect to the regular flow passageway 3620 to form a combined flow passageway configured to move with the second pushing surface 3636. A force-exerting member or an actuating member 3628 (e.g. a spring) is situated between the first pushing surface 3632 and second pushing surface 3636 and that actuating member 3628 is configured to simultaneously exert a force against both of these pushing surfaces to thereby urge the first pushing surface 3632 (along with the outer housing 3629) away from the second pushing surface 3636 (along with the combined flow passageway), thereby causing the extended flow passageway 3622 to approach—and the inner portion 3626b of the standard-facing end to more firmly seat against—an inner portion of any of a variety of standard connectors having different depths. In this context, it can be understood that a generalized embodiment can include a universal connector with an outer portion (e.g., the housing 3629 and in particular the standard-facing outer portion 3626) that can connect relatively firmly to a standard connector. This relatively firm connection can occur using a threaded luer lock, for example. The generalized embodiment can also have an inner portion (e.g., the extended flow passageway 3622) that can connect relatively firmly to a flow passageway (e.g., the regular flow passageway 3620). This relatively firm connection can occur using a connecting hub and/or adhesive, for example. At the same time, the generalized embodiment can include a resilient (as opposed to a relatively firm) connection between the inner portion and the standard connector, as the embodiment uses the first relatively firm connection and its own relatively rigid structure as a base against which to brace as it urges the inner portion into contact with the standard connector.

Figure 36H:
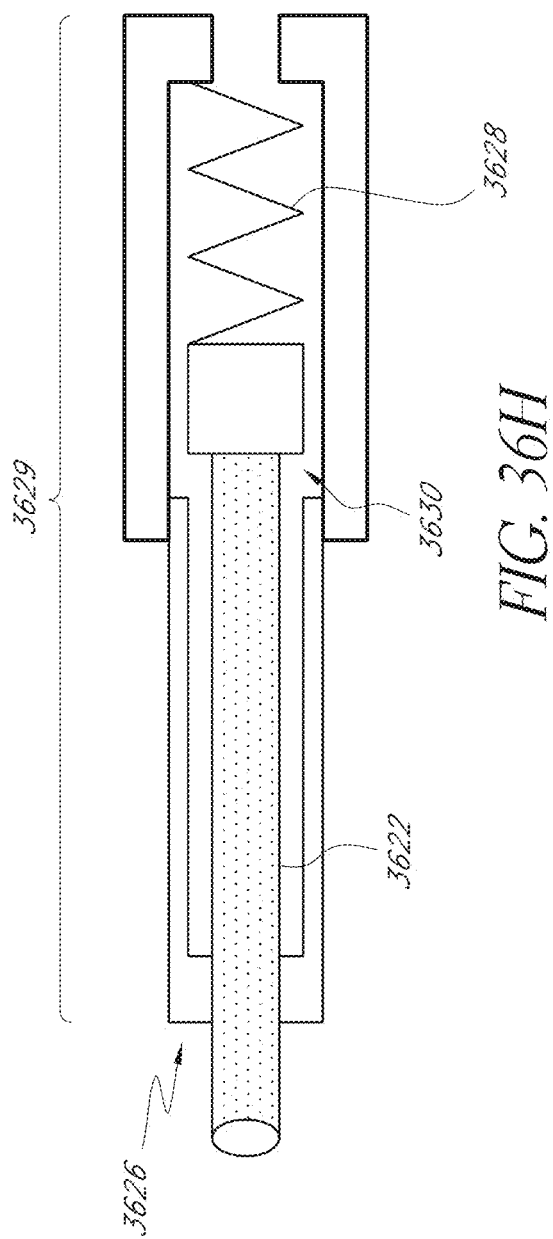

FIG. 36H illustrates a generalized view of a connector when it is not connected to or associated with any fluid lines. The connector can include an outer portion 3629 comprising at least one standard-facing end 3626; an inner portion 3630 comprising an extended flow passageway 3622; and an actuating member 3628 that is situated between the outer 3629 and the inner portion 3630 and configured to move the inner portion 3630 toward or away from the outer portion 3629 thereby causing the extended flow passageway 3622 to approach and seat against an inner portion of any of a variety of standard connectors (e.g. male or female Luer connectors) having different depths.

Analyte monitoring systems can be connected to a source of bodily fluid via a connector that is configured to reduce blood clotting risk. Blood clotting risk can be reduced, for example, by employing coatings in or on a connector, by reducing dead space volume in a connector, by using resiliency to improve fit, by extending a portion of one connector to better mate with a portion of another connector, etc.

As discussed above under the heading "SELF-ADJUSTING PATIENT CONNECTOR," it can be desirable to reduce the amount of dead space in and around connections along a fluid path. Such a reduction of dead space may reduce turbulence in a flowing fluid, for example. One way to reduce dead space is to include a sealing mass at or near an interface where fluid flows from a tube and into a connector. For example, a sealing mass can be placed on or around a tube that is part of the fluid path. The sealing mass may be placed anywhere along the length of the tube, and may be placed so that it partially or fully surrounds the tube. The sealing mass may be placed at specific locations along the tube where it may be most effective in reducing dead space. For example, the sealing mass may be placed such that it encircles a connecting tube near the tip of the connecting tube. Placing a sealing mass which encircles a connecting tube near the tip of the connecting tube that will connect to another tube may help reduce dead space at such a connection because the sealing mass can resiliently deform to fill cavities or crevices that may otherwise allow fluid pooling, stagnation, eddy currents, etc. If the sealing mass is placed near the tip of a connecting tube for this purpose, it may be desirable to minimize the distance between the sealing mass and the tip of the connecting tube because fluid may be more likely to leak out of the tip, so stopping the flow of leaked fluid advantageously occurs close to the original leak. For example, it may be advantageous to place a sealing mass within 0.001, 0.005, 0.01, 0.05 or 0.1 inches from the tip of a connecting tube. A sealing mass may be placed on one or both of the tubes that are to be connected.

A sealing mass may be especially useful on connectors which are intended to be used multiple times and for multiple fluid cycles.

A sealing mass may be made out of any type of material. The material used for a sealing mass may be chosen based upon any number of desirable characteristics, such as biological neutrality (or biological activity), affinity for the fluid in the fluid path (or lack of affinity), impermeability, resilience, compressibility, cost, ease of manufacture, ease of attaching to a tube, or other reasons. Various approaches can improve the sealing ability of a sealing mass. For example, a sealing mass may be made from the same type of material as the tube it surrounds. This can allow the mass and the tube to resiliently abut or conform to other surfaces and to each other in a similar manner. A sealing mass may be joined to the tube it surrounds. This can reduce the likelihood of fluid leakage between the sealing mass and the tube and also assist in urging the sealing mass against a mating connector. If the tube has a resilient force (e.g., from a spring) that may be urging the tube against a mating surface of another connector, coupling a resilient mass to the tube can cause the resilient force to also urge the sealing mass against the mating surface or adjacent surfaces. A sealing mass may be a unitary piece with the tube that it surrounds for similar reasons. It can be beneficial to make a sealing mass from a resilient or compressible material, as these materials may be useful to more effectively fill dead space and thereby reduce turbulence in a fluid path. These materials, when urged by a tube that has a resilient force (e.g., from a spring), may form a fluid-tight seal around the fluid path between the connector and a mating connector. In one particularly useful example, a sealing mass may be a plug or roughly frustoconical body made out of silicone.

If a sealing mass is placed such that it encircles a connecting tube near a tip of the connecting tube, a resilient or compressible material can help to create a seal between the connecting tube and a second tube. Compressible or resilient material may be preferable because such material may be able to form a tighter or larger seal near the connection between the connecting tube and the second tube. This tighter or larger seal may restrict a fluid traveling through the tube from entering dead space that may otherwise be present near the connection between the connecting tube and the second tube. A resilient or compressible sealing mass placed near the tip of a connecting tube may be especially effective in forming a tight, large seal in the presence of a force-exerting or an actuating member. A force-exerting member may be designed to apply pressure to firmly seat the connecting tube and the second tube. Such pressure may be sufficient to partially compress a resilient or compressible sealing mass that encircles the tip of the connecting tube.

A sealing mass that is placed around a tube may be any shape. The shape of the sealing mass may depend upon what type of material is used, where it is placed, and the anticipated use of the sealing mass. For example, if a sealing mass is placed encircling the tip of a tube which will connect to another tube, this may make some shapes more advantageous. A sealing mass with a radially symmetric shape may be desirable in order to create a larger or better seal. This can be especially helpful in a common medical setting where medical connectors (and the female openings therein) are radially symmetric. Thus, the shape, surface angles, and symmetries of the sealing mass can be made compatible with a wide variety of possible connectors. If it is known what type of connector a tube will connect to, the shape of the sealing mass may be based upon the shape of the corresponding connector. For example, if the corresponding connector is a standard female Luer connector, it may be useful if the sealing mass at the tip of the tube is in a frustoconical shape or has a generally frustoconical portion. This shape may allow a tight seal to be formed between the sealing mass and a corresponding female Luer connector, and thereby reduce leakage and/or turbulence at such a connection. Such a sealing mass may be extremely useful because it is able to be used with a standard connector, rather than requiring completely new connectors to be used. A patient connector with a sealing mass may be able to act as a male connector and connect to a standard female connector. Alternatively, a patient connector with a sealing mass may be able to act as a female connector and connect to a standard male connector. For example, a sealing mass may be placed around an inlet/outlet on a female connector in a location that is configured to come into contact with a standard male connector when the connectors are attached. Such a sealing mass may take on a shape that is suited to form a seal between the patient connector and the standard male connector. For example, a sealing mass may have an O-shape, designed to encircle the inlet/outlet that forms an interface with the standard male connector. A sealing mass may be created such that a patient connector may be able to reduce dead space and the incidence of blood clotting while working with existing, standard connectors. A sealing mass may allow a patient connector to be used as a medical device takes multiple samples of an individual.

FIG. 36I illustrates a generalized view of a patient connector 3652 that incorporates a sealing mass that can have some of the advantages and incorporate some of the principles discussed above. In this embodiment, an outer housing 3653 is configured to receive a regular flow passageway 3651. A connecting tube 3655 is connected to the to the regular flow passageway 3651 inside the outer housing 3653. The connecting tube includes a tip 3657 that is suitable for connecting with another connector which corresponds with the patient connector 3652. A sealing mass 3659 is positioned on the connecting tube 3655 near the tip 3657. The connecting tube 3655 extends through the sealing mass 3659 to the tip 3657.

FIG. 36J illustrates a generalized view of a patient connector 3654 that incorporates a sealing mass 3667, where the sealing mass 3667 has a shape configured to generally approximate a shape of the interface 3673 of the corresponding connector 3671 even when the patient connector 3654 is not mating with the corresponding connector. In this embodiment, an outer housing 3675 is configured to receive a regular flow passageway 3651. Inside the outer housing 3675, there is a first pushing surface 3661 and a second pushing surface 3663, with the regular flow passageway 3651 connected to a connecting tube 3655 through the second pushing surface 3663. A sealing mass 3667 is positioned on the connecting tube 3655 near the tip 3657. The connecting tube 3655 extends through the sealing mass 3667 to the tip 3657. A force-exerting member or an actuating member 3665 (e.g., a spring) is situated between the first pushing surface 3661 and second pushing surface 3663 and that actuating member 3665 is configured to simultaneously exert a force on both of these pushing surfaces to thereby urge the first pushing surface 3661 away from the second pushing surface 3663, thereby pushing the connecting tube 3655 towards a corresponding connector 3671. The corresponding connector 3671 will have an interface 3673. The sealing mass 3667 is configured to generally approximate a shape of the interface 3673 of the corresponding connector 3671 even when the patient connector is not mating with the corresponding connector, to allow for the sealing mass 3667 to minimize the dead space in the connection between the connecting tube 3655 and the corresponding connector 3671.

One or more coatings may be applied to any surface of a patient connector or an analyte monitoring system. For example, coatings may be applied to the inner or outer walls of connecting tubes in a patient connector, on the exterior of a patient connector, on a sealing mass on a patient connector, or any other surface of the patient connector. Such coatings may serve any number of purposes, such as making a connector last longer, preventing materials used in the connector from entering the fluid contained in a fluid path, increasing the accuracy of an analyte measurement, allowing for more flexibility in which materials are used in a patient connector, or reducing blood clotting in the patient connector. The purpose of a coating may determine where on a patient connector the coating is applied. For example, if a coating is designed to reduce or eliminate blood clotting in a patient connector, it may be advantageous to apply the coating to the inner and outer walls of a connecting tube, to a sealing mass placed near the tip of the connecting tube, and/or to any other surface that blood may come into contact with. A coating that is designed to reduce or eliminate blood clotting may be applied to any surface in an analyte monitoring system that may come into contact with blood. For example, a coating may be applied to an analyte monitoring system that is situated outside the body, either in the analyte monitoring system or in a tube that leads to the analyte monitoring system. For example, a coating may be applied near an intersection, such as the first connector 524 (C1) as illustrated in FIG. 5. An intersection such as this may be especially prone to turbulence because fluid flowing through the connector may be required to make a sharp 90-degree turn. Fluid that flows past a first connector 524 may be especially prone to turbulence when a valve 531 is closed, if the valve 531 is some distance away from the first connector 524. For example, when valve (e.g., a pinch valve, rotary valve, shuttle valve, etc.) is placed some distance from an intersection, fluid that is in the tube leading to the closed valve may be more likely to be turbulent. Therefore, to avoid such turbulence, it may be useful to apply a coating to such an intersection, especially when a valve is placed further away from the intersection. A coating may be applied to an analyte monitoring system that is designed to take multiple readings of analyte levels. Such a coating may be applied to a connector that is used during multiple readings from a medical device, and over multiple fluid withdrawal cycles. A coating may also be applied to an analyte monitoring system that is situated at least partly inside the body. A coating may also be applied to other systems that may come into contact with blood where it is desired to reduce friction and/or avoid blood clotting.

There are a number of ways that a coating may assist in reducing or eliminating blood clotting in a patient connector. For example, lubricious coatings can be used to reduce friction between the flowing fluid and the side-walls of the connector. Therapeutic drug delivery coatings can also be used (e.g., drug-eluting coatings). Some useful coatings include those that comprise heparin, which can be designed to reduce blood clotting against the side-walls of the connector by acting as an anticoagulant. A coating may be applied to the inner or outer walls of a connecting tube to reduce friction between a wall of the connecting tube and blood flowing within the tube. A reduction in friction may reduce the shear stress on blood that flows in a boundary area near the side-walls of the connector. The blood coagulation cascade is a very delicate process, and a reduction in shear stress can decrease the tendency for blood to begin to coagulate by reducing the turbulence in blood passing through the patient connector. Any number of lubricating agents may be suitable to form a lubricious coating on the inner or outer walls of the connecting tubes. A number of companies provide a wide array of active or inactive haemocompatible coatings that can be used in this context. Such companies include: AdvanSource biomaterials (e.g., HydroMed); AorTech Biomaterials; Applied Membrane Technology (e.g., Silglide, Fluorocarb); AST Products Inc. (LubriLAST); Bayer (e.g., Baymedix CL); Biocoat, Inc. (e.g., HYDAK); BioInteractions Ltd. (e.g., Assist); Cadence Inc.; Carmeda (e.g., CBAS); Coatings2Go LLC; Covalon Technologies Ltd.; Demax Medical; DSM Biomedical (e.g., ComfortCoat); Hemoteq (e.g., Lubriteq); Medkote; Merit Medical Systems Inc. (e.g., Endotek); SurModics Inc. (e.g., Rejoice, Harmony); and Tegra Medical. Lubricious coatings can be used to coat the inner or outer walls of the connecting tubes. Lubricious coatings such as this can dramatically reduce the friction between blood and the inner walls of the connecting tubes, and therefore reduce the shear stress on the blood. Lubricious coatings may be advantageous because they are less likely than some other coatings to interfere with analyte detection and measurement. Lubricious coatings may also be easier to apply to the inner and outer walls of a connecting tube, and may be more cost-effective than other types of coatings. Lubricious coatings may also present less danger than some types of drug-eluting coatings (as discussed above under the heading "SELF-ADJUSTING PATIENT CONNECTOR"), and therefore be easier to work with or more desirable than other types of coatings. Lubricious coatings can work with a patient connector design that minimizes dead space to reduce the incidents of clotting that are seen in the inner walls of the connecting tubes. It may be necessary to apply such a coating to a patient connector or other device as one of the later steps in production, as coatings may be somewhat more sensitive to temperatures encountered during manufacturing. For example, it maybe desirable to apply a coating to a patient connector as a final step in manufacturing a patient connector, to ensure that the heat needed to shape the patient connector does not adversely affect the coating and inhibit its function.

Coatings may reduce the need for detergent and/or heparin to flush the fluid system between draws and may allow for more frequent measurements. For example, a lubricious coating may ensure that less blood or other fluid remains in the fluid system after blood is drawn. If less blood remains in the fluid system after blood is drawn, this may reduce the amount of detergent and/or heparin (such as tergazyme A) that are needed to flush the system between blood draws. This may simplify the design of the system, may create less waste, and/or may make the system less expensive to create and to operate. Coatings may also allow for more frequent measurements, as less time may be needed between each measurement to flush the system and the system could be flushed more times with the same quantity of detergent and/or heparin.

FIG. 36K illustrates a cross-section view of a sealing mass 3675 that is positioned on a connecting tube 3655 near the tip 3657 of the connecting tube 3655. The sealing mass 3675 may have a frustoconical shape in a region 3679 that is near the tip 3657 of the connecting tube 3655. The remainder 3677 of the sealing mass 3675 may also have a frustoconical shape, although it may be less pronounced than the frustoconical shape in a region 3679 that is near the tip 3657 of the connecting tube 3655. The distance 3681 between the sealing mass 3655 and the tip 3657 of the connecting tube 3655 may be configured to be very small, thereby placing the sealing mass 3675 in close proximity to the tip 3657 of the connecting tube 3655. For example, the distance 3681 between the sealing mass 3655 and the tip 3657 of the connecting tube 3655 may be 0.001, 0.005, 0.01, 0.05 or 0.1 inches. It may also be beneficial to apply a coating to portions of the connecting tube 3655 and sealing mass 3675. For example, a coating may be applied to the inner walls 3683 of the connecting tube 3655, to the tip 3657 of the connecting tube 3655, or to any part of the sealing mass 3675.

FIG. 36L illustrates a different view sealing mass 3675 from FIG. 36K. In this head-on view, the sealing mass 3675 encircles the tip 3657 of the connecting tube. This views helps to illustrate the radial symmetry that a sealing mass 3675 may possess. This radial symmetry may allow a sealing mass 3675 to form a tighter, larger seal with a mating connector. A sealing mass 3675 may have a frustoconical shape in a region 3679 that is near the tip 3657 of the connecting tube. The remainder 3677 of the sealing mass 3675 may also have a frustoconical shape, although it may be less pronounced than the frustoconical shape in a region 3679 that is near the tip 3657 of the connecting tube. It may be beneficial, as before, to apply a coating to the tip 3657 of the connecting tube, as well as to the sealing mass 3675.

Figure 36M:
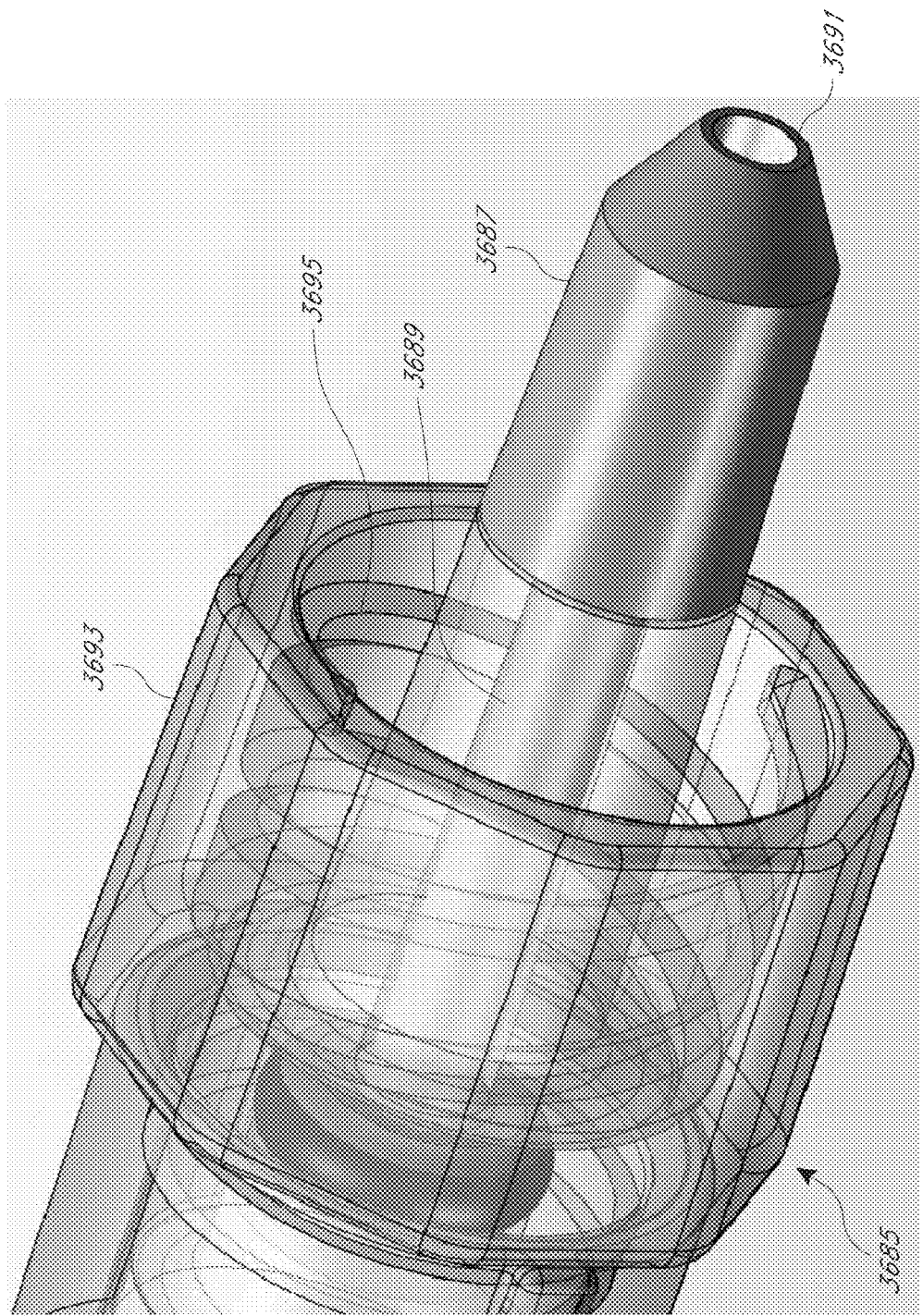
FIGS. 36M-36N are illustrations of self-adjusting connectors that have a sealing mass.

FIG. 36M illustrates a view of a patient connector 3685 that includes a sealing mass 3687. The sealing mass 3687 may encircle a connecting tube 3689 near the tip 3691 of the connecting tube 3689. The tip 3691 of the connecting tube 3689 may be configured to adjustably accommodate and firmly abut a mating connector. The sealing mass 3687 may be made of a resilient material (e.g., silicone) so that when the tip 3691 of the connecting tube 3689 firmly abuts a mating connector, the sealing mass 3687 may create a seal with the mating connector around a fluid flow inside the connecting tube 3689. The patient connector 3685 may have an outer housing 3693. The outer housing 3693 may have threads 3695, which may be used to attach the patient connector 3685 to a mating connector (not shown).

Figure 36N:
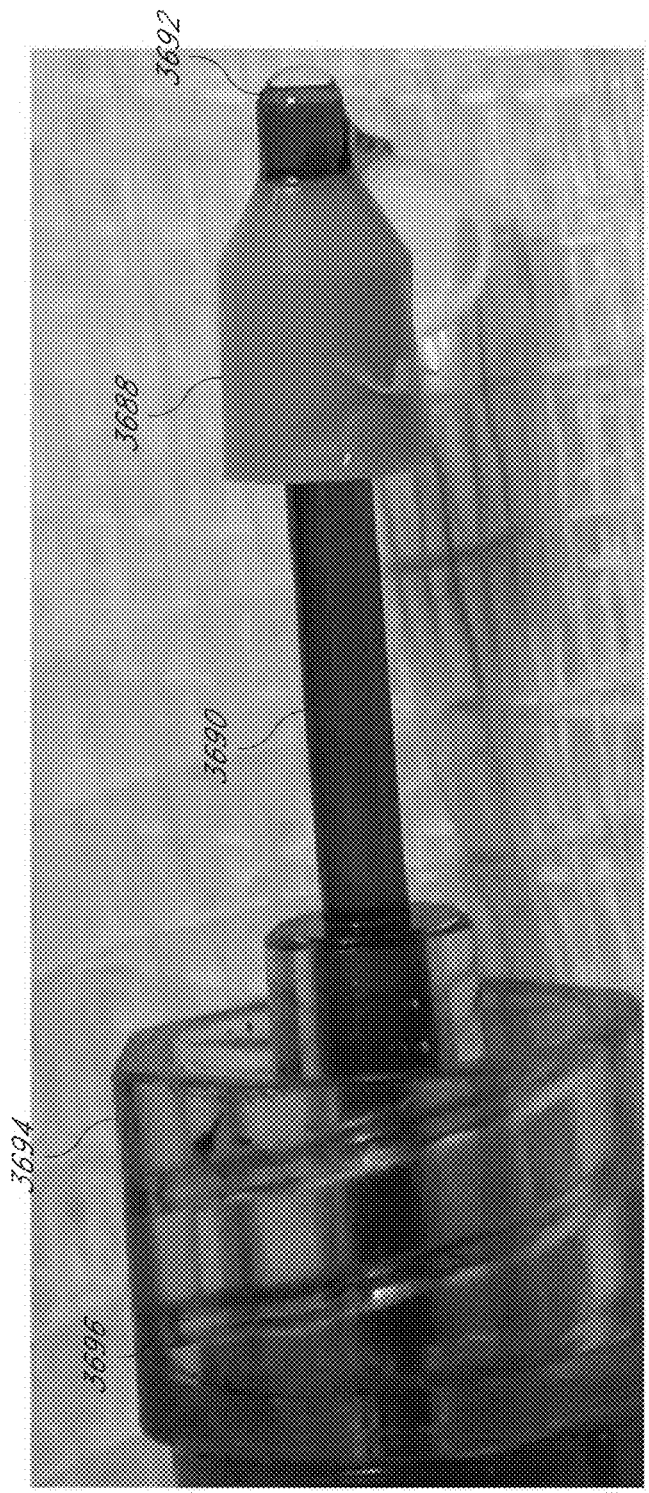

FIG. 36N illustrates a view of a patient connector 3686 that includes a sealing mass 3688. The sealing mass 3688 may be made out of silicone, or another resilient material. The sealing mass 3688 may encircle a connecting tube 3690 near the tip 3692 of the connecting tube 3690. It may be beneficial to apply a coating to an inner portion of the connecting tube 3690, to the tip 3692 of the connecting tube 3690, and/or to a portion of the sealing mass 3688. The patient connector 3686 may have an outer housing 3694. The outer housing may have threads 3696, which may be used to attach the patient connector 3686 to a mating connector.

In testing on sheep, placing a silicone sealing mass around the tip of a tube and coating the inner walls of the connecting tubes with a lubricious or heparin coating has been shown to significantly increase the length of time it takes before clotting is observed in a self-adjusting patient connector such as those described herein. A series of tests have been conducted, which show the efficacy of some embodiments at reducing the frequency of blood clotting. In each test, a catheter was attached to a sheep, and was used to draw blood every 15 minutes for the duration of the test. The blood drawn from the sheep flowed through a self-adjusting patient connector. In each test, the amount of time it took to withdraw a certain amount of blood was recorded, and this time was used to determine whether any anti-clotting measures were successful. A connector that is able to prevent blood clotting should ensure that successive blood draws will not take more time than previous blood draws through the same system. If a blood draw through the same system takes substantially longer than a previous blood draw, this may be a sign that a clot has begun to form within the connector.

In a first test, a sheep was attached to both a peripheral venous catheter (PVC) and a central venous catheter (CVC) using a self-adjusting patient connector without any coating or sealing mass to determine how long it would take for blood clots to form within the connector. In this test, clotting developed in the PVC after 3.4 hours, and clotting developed in the CVC after 5.6 hours. The results of this test may suggest a 10- to 12-hour useful life for human patients. In a second test, two different coatings were used on the inner and outer walls of the connecting tubes. Although the coatings used for this test happened to be the SurModics Rejoice Passive Hemocompatible Coating, a lubricious coating, and the SurModics Applause Heparin Coating, a drug-eluting coating, many other coatings can be used; see supra for a non-exhaustive partial list of example coating sources and coatings. In this second test, a sheep was attached to a CVC for 12 hours, to test both the lubricious and the drug-eluting coatings. During the 12 hour duration of the test, neither connecting tube showed any sign of clotting. Therefore, it appears that either a drug-eluting or a lubricious coating may be effective in reducing the frequency of blood clotting in fluid systems. In a third test, a lubricious coating was applied to the walls of the connecting tubes, and a silicone sealing mass was placed near the tip of the connecting tube. Although the lubricious coating used here was the SurModics Rejoice Passive Hemocompatible Coating, many other coatings could have been used; see supra for a non-exhaustive partial list of example coating sources and coatings. In this test, a patient connector was attached to a sheep through a CVC for 36 hours. During the 36 hours of this test, no clotting was observed. In a fourth test, three connecting tubes were used, each with a silicone sealing mass and each coated with a lubricious coating. Although the lubricious coating used here was the SurModics Rejoice Passive Hemocompatible Coating, many other coatings could have been used; see supra for a non-exhaustive partial list of example coating sources and coatings. The connecting tubes were attached to a sheep through a CVC for 42 hours. A measurement was taken for each blood draw from the fourth test, to determine the length of time that each blood draw took. Throughout the duration of the test, for each of the three self-adjusting patient connectors, each blood draw took a very consistent amount of time, between 35 and 45 seconds. No clotting was observed in any of the three self-adjusting patient connectors in this test.

In a fifth test, a 72-hour study was conducted using three connectors attached to two sheep. This test used patient connectors with a lubricious coating and silicone sealing masses. Although the lubricious coating used here was from SurModics, many other coatings or suppliers could have been used; see supra for a non-exhaustive partial list of example coating sources and coatings. In this test, one patient connector was able to successfully last 72 hours without any clots forming. The other two patient connectors were also able to last a long time before blood clots appeared, with the connectors lasting for 47 and 53 hours. It is possible that these connectors may have lasted even longer if the lubricious coating was applied to additional parts of the connector or an analyte monitoring system. In this way, these connectors may extend the length of time that a medical device connector can be used for repeated blood withdrawal. For example, these connectors are able to allow at least 12 hours of repeated blood draws without clot formation, whereas prior connectors suffered from clot formation in fewer than 6 hours.

In various embodiments, the patient connector can include fittings and lock assemblies that comply with ISO 594/1 and ISO 549-2 standards. In various embodiments, the patient connector can be configured and constructed to withstand up to and beyond 5 times normal operating pressure. As discussed above, various embodiments of the patient connector described herein can easily withstand about 1.5 psi over the back pressure. Back pressures can vary widely and can be correlated to a patient's blood pressure, for example. Normal arterial blood pressures can be in the range of 112/64 mmHg (2.17/1.24 psi), but diastolic pressures can be <60 mmHg (~1.16 psi) or >100 mmHg (~1.93 psi), and systolic pressures can be <90 mmHg (~1.74 psi) or >160 mmHg (~3.09 psi). Venous blood pressures can often be lower than arterial pressures. In various embodiments, the patient connector can be configured and constructed to withstand back pressures higher than the values mentioned above. For example, the connector can be useful to connect to different medical devices that do not have arterial or venous pressures but instead have pressures that are induced by pumps, gravity, and other device parameters.

Figure 37A:
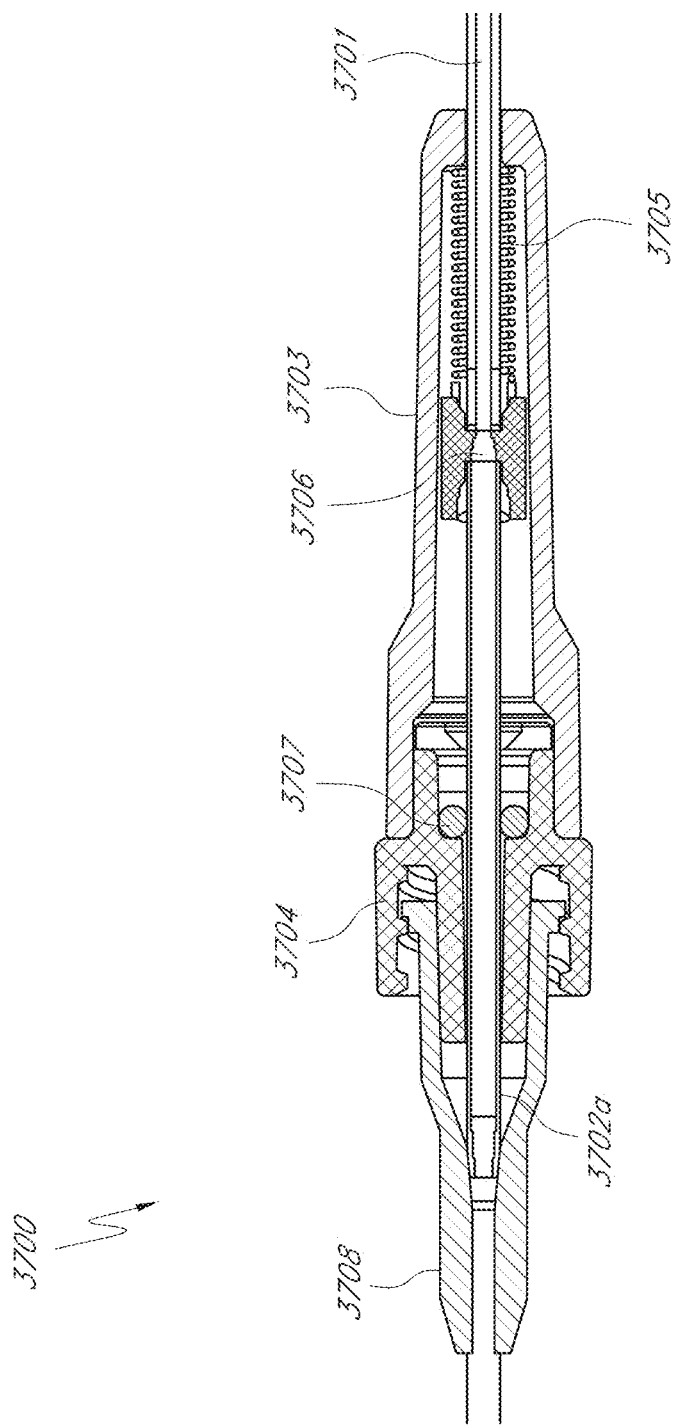

The patient connector 3600 can be compatible with a wide variety of CVCs and PICCs with depths ranging from approximately 0.270" to approximately 0.780" (approximately 6.9 mm to approximately 19.8 mm) and diameters up to 16 gauge (5 Fr). For example, FIG. 37A illustrates a cross-sectional view of the patient connector 3700 configured to connect a patient tube 3701 to an 18 ga CVC having a tapered tip. A first end of the extender tube 3702a connects to the patient tube 3701 via a hub 3706. The second end of the extender tube 3702a is tapered and connects to the 18 ga CVC having a tapered tip. As discussed above with reference to FIG. 36A, an "O-ring" may be disposed between the extender tube 3702a and the Luer base 3704. A standard Luer fitting 3708 that is matched to the Luer base 3704 can include a fluid line (e.g. a CVC or a PICC line) that is attached to the patient. In the embodiment illustrated in FIG. 37A, the Luer base 3704 is configured to match to a COOK type male Luer fitting 3708.

Figure 37B:
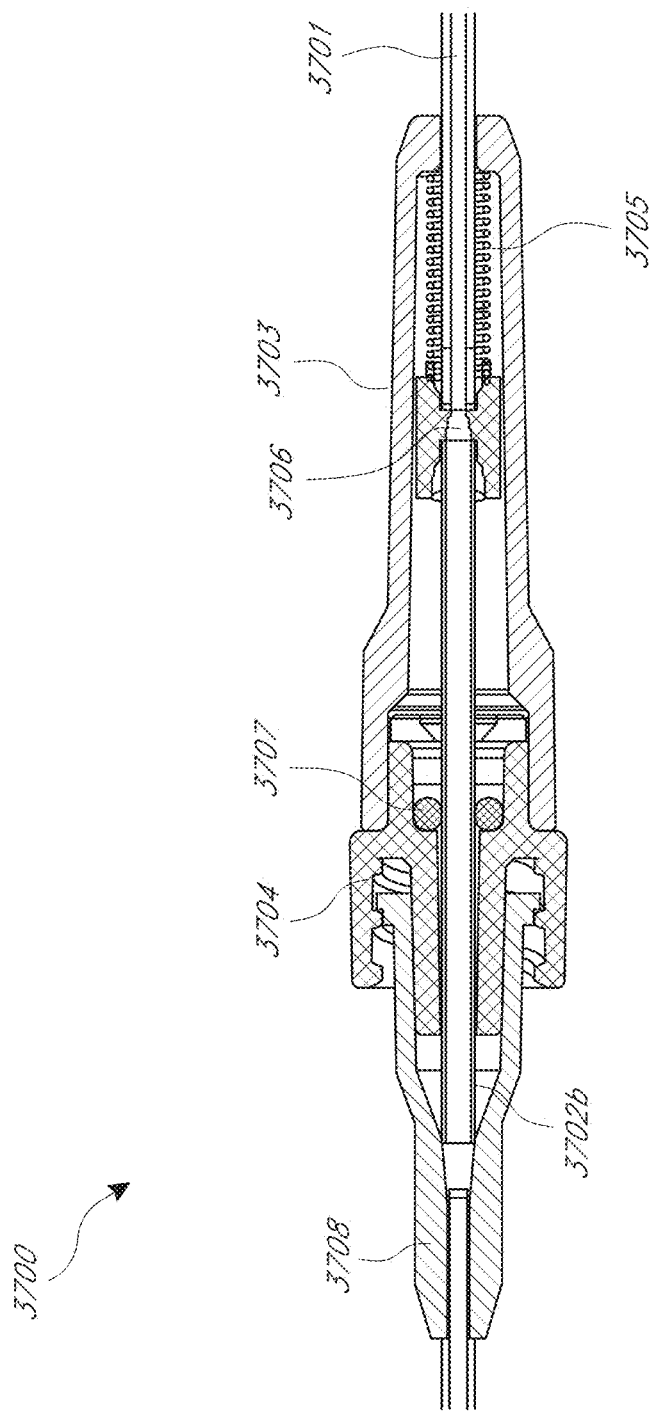

FIG. 37B illustrates a cross-sectional view of the patient connector 3700 configured to connect a patient tube 3701 to an 18 ga CVC having a square tip. In the embodiment illustrated in FIG. 37B, the second end of the extender tube 3702b is square. Similar to FIG. 37A, the Luer base 3704 is configured to match to a COOK type male Luer fitting 3708.

Figure 37C:
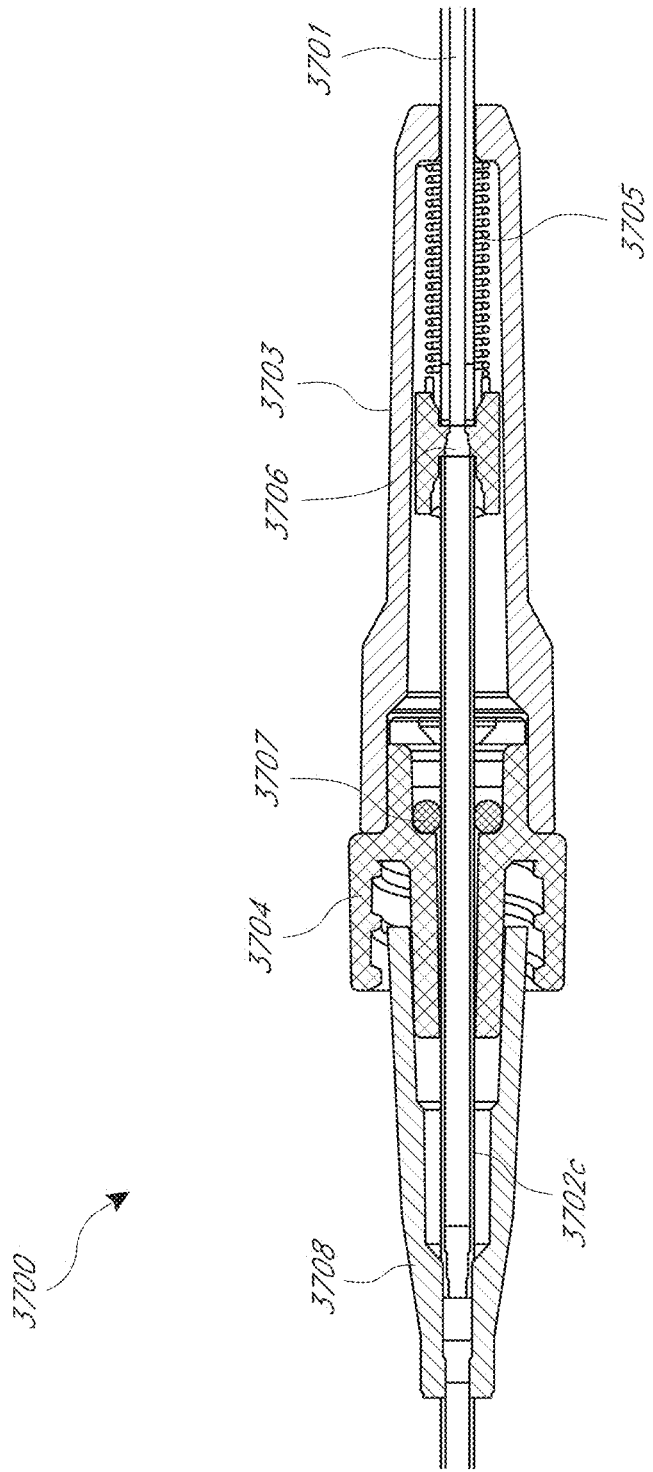

FIG. 37C illustrates a cross-sectional view of the patient connector 3700 configured to connect a patient tube 3701 to an 18 ga PICC line having a tapered tip. In the embodiment illustrated in FIG. 37C, the second end of the extender tube 3702c is tapered. In the embodiment illustrated in FIG. 37C, the Luer base 3704 is configured to match to a BD type male Luer fitting 3708.

Figure 37D:
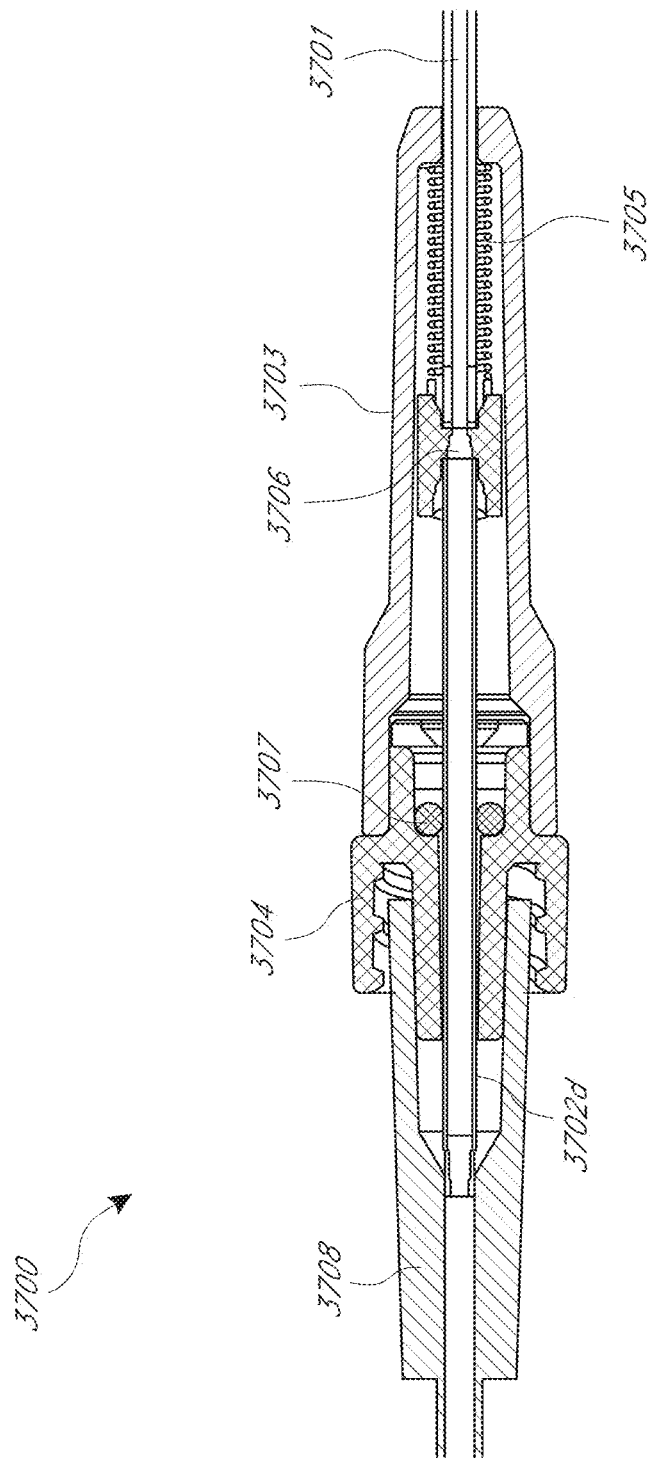

FIG. 37D illustrates a cross-sectional view of the patient connector 3700 configured to connect a patient tube 3701 to an 18 ga CVC having a tapered tip. In the embodiment illustrated in FIG. 37D, the second end of the extender tube 3702d is tapered. In the embodiment illustrated in FIG. 37D, the Luer base 3704 is configured to match to an Arrow type male Luer fitting 3708.

Figure 37E:
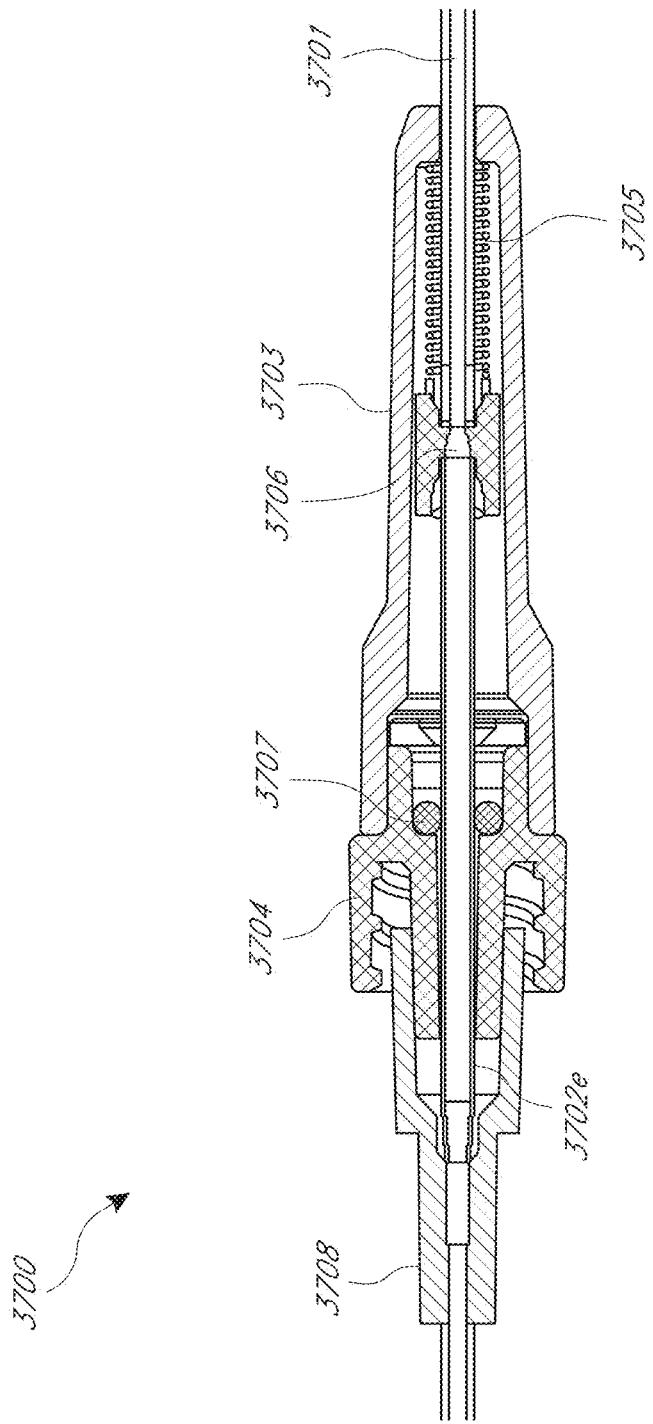

FIG. 37E illustrates a cross-sectional view of the patient connector 3700 configured to connect a patient tube 3701 to a 20 ga PICC line having a tapered tip. In the embodiment illustrated in FIG. 37E, the second end of the extender tube 3702e is tapered. In the embodiment illustrated in FIG. 37E, the Luer base 3704 is configured to match to a Johnson & Johnson type male Luer fitting 3708.

FIG. 37F illustrates a cross-sectional view of the patient connector 3700 configured to connect a patient tube 3701 to an 18 ga PICC line having a square tip. In the embodiment illustrated in FIG. 37F, the second end of the extender tube 3702f is square. In the embodiment illustrated in FIG. 37F, the Luer base 3704 is configured to match to a BD type male Luer fitting 3708.

Figure 37H:
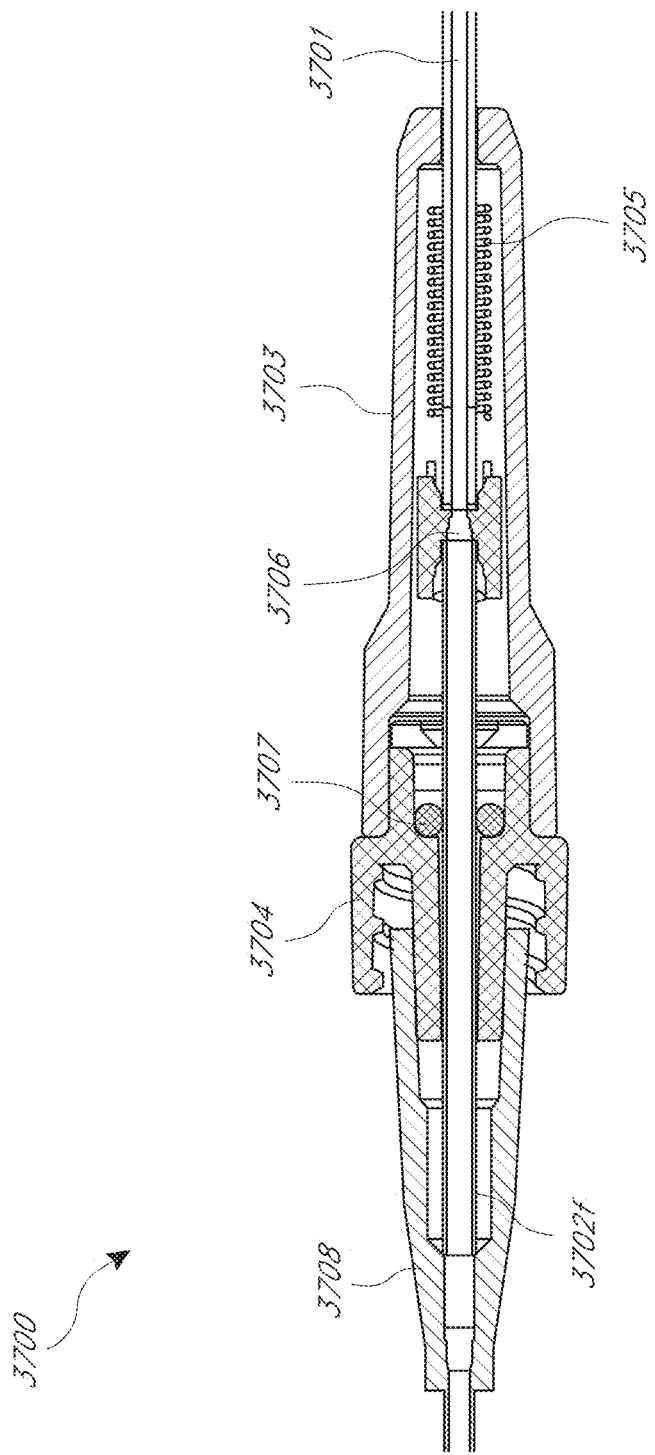
Figure 37G:
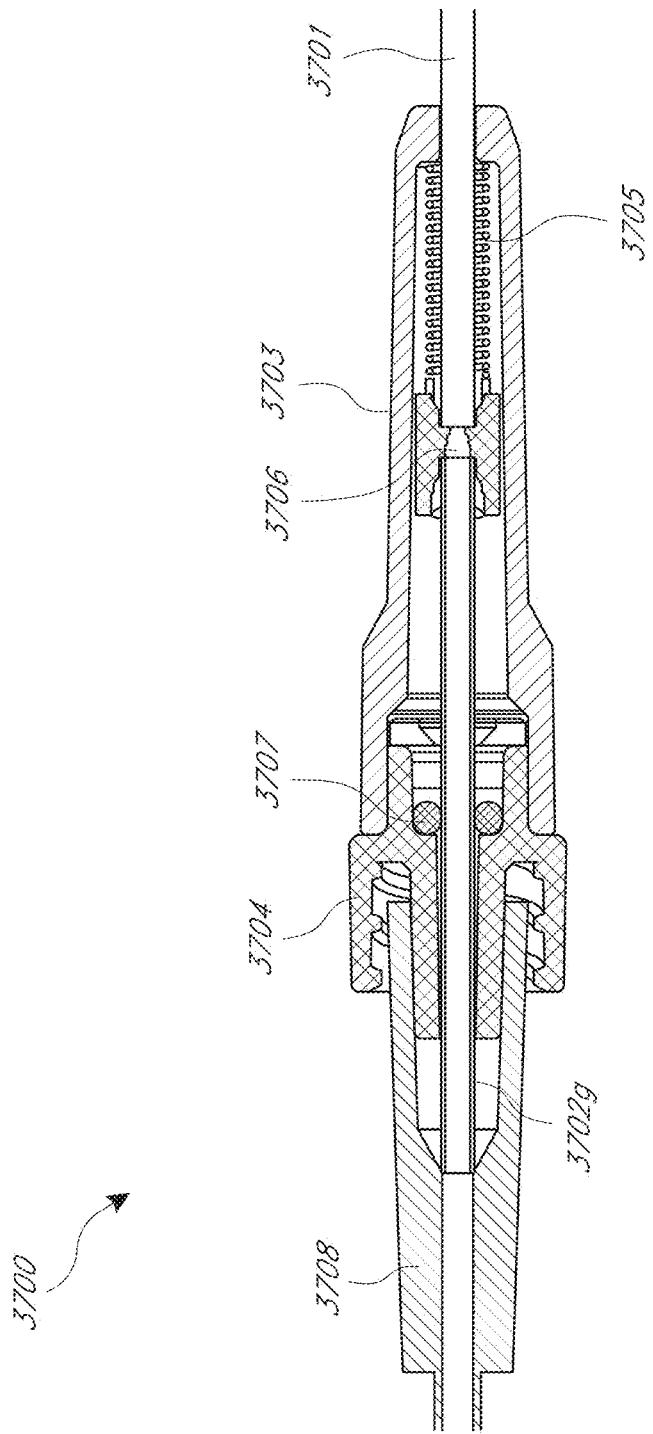
Figure 37H:
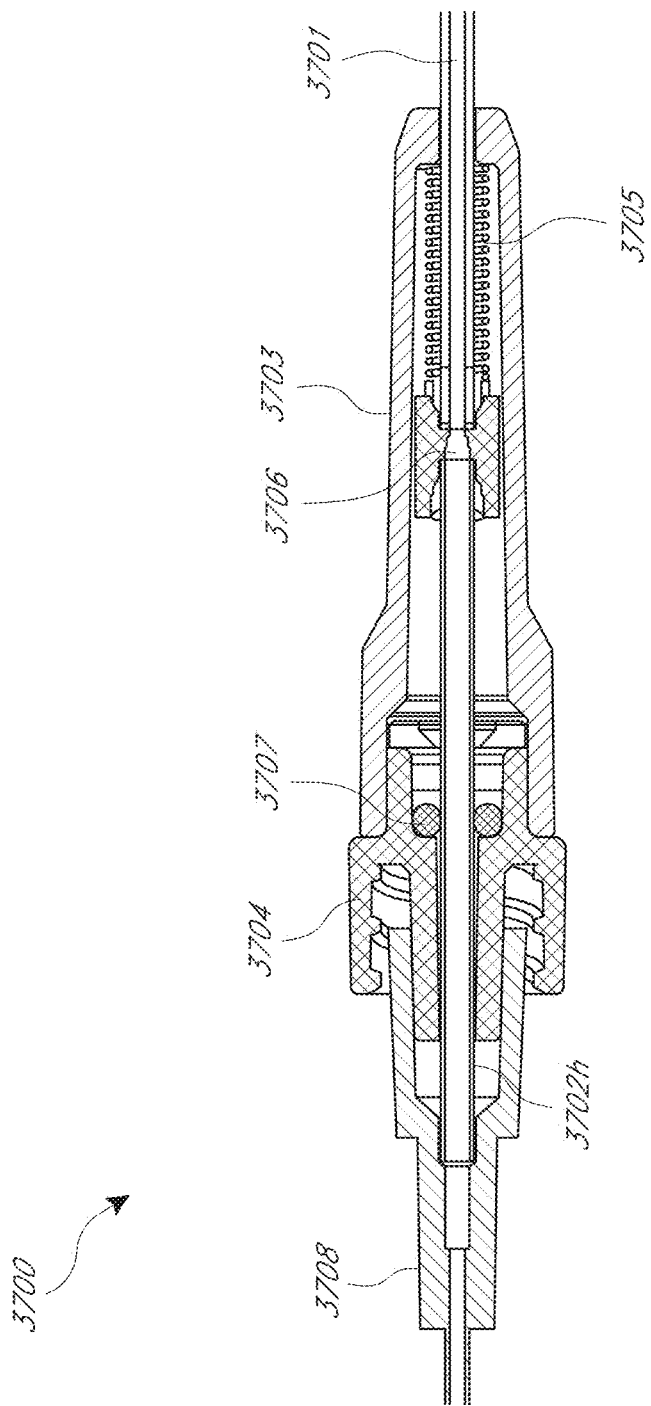

FIG. 37G illustrates a cross-sectional view of the patient connector 3700 configured to connect a patient tube 3701 to an 18 ga CVC having a square tip. In the embodiment illustrated in FIG. 37G, the second end of the extender tube 3702g is square. In the embodiment illustrated in FIG. 37G, the Luer base 3704 is configured to match to an Arrow type male Luer fitting 3708.

FIG. 37H illustrates a cross-sectional view of the patient connector 3700 configured to connect a patient tube 3701 to a 20 ga PICC line having a square tip. In the embodiment illustrated in FIG. 37H, the second end of the extender tube 3702h is square. In the embodiment illustrated in FIG. 37H, the Luer base 3704 is configured to match to a Johnson & Johnson type male Luer fitting 3708.

Figure 38A:
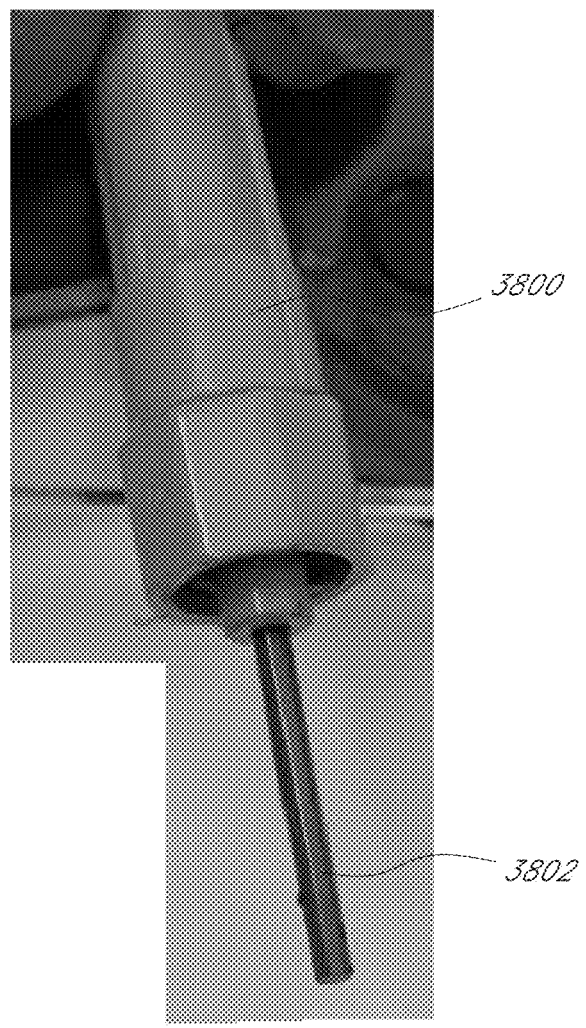
FIGS. 38A-38C and 39 illustrate the use of embodiments of a self-adjusting patient connector in a study to test for performance and compatibility.
Figure 38B:
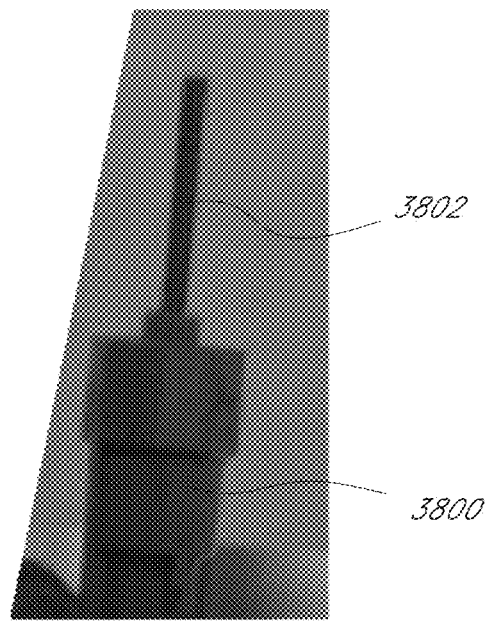

To understand and evaluate the performance of an example self-adjusting patient connector, and the compatibility of the various embodiments of the self-adjusting patient connector with other connectors, 12 healthy diabetic patients were connected to a medical device (e.g. the OPTISCANNER™) including an embodiment of the self-adjusting patient connector at its end for a period of about 74 hours. The other end of the self-adjusting patient connector was connected to a peripheral IV in each of the 12 patients. As illustrated in FIG. 38A, the self-adjusting patient connector 3800 included an extender tube 3802 and a spring (not shown) which maintained the structural integrity of the extender tube 3802 and the connector 3800 under constant spring force. The extender tube 3802 included polyimide for additional structural stability. As can be seen from FIGS. 38A and 38B, even after approximately 24 hours of operation (e.g. 23 hours 30 minutes), the fluid flow path in the extender tube 3802 remained open and was not clogged or occluded due to clotting of the blood. Additionally, FIGS. 38A and 38B illustrate that the extender tube maintained its shape even after approximately 24 hours of operation and that the extremity of the extender tube was not deformed.

Figure 38C:
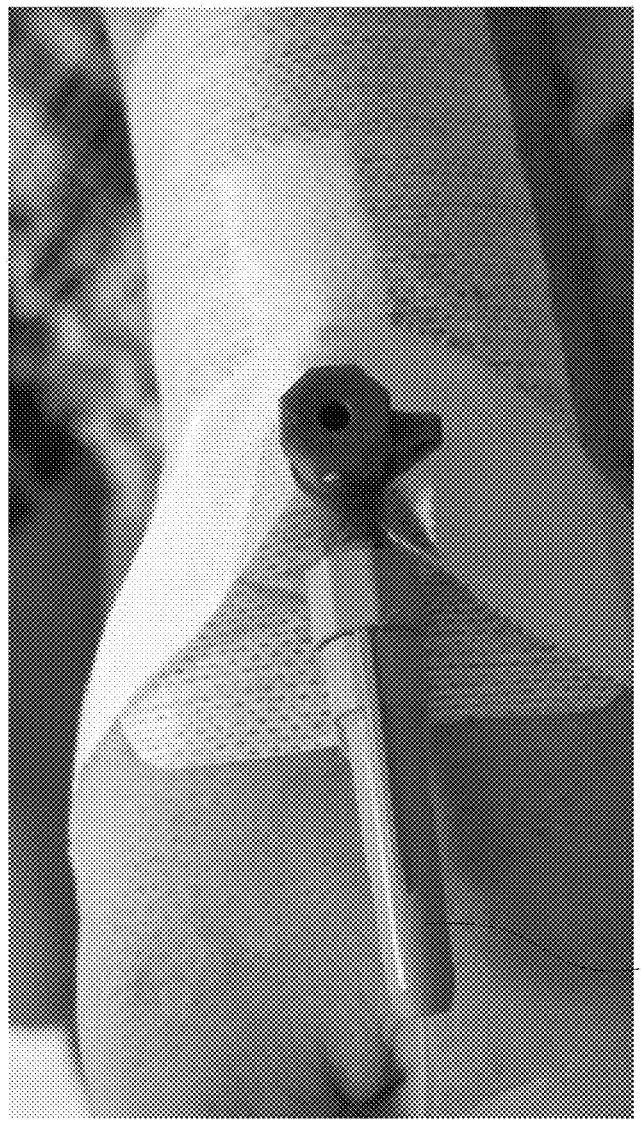

The self-adjusting patient connector was also tested for compatibility with various catheters. It was found that the self-adjusting patient connector was compatible with a BBraun Vasofix peripheral catheter as well as BD Angiocath Autogard catheter. FIG. 38C illustrates the self-adjusting patient connector 3800 connected to a BBraun Vasofix peripheral catheter.

Figure 39:
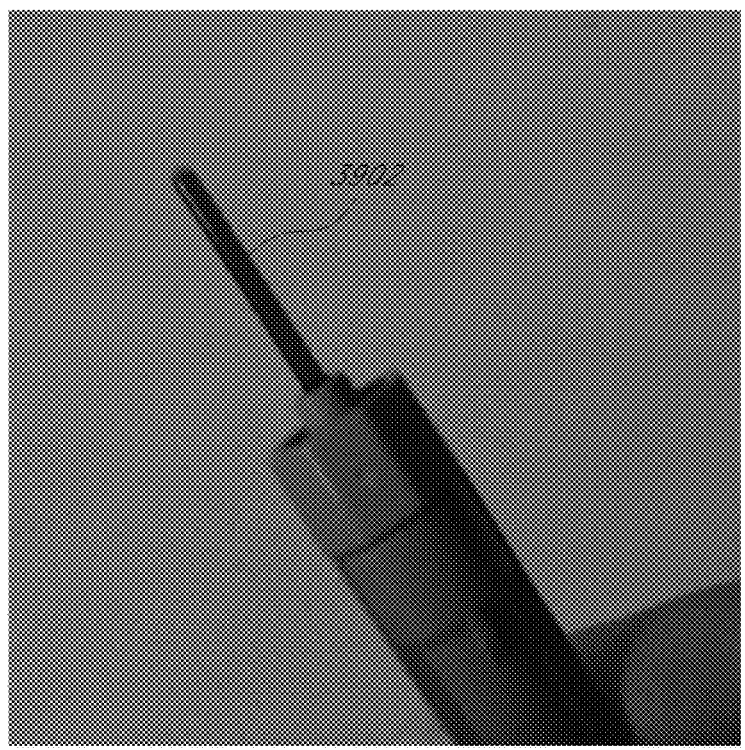

In another test, a medical device (e.g. the OPTISCANNER™) including an embodiment of the self-adjusting patient connector at its end was connected to a proximal port of a femoral venous catheter (e.g. Arrow triple lumen catheter) of a patient in the ICU for 12 hours. As seen from FIG. 39, even after 12 hours of continuous operation, the fluid flow path in the extender tube 3902 remained open and was not clogged or occluded due to clotting of the blood. The extender tube or the self-adjusting connector was not manually primed at any point during this test. The above tests indicate that some embodiments of the self-adjusting patient connector can be used over longer periods of time without requiring replacements due to structural deformation or occlusion of the fluid flow path as compared to other standard connectors.

Reference throughout this specification to "some embodiments" or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics may be combined in any suitable manner, as would be apparent to one of ordinary skill in the art from this disclosure, in one or more embodiments.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

Embodiments of the disclosed systems and methods may be used and/or implemented with local and/or remote devices, components, and/or modules. The term "remote" may include devices, components, and/or modules not stored locally, for example, not accessible via a local bus. Thus, a remote device may include a device which is physically located in the same room and connected via a device such as a switch or a local area network. In other situations, a remote device may also be located in a separate geographic area, such as, for example, in a different location, building, city, country, and so forth.

Methods and processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may be comprised of connected logic units, such as gates and flip-flops, and/or may be comprised of programmable units, such as programmable gate arrays, application specific integrated circuits, and/or processors. The modules described herein are preferably implemented as software modules, but may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with patients, health care practitioners, administrators, other systems, components, programs, and so forth.

A number of applications, publications, and external documents may be incorporated by reference herein. Any conflict or contradiction between a statement in the body text of this specification and a statement in any of the incorporated documents is to be resolved in favor of the statement in the body text.

Although described in the illustrative context of certain preferred embodiments and examples, it will be understood by those skilled in the art that the disclosure extends beyond the specifically described embodiments to other alternative embodiments and/or uses and obvious modifications and equivalents. Thus, it is intended that the scope of the claims which follow should not be limited by the particular embodiments described above.

What is claimed is:

1. An accommodating medical connector configured to resist blood clot formation, thereby extending a number of hours that the connector may be used for periodic blood withdrawals, the connector comprising:
   an outer housing having an elongate housing axis, a first side configured to accept standard medical tubing comprising an incoming fluid line, and a connecting side having an outer connecting structure configured to securely but removably interlock with an outer portion of a standard medical connector to form an interior volume;
   an elongate protruding cylindrical tube having a stiffness greater than the standard medical tubing and having an elongate tube axis, the protruding tube positioned so its elongate tube axis is generally aligned with and concentric to the elongate housing axis of the outer housing, an interior of the protruding tube forming a fluid path and terminating at a port, the protruding tube configured to:
   resiliently press against the standard medical connector when the standard medical connector is securely but removably interlocked with the outer connecting structure to provide a contiguous blood flow path; and
   minimize gaps between the standard medical connector and the protruding tube;
   a hub within the outer housing, axially aligned with both the incoming fluid line and the elongate tube axis and positioned between them to form a permanent secure connection such that any movement of the protruding tube in a direction of the elongate tube axis and the elongate housing axis causes corresponding movement of the incoming fluid line, the fluid path passing through the hub;

a lubricious coating applied to at least a portion of an inner lumen of the protruding tube, the coating configured to lubricate blood-contacting surfaces to reduce blood clotting; and a sealing mass positioned at or near the tip of the protruding tube, the sealing mass having a shape configured to correspond with a shape of the standard medical connector when the standard medical connector is securely but removably interlocked with the outer connecting structure such that the sealing mass prevents a fluid contained within the protruding tube from leaking out of the port and into the interior volume instead of proceeding into a corresponding lumen of the standard medical connector, and the sealing mass positioned and shaped to function together with the protruding tube, and the protruding tube is aligned with and has a width similar to a width of the corresponding lumen of the standard medical connector, to reduce blood clotting and confine a fluid flow to a fluid path while inhibiting leakage into and clotting within the interior volume outside the fluid path.

2. The accommodating connector of claim 1, wherein the sealing mass has a shape configured to correspond with a shape of the standard medical connector such that the sealing mass shape generally approximates the shape of an opening in the standard medical connector even when the accommodating connector is not mating with the standard medical connector.

3. The accommodating connector of claim 1, wherein at least a portion of the sealing mass has a generally frusto-conical shape.

4. The accommodating connector of claim 1, wherein the sealing mass is made from a resilient or compressible material.

5. The accommodating connector of claim 1, wherein the sealing mass is made from silicone.

6. The accommodating connector of claim 1, wherein the lubricious coating is applied to at least a portion of the sealing mass.

7. The accommodating connector of claim 1, wherein the lubricious coating is applied to a surface that is located near an interface between the port and the standard medical connector.

8. The accommodating connector of claim 1, wherein the incoming fluid line comprises a central venous catheter.

9. The accommodating connector of claim 1, wherein the incoming fluid line comprises a peripheral venous catheter.

10. The accommodating connector of claim 1, wherein the incoming fluid line has a width of up to 16 gauge.

11. The accommodating connector of claim 1, wherein the protruding tube comprises polyimide.

12. An accommodating medical connector configured to resist blood clot formation, thereby extending a number of hours that the connector may be used for periodic blood withdrawals, the connector comprising:

an outer housing having an elongate housing axis, a first side configured to accept standard medical tubing comprising an incoming fluid line, and a connecting side having an outer connecting structure configured to securely but removably interlock with an outer portion of a standard medical connector to form an interior volume;

an elongate protruding cylindrical tube having a stiffness greater than the standard medical tubing and having an elongate tube axis, the protruding tube positioned so its elongate tube axis is generally aligned with and concentric to the elongate housing axis of the outer housing, an interior of the protruding tube forming a fluid path and terminating at a port, the protruding tube configured to:

resiliently press against the standard medical connector when the standard medical connector is securely but removably interlocked with the outer connecting structure to provide a contiguous blood flow path; and minimize gaps between the standard medical connector and the protruding tube;

a hub within the outer housing, axially aligned with both the incoming fluid line and the elongate tube axis and positioned between them to form a permanent secure connection such that any movement of the protruding tube in a direction of the elongate tube axis and the elongate housing axis causes corresponding movement of the incoming fluid line, the fluid path passing through the hub;

a spring configured to exert force on the protruding tube or hub in a direction aligned with the fluid path such that the protruding tube protrudes into the interior volume and resiliently abuts a corresponding lumen of the standard medical connector such that when fluid passes through the interior volume and out of the port, it continues directly into the corresponding lumen of the standard medical connector, minimizing leakage; and a sealing mass positioned at or near the tip of the protruding tube, the sealing mass having a shape configured to correspond with a shape of the standard medical connector when the standard medical connector is securely but removably interlocked with the such that the sealing mass prevents a fluid contained within the tube from leaking out of the port and into the interior volume instead of proceeding into the corresponding lumen of the standard medical connector, and the sealing mass positioned and shaped to function together with the protruding tube, and the protruding tube is aligned with and has a width similar to a width of the corresponding lumen of the standard medical connector, to reduce blood clotting and confine a fluid flow to a fluid path while inhibiting leakage into and clotting within the interior volume outside the fluid path.

13. The accommodating connector of claim 12, wherein the sealing mass has a shape configured to correspond with a shape of the standard medical connector such that the sealing mass shape generally approximates the shape of an opening in the standard medical connector even when the accommodating connector is not mating with the standard medical connector.

14. The accommodating connector of claim 12, wherein at least a portion of the sealing mass has a generally frusto-conical shape.

15. The accommodating connector of claim 12, wherein the sealing mass is made from a resilient or compressible material.

16. The accommodating connector of claim 12, wherein the sealing mass is made from silicone.

17. The accommodating connector of claim 12, wherein the incoming fluid line comprises a central venous catheter.

18. The accommodating connector of claim 12, wherein the incoming fluid line comprises a peripheral venous catheter.

19. The accommodating connector of claim 12, wherein the incoming fluid line has a width of up to 16 gauge.

20. The accommodating connector of claim 12, wherein the protruding tube comprises polyimide.

21. An accommodating medical connector configured to resist blood clot formation, thereby extending a number of hours that the connector may be used for periodic blood withdrawals, the connector comprising:
an outer housing having an elongate housing axis, a first side configured to accept standard medical tubing comprising an incoming fluid line, and a connecting side having an outer connecting structure configured to securely but removably interlock with an outer portion of a standard medical connector to form an interior volume;
an elongate protruding cylindrical tube having a stiffness greater than the standard medical tubing and having an elongate tube axis, the protruding tube positioned so its elongate tube axis is generally aligned with and concentric to the elongate housing axis of the outer housing, an interior of the tube forming a fluid path and terminating at a port, the protruding tube configured to:
resiliently press against the standard medical connector when the standard medical connector is securely but removably interlocked with the outer connecting structure to provide a contiguous blood flow path; and
minimize gaps between the standard medical connector and the protruding tube;
a hub within the outer housing, axially aligned with both the incoming fluid line and the elongate tube axis and positioned between them to form a permanent secure connection such that any movement of the protruding tube in a direction of the elongate tube axis and the elongate housing axis causes corresponding movement of the incoming fluid line, the fluid path passing through the hub;
a spring configured to exert force on the protruding tube or hub in a direction aligned with the fluid path such that the protruding tube protrudes into the interior volume and resiliently abuts a corresponding lumen of the standard medical connector such that when fluid passes through the interior volume and out of the port, it continues directly into the corresponding lumen of the standard medical connector, minimizing leakage; and
a lubricious coating applied to at least a portion of an inner lumen of the protruding tube, the coating configured to lubricate blood-contacting surfaces to reduce blood clotting.

22. The accommodating connector of claim 21, wherein the lubricious coating is applied to at least a portion of the sealing mass.

23. The accommodating connector of claim 21, wherein the lubricious coating is applied to a surface that is located near an interface between the port and the standard medical connector.

24. The accommodating connector of claim 21, wherein the incoming fluid line comprises a central venous catheter.

25. The accommodating connector of claim 21, wherein the incoming fluid line comprises a peripheral venous catheter.

26. The accommodating connector of claim 21, wherein the incoming fluid line has a width of up to 16 gauge.

27. The accommodating connector of claim 21, wherein the protruding tube comprises polyimide.

28. An accommodating medical connector configured to resist blood clot formation, thereby extending a number of hours that the connector may be used for periodic blood withdrawals, the connector comprising:
an outer housing having an elongate housing axis, a first side configured to accept standard medical tubing comprising an incoming fluid line, and a connecting side having an outer connecting structure configured to securely but removably interlock with an outer portion of a standard medical connector to form an interior volume;
an elongate protruding cylindrical tube having a stiffness greater than the standard medical tubing and having an elongate tube axis, the protruding tube positioned so its elongate tube axis is generally aligned with and concentric to the elongate housing axis of the outer housing, an interior of the protruding tube forming a fluid path and terminating at a port, the protruding tube configured to:
resiliently press against the standard connector when the standard medical connector is securely but removably interlocked with the outer connecting structure to provide a contiguous blood flow path; and
minimize gaps between the standard medical connector and the protruding tube;
a hub within the outer housing, axially aligned with both the incoming fluid line and the elongate tube axis and positioned between them to form a permanent secure connection such that any movement of the protruding tube in a direction of the elongate tube axis and the elongate housing axis causes corresponding movement of the incoming fluid line, the fluid path passing through the hub; and
a sealing mass encircling the protruding tube on the protruding tube's outer surface, the sealing mass:
positioned at or near the tip of the protruding tube, thereby configured to provide an interface between the accommodating connector and the standard medical connector;
having a shape configured to correspond with a shape of the standard medical connector when the standard medical connector is removably interlocked with the accommodating connector such that the sealing mass prevents a fluid contained within the protruding tube from leaking out of the port and into the interior volume instead of proceeding into a corresponding lumen of the standard medical connector; and
configured to provide a seal only when the outer connecting structure is securely but removably interlocked with the standard medical connector such that the protruding tube protrudes into the interior volume, the sealing mass thereby positioned and shaped to function together with the protruding tube, and the protruding tube is aligned with and has a width similar to a width of the corresponding lumen of the standard medical connector to reduce blood clotting and confine a fluid flow to a fluid path while inhibiting leakage into and clotting within the interior volume outside the fluid path.

29. The accommodating connector of claim 28, wherein the sealing mass has a shape configured to correspond with a shape of the standard medical connector such that the sealing mass shape generally approximates the shape of an opening in the standard medical connector even when the accommodating connector is not mating with the standard medical connector.

30. The accommodating connector of claim 28, wherein at least a portion of the sealing mass has a generally frusto-conical shape.

31. The accommodating connector of claim 28, wherein the sealing mass is made from a resilient or compressible material.

32. The accommodating connector of claim 28, wherein the sealing mass is made from silicone.

33. The accommodating connector of claim 28, wherein the incoming fluid line comprises a central venous catheter.

34. The accommodating connector of claim 28, wherein the incoming fluid line comprises a peripheral venous catheter.

35. The accommodating connector of claim 28, wherein the incoming fluid line has a width of up to 16 gauge.

36. The accommodating connector of claim 28, wherein the protruding tube comprises polyimide.

\* \* \* \* \*